US010046048B2

(12) United States Patent
Skibinksi et al.

(10) Patent No.: US 10,046,048 B2
(45) Date of Patent: *Aug. 14, 2018

(54) HOMOGENOUS SUSPENSION OF IMMUNOPOTENTIATING COMPOUNDS AND USES THEREOF

(71) Applicant: GlaxoSmithKline Biologicals SA, Rixensart (BE)

(72) Inventors: David Skibinksi, Singapore (SG); Siddhartha Jain, Troy, NY (US); Manmohan Singh, Cary, NC (US); Derek O'Hagan, Winchester, MA (US)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,651

(22) Filed: Jul. 5, 2016

(65) Prior Publication Data

US 2016/0375132 A1    Dec. 29, 2016

Related U.S. Application Data

(62) Division of application No. 13/516,227, filed as application No. PCT/US2010/060621 on Dec. 15, 2010, now Pat. No. 9,408,907.

(60) Provisional application No. 61/286,754, filed on Dec. 15, 2009.

(51) Int. Cl.
| | | |
|---|---|---|
| *A61K 39/39* | (2006.01) | |
| *A61K 31/4745* | (2006.01) | |
| *A61K 31/7004* | (2006.01) | |
| *A61K 31/717* | (2006.01) | |
| *A61K 39/095* | (2006.01) | |
| *A61K 39/155* | (2006.01) | |
| *A61K 31/496* | (2006.01) | |
| *A61K 31/5377* | (2006.01) | |
| *A61K 31/675* | (2006.01) | |
| *A61K 31/683* | (2006.01) | |
| *A61K 39/12* | (2006.01) | |
| *A61K 39/00* | (2006.01) | |

(52) U.S. Cl.
CPC .......... *A61K 39/39* (2013.01); *A61K 31/4745* (2013.01); *A61K 31/496* (2013.01); *A61K 31/5377* (2013.01); *A61K 31/675* (2013.01); *A61K 31/683* (2013.01); *A61K 31/7004* (2013.01); *A61K 31/717* (2013.01); *A61K 39/095* (2013.01); *A61K 39/12* (2013.01); *A61K 39/155* (2013.01); *A61K 2039/55505* (2013.01); *A61K 2039/55511* (2013.01); *A61K 2039/55555* (2013.01); *A61K 2039/55561* (2013.01); *A61K 2039/55566* (2013.01); *C12N 2760/14134* (2013.01); *C12N 2760/18534* (2013.01)

(58) Field of Classification Search
CPC ................ A61K 31/4745; A61K 39/12; A61K 2039/55505
USPC ........................................................ 424/489
See application file for complete search history.

(56) References Cited

U.S. PATENT DOCUMENTS

| | | | |
|---|---|---|---|
| 4,726,912 | A | 2/1988 | Bishop et al. |
| 6,180,111 | B1 | 1/2001 | Stein et al. |
| 6,699,703 | B1 | 3/2004 | Doucette-Stamm et al. |
| 6,800,744 | B1 | 10/2004 | Doucette-Stamm et al. |
| 8,466,167 | B2 | 6/2013 | Wu et al. |
| 9,034,345 | B2 | 5/2015 | Granoff et al. |
| 2011/0053893 | A1 | 3/2011 | Wu et al. |
| 2011/0081365 | A1 | 4/2011 | Cortez et al. |
| 2013/0253002 | A1 | 9/2013 | Wu et al. |

FOREIGN PATENT DOCUMENTS

| | | |
|---|---|---|
| CA | 1142083 A | 3/1983 |
| CN | 101422437 | 5/2009 |
| EP | 0011243 B1 | 4/1982 |
| WO | WO 1996/029412 | 9/1996 |
| WO | WO 1997/037026 | 10/1997 |
| WO | WO 1997/043303 | 11/1997 |
| WO | WO 1998/018930 | 5/1998 |
| WO | WO 1998/018931 | 5/1998 |
| WO | WO 1998/056901 | 12/1998 |
| WO | WO 1999/010497 | 3/1999 |
| WO | WO 1999/024578 | 5/1999 |
| WO | WO 1999/027109 | 6/1999 |
| WO | WO 1999/036544 | 7/1999 |
| WO | WO 1999/053940 | 10/1999 |
| WO | WO 1999/057280 | 11/1999 |
| WO | WO 1999/058562 | 11/1999 |
| WO | WO 2000/006737 | 2/2000 |
| WO | WO 2000/006738 | 2/2000 |
| WO | WO 2000/012131 | 3/2000 |

(Continued)

OTHER PUBLICATIONS

Okumura et al; title: Interaction between Ebola Virus Glycoprotein and Host Toll-Like Receptor 4 Leads to Induction of Proinflammatory Cytokines and SOCS1; J Virol.; Jan. 2010 vol. 84 No. 1; pp. 27-33; Epub Oct. 21, 2009.*
Murawski et al,Title: Respiratory syncytial virus activates innate immunity through Toll-like receptor 2. J Virol.; vol. 83(3); pp. 1492-1500; Epub Nov. 19, 2008.*
Gohel et al.; Title: Pharmaceutical Suspensions: A review; published online May 1, 2007, down loaded on May 30, 2014 from: (http://www.pharmainfo.net).
Feinberg, Hadar, et al., "Scavenger Receptor C-type Lectin Binds to the Leukocyte Cell Surface Glycan Lewisx by a Novel Mechanism," J. Biol. Chem., 282{23}: 17250-17258 (2007).
definition of suspension, retrieved from http://www.thefreedictionary.com/suspension on Dec. 10, 2013.

Primary Examiner — Yanzhi Zhang
(74) Attorney, Agent, or Firm — Joseph Schuller

(57) ABSTRACT

The present invention generally relates to homogeneous suspensions of small molecule immune potentiators (SMIPs) that are capable of stimulating or modulating an immune response in a subject in need thereof. The homogeneous suspensions may be used in combinations with various antigens or adjuvants for vaccine therapies.

20 Claims, 13 Drawing Sheets

(56) References Cited

FOREIGN PATENT DOCUMENTS

| | | |
|---|---|---|
| WO | WO 2000/012689 | 3/2000 |
| WO | WO 2000/022430 | 4/2000 |
| WO | WO 2000/025811 | 5/2000 |
| WO | WO 2000/037105 | 6/2000 |
| WO | WO 2000/037494 | 6/2000 |
| WO | WO 2000/058475 | 10/2000 |
| WO | WO 2000/076540 | 12/2000 |
| WO | WO 2001/009350 | 2/2001 |
| WO | WO 2001/012219 | 2/2001 |
| WO | WO 2001/034642 | 5/2001 |
| WO | WO 2001/052885 | 7/2001 |
| WO | WO 2001/064920 | 9/2001 |
| WO | WO 2001/070955 | 9/2001 |
| WO | WO 2001/081380 | 11/2001 |
| WO | WO 2001/091788 | 12/2001 |
| WO | WO 2002/000974 | 1/2002 |
| WO | WO 2002/002606 | 1/2002 |
| WO | WO 2002/008426 | 1/2002 |
| WO | WO 2002/009643 | 2/2002 |
| WO | WO 2002/009746 | 2/2002 |
| WO | WO 2002/018595 | 3/2002 |
| WO | WO 2002/022167 | 3/2002 |
| WO | WO 2002/022168 | 3/2002 |
| WO | WO 2002/034771 | 5/2002 |
| WO | WO 2002/034773 | 5/2002 |
| WO | WO 2002/059148 | 8/2002 |
| WO | WO 2002/062378 | 8/2002 |
| WO | WO 2002/077183 | 10/2002 |
| WO | WO 2002/079241 | 10/2002 |
| WO | WO 2002/079243 | 10/2002 |
| WO | WO 2002/094851 | 11/2002 |
| WO | WO 2002/094868 | 11/2002 |
| WO | WO 2002/102829 | 12/2002 |
| WO | WO 2003/011899 | 2/2003 |
| WO | WO 2003/104272 | 2/2003 |
| WO | WO 2003/020756 | 3/2003 |
| WO | WO 2003/049762 | 6/2003 |
| WO | WO 2003/068811 | 8/2003 |
| WO | WO 2003/082183 | 10/2003 |
| WO | WO 2003/093306 | 11/2003 |
| WO | WO 2003/105890 | 12/2003 |
| WO | WO 2004/014417 | 2/2004 |
| WO | WO 2004/019977 | 3/2004 |
| WO | WO 2004/032958 | 4/2004 |
| WO | WO 2004/041157 | 5/2004 |
| WO | WO 2004/048404 | 6/2004 |
| WO | WO 2004/092209 | 10/2004 |
| WO | WO 2004/092360 | 10/2004 |
| WO | WO 2005/002619 | 1/2005 |
| WO | WO 2005/004908 | 1/2005 |
| WO | WO 2005/032582 | 4/2005 |
| WO | WO 2005/079315 | 9/2005 |
| WO | WO 2006/032472 | 3/2006 |
| WO | WO 2006/032475 | 3/2006 |
| WO | WO 2006/032500 | 3/2006 |
| WO | WO 2006/081259 | 8/2006 |
| WO | WO 2007/113222 | 10/2007 |
| WO | WO 2007/113223 | 10/2007 |
| WO | WO 2007/113224 | 10/2007 |
| WO | WO 2007/116322 | 10/2007 |
| WO | WO 2007/120362 | 10/2007 |
| WO | WO 2008/019162 | 2/2008 |
| WO | WO 2009/111337 | * 9/2009 |
| WO | WO 2010/144734 | 12/2010 |
| WO | WO 2011/024072 | 3/2011 |
| WO | WO 2011/049677 | 4/2011 |

* cited by examiner

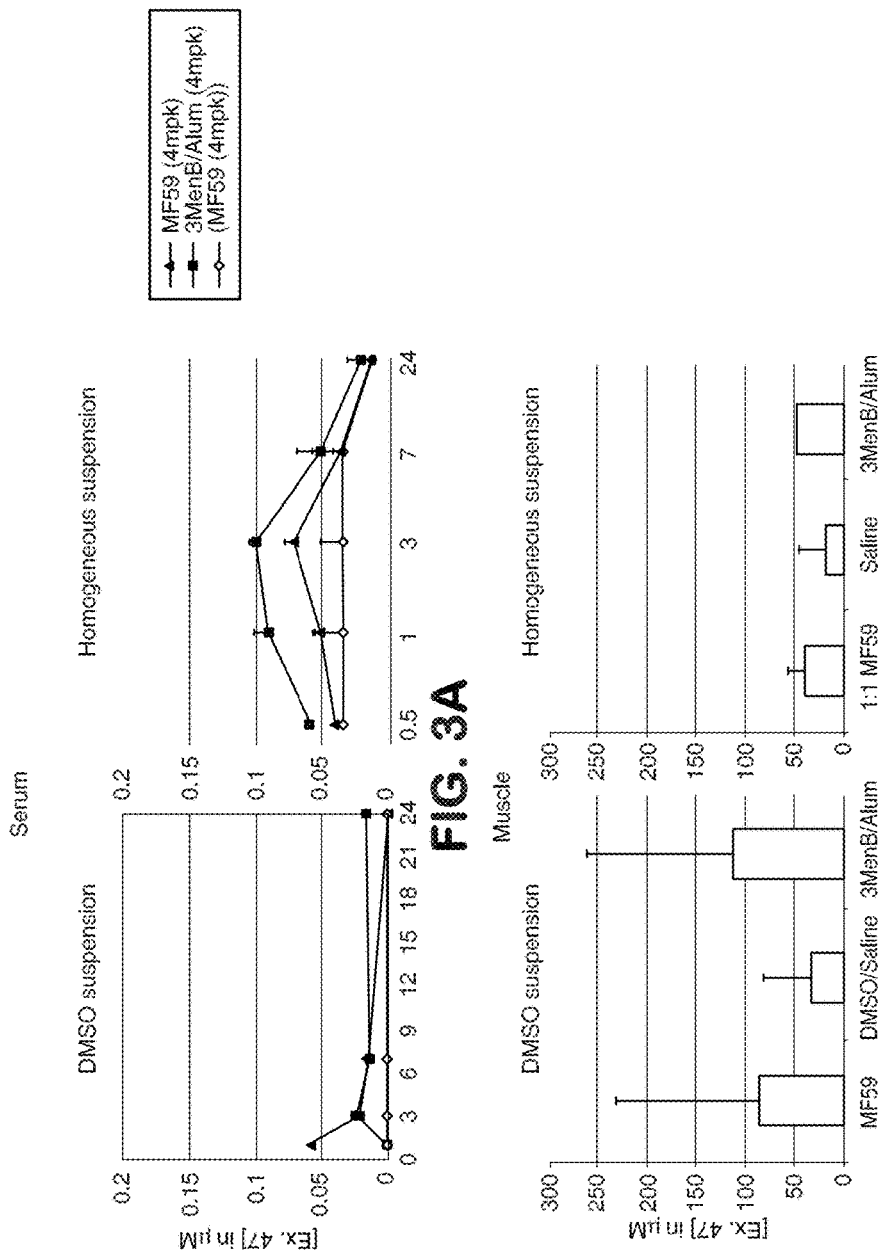

HOMOGENOUS SUSPENSION OF IMMUNOPOTENTIATING COMPOUNDS AND USES THEREOF

CROSS REFERENCE TO RELATED APPLICATIONS

This application is a divisional application of U.S. application Ser. No. 13/516,227, with an international filing date of Dec. 15, 2012, now U.S. Pat. No. 9,408,907, which is the U.S. National Stage of International Application No. PCT/US2010/060621, filed Dec. 15, 2010 and published in English, which claims the benefit of U.S. Provisional Application No. 61/286,754, filed Dec. 15, 2009. Each of the foregoing applications is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 303822018110SeqList.TXT, date recorded: Aug. 19, 2016, size: 29 KB).

BACKGROUND OF THE INVENTION

Recently developed attenuated pathogen or subunit protein vaccines, while offering significant advantages over the traditional whole pathogen vaccines in terms of safety and cost of production, generally have limited immunogenicity as compared to whole pathogens. As a result, these vaccines typically require adjuvants with significant immunostimulatory capability to reach their full potential in preventing diseases.

Efforts have been made to identify new immune modulators for use as adjuvants for vaccines and immunotherapies. In particular, an adjuvant formulation that elicits potent cell-mediated and humoral immune responses to a wide range of antigens in humans and domestic animals, but lacking the side effects of conventional adjuvants and other immune modulators, would be highly desirable. This need could be met by small molecule immune potentiators ("SMIPs") because the small molecule platform provides diverse compounds for the selective manipulation of the immune response, necessary for increasing the therapeutic index immune modulators.

Toll-like receptors (TLRs) are a group of pattern recognition receptors which bind to pathogen-associated molecular patterns (PAMPS) from bacteria, fungi, protozoa and viruses, and act as a first line of defense against invading pathogens. TLRs are essential to induce expression of genes involved in inflammatory responses, and TLRs and the innate immune system are a critical step in the development of antigen-specific acquired immunity.

Adaptive (humoral or cell-mediated) immunity is associated with the TLR signal mechanism of innate immunity. Innate immunity is a protective immune cell response that functions rapidly to fight environmental insults including, but not limited to, bacterial or viral agents. Adaptive immunity is a slower response, which involves differentiation and activation of naive T lymphocytes into T helper 1 (Th1) or T helper 2 (Th2) cell types. Th1 cells mainly promote cellular immunity, whereas Th2 cells mainly promote humoral immunity.

All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF-, interleukins, MIP-1 and MCP-1 which contribute to the killing and clearance of the pathogenic invasion.

Thirteen TLRs (named TLR1 to TLR13) have been identified in humans and mice together, and equivalent forms of many of these have been found in other mammalian species. In particular, the roles of TLR7 and TLR8 are to detect the presence of "foreign" single-stranded RNA within a cell, as a means to respond to viral invasion. Both TLR7 and TLR8 are structurally highly conserved proteins that recognize guanosine- or uridine-rich, single-stranded RNA (ssRNA) from viruses such as human immunodeficiency virus, vesicular stomatitis virus and influenza virus.

WO 2009/111337 discloses a series of compounds that bind to Toll-Like Receptors (TLR), including TLR7 and TLR8. The compounds are found to be useful as immunopotentiators, but contain a hydrophobic core and have low solubility.

It is therefore an object of this invention to provide homogeneous suspensions of SMIPs that are capable of stimulating or modulating an immune response in a subject in need thereof.

SUMMARY OF THE INVENTION

The present invention generally relates to homogeneous suspensions of small molecule immune potentiators (SMIPs; i.e. compounds of Formula I or Formula II) that are capable of stimulating or modulating an immune response in a subject in need thereof. The homogeneous suspensions may be used in combinations with various antigens or adjuvants for immunotherapy.

One exemplary approach is to use high pressure homogenization together with a surfactant and a viscosity-enhancing agent to create a stable homogeneous suspension of SMIP that contains particles in μm size range. The resulting suspensions are particularly suitable for co-delivery of SMIP with alum and oil-in-water emulsion based vaccines.

In one aspect, the invention provides a homogeneous suspension comprising (a) a Benzonaphthyridine compound of Formula I or Formula II, pharmaceutically acceptable salt, pharmaceutically acceptable solvate, N-oxide derivative, protected derivative, individual isomer or mixture of isomers thereof; (b) a surfactant, and (c) a suspension agent, wherein the suspension is stable for at least about four weeks at 4° C. In certain embodiments, the homogeneous suspension comprises about 0.5 mg/mL to about 50 mg/mL Benzonaphthyridine compound.

In certain embodiments, the Benzonaphthyridine compound is: 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine; 2-(4-methoxyphenethyl)-8-methylbenzo[f][1,7]naphthyridin-5-amine; or 2-(2-(4-(2-(5-amino-8-methylbenzo[f][1,7]naphthyridin-2-yl)ethyl)-3-methylphenoxy)ethoxy)ethanol.

In a preferred embodiment, the homogeneous suspension comprises (a) 2-(2,4-dimethylphenethyl)benzo[f][1,7]naphthyridin-5-amine, or a pharmaceutically acceptable salt or pharmaceutically acceptable solvate thereof, (b) a surfactant, and (c) a suspension agent, wherein the suspension is stable for at least about four weeks at 4° C.

In another preferred embodiment, the homogeneous suspension comprises (a) 2-(4-methoxy-2-methylphenethyl)-8-methylbenzo[f][1,7]naphthyridin-5-amine, or a pharmaceutically acceptable salt or pharmaceutically acceptable solvate thereof, (b) a surfactant, and (c) a suspension agent, wherein the suspension is stable for at least about four weeks at 4° C.

In another preferred embodiment, the homogeneous suspension comprises (a) 2-(2-(4-(2-(5-amino-8-methylbenzo[f][1,7]naphthyridin-2-yl)ethyl)-3-methylphenoxy)ethoxy)ethanol, or a pharmaceutically acceptable salt or pharmaceutically acceptable solvate thereof, (b) a surfactant, and (c) a suspension agent, wherein the suspension is stable for at least about four weeks at 4° C.

Exemplary surfactants include, e.g., Tween-80. In certain embodiments, the homogeneous suspension comprises about 0.1% to about 10% surfactant. Exemplary suspension agent includes, e.g., viscosity-enhancing agents such as carboxymethyl cellulose. In certain embodiments, the homogeneous suspension comprises about 0.1% to about 10% suspension agent.

In certain embodiments, at least about 50% of the suspension particles of the homogeneous suspension have a diameter of about 10 μm or less. In certain embodiments, at least about 50% of the suspension particles of the homogeneous suspension have a diameter of about 2 μm or less.

The homogeneous suspension of the invention can be used to potentiate an immune response and can be co-delivered with an antigen, immunogenic composition or vaccine to enhance the effectiveness of the induced immune response. An adjuvant (e.g., Alum or oil-in-water adjuvants) may also be used in combination with the homogeneous suspension of the invention.

Also provided herein are immunogenic compositions comprising (1) an antigen and (2) the homogeneous suspension of the invention.

In certain embodiments, the immunogenic composition further comprises an adjuvant. Exemplary adjuvants include, e.g., an aluminum-containing adjuvant (e.g., aluminum hydroxide, aluminum oxyhydroxide, or aluminum hydroxyphosphate), an oil-in-water emulsion (e.g., MF59), a liposome (e.g., an outer membrane vesicle), an oligonucleotide (e.g., an oligonucleotide comprising an unmethylated CpG motif).

In certain embodiments, the immunogenic composition comprises an antigen that is a bacterial antigen (e.g, an antigen from *Neisseria meningitides*), a viral antigen (e.g., an antigen from respiratory syncytial virus (RSV) or Ebola virus). In certain embodiment, the immunogenic composition comprises (1) a viral antigen (e.g., an antigen from Ebola virus) and (2) 2-(4-methoxy-2-methylphenethyl)-8-methylbenzo[f][1,7]naphthyridin-5-amine or 2-(2-(4-(2-(5-amino-8-methylbenzo[f][1,7]naphthyridin-2-yl)ethyl)-3-methylphenoxy)ethoxy)ethanol.

Also provided herein are methods of using the homogeneous suspension of the invention to potentiate an immune response in a subject in need thereof, and methods of producing the homogeneous suspension of the invention.

The invention also relates to a method for producing a homogeneous suspension that comprises a compound of Formula I or Formula II, a surfactant and a suspension agent.

The method comprises mixing the compound of Formula I or Formula II, a surfactant and a suspension agent, and homogenizing the mixture under high pressure, such as 15,000-20,000 psi, to produce a homogeneous suspension that preferably has a D50 of about 10 μm or less, more preferably, about 2 μm or less, and, optionally, a D90 of about 10 μm or less.

Also provided herein are methods of using the immunogenic composition of the invention to generating an immune response in a subject in need thereof.

The invention also relates to a homogeneous suspension as described herein for use in therapy, and to the use of a homogeneous suspension for the manufacture of a medicament for potentiating or inducing an immune response.

BRIEF DESCRIPTION OF THE DRAWINGS

FIG. 3A shows the serum levels of Example 47 (non-homogeneous/DMSO suspension versus homogeneous suspension) in mice after intramuscular injection at 4 mpk (miligram per kilogram) in the vehicles indicated with 3MenB/Alum. FIG. 3B shows the injection site muscle levels of Example 47 (non-homogeneous/DMSO suspension versus homogeneous suspension) in mice 24 hours after intramuscular injection at 4 mpk in the vehicles indicated with 3MenB/Alum.

FIG. 7A shows the IgG1, IgG2a, IgG2b and IgG3 titres for GNA2132-GNA1030. FIG. 7B shows the IgG1, IgG2a, IgG2b and IgG3 titres for GNA2091-GNA1870. FIG. 7C shows the IgG1, IgG2a, IgG2b and IgG3 titres for NadA.

DETAILED DESCRIPTION OF THE INVENTION

1. Overview

Figure 1:
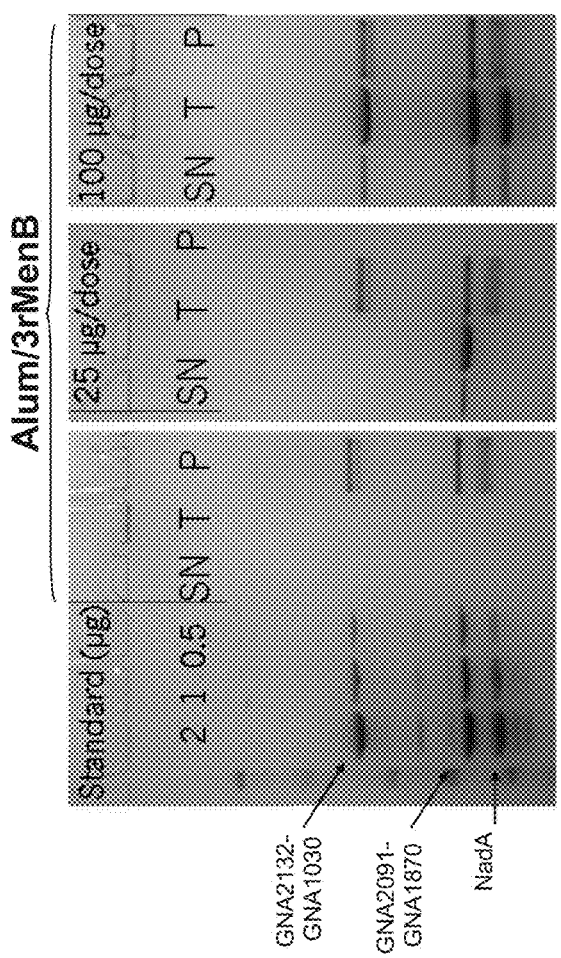
FIG. 1A shows the electrophoretic profiles (by SDS-PAGE) of three MenB antigens, alone or after adding different doses of Example 47 suspension to the Alum/3MenB formulations. Key: SN=unadsorbed antigen (representative of 20% of 10 μg dose); T=unadsorbed antigen (representative of 200% of 20 μg dose); P=adsorbed antigen recovery (representative of 10% of 10 μg dose).
FIG. 1B is a table showing the percentage of antigen adsorption onto alum.

In one aspect, this invention relates to homogeneous suspension of small molecule immune potentiators (SMIPs). The homogeneous suspensions can be used to potentiate an immune response.

As described herein, the inventors have evaluated the efficacy of homogeneous suspensions of an exemplary SMIP, dimethylphenethyl)benzo[f][1,7]naphthyridin-5-amine. These studies demonstrated that homogeneous suspensions of SMIP are more effective than non-homogeneous suspensions (in DMSO) in potentiating immune response.

One exemplary approach to produce the homogeneous suspensions is to use high pressure homogenization together with a surfactant and a viscosity-enhancing agent to create a stable homogeneous suspension of SMIP that contains particles in the 100 nm to 10 μm size range. The resulting suspensions are particularly suitable for co-delivery of SMIP with alum and oil-in-water emulsion based vaccines. A homogeneous suspension has a defined size distribution, allowing better uniformity of doses. Furthermore, the resulting particle size increases bioavailability of the SMIP to immune cells post administration. The suspensions also have the potential to be stable over time as measured by size distribution. Finally, a homogeneous suspension of SMIP provide immuno-stimulatory effect at lower doses (e.g., 10 μg/dose or less) as compared to a non-homogeneous suspension at the same dosage.

In a preferred embodiment, the homogeneous suspension comprises (a) 2-(2,4-dimethylphenethyl)benzo[f][1,7]naphthyridin-5-amine, or pharmaceutically acceptable salt or pharmaceutically acceptable solvate thereof, (b) a surfactant, and (c) a suspension agent, wherein the suspension is stable for at least about four weeks at 4° C.

In another preferred embodiment, the homogeneous suspension comprises (a) 2-(4-methoxy-2-methylphenethyl)-8-methylbenzo[f][1,7]naphthyridin-5-amine, or a pharmaceutically acceptable salt or pharmaceutically acceptable solvate thereof, (b) a surfactant, and (c) a suspension agent, wherein the suspension is stable for at least about four weeks at 4° C.

In another preferred embodiment, the homogeneous suspension comprises (a) 2-(2-(4-(2-(5-amino-8-methylbenzo[f][1,7]naphthyridin-2-yl)ethyl)-3-methylphenoxy)ethoxy)ethanol, or a pharmaceutically acceptable salt or pharmaceutically acceptable solvate thereof, (b) a surfactant, and (c) a suspension agent, wherein the suspension is stable for at least about four weeks at 4° C.

The homogeneous suspension of the invention can be used to potentiate an immune response and can be co-delivered with an antigen, immunogenic composition or vaccine to enhance the effectiveness of the induced immune response.

Also provided herein are methods of using the homogeneous suspension of the invention to potentiate an immune response in a subject in need thereof, and methods of producing the homogeneous suspension of the invention.

2. Definitions

As used herein, the singular forms "a," "an" and "the" include plural references unless the content clearly dictates otherwise.

The term "about", as used here, refers to +/−10% of a value.

The term "alkenyl," as used herein, refers to a partially unsaturated branched or straight chain hydrocarbon having at least one carbon-carbon double bond. Atoms oriented about the double bond are in either the cis (Z) or trans (E) conformation. An alkenyl group can be optionally substituted. As used herein, the terms "$C_2$-$C_3$alkenyl", "$C_2$-$C_4$alkenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. If not otherwise specified, an alkenyl group generally is a $C_2$-$C_6$ alkenyl. Non-limiting examples of alkenyl groups, as used herein, include ethenyl, propenyl, butenyl, pentenyl, hexenyl, heptenyl, octenyl, nonenyl, decenyl and the like.

The term "alkenylene," as used herein, refers to a partially unsaturated branched or straight chain divalent hydrocarbon radical derived from an alkenyl group. An alkenylene group can be optionally substituted. As used herein, the terms "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. If not otherwise specified, an alkenylene group generally is a $C_1$-$C_6$ alkenylene. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. An alkyl group can be optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. If not otherwise specified, an alkyl group generally is a $C_1$-$C_6$ alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. An alkylene group can be optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. If not otherwise specified, an alkylene group generally is a $C_1$-$C_6$ alkylene. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl," as used herein, refers to a partially unsaturated branched or straight chain hydrocarbon having at least one carbon-carbon triple bond. An alkynyl group can be optionally substituted. As used herein, the terms "$C_2$-$C_3$alkynyl", "$C_2$-$C_4$alkynyl", "$C_2$-$C_5$alkynyl", "$C_2$-$C_6$alkynyl", "$C_2$-$C_7$alkynyl", and "$C_2$-$C_8$alkynyl" refer to an alkynyl group containing at least 2, and at most 3, 4, 5, 6, 7 or 8 carbon atoms, respectively. If not otherwise specified, an alkynyl group generally is a $C_2$-$C_6$ alkynyl. Non-limiting examples of alkynyl groups, as used herein, include ethynyl, propynyl, butynyl, pentynyl, hexynyl, heptynyl, octynyl, nonynyl, decynyl and the like.

The term "alkynylene," as used herein, refers to a partially unsaturated branched or straight chain divalent hydrocarbon radical derived from an alkynyl group. An alkynylene group can be optionally substituted. As used herein, the terms "$C_2$-$C_3$alkynylene", "$C_2$-$C_4$alkynylene", "$C_2$-$C_5$alkynylene", "$C_2$-$C_6$alkynylene", "$C_2$-$C_7$alkynylene", and "$C_2$-$C_8$alkynylene" refer to an alkynylene group containing at least 2, and at most 3, 4, 5, 6, 7 or 8 carbon atoms respectively. If not otherwise specified, an alkynylene group generally is a $C_2$-$C_6$ alkynylene. Non-limiting examples of alkynylene groups as used herein include, ethynylene, propynylene, butynylene, pentynylene, hexynylene, heptynylene, octynylene, nonynylene, decynylene and the like.

The term "alkoxy," as used herein, refers to the group —$OR_a$, where $R_a$ is an alkyl group as defined herein. An alkoxy group can be optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. An aryl group can be optionally substituted. Non-limiting examples of aryl groups, as used herein, include phenyl, naphthyl, fluorenyl, indenyl, azulenyl, anthracenyl and the like.

The term "arylene," as used means a divalent radical derived from an aryl group. An arylene group can be optionally substituted.

The term "cyano," as used herein, refers to a —CN group.

The term "cycloalkyl," as used herein, refers to a saturated or partially unsaturated, monocyclic, fused bicyclic, fused tricyclic or bridged polycyclic ring assembly. As used herein, the terms "$C_3$-$C_5$ cycloalkyl", "$C_3$-$C_6$ cycloalkyl", "$C_3$-$C_7$ cycloalkyl", "$C_3$-$C_8$ cycloalkyl, "$C_3$-$C_9$ cycloalkyl and "$C_3$-$C_{10}$ cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. A cycloalkyl group can be optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The terms "haloalkenyl" or "halo-substituted alkenyl," as used herein, refers to an alkenyl group as defined herein, substituted with one or more halogen groups, wherein the halogen groups are the same or different. A haloalkenyl group can be optionally substituted. Non-limiting examples of such branched or straight chained haloalkenyl groups, as used herein, include ethenyl, propenyl, butenyl, pentenyl, hexenyl, heptenyl, octenyl, nonenyl, decenyl and the like substituted with one or more halogen groups, wherein the halogen groups are the same or different.

The terms "haloalkynyl" or "halo-substituted alkynyl," as used herein, refers to an alkynyl group as defined above, substituted with one or more halogen groups, wherein the halogen groups are the same or different. A haloalkynyl group can be optionally substituted. Non-limiting examples of such branched or straight chained haloalkynyl groups, as used herein, include ethynyl, propynyl, butynyl, pentynyl, hexynyl, heptynyl, octynyl, nonynyl, decynyl, and the like substituted with one or more halogen groups, wherein the halogen groups are the same or different.

The term "haloalkoxy," as used herein, refers to an alkoxy group as defined herein, substituted with one or more halogen groups, wherein the halogen groups are the same or different. A haloalkoxy group can be optionally substituted. Non-limiting examples of such branched or straight chained haloalkynyl groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like, substituted with one or more halogen groups, wherein the halogen groups are the same or different.

The term "heteroalkyl," as used herein, refers to an alkyl group as defined herein wherein one or more carbon atoms are independently replaced by one or more of oxygen, sulfur, nitrogen, or combinations thereof.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. A heteroaryl group may contain one or more substituents. A heteroaryl group can be optionally substituted. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term "heterocycloalkyl," as used herein, refers to a cycloalkyl, as defined herein, wherein one or more of the ring carbons are replaced by a moiety selected from —O—, —N═, —NR—, —C(O)—, —S—, —S(O)— or —S(O)2-, wherein R is hydrogen, $C_1$-$C_4$alkyl or a nitrogen protecting group, with the proviso that the ring of said group does not contain two adjacent O or S atoms. A heterocycloalkyl group can be optionally substituted. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "isocyanato," as used herein, refers to a —N═C═O group.

The term "isothiocyanato," as used herein, refers to a —N═C═S group

The term "mercaptyl," as used herein, refers to an (alkyl) S— group.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, ═O, ═N—OH, ═N—OR, ═N—R, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$NR$_2$, —NRS(O)$_2$NR$_2$, —NHS(O)$_2$R, —NRS(O)$_2$R, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substituent groups is done in accordance with the well-understood valence limitations of each group, for example ═O is a suitable substituent for an alkyl group but not for an aryl group.

The term "prodrug," as used herein, refers to an agent that is converted into the parent drug in vivo. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, "treatment" refers to any of (i) the prevention of a condition (e.g., a disease or disorder) in question (e.g. cancer or a pathogenic infection, as in a traditional vaccine), (ii) the reduction or elimination of symptoms associated with the condition in question, and (iii) the substantial or complete elimination of the condition in question. Treatment may be effected prophylactically (prior to arrival of the condition in question) or therapeutically (following arrival of the same).

The terms "effective amount" or "pharmaceutically effective amount" of a homogeneous suspension of the present invention refers to an amount sufficient to potentiate an immune response, for example by at least about 10%, as described herein. The terms "effective amount" or "pharmaceutically effective amount" of an immunogenic composition of the present invention refer herein to a sufficient amount of the immunogenic composition for the treatment or diagnosis of a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "pharmaceutically acceptable" or "pharmacologically acceptable" is meant a material which is not biologically or otherwise undesirable, e.g., the material may be administered to an individual without causing any unduly undesirable biological effects or interacting in an unduly deleterious manner with any of the components of the composition in which it is contained.

By "physiological pH" or a "pH in the physiological range" is meant a pH in the range of approximately 6.5 to 8.0 inclusive, more typically in the range of approximately 7.2 to 7.6 inclusive.

As used here, the term "injectable composition", or variants thereof, refers to pharmaceutically acceptable compositions suitable for injection into a vertebrate subject, which compositions are typically sterile, pyrogen-free, and possess specific pH and isotonicity values suitable for injection.

As used herein, the term "particle" refers to a particle of about 10 nm or less to about 150 μm in diameter, for example, ranging from 10 nm to 25 nm to 50 nm to 100 nm to 250 nm to 500 nm to 1 μm to 2.5 μm to 5 μm to 10 μm to 25 μm to 50 μm to 100 μm. The term "particle" as used herein thus includes "nanoparticle," which is defined herein as a particle having a diameter less than 1000 nm, and "microparticle," which is defined herein as a particle having a diameter ranging from 1 μm to 1000 μm. In some embodiments, the polymeric particles described herein can be generally spherical.

The term "polypeptide" refers to a polymer of amino acid residues and is not limited to a minimum length of the product. Thus, full length proteins, peptides, oligopeptides, dimers, multimers, and the like, are included within the definition.

A "polypeptide-containing species" is a molecule, at least a portion of which is a polypeptide. Examples include polypeptides, proteins including glycoproteins, metalloproteins and lipoproteins, polysaccharide antigens conjugated to carrier proteins, and so forth. Proteins for use herein include full-length proteins and fragments thereof. In certain embodiments, modifications to the native sequence, such as deletions, additions and substitutions (generally conservative in nature), are employed.

The term "fragment" as used herein refers to a physically contiguous portion of the primary structure of a biomolecule. In the case of proteins, a fragment may be defined by a contiguous portion of the amino acid sequence of that protein and may be at least 3-5 amino acids, at least 6-10 amino acids, at least 11-15 amino acids, at least 16-24 amino acids, at least 25-30 amino acids, and at least 30-45 amino acids. In the case of polynucleotide, a fragment is defined by a contiguous portion of the nucleic acid sequence of that polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

A "polynucleotide" is a nucleic acid polymer. A polynucleotide can include as few as 5, 6, 7 or 8 nucleotides. Furthermore, a "polynucleotide" can include both double- and single-stranded sequences and refers to, but is not limited to, cDNA from viral, procaryotic or eukaryotic mRNA, genomic RNA and DNA sequences from viral (e.g. RNA and DNA viruses and retroviruses), prokaryotic or eukaryotic organisms, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

A "polynucleotide-containing species" is a molecule, at least a portion of which is a polynucleotide. Examples include RNA vector constructs, DNA vector constructs and so forth.

As used herein the term "saccharide" encompasses monosaccharides, oligosaccharides and polysaccharides. A "saccharide-containing species" is a molecule, at least a portion of which is a saccharide. Examples include saccharide antigens, antigens comprising saccharides conjugated to carrier peptides, and so forth.

As used herein the term "isolated" refers to a chemical species such as a polynucleotide, a polypeptide, and an antibody, etc. that is in an environment different from that in which the chemical species naturally occurs. A chemical species which is isolated is generally substantially purified. Methods of isolating cells are also well known to those skilled in the art.

A "purified" protein is a protein which is produced (e.g., recombinantly or synthetically) or isolated from its natural host, such that the amount of protein present in a composition is substantially higher than that present in a crude preparation. In general, a purified protein will be at least about 50% homogeneous, more preferably at least about 80%, about 85%, about 90%, about 95%, about 97%, about 98%, about 99%, or more, homogeneous.

As used herein, an "immunological response" or "immune response" is the development in a subject of a humoral and/or a cellular immune response to the immunogenic species.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Reported TLRs (along with examples of some reported ligands, which may be used as immunogenic species in various embodiments of the invention) include the following: TLR1 (bacterial lipoproteins from *Mycobacteria, Neisseria*), TLR2 (zymosan yeast particles, peptidoglycan, lipoproteins, glycolipids, lipopolysaccharide), TLR3 (viral double-stranded RNA, poly:IC), TLR4 (bacterial lipopolysaccharides, plant product taxol), TLR5 (bacterial flagellins), TLR6 (yeast zymosan particles, lipotechoic acid, lipopeptides from *mycoplasma*), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others. Dendritic cells are recognized as some of the most important cell types for initiating the priming of naive CD4$^+$ helper T (T$_H$) cells and for inducing CD8$^+$ T cell differentiation into killer cells. TLR signaling has been reported to play an important role in determining the quality of these helper T cell responses, for instance, with the nature of the TLR signal determining the specific type of T$_H$ response that is observed (e.g., T$_H$1 versus T$_H$2 response). A combination of antibody (humoral) and cellular immunity are produced as part of a T$_H$1-type response, whereas a T$_H$2-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer, *Nature Medicine*, 11, S63-S68 (2005), K. S. Rosenthal and D. H. Zimmerman, *Clinical and Vaccine Immunology*, 13(8), 821-829 (2006), and the references cited therein.

For purposes of the present invention, a humoral immune response refers to an immune response mediated by antibody molecules, while a cellular immune response is one mediated by T-lymphocytes and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4$^+$ and CD8$^+$ T-cells.

A composition such as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) *J. Immunol.* 151:4189-4199; Doe et al. (1994) *Eur. J. Immunol.* 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve, for example, to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "antigen" refers to a molecule containing one or more epitopes (either linear, conformational or both) that elicit an immunological response. The term may be used interchangeably with the term "immunogen." An "epitope" is that portion of given species (e.g., an antigenic molecule or antigenic complex) that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids. The term "antigen" denotes both subunit antigens, i.e., antigens which are separate and discrete from a whole organism or cell with which the antigen is associated in nature, as well as killed, attenuated or inactivated bacteria, viruses, fungi, parasites or other microbes or tumor cells. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

Thus, for purposes of the present invention, antigens can be derived from any of the various viruses, bacteria, parasites, fungi and other microbes, as well as any of the various tumor antigens. Antigens also include nucleic acids which express an antigen or antigenic determinant in vivo. As a few specific examples, antigens may be proteins from or derived from the herpes virus family, including proteins derived from herpes simplex virus (HSV) types 1 and 2, such as HSV-1 and HSV-2 glycoproteins gB, gD and gH; proteins derived from cytomegalovirus (CMV) including CMV gB and gH; proteins derived from hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV); proteins, including gp120, gp160, gp41, p24gag and p55gag envelope proteins, derived from HIV, including members of the various genetic subtypes of HIV isolates HIV$_{IIIb}$, HIV$_{SF2}$, HIV$_{LAV}$, HIV$_{LAI}$, HIV$_{MN}$, HIV-1$_{CM235}$, HIV-1$_{US4}$, HIV-2; proteins derived from simian immunodeficiency virus (SIV); and proteins derived from *Neisseria meningitidis* (A, B, C, Y), *Hemophilus influenza* type B (HIB), *Helicobacter pylori*; human serum albumin and ovalbumin, among many others.

An immunogenic composition which contains an antigen in accordance with the present invention displays "enhanced immunogenicity" when it possesses a greater capacity to elicit an immune response than the immune response elicited by an equivalent amount of the antigen administered using a different delivery system, e.g., wherein the antigen is administered as a soluble protein. Thus, an immunogenic or vaccine composition may display "enhanced immunogenicity" because the antigen is more strongly immunogenic or because a lower dose or fewer doses of antigen are necessary to achieve an immune response in the subject to which the antigen is administered. Such enhanced immunogenicity can be determined by administering the antigen composition and antigen controls to animals and comparing antibody titers and/or cellular-mediated immunity against the two using standard assays described herein.

The term "adjuvant" or "immunological adjuvant" refers to any substance that assists or modifies the action of an antigen in the immune system. Adjuvants can potentiate humoral and/or cellular immunity.

The term "excipient" refers to any essentially accessory substance that may be present in the finished dosage form. For example, the term "excipient" includes vehicles, binders, disintegrants, fillers (diluents), suspending/dispersing agents, and so forth.

As used herein, the phrase "vector construct" generally refers to any assembly that is capable of directing the expression of a nucleic acid sequence(s) or gene(s) of interest. A "DNA vector construct" refers to a DNA molecule that is capable of directing the expression of a nucleic acid sequence(s) or gene(s) of interest. One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

The term "homogeneous" refers to a mixture or blend of components that is generally uniform in structure and composition with little variability throughout the mixture. Different portions of a homogeneous mixture exhibit essentially the same physical and chemical properties substantially at every place throughout the mixture. The stoichiometry in a homogeneous mixture is also substantially constant throughout the mixture.

The terms "suspension" refers to particles that are dispersed in a liquid.

The term "aqueous suspension" refers to particles that are suspended in an aqueous (continuous) phase liquid that contains water.

A "stable" homogeneous suspension is a suspension in which the size of the suspended particles does not substantially change (e.g., change by no more that about 10%) over time.

3. Homogeneous Suspension of Immune-Potentiating Compounds

In one aspect, the invention is a homogeneous suspension comprising (a) a Benzonaphthyridine compound of Formula I or Formula II, pharmaceutically acceptable salt, pharmaceutically acceptable solvate, N-oxide derivative, protected derivative, individual isomer or mixture of isomers thereof; (b) a surfactant, and (c) a suspension agent. The homogeneous suspension contain an aqueous phase, that can be water or any other suitable aqueous phase, such as buffered aqueous solutions.

Preferably, the homogeneous suspension is stable for at least about 2 weeks, at least about 4 weeks, at least about 2 months, at least about 3 months, at least about 4 months, at least about 5 months, at least about 6 months, at least about 7 months, at least about 8 months, at least about 9 months, at least about 10 months, at least about 11 months, at least about 1 year or longer, at 4° C.

The homogeneous suspensions preferably have a size distribution wherein 50% of the particles (D50) are smaller than about 10 µM, smaller than about 9 µM, smaller than about 8 µM, smaller than about 7 µM, smaller than about 6 µM, smaller than about 5 µM, smaller than about 4 µM, smaller than about 3 µM, smaller than about 2 µM, smaller than about 1 µM, or smaller than about 0.9 µM. Alternatively or in addition, the homogeneous suspensions can have a size distribution wherein 90% of the particles (D90) are smaller than about 10 µM, smaller than about 9 µM, smaller than about 8 µM, smaller than about 7 µM, smaller than about 6 µM, smaller than about 5 µM, smaller than about 4 µM, smaller than about 3 µM, or smaller than about 2 µM.

The homogeneous suspension can contain any suitable surfactant, such as an anionic surfactant, a cationic surfactant, zwitterionic (amphoteric) surfactants, or a non-ionic surfactant. Exemplary anionic surfactants include, e.g., perfluorooctanoate (PFOA or PFO), perfluorooctanesulfonate (PFOS), alkyl sulfate salts such as sodium dodecyl sulfate (SDS) or ammonium lauryl sulfate, sodium laureth sulfate (also known as sodium lauryl ether sulfate, SLES), alkyl benzene sulfonate, and fatty acid salts. Exemplary cationic surfactants include, e.g., alkyltrimethylammonium salts such as cetyl trimethylammonium bromide (CTAB, or hexadecyl trimethyl ammonium bromide), cetylpyridinium chloride (CPC), polyethoxylated tallow amine (POEA), benzalkonium chloride (BAC), benzethonium chloride (BZT). Exemplary zwitterionic (amphoteric) surfactants include, e.g., dodecyl betaine, cocamidopropyl betaine, and coco ampho glycinate. Exemplary nonionic surfactants include, e.g., alkyl poly(ethylene oxide), alkylphenol poly(ethylene oxide), copolymers of poly(ethylene oxide) and poly(propylene oxide) (commercially called Poloxamers or Poloxamines), Aayl polyglucosides (e.g., octyl glucoside or decyl maltoside), fatty alcohols (e.g., cetyl alcohol or oleyl alcohol), cocamide MEA, cocamide DEA, Pluronic F-68, and Polysorbates, such as Tween 20 (Polysorbate 20), Tween 80 (polysorbate 80), and dodecyl dimethylamine oxide. The homogeneous suspensions can contain two or more surfactants in any combination, if desired.

The homogeneous suspensions can contain from about 0.1% to about 10% surfactant (v/v or w/v), about 0.1% to about 5% surfactant, 0.1% to about 4% surfactant, 0.1% to about 3% surfactant, 0.1% to about 2% surfactant, 0.1% to about 1% surfactant, 0.1% to about 0.5% surfactant, about 0.1% surfactant, about 0.2% surfactant, about 0.3% surfactant, about 0.4% surfactant, about 0.5% surfactant, about 0.6% surfactant, about 0.7% surfactant, about 0.8% surfactant, about 0.9% surfactant, or about 1% surfactant.

A preferred surfactant for use in the homogeneous suspensions described herein is Tween 80 (polysorbate 80). Preferably, the homogeneous suspension contains about 0.1% to about 5%, 0.1% to about 4%, 0.1% to about 3%, 0.1% to about 2%, 0.1% to about 1%, 0.1% to about 0.5%, about 0.1%, about 0.2%, about 0.3%, about 0.4%, about 0.5%, about 0.6%, about 0.7%, about 0.8%, about 0.9%, or about 1% Tween 80.

The homogeneous suspension can contain any suitable suspension agent, such as a suspension agent that increases viscosity. A variety of such agents are well-known in the art including, for example, cellulose derivatives (such as carboxymethyl cellulose, hydroxypropyl cellulose, hydroxypropylmethyl cellulose), xanthan gum, sodium alginate, carrageenan, tragacanth, cooked starch (e.g., potato starch), guar gum, fumed silica, citronellol, geraniol, dihydro mercinol, linalool, nerol, rhodinal, alphaterpineol, beta-citronellol, rhodinol, citronella nitrile, carvone, fenchone, menthol, and isoborneol. The homogeneous suspensions can contain two or more suspension agents in any combination, if desired.

The homogeneous suspensions can contain from about 0.1% to about 10% suspension agent (v/v or w/v), about 0.1% to about 5% suspension agent, 0.1% to about 4% suspension agent, 0.1% to about 3% suspension agent, 0.1% to about 2% suspension agent, 0.1% to about 1% suspension agent, 0.1% to about 0.5% suspension agent, about 0.1% suspension agent, about 0.2% suspension agent, about 0.3% suspension agent, about 0.4% suspension agent, about 0.5% suspension agent, about 0.6% suspension agent, about 0.7% suspension agent, about 0.8% suspension agent, about 0.9% suspension agent, or about 1% suspension agent.

A preferred suspension agent for use in the homogeneous suspensions described herein is carboxymethyl cellulose (CMC). Preferably, the homogeneous suspension contains about 0.1% to about 5%, 0.1% to about 4%, 0.1% to about 3%, 0.1% to about 2%, 0.1% to about 1%, 0.1% to about 0.5%, about 0.1%, about 0.2%, about 0.3%, about 0.4%, about 0.5%, about 0.6%, about 0.7%, about 0.8%, about 0.9%, or about 1% carboxymethyl cellulose (CMC).

The homogeneous suspensions also contain a Benzonaphthyridine compound of Formula I or Formula II, pharmaceutically acceptable salt, pharmaceutically acceptable solvate, N-oxide derivative, protected derivative, individual isomer or mixture of isomers thereof. The homogeneous suspensions can contain Benzonaphthyridine compound at a concentration of from about 0.1 mg/mL to about 50 mg/ml, about 0.1 mg/mL to about 40 mg/ml, about 0.1 mg/mL to about 30 mg/ml, about 0.1 mg/mL to about 20 mg/ml, about 0.1 mg/mL to about 10 mg/ml, about 0.1 mg/mL to about 5 mg/ml, about 0.5 mg/mL, about 1.0 mg/mL, about 1.5 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 15 mg/ml, or about 20 mg/mL.

In preferred embodiments, the homogeneous suspensions contain a Benzonaphthyridine compound selected from 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; dimethylphenethyl)benzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine, and 2-(4-methoxyphenethyl)-8-methylbenzo[f][1,7]naphthyridin-5-amine.

In another preferred embodiments, the homogeneous suspensions contain a Benzonaphthyridine compound selected from 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; dimethylphenethyl)benzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine, 2-(4-methoxyphenethyl)-8-methylbenzo[f][1,7]naphthyridin-5-amine, and 2-(2-(4-(2-(5-amino-8-methylbenzo[f][1,7]naphthyridin-2-yl)ethyl)-3-methylphenoxy)ethoxy)ethanol.

In particularly preferred embodiments, the homogeneous formulation comprises 2-(2,4-dimethylphenethyl)benzo[f][1,7]naphthyridin-5-amine.

In another particularly preferred embodiments, the homogeneous formulation comprises 2-(2,4-dimethylphenethyl)benzo[f][1,7]naphthyridin-5-amine, 2-(4-methoxy-2-methylphenethyl)-8-methylbenzo[f][1,7]naphthyridin-5-amine, or 2-(2-(4-(2-(5-amino-8-methylbenzo[f][1,7]naphthyridin-2-yl)ethyl)-3-methylphenoxy)ethoxy)ethanol.

In certain embodiments, the homogeneous formulation comprises (a) a Benzonaphthyridine compound of Formula I or Formula II, pharmaceutically acceptable salt, pharmaceutically acceptable solvate, N-oxide derivative, protected derivative, individual isomer or mixture of isomers thereof; (b) 0.1% to about 5% Tween 80, and (c) 0.1% to about 10% carboxymethyl cellulose, and is stable. In certain examples of these embodiments, the homogeneous formulation has a D50 of about 1 and, optionally, a D90 of about 2. Preferably, the homogeneous formulations are stable for at least about one month. For example, the homogeneous formulations can be stable for at least about one month, at least about two months, at least about three months, at least about four months, at least about five months, at least about six months, at least about seven months, at least about eight months, at least about nine months, at least about ten months, at least about eleven months, or at least about twelve months in some embodiments.

Benzonaphthyridine Compounds

Benzonaphthyridine compounds suitable for use in the invention include the compounds of Formula (I) or Formula (II), pharmaceutically acceptable salts, pharmaceutically acceptable solvates (e.g. hydrates), the N-oxide derivatives, prodrug derivatives, protected derivatives, individual isomers and mixture of isomers thereof.

In certain embodiments of the immunogenic compositions provided herein, the benzonaphthyridine compound is a compound having the structure of Formula (I), or a pharmaceutically acceptable salt thereof:

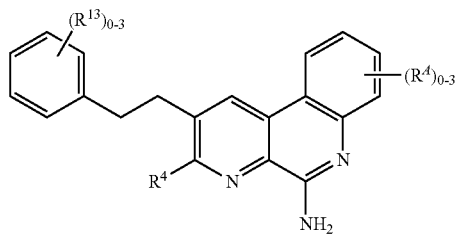

Formula (I)

wherein:
R$^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)—R$^7$, -LR$^{10}$, —OLR$^8$, —OLR$^{10}$, C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl groups of R$^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, C$_1$-C$_6$alkyl, C$_2$-C$_6$alkenylene and C$_2$-C$_6$alkynylene, wherein the C$_1$-C$_6$alkyl, C$_2$-C$_6$alkenylene and C$_2$-C$_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

R$^7$ is selected from H, C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl, wherein the C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl groups of R$^7$ are each optionally substituted with 1 to 3 R$^{13}$ groups;

each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^9$ is independently selected from H, —C(O)R$^8$, —C(O)OR$^8$, —C(O)R$^{10}$, —C(O)OR$^{10}$, —S(O)$_2$R$^{10}$, —C$_1$-C$_6$ alkyl, C$_1$-C$_6$ heteroalkyl and C$_3$-C$_6$ cycloalkyl, or each R$^9$ is independently a C$_1$-C$_6$alkyl that together with N they are attached to form a C$_3$-C$_8$heterocycloalkyl, wherein the C$_3$-C$_8$heterocycloalkyl ring optionally contains an additional heteroatom selected from N, O and S, and wherein the C$_1$-C$_6$ alkyl, C$_1$-C$_6$ heteroalkyl, C$_3$-C$_6$ cycloalkyl, or C$_3$-C$_8$heterocycloalkyl groups of R$^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR$^{11}$OH, —S(O)$_2$R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —R$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

R$^{11}$ and R$^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_1$-C$_8$heterocycloalkyl groups of R$^{11}$ and R$^{12}$ are each optionally substituted with 1 to 3 substituents independently selected from halogen, —CN, R$^8$, —OR$^8$, —C(O)R$^8$, —OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, C$_3$-C$_8$heterocycloalkyl, —S(O)$_2$R$^8$, —S(O)$_2$N(R$^9$)$_2$, —NR$^9$S(O)$_2$R$^8$, C$_1$-C$_6$haloalkyl and C$_1$-C$_6$haloalkoxy;

or R$^{11}$ and R$^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;

each R$^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)OR$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$;

each R$^A$ is independently selected from —R$^8$, —R$^7$, —OR$^8$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH═CHCO$_2$R$^8$, —C(═NH)—N(R$^9$)$_2$, and —(CH$_2$)—NHC(O)R$^8$; or two adjacent R$^A$ substituents on on the ring to which they are bonded form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In other embodiments, the benzonaphthyridine compound is a compound having the structure of Formula (II), or a pharmaceutically acceptable salt thereof:

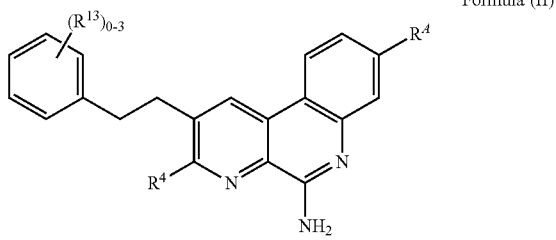

Formula (II)

wherein:
$R^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$—R$^7$, -LR$^8$, —OLR$^8$, —OLR$^{10}$, C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl groups of $R^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;
each L is independently selected from a bond, —(O(CH$_2$)$_m$)$_t$—, C$_1$-C$_6$alkyl, C$_2$-C$_6$alkenylene and C$_2$-C$_6$alkynylene, wherein the C$_1$-C$_6$alkyl, C$_2$-C$_6$alkenylene and C$_2$-C$_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;
$R^7$ is selected from H, C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl, wherein the C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl groups of $R^7$ are each optionally substituted with 1 to 3 $R^{13}$ groups;
each $R^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of $R^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;
each $R^9$ is independently selected from H, —C(O)R$^8$, —C(O)OR$^8$, —C(O)R$^{10}$, —C(O)OR$^{10}$, —S(O)$_2$R$^{10}$, —C$_1$-C$_6$ alkyl, C$_1$-C$_6$ heteroalkyl and C$_3$-C$_6$ cycloalkyl, or each $R^9$ is independently a C$_1$-C$_6$alkyl that together with N they are attached to form a C$_3$-C$_8$heterocycloalkyl, wherein the C$_3$-C$_8$heterocycloalkyl ring optionally contains an additional heteroatom selected from N, O and S, and wherein the C$_1$-C$_6$ alkyl, C$_1$-C$_6$ heteroalkyl, C$_3$-C$_6$ cycloalkyl, or C$_3$-C$_8$heterocycloalkyl groups of $R^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR$^{11}$OH, —S(O)$_2$R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;
each $R^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;
$R^{11}$ and $R^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl groups of $R^{11}$ and $R^{12}$ are each optionally substituted with 1 to 3 substituents independently selected from halogen, —CN, R$^8$, —OR$^8$, —C(O)R$^8$, ⁻OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, C$_3$-C$_8$heterocycloalkyl, —S(O)$_2$R$^8$, —S(O)$_2$N(R$^9$)$_2$, —NR$^9$S(O)$_2$R$^8$, C$_1$-C$_6$haloalkyl and C$_1$-C$_6$haloalkoxy;
or $R^{11}$ and $R^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;
each $R^{13}$ is independently selected from halogen, —CN, -LR$^9$, -LOR$^9$, —OLR$^9$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)OR$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$;
$R^A$ is selected from —R$^8$, —R$^7$, —OR$^8$, —OR$^8$, —R$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$—CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH═CHCO$_2$R$^8$, —C(═NH)—N(R$^9$)$_2$, and —(CH$_2$)$_n$—NHC(O)R$^8$;
n is, independently at each occurrence, 0, 1, 2, 3, 4, 5, 6, 7 or 8;
each m is independently selected from 1, 2, 3, 4, 5 and 6, and t is 1, 2, 3, 4, 5, 6, 7 or 8.

In certain embodiments of the benzonaphthyridine compounds of Formula I or Formula II, each $R^{13}$ is selected from -LR$^9$, -LOR$^9$, —OLR$^9$, -LR$^{10}$, -LOR$^{10}$, —OLR$^{10}$, -LR$^8$, -LOR$^8$, -LOR$^8$, —OLR$^8$, -LSR$^8$, -LSR$^{10}$, -LC(O)R$^8$, —OLC(O)R$^8$, -LC(O)OR$^8$, -LC(O)R$^{10}$, -LOC(O)R$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$, and each R$^A$ is independently selected from —R$^7$, —OR$^7$, —R$^8$, —OR$^8$, —R$^{10}$, —OR$^{10}$, —SR$^8$, —N(R$^9$)$_2$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —CH═CHCO$_2$R$^8$, (CH$_2$)$_n$—CO$_2$R$^8$, —NR$^9$SO$_2$R$^8$, —P(O)(OR$^8$)$_2$, —OP(O)(OR$^8$)$_2$, —P(O)(OR$^{10}$)$_2$, and —OP(O)(OR$^{10}$)$_2$.

In certain embodiments of the benzonaphthyridine compounds of Formula I or Formula II, each L is independently selected from a —(O(CH$_2$)$_m$)$_t$—, and C$_1$-C$_6$alkyl, wherein the C$_1$-C$_6$alkyl of L is optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and OP(O)(OR$^{10}$)$_2$.

In certain embodiments of the benzonaphthyridine compounds of Formula I or Formula II, R$^A$ is H or C$_1$-C$_6$alkyl.

In certain embodiments of the benzonaphthyridine compounds of Formula I or Formula II, R$^A$ is H, —CH$_3$ or —CH$_2$CH$_3$; and each R$^{13}$ is independently selected from H, —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$ and C$_2$-C$_6$ alkyl substituted with 1-3 substituents selected from —OH, —CH$_3$, —COOH, —COOCH$_3$, cyclopropyl, —O(CH$_2$)$_{2-4}$—COOH, —O(CH$_2$)$_{2-4}$(PO$_3$H$_2$), and —COOCH$_2$CH$_3$.

In certain embodiments of the benzonaphthyridine compounds of Formula I or Formula II, each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$.

In certain embodiments of the benzonaphthyridine compounds of Formula I or Formula II, R$^8$ is H or C$_1$-C$_6$alkyl.

In certain embodiments of the benzonaphthyridine compounds of Formula I or Formula II, R$^9$ is H or C$_1$-C$_6$alkyl.

In certain embodiments of the benzonaphthyridine compounds of Formula I or Formula II, R$^A$ is H or —CH$_3$.

In certain embodiments of the benzonaphthyridine compounds of Formula I or Formula II, R$^4$ is H.

In certain embodiments, the benzonaphthyridine compounds is selected from:
2-(4-(2-(5-amino-8-methylbenzo[f][1,7]naphthyridin-2-yl)ethyl)-3-methylphenyl)propan-2-ol;
2-(4-methoxy-2-methylphenethyl)-8-methylbenzo[f][1,7]naphthyridin-5-amine;
2-(2,4-dimethylphenethyl)benzo[f][1,7]naphthyridin-5-amine;
ethyl 4-(2-(5-amino-8-methylbenzo[f][1,7]naphthyridin-2-yl)ethyl)-3-methylbenzoate;
2-(4-(dimethylamino)phenethyl)-8-methylbenzo[f][1,7]naphthyridin-5-amine,
and 2-(4-methoxyphenethyl)-8-methylbenzo[f][1,7]naphthyridin-5-amine.

Benzonaphthyridine compounds of Formula (I) or Formula (II) can be prepared using suitable methods, such as the methods disclosed in WO 2009/111337, the entire contents of which are incorporated herein by reference. The person of ordinary skill is directed to WO 2009/111337 at pages 71 to 83 which disclose Schemes I-XIX, which are exemplary schemes suitable for producing compounds of Formula (1) or Formula (II).

The compounds of Formula (I) or Formula (II), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound provided herein or a pharmaceutically acceptable salt thereof is defined as one in which at least one atom is replaced by an atom having the same atomic number but an atomic mass different from the atomic mass usually found in nature. Examples of isotopes that may be incorporated into the compounds provided herein and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds provided herein and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

4. Immune Potentiation and Immunogenic Compositions

The homogeneous suspension of SMIPs, i.e. compounds of Formula I or Formula II, described herein can be used as immune potentiators. Compounds of Formula I or Formula II contain a hydrophobic core, and the homogeneous suspensions provide the advantage of allowing an effective amount of SMIP to be conveniently administered to a subject in need thereof.

In one aspect, the invention is a method for potentiation an immune response, comprising administering an effective amount of a homogeneous suspension of the invention to a subject in need thereof. The immune response can be a naturally occurring immune response, or an induced immune response, for example induced by immunization. When the homogeneous suspension is administered to potentiate an induced immune response, it is preferred that it is administered at substantially the same time as the agent that induces the immune response. For example, an effective amount of a homogeneous suspension can be administered concurrently with an immunogenic composition or vaccine, or administered within a period of about 1 day before or after the immunogenic composition or vaccine is administered.

In another aspect, the invention provides an immunogenic composition comprising an antigen and a homogeneous suspension of a SMIP, i.e. compounds of Formula I or Formula II. In certain embodiments, the immunogenic composition further comprises another immunostimulatory agent, such as an adjuvant. The immunogenic composition can contain any desired antigen and/or adjuvant. For example, the immunogenic composition can contain a bacterial antigen, bacterial vesicle antigen, viral antigen, fungal antigen, protozoan antigen, plant antigen, STD antigen, respiratory antigen, pediatric vaccine antigen, antigen suitable for elderly or immunocompromized individuals, antigen suitable for use in adolescent vaccines, or tumor antigen, as described herein. The immunogenic composition can also contain an adjuvant (e.g., alum, MF59) as described herein.

In certain embodiments, the immunogenic composition contains an amount of homogeneous composition that is sufficient to enhance an immune response to the antigen. Such immunogenic compositions can be used to produce vaccines. In certain embodiments, the vaccines are prophylactic (i.e. to prevent infection), while in other embodiments, such vaccines are therapeutic (i.e. to treat infection).

The immunostimulatory effect referred to herein is often an enhancement of the immunogenic composition's effect. In certain embodiments the enhancement of the efficacy of the immunogenic composition is by at least about 10%, at least about 20%, at least about 30%, at least about 40%, at least about 50%, at least about 60%, at least about 70%, at least about 80%, at least about 90%, or at least about 100%, relative to the effect of the immunogenic composition in the absence of the homogeneous suspension of SMIP.

In certain embodiments, the enhancement of the immunogenic composition's effect is measured by the increased effectiveness of the immunogenic composition for achieving its protective effects. In certain embodiments, this increased effectiveness is measured as a decreased probability that a subject receiving the immunogenic composition will experience a condition for which the immunogenic composition is considered protective, or a decrease in duration or severity of the effects of such condition. In other embodiments, this increased effectiveness is measured as an increase in a titer of an antibody elicited by the immunogenic composition in a treated subject.

The immunogenic compositions may further comprise a pharmaceutically acceptable carrier. Such carriers are include, but are not limited to, proteins, polysaccharides, polylactic acids, polyglycolic acids, polymeric amino acids, amino acid copolymers, sucrose, trehalose, lactose, lipid aggregates (such as oil droplets or liposomes), and inactive virus particles. The immunogenic compositions typically also contain diluents, such as water, saline, and glycerol, and optionally contain other excipients, such as wetting or emulsifying agents, and pH buffering substances.

(a) Adjuvants

In certain embodiments, immunogenic compositions optionally include one or more immunoregulatory agents. In certain embodiments, one or more of the immunoregulatory agents include one or more adjuvants. Such adjuvants include, but are not limited to, a TH1 adjuvant and/or a TH2 adjuvant, further discussed below. In certain embodiments, the adjuvants used in immunogenic compositions provide herein include, but are not limited to:

1. Mineral-Containing Compositions;
2. Oil Emulsions;
3. Saponin Formulations;
4. Virosomes and Virus-Like Particles;
5. Bacterial or Microbial Derivatives;
6. Human Immunomodulators;
7. Bioadhesives and Mucoadhesives;
8. Microparticles;
9. Liposomes;
10. Polyoxyethylene Ether and Polyoxyethylene Ester Formulations;
11. Polyphosphazene (PCPP);
12. Muramyl Peptides, and
13. Imidazoquinolone Compounds.

Mineral-containing compositions suitable for use as adjuvants include, but are not limited to, mineral salts, such as aluminium salts and calcium salts. By way of example only, such mineral salts include, hydroxides (e.g. oxyhydroxides, including aluminium hydroxides and aluminium oxyhydroxides), phosphates (e.g. hydroxyphosphates and orthophosphates, including aluminium phosphates, aluminium hydroxyphosphates, aluminium orthophosphates and calcium phosphate), sulfates (e.g. aluminium sulfate), or mixtures of different mineral compounds. Such mineral salts are in any suitable form, such as, by way of example only, gel, crystalline, and amorphous forms. In certain embodiments, such mineral containing compositions are formulated as a particle of the metal salt. In certain embodiments, components of the immunogenic compositions described herein are adsorbed to such mineral salts. In certain embodiments, an aluminium hydroxide and/or aluminium phosphate adjuvant is used in the immunogenic compositions described herein. In other embodiments, antigens used in an immunogenic composition described herein are adsorbed to such aluminium hydroxide and/or aluminium phosphate adjuvants. In certain embodiments, a calcium phosphate adjuvant is used in the immunogenic compositions described herein. In other embodiments, antigens used in an immunogenic composition described herein are adsorbed to such calcium phosphate adjuvants.

In certain embodiments, aluminum phosphates are used as an adjuvant in the immunogenic compositions described herein. In other embodiments, aluminum phosphates are used as an adjuvant in the immunogenic compositions described herein, wherein such compositions include a *H. influenzae* saccharide antigen. In certain embodiments, the adjuvant is amorphous aluminium hydroxyphosphate with a $PO_4/Al$ molar ratio between 0.84 and 0.92, included at 0.6 mg $Al^{3+}$/ml. In other embodiments, adsorption with a low dose of aluminium phosphate is used, by way of example only, between 50 and 100 μg $Al^{3+}$ per conjugate per dose. Where there is more than one conjugate in a composition, not all conjugates need to be adsorbed.

Oil emulsions suitable for use as adjuvants include, but are not limited to, squalene-water emulsions (such as MF59 (5% Squalene, 0.5% Tween 80, and 0.5% Span 85, formulated into submicron particles using a microfluidizer), Complete Freund's adjuvant (CFA) and incomplete Freund's adjuvant (IFA).

Saponins are a heterologous group of sterol glycosides and triterpenoid glycosides that are found in the bark, leaves, stems, roots and even flowers of a wide range of plant species. Saponin formulations suitable for use as adjuvants include, but are not limited to, saponins from the bark of the *Quillaia saponaria* Molina tree, from *Smilax ornata* (sarsaprilla), *Gypsophilla paniculata* (brides veil), and *Saponaria officianalis* (soap root). In certain embodiments, saponin formulations suitable for use as adjuvants include, but are not limited to, purified formulations including, but are not limited to, QS7, QS17, QS18, QS21, QH-A, QH-B and QH-C. QS21 is marketed as STIMULOM™. In other embodiments, saponin formulations include sterols, cholesterols and lipid formulations, such as unique particles formed by the combinations of saponins and cholesterols called immunostimulating complexes (ISCOMs). In certain embodiments, the ISCOMs also include a phospholipid such as phosphatidylethanolamine or phosphatidylcholine. Any known saponin can be used in ISCOMs. In certain embodiments, the ISCOM includes one or more of QuilA, QHA & QHC. In other embodiments, the ISCOMS are optionally devoid of an additional detergent.

Virosomes and virus-like particles (VLPs) suitable for use as adjuvants include, but are not limited to, one or more proteins from a virus optionally combined or formulated with a phospholipid. Such virosomes and VLPs are generally non-pathogenic, non-replicating and generally do not contain any of the native viral genome. In certain embodiments, the viral proteins are recombinantly produced, while in other embodiments the viral proteins are isolated from whole viruses.

The viral proteins suitable for use in virosomes or VLPs include, but are not limited to, proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Q☐-phage (such as coat proteins), GA-phage, fr-phage, AP205 phage, and Ty (such as retrotransposon Ty protein p1).

Bacterial or microbial derivatives suitable for use as adjuvants include, but are not limited to, bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Such non-toxic derivatives of LPS include, but are not limited to, monophosphoryl lipid A (MPL) and 3-O-deacylated MPL (3dMPL). 3dMPL is a mixture of 3 de-O-acylated monophosphoryl lipid A with 4, 5 or 6 acylated chains. Other non-toxic LPS derivatives include monophosphoryl lipid A mimics, such as aminoalkyl glucosaminide phosphate derivatives (e.g. RC-529). Lipid A derivatives include, but are not limited to, derivatives of lipid A from *Escherichia coli* (e.g. OM-174).

Immunostimulatory oligonucleotides used as adjuvants include, but are not limited to, nucleotide sequences containing a CpG motif (a dinucleotide sequence containing an unmethylated cytosine linked by a phosphate bond to a guanosine). Such CpG sequences can be double-stranded or single-stranded. In certain embodiments, such nucleotide sequences are double-stranded RNAs or oligonucleotides containing palindromic or poly(dG) sequences. In other embodiments, the CpG's include nucleotide modifications/analogs such as phosphorothioate modifications.

In certain embodiments the CpG sequence are directed to TLR9, and in certain embodiments the motif is GTCGTT or TTCGTT. In certain embodiments the CpG sequence is specific for inducing a Th1 immune response, such as, by way of example only, a CpG-A ODN, or in other embodiments the CpG sequence is more specific for inducing a B cell response, such as, by way of example only, a CpG-B ODN. In certain embodiments the CpG is a CpG-A ODN.

In certain embodiments the CpG oligonucleotide is constructed so that the 5' end is accessible for receptor recognition. In other embodiments two CpG oligonucleotide sequences are optionally attached at their 3' ends to form "immunomers".

A particularly useful adjuvant based around immunostimulatory oligonucleotides is known as IC-31™. In certain embodiments, an adjuvant used with immunogenic compositions described herein, includes a mixture of (i) an oligonucleotide (such as, by way of example only, between 15-40 nucleotides) including at least one (and preferably multiple) CpI motifs (such as, by way of example only, a cytosine linked to an inosine to form a dinucleotide), and (ii) a polycationic polymer, such as, by way of example only, an oligopeptide (such as, by way of example only, between 5-20 amino acids) including at least one (and preferably multiple) Lys-Arg-Lys tripeptide sequence(s). In certain embodiments, the oligonucleotide is a deoxynucleotide comprising 26-mer sequence 5'-(IC)$_{13}$-3'. In other embodiments, the polycationic polymer is a peptide comprising 11-mer amino acid sequence KLKLLLLLKLK.

In certain embodiments, bacterial ADP-ribosylating toxins and detoxified derivatives thereof are used as adjuvants in the immunogenic compositions described herein. In certain embodiments, such proteins are derived from *E. coli* (*E. coli* heat labile enterotoxin "LT"), cholera ("CT"), or pertussis ("PT"). In other embodiments, the toxin or toxoid is in the form of a holotoxin, comprising both A and B subunits. In other embodiments, the A subunit contains a detoxifying mutation; whereas the B subunit is not mutated. In other embodiments, the adjuvant is a detoxified LT mutant such as LT-K63, LT-R72, and LT-G192.

The human immunomodulators suitable for use as adjuvants include, but are not limited to, cytokines, such as, by way of example only, interleukins (IL-1, IL-2, IL-4, IL-5, IL-6, IL-7, IL-12), interferons (such as, by way of example only, interferon-γ), macrophage colony stimulating factor, and tumor necrosis factor.

The bioadhesives and mucoadhesives used as adjuvants in the immunogenic compositions described herein include, but are not limited to, esterified hyaluronic acid microspheres, and cross-linked derivatives of poly(acrylic acid), polyvinyl alcohol, polyvinyl pyrollidone, polysaccharides and carboxymethylcellulose. In certain embodiments, chitosan and derivatives thereof are used as in the vaccine compositions described herein adjuvants.

The microparticles suitable for use as adjuvants include, but are not limited to, microparticles formed from materials that are biodegradable and non-toxic (e.g. a poly(.alpha.-hydroxy acid), a polyhydroxybutyric acid, a polyorthoester, a polyanhydride, a polycaprolactone, etc.), with poly(lactide-co-glycolide). In certain embodiments, such microparticles are treated to have a negatively-charged surface (e.g. with SDS) or a positively-charged surface (e.g. with a cationic detergent, such as CTAB). The microparticles suitable for use as adjuvants have a particle diameter of about 100 nm to about 150 μm in diameter. In certain embodiments, the particle diameter is about 200 nm to about 30 μm, and in other embodiments the particle diameter is about 500 nm to 10 μm.

The polyoxyethylene ether and polyoxyethylene ester formulations suitable for use as adjuvants include, but are not limited to, polyoxyethylene sorbitan ester surfactants in combination with an octoxynol, and polyoxyethylene alkyl ethers or ester surfactants in combination with at least one additional non-ionic surfactant such as an octoxynol. In certain embodiments, the polyoxyethylene ethers are selected from polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

The muramyl peptides suitable for use as adjuvants include, but are not limited to, N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-s-n-glycero-3-hydroxyphosphoryloxy)-ethylamine MTP-PE).

In certain embodiments, one or more compounds of Formula (I) used as an immune potentiator are included in compositions having combinations of one or more of the adjuvants identified above. Such combinations include, but are not limited to,
  (1) a saponin and an oil-in-water emulsion;
  (2) a saponin (e.g. QS21)+a non-toxic LPS derivative (e.g. 3dMPL);
  (3) a saponin (e.g. QS21)+a non-toxic LPS derivative (e.g. 3dMPL)+a cholesterol;
  (4) a saponin (e.g. QS21)+3dMPTL+IL-12 (optionally including a sterol);
  (5) combinations of 3dMPL with, for example, QS21 and/or oil-in-water emulsions;
  (6) SAF, containing 10% squalane, 0.4% Tween 80™, 5% pluronic-block polymer L121, and thr-MDP, either microfluidized into a submicron emulsion or vortexed to generate a larger particle size emulsion.
  (7) RIBI™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and
  (8) one or more mineral salts (such as an aluminum salt)+a non-toxic derivative of LPS (such as 3dMPL).

In other embodiments, the adjuvant combinations used in the immunogenic combinations provided herein include combinations of Th1 and Th2 adjuvants such as, by way of example only, CpG and alum or resiquimod and alum.

In certain embodiments, the immunogenic compositions provided herein elicit both a cell mediated immune response as well as a humoral immune response. In other embodiments, the immune response induces long lasting (e.g. neutralising) antibodies and a cell mediated immunity that quickly responds upon exposure to the infectious agent.

TH1 adjuvants can be used to elicit a TH1 immune response. A TH1 adjuvant will generally elicit increased levels of IgG2a production relative to immunization of the antigen without adjuvant. TH1 adjuvants suitable for use in immunogenic compositions provided herein include, but are not limited to, saponin formulations, virosomes and virus like particles, non-toxic derivatives of enterobacterial lipopolysaccharide (LPS), immunostimulatory oligonucleotides. In certain embodiments, the immunostimulatory oligonucleotides used as TH1 adjuvants in the immunogenic compositions provided herein contain a CpG motif.

TH2 adjuvants can be used to elicit a TH2 immune response. A TH2 adjuvant will generally elicit increased levels of IgG1 production relative to immunization of the antigen without adjuvant. TH2 adjuvants suitable for use in immunogenic compositions provided herein include, but are not limited to, mineral containing compositions, oil-emulsions, and ADP-ribosylating toxins and detoxified derivatives thereof. In certain embodiments, the mineral containing compositions used as TH2 adjuvants in the immunogenic compositions provided herein are aluminium salts.

In certain embodiments, the immunogenic compositions provided herein include a TH1 adjuvant and a TH2 adjuvant. In other embodiments, such compositions elicit an enhanced TH1 and an enhanced TH2 response, such as, an increase in the production of both IgG1 and IgG2a production relative to immunization without an adjuvant. In still other embodiments, such compositions comprising a combination of a TH1 and a TH2 adjuvant elicit an increased TH1 and/or an increased TH2 immune response relative to immunization with a single adjuvant (i.e., relative to immunization with a TH1 adjuvant alone or immunization with a TH2 adjuvant alone).

In certain embodiments, the immune response is one or both of a TH1 immune response and a TH2 response. In other embodiments, the immune response provides for one or both of an enhanced TH1 response and an enhanced TH2 response.

In certain embodiments, the enhanced immune response is one or both of a systemic and a mucosal immune response. In other embodiments, the immune response provides for one or both of an enhanced systemic and an enhanced mucosal immune response. In certain embodiments, the mucosal immune response is a TH2 immune response. In certain embodiments, the mucosal immune response includes an increase in the production of IgA.

(b) Antigens

In certain embodiments, the immunogenic composition comprises at least one antigen, which may be a bacterial antigen or a cancer-associated antigen, or a viral antigen. In certain embodiments, the homogeneous suspensions provided herein are included in prophylactic vaccines or used in combination with prophylactic vaccines. In certain embodiments, the homogeneous suspensions provided herein are included in, or are used in combination with, therapeutic viral vaccines. In certain embodiments, the homogeneous suspensions provided herein are included in, or are used in combination with, with cancer vaccines.

Antigens for use with the immunogenic compositions provided herein include, but are not limited to, one or more of the following antigens set forth below, or antigens derived from one or more of the pathogens set forth below.

Bacterial Antigens

Bacterial antigens suitable for use in immunogenic compositions provided herein include, but are not limited to, proteins, polysaccharides, lipopolysaccharides, and outer membrane vesicles which are isolated, purified or derived from a bacteria. In certain embodiments, the bacterial antigens include bacterial lysates and inactivated bacteria formulations. In certain embodiments, the bacterial antigens are produced by recombinant expression. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis: Meningitidis* antigens include, but are not limited to, proteins, saccharides (including a polysaccharide, oligosaccharide, lipooligosaccharide or lipopolysaccharide), or outer-membrane vesicles purified or derived from *N. meningitides* serogroup such as A, C, W135, Y, X and/or B. In certain embodiments *meningitides* protein antigens are be selected from adhesions, autotransporters, toxins, Fe acquisition proteins, and membrane associated proteins (preferably integral outer membrane protein).

*Streptococcus pneumoniae: Streptococcus pneumoniae* antigens include, but are not limited to, a saccharide (including a polysaccharide or an oligosaccharide) and/or protein from *Streptococcus pneumoniae*. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. An immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. No. 6,699,703, U.S. Pat. No. 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm. (2006) 74:2453-2456, Hoskins et al., J. Bacteriol. (2001) 183:5709-5717, Adamou et al., Infect. Immun. (2001) 69(2):949-958, Briles et al., J. Infect. Dis. (2000) 182:1694-1701, Talkington et al., Microb. Pathog. (1996) 21(1):17-22, Bethe et al., FEMS Microbiol. Lett. (2001) 205(1):99-104, Brown et al., Infect. Immun. (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SplOl, Spl30, Spl25, Spl33, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis*: *Moraxella* antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis holotoxin (PT) and filamentous haemagglutinin (FHA) from *B. pertussis*, optionally also combination with pertactin and/or agglutinogens 2 and 3.

*Burkholderia*: *Burkholderia* antigens include, but are not limited to *Burkholderia mallei*, *Burkholderia pseudomallei* and *Burkholderia cepacia*.

*Staphylococcus aureus*: Staph aureus antigens include, but are not limited to, a polysaccharide and/or protein from *S. aureus*. *S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis*: *S. epidermidis* antigens include, but are not limited to, slime-associated antigen (SAA).

*Clostridium tetani* (Tetanus): Tetanus antigens include, but are not limited to, tetanus toxoid (TT). In certain embodiments such antigens are used as a carrier protein in conjunction/conjugated with the immunogenic compositions provided herein.

*Clostridium perfringens*: Antigens include, but are not limited to, Epsilon toxin from *Clostridium perfringen*.

*Clostridium botulinums* (Botulism): Botulism antigens include, but are not limited to, those derived from *C. botulinum*.

*Cornynebacterium diphtherias* (Diphtheria): Diphtheria antigens include, but are not limited to, diphtheria toxin, preferably detoxified, such as $CRM_{197}$. Additionally antigens capable of modulating, inhibiting or associated with ADP ribosylation are contemplated for combination/co-administration/conjugation with the immunogenic compositions provided herein. In certain embodiments, the diphtheria toxoids are used as carrier proteins.

*Haemophilus influenzae* B (Hib): Hib antigens include, but are not limited to, a Hib saccharide antigen.

*Pseudomonas aeruginosa*: Pseudomonas antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Legionella pneumophila*. Bacterial antigens derived from *Legionella pneumophila*.

*Coxiella burnetii*. Bacterial antigens derived from *Coxiella burnetii*.

*Brucella*. Bacterial antigens derived from *Brucella*, including but not limited to, *B. abortus*, *B. canis*, *B. melitensis*, *B. neotomae*, *B. ovis*, *B. suis* and *B. pinnipediae*.

*Francisella*. Bacterial antigens derived from *Francisella*, including but not limited to, *F. novicida*, *F. philomiragia* and *F. tularensis*.

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae: Gonorrhoeae* antigens include, but are not limited to, Por (or porin) protein, such as PorB (see Zhu et al., *Vaccine* (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis: Chlamydia trachomatis* antigens include, but are not limited to, antigens derived from serotypes A, B, Ba and C (agents of trachoma, a cause of blindness), serotypes $L_1$, $L_2$ & $L_3$ (associated with Lymphogranuloma venereum), and serotypes, D-K. In certain embodiments, *chlamydia* trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): Ducreyi antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori: H pylori* antigens include, but are not limited to, Cag, Vac, Nap, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli: E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6 optionally formulated in cationic lipid vesicles, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, VlsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the immunogenic compositions provided herein include, but are not limited to, capsular antigens, polysaccharide antigens or protein antigens of any of the above. Other bacterial antigens used in the immunogenic compositions provided herein include, but are not limited to, an outer membrane vesicle (OMV) preparation. Additionally, Other bacterial antigens used in the immunogenic compositions provided herein include, but are not limited to, live, attenuated, and/or purified versions of any of the aforementioned bacteria. In certain embodiments, the bacterial antigens used in the immunogenic compositions provided herein are derived from gram-negative, while in other embodiments they are derived from gram-positive bacteria. In certain embodiments, the bacterial antigens used in the immunogenic compositions provided herein are derived from aerobic bacteria, while in other embodiments they are derived from anaerobic bacteria.

In certain embodiments, any of the above bacterial-derived saccharides (polysaccharides, LPS, LOS or oligosaccharides) are conjugated to another agent or antigen, such as a carrier protein (for example $CRM_{197}$). In certain embodiments, such conjugations are direct conjugations effected by reductive amination of carbonyl moieties on the saccharide to amino groups on the protein. In other embodiments, the saccharides are conjugated through a linker, such as, with succinamide or other linkages provided in *Bioconjugate Techniques*, 1996 and CRC, *Chemistry of Protein Conjugation and Cross-Linking*, 1993.

In certain embodiments useful for the treatment or prevention of *Neisseria* infection and related diseases and disorders, recombinant proteins from *N. meningitidis* for use in the immunogenic compositions provided herein may be found in WO99/24578, WO99/36544, WO99/57280, WO00/22430, WO96/29412, WO01/64920, WO03/020756, WO2004/048404, and WO2004/032958. Such antigens may be used alone or in combinations. Where multiple purified proteins are combined then it is helpful to use a mixture of 10 or fewer (e.g. 9, 8, 7, 6, 5, 4, 3, 2) purified antigens.

A particularly useful combination of antigens for use in the immunogenic compositions provided herein is disclosed in Giuliani et al. (2006) *Proc Natl Acad Sci USA* 103(29): 10834-9 and WO2004/032958, and so an immunogenic composition may include 1, 2, 3, 4 or 5 of: (1) a 'NadA' protein (aka GNA1994 and NMB1994); (2) a 'fHBP' protein (aka '741', LP2086, GNA1870, and NMB1870); (3) a '936' protein (aka GNA2091 and NMB2091); (4) a '953' protein (aka GNA1030 and NMB1030); and (5) a '287' protein (aka GNA2132 and NMB2132). Other possible antigen combinations may comprise a transferrin binding protein (e.g. TbpA and/or TbpB) and an Hsf antigen. Other possible purified antigens for use in the immunogenic compositions provided herein include proteins comprising one of the following amino acid sequences: SEQ ID NO:650 from WO99/24578; SEQ ID NO:878 from WO99/24578; SEQ ID NO:884 from WO99/24578; SEQ ID NO:4 from WO99/36544; SEQ ID NO:598 from WO99/57280; SEQ ID NO:818 from WO99/57280; SEQ ID NO:864 from WO99/57280; SEQ ID NO:866 from WO99/57280; SEQ ID NO:1196 from WO99/57280; SEQ ID NO:1272 from WO99/57280; SEQ ID NO:1274 from WO99/57280; SEQ ID NO:1640 from WO99/57280; SEQ ID NO:1788 from WO99/57280; SEQ ID NO:2288 from WO99/57280; SEQ ID NO:2466 from WO99/57280; SEQ ID NO:2554 from WO99/57280; SEQ ID NO:2576 from WO99/57280; SEQ ID NO:2606 from WO99/57280; SEQ ID NO:2608 from WO99/57280; SEQ ID NO:2616 from WO99/57280; SEQ ID NO:2668 from WO99/57280; SEQ ID NO:2780 from WO99/57280; SEQ ID NO:2932 from WO99/57280; SEQ ID NO:2958 from WO99/57280; SEQ ID NO:2970 from WO99/57280; SEQ ID NO:2988 from WO99/57280 (each of the forgoing amino acid sequences is hereby incorporated by reference from the cited document), or a polypeptide comprising an amino acid sequence which: (a) has 50% or more identity (e.g., 60%, 70%, 80%, 90%, 95%, 99% or more) to said sequences; and/or (b) comprises a fragment of at least n consecutive amino acids from said sequences, wherein n is 7 or more (e.g., 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g., 2, 3, 4, 5, 6) of these polypeptides may be included in the immunogenic compositions.

The fHBP antigen falls into three distinct variants (WO2004/048404). An *N. meningitidis* serogroup vaccine based upon the immunogenic compositions disclosed herein utilizing one of the compounds disclosed herein may include a single fHBP variant, but is will usefully include an fHBP from each of two or all three variants. Thus the immunogenic composition may include a combination of two or three different purified fHBPs, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: 1; (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least z contiguous amino acids from SEQ ID NO: 3

SEQ ID NO: 1
VAADIGAGLADALTAPLDHKDKGLQSLTLDQSVRKNEKLKLAAQGAEKTY
GNGDSLNTGKLKNDKVSRFDFIRQIEVDGQLITLESGEFQVYKQSHSALT
AFQTEQIQDSEHSGKMVAKRQFRIGDIAGEHTSFDKLPEGGRATYRGTAF
GSDDAGGKLTYTIDFAAKQGNGKIEHLKSPELNVDLAAADIKPDGKRHAV
ISGSVLYNQAEKGSYSLGIFGGKAQEVAGSAEVKTVNGIRHIGLAAKQ

SEQ ID NO: 2
VAADIGAGLADALTAPLDHKDKSLQSLTLDQSVRKNEKLKLAAQGAEKTY
GNGDSLNTGKLKNDKVSRFDFIRQIEVDGQLITLESGEFQIYKQDHSAVV
ALQIEKINNPDKIDSLINQRSFLVSGLGGEHTAFNQLPDGKAEYHGKAFS
SDDAGGKLTYTIDFAAKQGHGKIEHLKTPEQNVELAAAELKADEKSHAVI
LGDTRYGSEEKGTYHLALFGDRAQEIAGSATVKIGEKVHEIGIAGKQ

SEQ ID NO: 3
VAADIGTGLADALTAPLDHKDKGLKSLTLEDSIPQNGTLTLSAQGAEKTF
KAGDKDNSLNTGKLKNDKISRFDFVQKIEVDGQTITLASGEFQIYKQNHS
AVVALQIEKINNPDKTDSLINQRSFLVSGLGGEHTAFNQLPGGKAEYHGK
AFSSDDPNGRLHYSIDFTKKQGYGRIEHLKTLEQNVELAAAELKADEKSH
AVILGDTRYGSEEKGTYHLALFGDRAQEIAGSATVKIGEKVHEIGIAGKQ.

The value of a is at least 85, e.g., 86, 87, 88, 89, 90, 91, 92, 93, 94, 95, 96, 97, 98, 99, 99.5, or more. The value of b is at least 85, e.g., 86, 87, 88, 89, 90, 91, 92, 93, 94, 95, 96, 97, 98, 99, 99.5, or more. The value of c is at least 85, e.g., 86, 87, 88, 89, 90, 91, 92, 93, 94, 95, 96, 97, 98, 99, 99.5, or more. The values of a, b and c are not intrinsically related to each other.

The value of x is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

In some embodiments, the immunogenic compositions as disclosed herein will include fHBP protein(s) that are lipidated, e.g., at a N-terminal cysteine. In other embodiments they will not be lipidated A useful immunogenic composition as disclosed herein includes purified proteins comprises a mixture of: (i) a first polypeptide having amino acid sequence SEQ ID NO: 4; (ii) a second polypeptide having amino acid sequence SEQ ID NO: 5; and (iii) a third polypeptide having amino acid sequence SEQ ID NO: 6. See Giuliani et al. (2006) *Proc Natl Acad Sci USA* 103(29):10834-9 and WO2004/032958. A useful immunogenic composition as disclosed herein includes purified proteins comprises a mixture of: (i) a first polypeptide having at least a % sequence identity to amino acid sequence SEQ ID NO: 4; (ii) a second polypeptide having at least b % sequence identity to amino acid sequence SEQ ID NO: 5; and (iii) a third polypeptide having at least a % sequence identity to amino acid sequence SEQ ID NO: 6.

SEQ ID NO: 4
MASPDVKSADTLSKPAAPVVSEKETEAKEDAPQAGSQGQGAPSAQGGQDM

AAVSEENTGNGGAAATDKPKNEDEGAQNDMPQNAADTDSLTPNHTPASNM

PAGNMENQAPDAGESEQPANQPDMANTADGMQGDDPSAGGENAGNTAAQG

TNQAENNQTAGSQNPASSTNPSATNSGGDFGRTNVGNSVVIDGPSQNITL

THCKGDSCSGNNFLDEEVQLKSEFEKLSDADKISNYKKDGKNDGKNDKFV

GLVADSVQMKGINQYIIFYKPKPTSFARFRRSARSRRSLPAEMPLIPVNQ

ADTLIVDGEAVSLTGHSGNIFAPEGNYRYLTYGAEKLPGGSYALRVQGEP

SKGEMLAGTAVYNGEVLHFHTENGRPSPSRGRFAAKVDFGSKSVDGIIDS

GDGLHMGTQKFKAAIDGNGFKGTWTENGGGDVSGKFYGPAGEEVAGKYSY

RPTDAEKGGFGVFAGKKEQDGSGGGATYKVDEYHANARFAIDHFNTSTN

VGGFYGLTGSVEFDQAKRDGKIDITIPVANLQSGSQHFTDHLKSADIFDA

AQYPDIRFVSTKFNFNGKKLVSVDGNLTMHGKTAPVKLKAEKFNCYQSPM

AKTEVCGGDFSTTIDRTKWGVDYLVNVGMTKSVRIDIQIEAAKQ

SEQ ID NO: 5
MVSAVIGSAAVGAKSAVDRRTTGAQTDDNVMALRIETTARSYLRQNNQTK

GYTPQISVVGYNRHLLLLGQVATEGEKQFVGQIARSEQAAEGVYNYITVA

SLPRTAGDIAGDTWNTSKVRATLLGISPATQARVKIVTYGNVTYVMGILT

PEEQAQITQKVSTTVGVQKVITLYQNYVQRGSGGGVAADIGAGLADALT

APLDHKDKGLQSLTLDQSVRKNEKLKLAAQGAEKTYGNGDSLNTGKLKND

KVSRFDFIRQIEVDGQLITLESGEFQVYKQSHSALTAFQTEQIQDSEHSG

KMVAKRQFRIGDIAGEHTSFDKLPEGGRATYRGTAFGSDDAGGKLTYTID

FAAKQGNGKIEHLKSPELNVDLAAADIKPDGKRHAVISGSVLYNQAEKGS

YSLGIFGGKAQEVAGSAEVKTVNGIRHIGLAAKQ

SEQ ID NO: 6
ATNDDDVKKAATVAIAAAYNNGQEINGFKAGETIYDIDEDGTITKKDATA

ADVEADDFKGLGLKKVVTNLTKTVNENKQNVDAKVKAAESEIEKLTTKLA

DTDAALADTDAALDATTNALNKLGENITTFAEETKTNIVKIDEKLEAVAD

TVDKHAEAFNDIADSLDETNTKADEAVKTANEAKQTAEETKQNVDAKVKA

AETAAGKAEAAAGTANTAADKAEAVAAKVTDIKADIATNKDNIAKKANSA

DVYTREESDSKFVRIDGLNATTEKLDTRLASAEKSIADHDTRLNGLDKTV

SDLRKETRQGLAEQAALSGLFQPYNVG.

Bacterial Vesicle Antigens

The immunogenic compositions as disclosed herein may include outer membrane vesicles. Such outer membrane vesicles may be obtained from a wide array of pathogenic bacteria and used as antigenic components of the immunogenic compositions as disclosed herein. Vesicles for use as antigenic components of such immunogenic compositions include any proteoliposomic vesicle obtained by disrupting a bacterial outer membrane to form vesicles therefrom that include protein components of the outer membrane. Thus the term includes OMVs (sometimes referred to as 'blebs'), microvesicles (MVs, see, e.g., WO02/09643) and 'native OMVs' ('NOMVs' see, e.g., Katial et al. (2002) Infect. Immun. 70:702-707). Immnogenic compositions as disclosed herein that include vesicles from one or more pathogenic bacteria can be used in the treatment or prevention of infection by such pathogenic bacteria and related diseases and disorders.

MVs and NOMVs are naturally-occurring membrane vesicles that form spontaneously during bacterial growth and are released into culture medium. MVs can be obtained by culturing bacteria such as Neisseria in broth culture medium, separating whole cells from the smaller MVs in the broth culture medium (e.g., by filtration or by low-speed centrifugation to pellet only the cells and not the smaller vesicles), and then collecting the MVs from the cell-depleted medium (e.g., by filtration, by differential precipitation or aggregation of MVs, by high-speed centrifugation to pellet the MVs). Strains for use in production of MVs can generally be selected on the basis of the amount of MVs produced in culture (see, e.g., U.S. Pat. No. 6,180,111 and WO01/34642 describing Neisseria with high MV production).

OMVs are prepared artificially from bacteria, and may be prepared using detergent treatment (e.g., with deoxycholate), or by non detergent means (see, e.g., WO04/019977). Methods for obtaining suitable OMV preparations are well known in the art. Techniques for forming OMVs include treating bacteria with a bile acid salt detergent (e.g., salts of lithocholic acid, chenodeoxycholic acid, ursodeoxycholic acid, deoxycholic acid, cholic acid, ursocholic acid, etc., with sodium deoxycholate (EP0011243 and Fredriksen et al. (1991) NIPH Ann. 14(2):67-80) being preferred for treating Neisseria) at a pH sufficiently high not to precipitate the detergent (see, e.g., WO01/91788). Other techniques may be performed substantially in the absence of detergent (see, e.g., WO04/019977) using techniques such as sonication, homogenisation, microfluidisation, cavitation, osmotic shock, grinding, French press, blending, etc. Methods using no or low detergent can retain useful antigens such as NspA in Neisserial OMVs. Thus a method may use an OMV extraction buffer with about 0.5% deoxycholate or lower, e.g., about 0.2%, about 0.1%, <0.05% or zero.

A useful process for OMV preparation is described in WO05/004908 and involves ultrafiltration on crude OMVs, rather than instead of high speed centrifugation. The process may involve a step of ultracentrifugation after the ultrafiltration takes place.

Vesicles can be prepared from any pathogenic strain such as Neisseria minigtidis for use with the invention. Vesicles from Neisserial meningitidis serogroup B may be of any serotype (e.g., 1, 2a, 2b, 4, 14, 15, 16, etc.), any serosubtype, and any immunotype (e.g., L1; L2; L3; L3, 3, 7; L10; etc.). The meningococci may be from any suitable lineage, including hyperinvasive and hypervirulent lineages, e.g., any of the following seven hypervirulent lineages: subgroup I; subgroup III; subgroup IV 1; ET 5 complex; ET 37 complex; A4 cluster; lineage 3. These lineages have been defined by multilocus enzyme electrophoresis (MLEE), but multilocus sequence typing (MLST) has also been used to classify meningococci, e.g., the ET 37 complex is the ST 11 complex by MLST, the ET 5 complex is ST-32 (ET-5), lineage 3 is ST 41/44, etc. Vesicles can be prepared from strains having one of the following subtypes: P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14.

Vesicles included in the immunogenic compositions disclosed herein may be prepared from wild type pathogenic strains such as N. meningitidis strains or from mutant strains. By way of example, WO98/56901 discloses preparations of vesicles obtained from N. meningitidis with a modified fur gene. WO02/09746 teaches that nspA expression should be up regulated with concomitant porA and cps knockout. Further knockout mutants of N. meningitidis for OMV production are disclosed in WO02/0974, WO02/062378, and WO04/014417. WO06/081259 discloses vesicles in which fHBP is upregulated. Claassen et al. (1996) 14(10): 1001-8, disclose the construction of vesicles from strains modified to express six different PorA subtypes. Mutant *Neisseria* with low endotoxin levels, achieved by knockout of enzymes involved in LPS biosynthesis, may also be used (see, e.g., WO99/10497 and Steeghs et al. (2001) i20:6937-6945). These or others mutants can all be used with the invention.

Thus *N. meningitidis* serogroup B strains included in the immunogenic compositions disclosed herein may in some embodiments express more than one PorA subtype. Six valent and nine valent PorA strains have previously been constructed. The strain may express 2, 3, 4, 5, 6, 7, 8 or 9 of PorA subtypes: P1.7,16; P1.5-1,2-2; P1.19,15-1; P1.5-2,10; P1.12 1,13; P1.7-2,4; P1.22,14; P1.7-1,1 and/or P1.18-1,3,6. In other embodiments a strain may have been down regulated for PorA expression, e.g., in which the amount of PorA has been reduced by at least 20% (e.g., >30%, >40%, >50%, >60%, >70%, >80%, >90%, >95%, etc.), or even knocked out, relative to wild type levels (e.g., relative to strain H44/76, as disclosed in WO03/105890).

In some embodiments *N. meningitidis* serogroup B strains may over express (relative to the corresponding wild-type strain) certain proteins. For instance, strains may over express NspA, protein 287 (WO01/52885—also referred to as NMB2132 and GNA2132), one or more fHBP (WO06/081259 and U.S. Pat. Pub. 2008/0248065—also referred to as protein 741, NMB1870 and GNA1870), TbpA and/or TbpB (WO00/25811), Cu,Zn-superoxide dismutase (WO00/25811), etc.

In some embodiments *N. meningitidis* serogroup B strains may include one or more of the knockout and/or over expression mutations. Preferred genes for down regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB (WO01/09350); (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB (WO02/09746); (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB (WO02/062378); and (d) CtrA, CtrB, CtrD, FrpB, OpA, OpC, PilC, PorB, SiaD, SynA, SynB, and/or SynC (WO04/014417).

Where a mutant strain is used, in some embodiments it may have one or more, or all, of the following characteristics: (i) down regulated or knocked-out LgtB and/or GalE to truncate the meningococcal LOS; (ii) up regulated TbpA; (iii) up regulated Hsf; (iv) up regulated Omp85; (v) up regulated LbpA; (vi) up regulated NspA; (vii) knocked-out PorA; (viii) down regulated or knocked-out FrpB; (ix) down regulated or knocked-out Opa; (x) down regulated or knocked-out Opc; (xii) deleted cps gene complex. A truncated LOS can be one that does not include a sialyl-lacto-N-neotetraose epitope, e.g., it might be a galactose-deficient LOS. The LOS may have no $\alpha$ chain.

If LOS is present in a vesicle then it is possible to treat the vesicle so as to link its LOS and protein components ("intra-bleb" conjugation (WO04/014417)).

The immunogenic compositions as disclosed herein may include mixtures of vesicles from different strains. By way of example, WO03/105890 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. WO06/024946 discloses useful combinations of different vesicles. A combination of vesicles from strains in each of the L2 and L3 immunotypes may be used in some embodiments.

Vesicle-based antigens can be prepared from *N. meningitidis* serogroups other than serogroup B (e.g., WO01/91788 discloses a process for serogroup A). The immunogenic compositions disclosed herein accordingly can include vesicles prepared serogroups other than B (e.g. A, C, W135 and/or Y) and from bacterial pathogens other than *Neisseria.*

Viral Antigens

Viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, and Virus Like Particles (VLPs). In certain embodiments, viral antigens are derived from viruses propagated on cell culture or other substrate. In other embodiments, viral antigens are expressed recombinantly. In certain embodiments, viral antigens preferably include epitopes which are exposed on the surface of the virus during at least one stage of its life cycle. Viral antigens are preferably conserved across multiple serotypes or isolates. Viral antigens suitable for use in the immunogenic compositions provided herein include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M. In certain embodiments, pneumovirus antigens are also formulated in or derived from chimeric viruses, such as, by way of example only, chimeric RSV/PIV viruses comprising components of both RSV and PIV.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are also formulated in or derived from chimeric viruses, such as, by way of example only, chimeric RSV/PIV viruses comprising components of both RSV and PIV. Commercially available mumps vaccines include live attenuated mumps virus, in either a monovalent form or in combination with measles and rubella vaccines (MMR). In other embodiments, the Paramyxovirus is Nipahvirus or Henipavirus and the antigens are selected from one or more of the following proteins: Fusion (F) protein, Glycoprotein (G) protein, Matrix (M) protein, Nucleocapsid (N) protein, Large (L) protein and Phosphoprotein (P).

Poxviridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are also formulated in or derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses. In certain embodiments, the antigens are formulated into virus-like particles (VLPs).

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4. Commercially available polio vaccines include Inactivated Polio Vaccine (IPV) and Oral poliovirus vaccine (OPV). In certain embodiments, the antigens are formulated into virus-like particles.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limited to, those derived from rhinovirus. In certain embodiments, the rhinovirus antigens are selected from one or more of the following Capsid proteins: VP0, VP1, VP2, VP2 and VP4. In certain embodiments, the antigens are formulated into virus-like particles (VLPs).

Heparnavirus: Viral antigens include, but are not limited to, those derived from a Heparnavirus, such as, by way of example only, Hepatitis A virus (HAV). Commercially available HAV vaccines include inactivated HAV vaccine.

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3. Commercially available Rubella vaccines include a live cold-adapted virus, typically in combination with mumps and measles vaccines (MMR).

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E. Commercially available TBE vaccine includes inactivated virus vaccines. In certain embodiments, the antigens are formulated into virus-like particles (VLPs).

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe). Commercially available HBV vaccines include subunit vaccines comprising the surface antigen S protein.

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the non-structural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity. In certain embodiments, the antigens are formulated into virus-like particles (VLPs).

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens include, but are not limited to, those derived from Calciviridae, such as Norwalk virus, and Norwalk-like Viruses, such as Hawaii Virus and Snow Mountain Virus. In certain embodiments, the antigens are formulated into virus-like particles (VLPs).

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J. K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: $HIV_{IIIb}$, $HIV_{SF2}$, $HIV_{LAV}$, $HIV_{LAI}$, $HIV_{MN}$, HIV-$1_{CM235}$, HIV-$1_{US4}$, HIV-$1_{SF162}$, HIV-$1_{TV1}$, HIV-$1_{MJ4}$. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins λ1, λ2, λ3, μ1, μ2, σ1, σ2, or σ3, or nonstructural proteins σNS, μNS, or σ1s. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B 19. In certain embodiments, the Parvovirus antigens are selected from VP-1, VP-2, VP-3, NS-1 and NS-2. In certain embodiments, the Parvovirus antigen is capsid protein VP1 or VP-2. In certain embodiments, the antigens are formulated into virus-like particles (VLPs).

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (α), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp65/IE1 (Reap et al., *Vaccine* (2007) 25:7441-7449). In certain embodiments, the antigens are formulated into virus-like particles (VLPs).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Further provided are antigens, compositions, methods, and microbes included in Vaccines, 4th Edition (Plotkin and Orenstein ed. 2004); *Medical Microbiology* 4th Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the immunogenic compositions provided herein.

Fungal Antigens

Fungal antigens for use in the immunogenic compositions provided herein include, but are not limited to, those derived from one or more of the fungi set forth below.

Fungal antigens are derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T verrucosum* var. *album*, var. *discoides*, var. *ochraceum, Trichophyton violaceum*, and/or *Trichophyton faviforme*.

Fungal pathogens are derived from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In certain embodiments, the process for producing a fungal antigen includes a method wherein a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Protazoan Antigens/Pathogens

Protazoan antigens/pathogens for use in the immunogenic compositions provided herein include, but are not limited to, those derived from one or more of the following protozoa: *Entamoeba histolytica, Giardia lambli, Cryptosporidium parvum, Cyclospora cayatanensis* and *Toxoplasma*.

Plant Antigens/Pathogens

Plan antigens/pathogens for use in the immunogenic compositions provided herein include, but are not limited to, those derived from *Ricinus communis*.

STD Antigens

In certain embodiments, the immunogenic compositions provided herein include one or more antigens derived from a sexually transmitted disease (STD). In certain embodiments, such antigens provide for prophylactis for STD's such as *chlamydia*, genital herpes, hepatitis (such as HCV), genital warts, gonorrhea, syphilis and/or chancroid. In other embodiments, such antigens provide for therapy for STD's such as *chlamydia*, genital herpes, hepatitis (such as HCV), genital warts, gonorrhea, syphilis and/or chancroid. Such antigens are derived from one or more viral or bacterial STD's. In certain embodiments, the viral STD antigens are derived from HIV, herpes simplex virus (HSV-1 and HSV-2), human papillomavirus (HPV), and hepatitis (HCV). In certain embodiments, the bacterial STD antigens are derived from *Neiserria gonorrhoeae, Chlamydia trachomatis, Treponema pallidum, Haemophilus ducreyi, E. coli*, and *Streptococcus agalactiae*. Examples of specific antigens derived from these pathogens are described above.

Respiratory Antigens

In certain embodiments, the immunogenic compositions provided herein include one or more antigens derived from a pathogen which causes respiratory disease. By way of example only, such respiratory antigens are derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). In certain embodiments, the respiratory antigens are derived from a bacteria which causes respiratory disease, such as, by way of example only, *Streptococcus pneumoniae, Pseudomonas aeruginosa, Bordetella pertussis, Mycobacterium tuberculosis, Mycoplasma pneumoniae, Chlamydia pneumoniae, Bacillus anthracis*, and *Moraxella catarrhalis*. Examples of specific antigens derived from these pathogens are described above.

Pediatric Vaccine Antigens

In certain embodiments, the immunogenic compositions provided herein include one or more antigens suitable for use in pediatric subjects. Pediatric subjects are typically less than about 3 years old, or less than about 2 years old, or less than about 1 years old. Pediatric antigens are administered multiple times over the course of 6 months, 1, 2 or 3 years. Pediatric antigens are derived from a virus which may target pediatric populations and/or a virus from which pediatric populations are susceptible to infection. Pediatric viral antigens include, but are not limited to, antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli*. Examples of specific antigens derived from these pathogens are described above.

Antigens Suitable for Use in Elderly or Immunocompromised Individuals

In certain embodiments, the immunogenic compositions provided herein include one or more antigens suitable for use in elderly or immunocompromised individuals. Such individuals may need to be vaccinated more frequently, with higher doses or with adjuvanted formulations to improve their immune response to the targeted antigens. Antigens which are targeted for use in Elderly or Immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Chlamydia pneumoniae*, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicellazoster virus (VZV), Epstein Barr virus (EBV), Cytomegalovirus (CMV). Examples of specific antigens derived from these pathogens are described above.

Antigens Suitable for Use in Adolescent Vaccines

In certain embodiments, the immunogenic compositions provided herein include one or more antigens suitable for use in adolescent subjects. Adolescents are in need of a boost of a previously administered pediatric antigen. Pediatric antigens which are suitable for use in adolescents are described above. In addition, adolescents are targeted to receive antigens derived from an STD pathogen in order to ensure protective or therapeutic immunity before the beginning of sexual activity. STD antigens which are suitable for use in adolescents are described above.

Tumor Antigens

In certain embodiments, a tumor antigen or cancer antigen is used in conjunction with the immunogenic compositions provided herein. In certain embodiments, the tumor antigens is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA.

Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including polysaccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Horn/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

Polynucleotide-containing antigens used in conjunction with the immunogenic compositions provided herein include polynucleotides that encode polypeptide cancer antigens such as those listed above. In certain embodiments, the polynucleotide-containing antigens include, but are not limited to, DNA or RNA vector constructs, such as plasmid vectors (e.g., pCMV), which are capable of expressing polypeptide cancer antigens in vivo.

In certain embodiments, the tumor antigens are derived from mutated or altered cellular components. After alteration, the cellular components no longer perform their regulatory functions, and hence the cell may experience uncontrolled growth. Representative examples of altered cellular components include, but are not limited to ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Additionally, bacterial and viral antigens, are used in conjunction with the immunogenic compositions provided herein for the treatment of cancer. In certain embodiments, the, carrier proteins, such as $CRM_{197}$, tetanus toxoid, or *Salmonella typhimurium* antigen are used in conjunction/conjugation with compounds provided herein for treatment of cancer. The cancer antigen combination therapies will show increased efficacy and bioavailability as compared with existing therapies.

In certain embodiments, the immunogenic compositions containing at least one compound of Formula (I) include capsular saccharides from at least two of serogroups A, C, W135 and Y of *Neisseria meningitides*. In other embodiments, such vaccines further comprise an antigen from one or more of the following: (a) serogroup B *N. meningitidis*; (b) *Haemophilus influenzae* type B; and/or (c) *Streptococcus pneumoniae*.

In certain embodiments the immunogenic compositions containing at least one compound of Formula (I) include serogroups C, W135 & Y of *N. meningitides*. In certain embodiments the immunogenic compositions containing at least one compound of Formula (I) include serogroups A, C, W135 & Y of *N. meningitides*. In certain embodiments the immunogenic compositions containing at least one compound of Formula (I) include serogroups B, C, W135 & Y of *N. meningitides*. In certain embodiments the immunogenic compositions containing at least one compound of Formula (I) include serogroups A, B, C, W135 & Y of *N. meningitides*. In certain embodiments the immunogenic compositions containing at least one compound of Formula (I) include *H. influenzae* type B and serogroups C, W135 & Y of *N. meningitides*. In certain embodiments the immunogenic compositions containing at least one compound of Formula (I) include *H. influenzae* type B and serogroups A, C, W135 & Y of *N. meningitides*. In certain embodiments the immunogenic compositions containing at least one compound of Formula (I) include *H. influenzae* type B and serogroups B, C, W135 & Y of *N. meningitides*. In certain embodiments the immunogenic compositions containing at least one compound of Formula (I) include *H. influenzae* type B and serogroups A, B, C, W135 & Y of *N. meningitides*. In certain embodiments the immunogenic compositions containing at least one compound of Formula (I) include *S. pneumoniae* and serogroups C, W135 & Y of *N. meningitides*. In certain embodiments the immunogenic compositions containing at least one compound of Formula (I) include *S. pneumoniae* and serogroups A, C, W135 & Y of *N. meningitides*. In certain embodiments the immunogenic compositions containing at least one compound of Formula (I) include *S. pneumoniae* and serogroups B, C, W135 & Y of *N. meningitides*. In certain embodiments the immunogenic compositions containing at least one compound of Formula (I) include *S. pneumoniae* and serogroups A, B, C, W135 & Y of *N. meningitides*. In certain embodiments the immunogenic compositions containing at least one compound of Formula (I) include *H. influenzae* type B, *S. pneumoniae* and serogroups C, W135 & Y of *N. meningitides*. In certain embodiments the immunogenic compositions containing at least one compound of Formula (I) include *H. influenzae* type B, *S. pneumoniae* and serogroups A, C, W135 & Y of *N. meningitides*. In certain embodiments the immunogenic compositions containing at least one compound of Formula (I) include *H. influenzae* type B, *S. pneumoniae* and serogroups B, C, W135 & Y of *N. meningitides*. In certain embodiments the immunogenic compositions containing at least one compound of Formula (I) include *H. influenzae* type B, *S. pneumoniae* and serogroups A, B, C, W135 & Y of *N. meningitidis*.

5. Pharmaceutical Compositions and Administration

In another aspect, the invention provides a pharmaceutical composition comprising the homogeneous suspension of SMIP, and may further comprise one or more pharmaceutically acceptable carriers, diluents, or excipients.

The pharmaceutical compositions provided herein may be administered singly or in combination with one or more additional therapeutic agents. The method of administration include, but are not limited to, oral administration, rectal administration, parenteral, intravenous administration, intravitreal administration, intramuscular administration, inhalation, intranasal administration, topical administration, ophthalmic administration or otic administration.

The therapeutically effective amount of a SMIP will vary depending on, among others, the disease indicated, the severity of the disease, the age and relative health of the subject, the potency of the compound administered, the mode of administration and the treatment desired.

In other embodiments, the homogeneous suspension described herein, the immunogenic composition described herein, or a pharmaceutical composition thereof, is administered in combination with one or more additional therapeutic agents. The additional therapeutic agents may include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, and other toll-like receptor modulators, immunoglobulins (Igs), and antibodies modulating Ig function (such as anti-IgE (omalizumab)).

In certain embodiments, the pharmaceutical compositions provided herein are used in the treatment of infectious diseases including, but not limited to, viral diseases such as genital warts, common warts, plantar warts, respiratory syncytial virus (RSV), hepatitis B, hepatitis C, Dengue virus, herpes simplex virus (by way of example only, HSV-I, HSV-II, CMV, or VZV), molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, para-influenza, mumps virus, measles virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marbug virus).

In certain embodiments, the pharmaceutical compositions provided herein are used in the treatment of bacterial, fungal, and protozoal infections including, but not limited to, tuberculosis and *mycobacterium avium*, leprosy; *pneumocystis* carnii, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, cryptococcal meningitis.

In certain embodiments, the immunogenic compositions provided herein are used in the treatment of respiratory diseases and/or disorders, dermatological disorders, ocular diseases and/or disorders, genitourinary diseases and/or disorders including, allograft rejection, auto-immune and allergic, cancer, or damaged or ageing skin such as scarring and wrinkles.

In another aspect, the invention provides a method for generating an immune response in a subject in need thereof, such as a mammal, comprising administering an effective amount of an immunogenic composition as disclosed herein. The immune response is preferably protective and preferably involves antibodies and/or cell-mediated immunity. The method may raise a booster response.

In other aspects, the homogeneous suspensions and/or immunogenic compositions provided herein are used to induce or potentiate an immune response, for example, in the treatment of treatment of bacterial, fungal, and protozoal infections including, but not limited to meneingococcemia, meningitis, meningococcal pneumonia, meningococcal pericarditis, meningococcal myocarditis, meningococcal pharyngitis, meningococcal conjunctivitis, meningococcal osteomyelitis, meningococcal endophthalmitis, meningococcal urethritis, *Neisseria meningitides* infection, tuberculosis and *mycobacterium avium*, leprosy; *pneumocystis* carnii, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, cryptococcal meningitis.

In certain embodiments, the homogeneous suspensions and/or immunogenic compositions provided herein are used to induce or potentiate an immune response, for example, in the treatment of treatment of respiratory diseases and/or disorders (e.g., RSV), meningococcal disease (e.g., meneingococcemia, meningitis, meningococcal pneumonia, meningococcal pericarditis, meningococcal myocarditis, meningococcal pharyngitis, meningococcal conjunctivitis, meningococcal osteomyelitis, meningococcal endophthalmitis, meningococcal urethritis) dermatological disorders, ocular diseases and/or disorders, genitourinary diseases and/or disorders including, allograft rejection, auto-immune and allergic, cancer, or damaged or ageing skin such as scarring and wrinkles.

In some preferred embodiments, the homogeneous suspensions and/or immunogenic compositions provided herein are used to induce or potentiate an immune response, e.g., a protective immune response, against RSV, Ebola, or *N. meningitides*.

In some embodiments, the invention provides a method for generating or potentiating an immune response, comprising administering an effective amount of an immunogenic composition or a homogeneous suspension, as described herein, to a subject in need thereof. The immune response can be a naturally occurring immune response, or an induced immune response, for example, induced by immunization.

When a homogeneous suspension of the Benzonaphthyridine compound of formula I and II is administered to potentiate an induced immune response, it is preferred that it is administered at substantially the same time as the agent that induces the immune response. For example, an effective amount of a homogeneous suspension can be administered concurrently with an immunogenic composition or vaccine, or administered within a period of about 1 day before or after the immunogenic composition or vaccine is administered.

In certain embodiments, if an aluminum-containing adjuvant is used, it may be desirable to package the alum-adsorbed antigen and the homogeneous suspension of the Benzonaphthyridine compound of formula I and II separately. The two components may be combined, e.g., within about 72 hours prior to administration, so that the desorption of the antigen from the aluminum-containing adjuvant is reduced. For example, the alum-adsorbed antigen and the homogeneous suspension can be combined at a patient's bedside. Preferably, the alum-adsorbed antigen and the homogeneous suspension are combined within about 72 hours, about 48 hours, about 24 hours, about 12 hours, about 10 hours, about 9 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, or about 5 minutes prior to administration.

In certain embodiments, the immunogenic compositions disclosed herein may be used as a medicament, e.g., for use in raising or enhancing an immune response in a subject in need thereof, such as a mammal.

In certain embodiments, the immunogenic compositions disclosed herein may be used in the manufacture of a medicament for raising an immune response in a subject in need thereof, such as a mammal. The invention also provides a delivery device pre-filled with an immunogenic composition disclosed herein.

The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant) or a teenager; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the immunogenic compositions disclosed herein. One way of checking efficacy of prophylactic treatment involves monitoring immune responses, systemically (such as monitoring the level of IgG1 and IgG2a production) and/or mucosally (such as monitoring the level of IgA production), against the antigens included in or administered in conjunction with the immunogenic compositions disclosed herein after administration of the immunogenic composition (and the antigen if administered separately). Typically, antigen-specific serum antibody responses are determined post-immunisation but pre-challenge whereas antigen-specific mucosal antibody responses are determined post-immunisation and post-challenge.

Another way of assessing the immunogenicity of the immunogenic compositions disclosed herein where the antigen is a protein is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the immunogenic compositions can also be determined in vivo by challenging appropriate animal models of the pathogen of interest infection.

Dosage can be by a single dose schedule or a multiple dose schedule. Multiple doses may be used in a primary immunisation schedule and/or in a booster immunisation schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The immunogenic compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving such immunogenic compositions are the elderly (e.g., >50 years old, >60 years old, and preferably >65 years), the young (e.g., <5 years old), hospitalised patients, healthcare workers, armed service and military personnel, pregnant women, the chronically ill, or immunodeficient patients. The immunogenic compositions are not suitable solely for these groups, however, and may be used more generally in a population.

The immunogenic compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

6. Kits

The invention also provides kits comprising a homogeneous suspension and a composition comprising an antigen in separate containers. For example, the kit can contain a first container comprising a homogeneous suspension, and a second container comprising a composition that comprises an antigen. The composition that comprises an antigen can be in liquid form or can be in solid form (e.g., lyophilized), as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a third container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a fourth container comprising an adjuvant (such as an aluminum containing adjuvant or MF59).

The kit can also comprise a package insert containing written instructions for methods of inducing immunity or for treating infections. The package insert can be an unapproved draft package insert or can be a package insert approved by the Food and Drug Administration (FDA) or other regulatory body.

EXEMPLIFICATION

The invention now being generally described, it will be more readily understood by reference to the following examples, which are included merely for purposes of illustration of certain aspects and embodiments of the present invention, and are not intended to limit the invention.

Example (I): Preparation of Selected Benzo[F][1,7] Naphthyridin-5-Amine Analogs

The following examples illustrate methods for preparing certain compounds useful in the compositions and methods of the invention. The skilled person would be able to make a wide range of other compounds for use in the instant methods based on these examples.

Example 1

Benzo[f][1,7]naphthyridin-5-amine

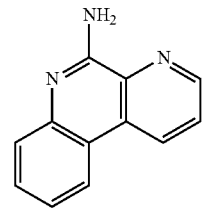 [SMILES: Nc1nc2ccccc2c2cccnc12]

A solution of 2-(tert-butoxycarbonylamino)phenylboronic acid (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-80% ethyl acetate in hexane to give a white solid. $^1$H NMR (acetone d-6): δ 9.04 (d, 1H), 8.91 (d, 1H), 8.45 (d, 1H), 7.86 (dd, 1H), 7.53-7.62 (m, 2H), 7.35 (t, 1H), 6.65 (br, 2H). LRMS [M+H]=196.1

Example 3

9-chlorobenzo[f][1,7]naphthyridin-5-amine

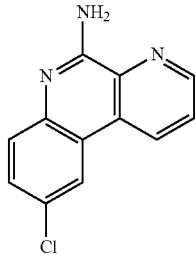 [SMILES: Nc1nc2ccc(Cl)cc2c2cccnc12]

Step 1: tert-butyl 2-bromo-4-chlorophenylcarbamate

To a solution of 2-bromo-4-chloroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified y by flash chromatography on a COMBIFLASH® system (ISCO) using 0-5% ethyl acetate in hexane to give the product as light yellow oil.

Step 2: tert-butyl 4-chloro-2-(4,4,5,5-tetramethyl-1,3,2-dioxaborolan-2-yl)phenyl-carbamate Tert-butyl 2-bromo-4-chlorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-10% ethyl acetate in hexane to give tert-butyl 4-chloro-2-(4,4,5,5-tetramethyl-1,3,2-dioxaborolan-2-yl)phenyl-carbamate.

Step 3: 9-chlorobenzo[f][1,7]naphthyridin-5-amine

A solution of tert-butyl 4-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane and then re-purified using 0-5% methanol in dichloromethane to give a solid. $^1$H NMR (acetone d-6): δ 9.08 (d, 1H), 8.96 (d, 1H), 8.45 (s, 1H), 7.86-7.89 (dd, 1H), 7.60 (d, 1H), 7.54 (d, 1H), 6.78 (br, 2H). LRMS [M+H]=230.1

Example 4

8-chlorobenzo[f][1,7]naphthyridin-5-amine

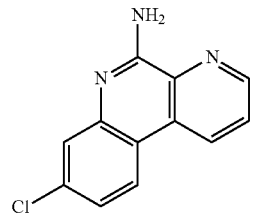 [SMILES: Nc1nc2cc(Cl)ccc2c2cccnc12]

Step 1: tert-butyl 2-bromo-5-chlorophenylcarbamate

To a solution of 2-bromo-5-chloroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give the product as light yellow oil.

Step 2: tert-butyl 5-chloro-2-(4,4,5,5-tetramethyl-1,3,2-dioxaborolan-2-yl)phenyl-carbamate Tert-butyl 2-bromo-5-chlorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-5% ethyl acetate in hexane to give tert-butyl 5-chloro-2-(4,4,5,5-tetramethyl-1,3,2-dioxaborolan-2-yl)phenyl-carbamate.

Step 3: 8-chlorobenzo[f][1,7]naphthyridin-5-amine

A solution of tert-butyl 5-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-5% methanol in dichloromethane to give a semipure solid, which was then stirred in hot 10% ethyl acetate in hexane, filtered, and dried to give a pure solid. $^1$H NMR (acetone d-6): δ 9.03 (d, 1H), 8.93 (d, 1H), 8.46 (d, 1H), 7.85-7.88 (dd, 1H), 7.57 (s, 1H), 7.32 (d, 1H), 6.94 (br, 2H). LRMS [M+H]=230.1

Example 5

8-methylbenzo[f][1,7]naphthyridin-5-amine

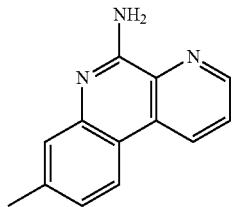 [SMILES: Cc1ccc2c(c1)nc(N)c1ncccc12]

Step 1: tert-butyl 2-bromo-5-methylphenylcarbamate

To a solution of 2-bromo-5-methylaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2: tert-butyl 5-methyl-2-(4,4,5,5-tetramethyl-1,3,2-dioxaborolan-2-yl)phenylcarbamate Tert-butyl 2-bromo-5-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 5-methyl-2-(4,4,5,5-tetramethyl-1,3,2-dioxaborolan-2-yl)phenylcarbamate.

Step 3: 8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-40% ethyl acetate in toluene to give a pure solid. $^1$H NMR (acetone d-6): δ 8.98 (d, 1H), 8.87 (d, 1H), 8.32 (d, 1H), 7.79-7.82 (dd, 1H), 7.42 (s, 1H), 7.18 (d, 1H), 6.6 (br, 2H), 2.45 (s, 3H). LRMS [M+H]=210.1

Example 6

9-methylbenzo[f][1,7]naphthyridin-5-amine

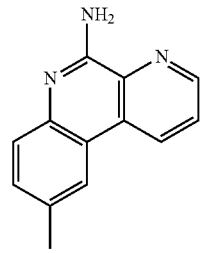 [SMILES: Cc1ccc2nc(N)c3ncccc3c2c1]

Step 1: tert-butyl 2-bromo-4-methylphenylcarbamate

To a solution of 2-bromo-4-methylaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2: tert-butyl 4-methyl-2-(4,4,5,5-tetramethyl-1,3,2-dioxaborolan-2-yl)phenylcarbamate Tert-butyl 2-bromo-4-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBI-FLASH® system (ISCO) using 0-8% ether in hexane to give tert-butyl 4-methyl-2-(4,4,5,5-tetramethyl-1,3,2-dioxaborolan-2-yl)phenylcarbamate.

Step 3: 9-methylbenzo[f][1,7]naphthyridin-5-amine

A solution of tert-butyl 4-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-5% methanol in dichloromethane to give a semipure solid, which was then swirled in hot ethyl acetate, filtered, and dried to give a pure solid. $^1$H NMR (acetone d-6): δ 9.02 (d, 1H), 8.89 (d, 1H), 8.25 (s, 1H), 7.80-7.84 (dd, 1H), 7.52 (d, 1H), 7.40 (d, 1H), 6.5 (br, 2H), 2.48 (s, 3H). LRMS [M+H]=210.2

Example 7

10-methylbenzo[f][1,7]naphthyridin-5-amine

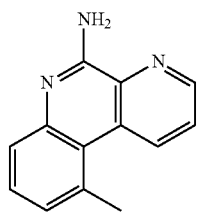 [SMILES: Cc1cccc2nc(N)c3ncccc3c12]

Step 1: tert-butyl 2-bromo-3-methylphenylcarbamate

To a solution of 2-bromo-3-methylaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2: tert-butyl 3-methyl-2-(4,4,5,5-tetramethyl-1,3,2-dioxaborolan-2-yl)phenylcarbamate Tert-butyl 2-bromo-3-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to tert-butyl 3-methyl-2-(4,4,5,5-tetramethyl-1,3,2-dioxaborolan-2-yl)phenylcarbamate.

Step 3: 10-methylbenzo[f][1,7]naphthyridin-5-amine

A solution of tert-butyl 3-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1$H NMR (acetone d-6): δ 9.22 (d, 1H), 8.90 (d, 1H), 7.82-7.85 (dd, 1H), 7.54 (d, 1H), 7.45 (t, 1H), 7.19 (d, 1H), 6.6 (br, 2H), 2.98 (s, 3H). LRMS [M+H]=210.2.

Example 8

Ethyl 5-aminobenzo[f][1,7]naphthyridine-9-carboxylate

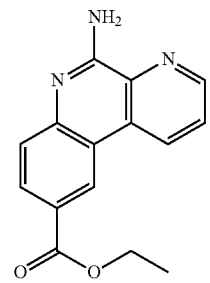 [SMILES: CCOC(=O)c1ccc2nc(N)c3ncccc3c2c1]

Step 1: ethyl 3-bromo-4-(tert-butoxycarbonylamino)benzoate

To a solution of 4-amino-3-bromobenzoate (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2: Ethyl 4-(tert-butoxycarbonylamino)-3-(4,4,5,5-tetramethyl-1,3,2-dioxaborolan-2-yl)benzoate Ethyl 3-bromo-4-(tert-butoxycarbonylamino)benzoate (from step 1) (1.0 eq.), 4,4,4',4',5,5,5',5'-octamethyl-2,2'-bi (1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give ethyl 4-(tert-butoxycarbonylamino)-3-(4,4,5,5-tetramethyl-1,3,2-dioxaborolan-2-yl)benzoate.

Step 3: ethyl 5-aminobenzo[f][1,7]naphthyridine-9-carboxylate

A solution of ethyl 4-(tert-butoxycarbonylamino)-3-(4,4,5,5-tetramethyl-1,3,2-dioxaborolan-2-yl)benzoate (from step 2) (1.0 eq.) and 3-bromopicolino-nitrile (1.0 eq.) in toluene/ethanol (10:1, 0.23 M) was mixed with tetrakis (triphenyl-phosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude material was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1$H NMR (acetone d-6): δ 9.11 (d, 1H), 9.05 (s, 1H), 8.95 (d, 1H), 8.14 (d, 1H), 7.89-7.92 (dd, 1H), 7.63 (d, 1H), 4.38 (q, 2H), 1.40 (t, 3H). LRMS [M+H]=268.2.

Example 9

5-aminobenzo[f][1,7]naphthyridine-9-carboxylic acid

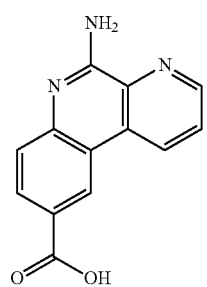 [SMILES: Nc1nc2ccc(C(=O)O)cc2c2cccnc12]

Ethyl 5-aminobenzo[f][1,7]naphthyridine-9-carboxylate (Example 8) (1.0 eq.) was mixed with 1N NaOH (2.0 eq.) in ethanol (0.12 M). The reaction was heated to 80° C. and stirred for 36 hours. The solvent was removed en vacuo. The residue was suspended in water, and the pH was adjusted to neutral using 5% citric acid aqueous solution. The suspension was centrifuged (2500 rpm, 5 min), and the supernatant was removed. The resulting solids was re-suspended in water by vortexing, centrifuged (2500 rpm, 5 min), and the supernatant was removed. The re-suspension, centrifugation, and removal of supernatant steps were repeated with hot methanol, hot ethyl acetate, and ether to give a pure solid. $^1$H NMR (DMSO): δ 12.86 (s, 1H), 9.15 (d, 1H), 9.00 (s, 1H), 8.97 (d, 1H), 8.07 (d, 1H), 7.88-7.91 (dd, 1H), 7.56-7.59 (m, 3H). LRMS [M+H]=240.1

Example 10

8-methoxybenzo[f][1,7]naphthyridin-5-amine

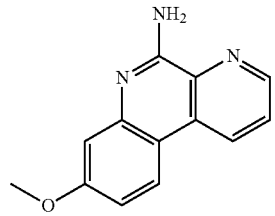 [SMILES: COc1ccc2c(c1)nc(N)c1ncccc12]

Step 1: 2-bromo-5-methoxyaniline

A solution of 1-bromo-4-methoxy-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous MgSO$_4$, and concentrated en vacuo. The crude material was purified by flash chromatography on a COMBIFLASH® system (ISCO) using 0-15% ethyl acetate in hexane to give the product as oil.

Step 2: tert-butyl 2-bromo-5-methoxyphenylcarbamate

To a solution of 2-bromo-5-methoxyaniline (1.0 eq.) (from step 1) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 3: tert-butyl 5-methoxy-2-(4,4,5,5-tetramethyl-1,3,2-dioxaborolan-2-yl)phenylcarbamate Tert-butyl 2-bromo-5-methoxyphenylcarbamate (from step 2) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N₂ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-15% ether in hexane to give tert-butyl 5-methoxy-2-(4,4,5,5-tetramethyl-1,3,2-dioxaborolan-2-yl)phenylcarbamate.

Step 4: 8-methoxybenzo[f][1,7]naphthyridin-5-amine

A solution of tert-butyl 5-methoxy-2-(4,4,5,5-tetramethyl-1,3,2-dioxaborolan-2-yl)phenylcarbamate (from step 3) (1.0 eq.) and 3-bromopicolino-nitrile (1.0 eq.) in toluene/ethanol (10:1, 0.23 M) was mixed with tetrakis(triphenylphosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-5% methanol in dichloromethane to give a semipure solid, which was then recrystalized in ethyl acetate, filtered, and dried to give a pure solid. ¹H NMR (acetone d-6): δ 8.91 (d, 1H), 8.82 (d, 1H), 8.33 (d, 1H), 7.76-7.79 (dd, 1H), 7.07 (s, 1H), 6.96 (d, 1H), 6.6 (br, 2H), 3.90 (s, 3H). LRMS [M+H]=226.1

Example 11

7-fluorobenzo[f][1,7]naphthyridin-5-amine

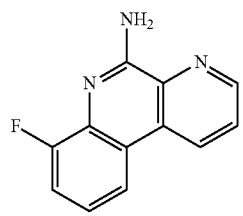 [SMILES: Nc1nc2c(F)cccc2c2cccnc12]

Step 1: tert-butyl 2-fluorophenylcarbamate

To a solution of 2-fluoroaniline (1.0 eq.) in tetrahydrofuran (0.2 M) at 0° C. under N₂ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO₄, and concentrated en vacuo. The crude material was purified by flash chromatography on a COMBIFLASH® system (ISCO) using 0-5% ethyl acetate in hexane to give product as light yellow oil.

Step 2: 2-(tert-butoxycarbonylamino)-3-fluorophenylboronic acid

To a solution of tert-butyl 2-fluorophenylcarbamate (from step 1) (1.0 eq.) in tetrahydrofuran (0.25 M) at −78° C. under N₂ atmosphere was added dropwise 1.7 M tert-butyllithium (2.4 eq.). The reaction was warmed to −40° C. slowly over 2 hours, and neat trimethyl borate (3.8 eq.) was added. The reaction was warmed to room temperature over 30 minutes. An aqueous solution of 1N NaOH was slowly added to the reaction and stirred for 15 minutes. The mixture was poured into ethyl acetate and acidified with 3N HCl to dissolve the solids. The aqueous layer was extracted twice with ethyl acetate, and the combined organic layers were washed with brine, dried over anhydrous MgSO₄, and concentrated en vacuo. The resulting solids were stirred in 1:1 ether/hexane, filtered, and dried. The solids were carried onto the next step without further purification.

Step 3: 7-fluorobenzo[f][1,7]naphthyridin-5-amine

A solution of 2-(tert-butoxycarbonylamino)-3-fluorophenylboronic acid (from step 2) (1.0 eq.) and 3-bromopicolinonitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. After workup, the crude product was suspended in hot toluene, centrifuged (2500 rpm, 5 min), and the supernatant was removed. The suspension, centrifugation, and removal of supernatant steps were repeated with hot ethyl acetate, ether, and hexane to give a pure solid. ¹H NMR (acetone d-6): δ 9.04 (d, 1H), 8.96 (d, 1H), 8.27 (d, 1H), 7.86-7.90 (dd, 1H), 7.28-7.34 (m, 2H), 6.9 (br, 2H). LRMS [M+H]=214.1

Example 12

8-(methylsulfonyl)benzo[f][1,7]naphthyridin-5-amine

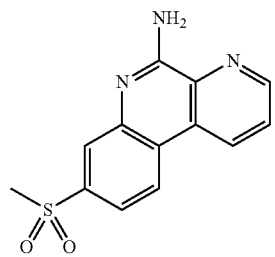 [SMILES: CS(=O)(=O)c1ccc2c(c1)nc(N)c1ncccc12]

Step 1: 2-bromo-5-(methylsulfonyl)aniline

A solution of 1-bromo-4-(methylsulfonyl)-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous $MgSO_4$, and concentrated en vacuo. The crude material was purified by triturating in 1:1 hexane/ether to give a light yellow solid.

Step 2: tert-butyl 2-bromo-5-(methylsulfonyl)phenylcarbamate

To a solution of 2-bromo-5-(methylsulfonyl)aniline (from step 1) (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give tert-butyl 2-bromo-5-(methylsulfonyl) phenylcarbamate.

Step 3: tert-butyl 5-(methylsulfonyl)-2-(4,4,5,5-tetramethyl-1,3,2-dioxaborolan-2-yl)phenylcarbamate Tert-butyl 2-bromo-5-(methylsulfonyl)phenylcarbamate (from step 2) (1.0 eq.), 4,4,4',4',5,5,5',5'-octamethyl-2,2'-bi (1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-50% ethyl acetate in hexane to give a solid which was then triturated in 10% ether/hexane to give tert-butyl 5-(methylsulfonyl)-2-(4,4,5, 5-tetramethyl-1,3,2-dioxaborolan-2-yl)phenylcarbamate as a white solid.

Step 4: 8-(methylsulfonyl)benzo[f][1,7]naphthyridin-5-amine

A solution of tert-butyl 5-(methylsulfonyl)-2-(4,4,5,5-tetramethyl-1,3,2-dioxaborolan-2-yl)phenylcarbamate (from step 3) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-5% methanol in dichloromethane to give a solid which was then triturated in 1:1 hexane/ethyl acetate to give 8-(methylsulfonyl)benzo[f][1,7]naphthyridin-5-amine. $^1$H NMR (acetone d-6): δ 9.16 (d, 1H), 9.03 (d, 1H), 8.71 (d, 1H), 8.11 (s, 1H), 7.93-7.96 (dd, 1H), 7.81 (d, 1H), 7.0 (br, 2H), 3.19 (s, 3H). LRMS [M+H]=274.1

Example 13

8-(trifluoromethyl)benzo[f][1,7]naphthyridin-5-amine

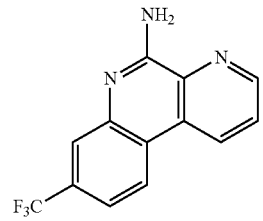 [SMILES: Nc1nc2cc(C(F)(F)F)ccc2c2cccnc12]

Step 1: tert-butyl 2-bromo-5-(trifluoromethyl)phenylcarbamate

To a solution of 2-bromo-5-(trifluoromethyl)aniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 2-(4,4,5,5-tetramethyl-1,3,2-dioxaborolan-2-yl)-5-(trifluoromethyl)phenylcarbamate Tert-butyl 2-bromo-5-(trifluoromethyl)phenylcarbamate (from step 1) (1.0 eq.), 4,4,4',4',5,5,5',5'-octamethyl-2,2'-bi (1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give an impure product which was carried onto the next step without further purification.

Step 3: 8-(trifluoromethyl)benzo[f][1,7]naphthyridin-5-amine

A solution of tert-butyl 2-(4,4,5,5-tetramethyl-1,3,2-dioxaborolan-2-yl)-5-(trifluoromethyl)phenylcarbamate (from step 2) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-(trifluoromethyl)benzo[f][1,7]naphthyridin-5-amine. $^1$H NMR (acetone d-6): δ 9.13 (d, 1H), 9.00 (d, 1H), 8.67 (d, 1H), 7.91-7.94 (dd, 1H), 7.86 (s, 1H), 7.58 (d, 1H), 6.9 (br, 2H). LRMS [M+H]=264.1

Example 14

8-fluorobenzo[f][1,7]naphthyridin-5-amine

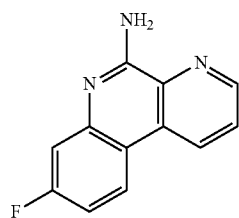 [SMILES: Nc1nc2cc(F)ccc2c2cccnc12]

Step 1: tert-butyl 2-bromo-5-fluorophenylcarbamate

To a solution of 2-bromo-5-fluoroaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give the product as light yellow oil.

Step 2: tert-butyl 5-fluoro-2-(4,4,5,5-tetramethyl-1,3,2-dioxaborolan-2-yl)phenylcarbamate Tert-butyl 2-bromo-5-fluorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-5% ether in hexane to give the product as a yellow solid.

Step 3: 8-fluorobenzo[f][1,7]naphthyridin-5-amine

A solution of tert-butyl 5-fluoro-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-fluorobenzo[f][1,7]naphthyridin-5-amine. $^1$H NMR (acetone d-6): δ 9.00 (d, 1H), 8.90 (d, 1H), 8.46-8.50 (dd, 1H), 7.83-7.87 (dd, 1H), 7.26 (d, 1H), 7.15 (t, 1H), 6.9 (br, 2H). LRMS [M+H]=214.1

Example 16

3-methoxybenzo[f][1,7]naphthyridin-5-amine

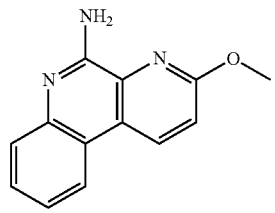 [SMILES: COc1ccc2c(n1)c(N)nc1ccccc12]

Step 1: 3-bromo-6-methoxypicolinonitrile

A solution of 3-bromo-6-oxo-1,6-dihydropyridine-2-carbonitrile (from Example 15/Step 2) (1.0 eq.), silver carbonate (1.3 eq.), and iodomethane (1.2 eq.) in toluene (0.2 M) was stirred in the dark at room temperature overnight. The solvent was concentrated en vacuo, and the resulting residue was purified by a COMBIFLASH® system (ISCO) using 0-80% ethyl acetate in hexane to give 3-bromo-6-methoxypicolinonitrile.

Step 2: 3-methoxybenzo[f][1,7]naphthyridin-5-amine

A solution of 2-(tert-butoxycarbonylamino)phenylboronic acid (1.0 eq.) and 3-bromo-6-methoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-50% ethyl acetate in hexane to give 3-methoxybenzo[f][1,7]naphthyridin-5-amine as a yellow solid. ¹H NMR (acetone d-6): δ 8.91 (d, 1H), 8.34 (d, 1H), 7.63 (d, 1H), 7.51-7.53 (dd, 1H), 7.27-7.33 (m, 2H), 6.65 (br, 2H), 4.11 (s, 3H). LRMS [M+H]=226.1

Example 17

3-butoxybenzo[f][1,7]naphthyridin-5-amine

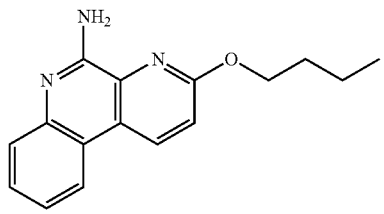 [SMILES: CCCCOc1ccc2c(n1)c(N)nc1ccccc12]

Step 1: 3-bromo-6-butoxypicolinonitrile

A solution of 3-bromo-6-oxo-1,6-dihydropyridine-2-carbonitrile (from Example 15/Step 2) (1.0 eq.), potassium carbonate (1.3 eq.), and 1-iodobutane (1.2 eq.) in acetone (0.3 M) was stirred at 70° C. overnight. The solvent was concentrated en vacuo, and the resulting residue was taken up in water and ethyl acetate. The aqueous layer was extracted with ethyl acetate three times. The combined organic layers were washed with brine, dried over anhydrous MgSO₄, and concentrated en vacuo. The crude product was purified by a COMBIFLASH® system (ISCO) using 0-30% ethyl acetate in hexane to give a colorless solid.

Step 2: 3-butoxybenzo[f][1,7]naphthyridin-5-amine

A solution of 2-(tert-butoxycarbonylamino)phenylboronic acid (1.0 eq.) and 3-bromo-6-butoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-5% ethyl acetate in methanol to give 3-butoxybenzo[f][1,7]naphthyridin-5-amine as a white solid. ¹H NMR (acetone d-6): δ 8.91 (d, 1H), 8.34 (d, 1H), 7.61 (d, 1H), 7.48-7.52 (dd, 1H), 7.27-7.33 (m, 2H), 6.51 (br, 2H), 6.55 (t, 2H), 1.81-1.88 (m, 2H), 1.50-1.59 (m, 2H), 1.00 (t, 3H). LRMS [M+H]=268.1

Example 18

3-(benzyloxy)benzo[f][1,7]naphthyridin-5-amine

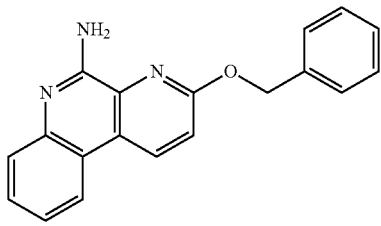 [SMILES: Nc1nc2ccccc2c2ccc(OCc3ccccc3)nc12]

Step 1: 6-(benzyloxy)-3-bromopicolinonitrile

A solution of 3-bromo-6-oxo-1,6-dihydropyridine-2-carbonitrile (from Example 15/Step 2) (1.0 eq.), silver carbonate (1.3 eq.), and benzyl bromide (1.2 eq.) in toluene (0.16 M) was stirred in the dark at 50° C. overnight. The solvent was concentrated en vacuo, and the resulting residue was purified by a COMBIFLASH® system (ISCO) using 0-20% ethyl acetate in hexane to give 6-(benzyloxy)-3-bromopicolinonitrile.

Step 2: 3-(benzyloxy)benzo[f][1,7]naphthyridin-5-amine

A solution of 2-(tert-butoxycarbonylamino)phenylboronic acid (1.0 eq.) and 6-(benzyloxy)-3-bromopicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-50% ethyl acetate in hexane to give 3-(benzyloxy)benzo[f][1,7]naphthyridin-5-amine as a yellow solid. ¹H NMR (acetone d-6): δ 8.95 (d, 1H), 8.35 (d, 1H), 7.58-7.63 (m, 2H), 7.49-7.53 (dd, 1H), 7.30-7.44 (m, 5H), 6.61 (br, 2H), 5.64 (s, 2H). LRMS [M+H]=302.1

Example 19

3-methylbenzo[f][1,7]naphthyridin-5-amine

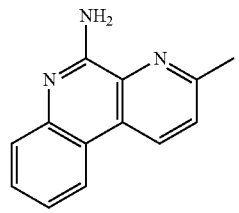 [SMILES: Cc1ccc2c(n1)c(N)nc1ccccc12]

Step 1: 5-bromo-2-methylpyridine 1-oxide

To a solution of 5-bromo-2-methylpyridine (1.0 eq.) in chloroform (0.38 M) was added 77% meta-chloroperbenzoic acid (mCPBA) (4.0 eq.) and heated at 60° C. for 20 hours. After cooling to room temperature, Ca(OH)$_2$ (5.3 eq.) was added, and the resulting precipitate was stirred for 30 minutes. The precipitate was filtered and washed with 3:1 CHCl$_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-methylpicolinonitrile

To a solution of 5-bromo-2-methylpyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-50% ethyl acetate in hexane to give 3-bromo-6-methylpicolinonitrile.

Step 3: 3-methylbenzo[f][1,7]naphthyridin-5-amine

A solution of 2-(tert-butoxycarbonylamino)phenylboronic acid (1.0 eq.) and 3-bromo-6-methylpicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-70% ethyl acetate in hexane to give 3-methylbenzo[f][1,7]naphthyridin-5-amine as a yellow solid. $^1$H NMR (methanol d-4): δ 8.85 (d, 1H), 8.38 (d, 1H), 7.72 (d, 1H), 7.53-7.61 (m, 2H), 7.34-7.38 (dd, 1H), 2.76 (s, 3H). LRMS [M+H]=210.1

Example 20

3-chlorobenzo[f][1,7]naphthyridin-5-amine

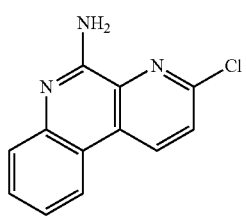 [SMILES: Nc1nc2ccccc2c2ccc(Cl)nc12]

Step 1: 5-bromo-2-chloropyridine 1-oxide

To a solution of 5-bromo-2-chloropyridine (1.0 eq.) in chloroform (0.38 M) was added 77% meta-chloroperbenzoic acid (mCPBA) (4.0 eq.) and heated at 60° C. for 20 hours. After cooling to room temperature, Ca(OH)$_2$ (5.3 eq.) was added, and the resulting precipitate was stirred for 30 minutes. The precipitate was filtered and washed with 3:1 CHCl$_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-chloropicolinonitrile

To a solution of 5-bromo-2-chloropyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-40% ethyl acetate in hexane to give 3-bromo-6-chloropicolinonitrile.

Step 3: 3-chlorobenzo[f][1,7]naphthyridin-5-amine

A solution of 2-(tert-butoxycarbonylamino)phenylboronic acid (1.0 eq.) and 3-bromo-6-chloropicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give a solid, which was then triturated in 10% ethyl acetate in hexane to give 3-chlorobenzo[f][1,7]naphthyridin-5-amine. $^1$H NMR (acetone d-6): δ 9.10 (d, 1H), 8.45 (d, 1H), 7.89 (d, 1H), 7.58-7.65 (m, 2H), 7.35-7.39 (dd, 1H), 6.67 (br, 2H). LRMS [M+H]=230.1

Example 21

N$^3$,N$^3$-dimethylbenzo[f][1,7]naphthyridine-3,5-diamine

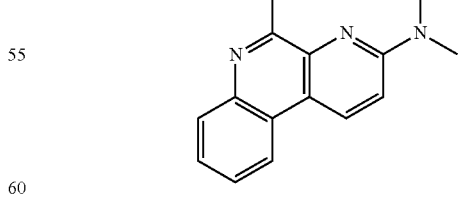

A solution of 3-chlorobenzo[f][1,7]naphthyridin-5-amine (Example 20) (1.0 eq.) was dissolved in 40% aqueous dimethylamine (0.26 M) and heated in a microwave reactor at 100° C. for 30 minutes. The reaction mixture was concentrated en vacuo, and the residue was purified by a COMBIFLASH® system (ISCO) using 0-90% ethyl acetate in hexane to give N³,N³-dimethylbenzo[f][1,7]naphthyridine-3,5-diamine. ¹H NMR (methanol d-4): δ 8.63 (d, 1H), 8.20 (d, 1H), 7.55 (d, 1H), 7.41-7.45 (dd, 1H), 7.29-7.33 (dd, 1H), 7.27 (d, 1H), 3.26 (s, 6H). LRMS [M+H]=239.1

Example 22

N³-butylbenzo[f][1,7]naphthyridine-3,5-diamine

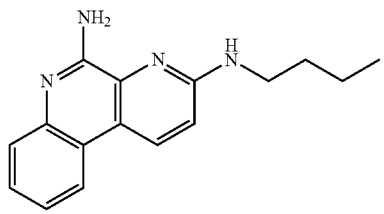 [SMILES: CCCCNc1ccc2c(n1)c(N)nc1ccccc12]

A solution of 3-chlorobenzo[f][1,7]naphthyridin-5-amine (Example 20) (1.0 eq.) was dissolved in n-butylamine (0.1 M) and heated at 110° C. overnight. The reaction mixture was concentrated en vacuo, and the residue was purified by a COMBIFLASH® system (ISCO) using 0-90% ethyl acetate in hexane to give N³-butylbenzo[f][1,7]naphthyridine-3,5-diamine. ¹H NMR (methanol d-4): δ 8.42 (d, 1H), 8.13 (d, 1H), 7.53 (d, 1H), 7.38-7.42 (dd, 1H), 7.25-7.29 (dd, 1H), 6.96 (d, 1H), 3.48 (t, 2H), 1.63-1.71 (m, 2H), 1.43-1.52 (m, 2H), 0.99 (t, 3H). LRMS [M+H]=267.2

Example 23

3-vinylbenzo[f][1,7]naphthyridin-5-amine

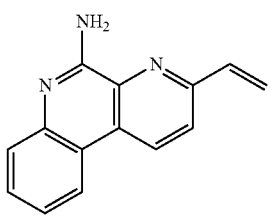 [SMILES: C=Cc1ccc2c(n1)c(N)nc1ccccc12]

A solution of 3-chlorobenzo[f][1,7]naphthyridin-5-amine (Example 20) (1.0 eq.), 4,4,5,5-tetramethyl-2-vinyl-1,3,2-dioxaborolane (1.2 eq.), tetrakis(triphenyl-phosphine)palladium (5 mol %), and 2N aqueous potassium carbonate solution (2.0 eq.) in toluene/ethanol (4:1, 0.1 M) was heated to 100° C. and stirred overnight. After cooling to ambient temperature, the reaction content was diluted with ethyl acetate and water. The two phases were separated, and the aqueous layer was extracted with ethyl acetate three times. The combined organic layers were washed with brine, dried over anhydrous MgSO₄, and concentrated en vacuo. The crude material was purified by flash chromatography on a COMBIFLASH® system (ISCO) using 0-50% ethyl acetate in hexane to give a solid, which was then triturated in 10% ethyl acetate in hexane to give 3-vinylbenzo[f][1,7]naphthyridin-5-amine. ¹H NMR (acetone d-6): δ 8.99 (d, 1H), 8.42 (d, 1H), 8.01 (d, 1H), 7.53-7.62 (m, 2H), 7.30-7.35 (dd, 1H), 7.03-7.10 (dd, 1H), 6.77 (br, 2H), 6.56 (d, 1H), 5.66 (d, 1H). LRMS [M+H]=222.1

Example 24

3-ethylbenzo[f][1,7]naphthyridin-5-amine

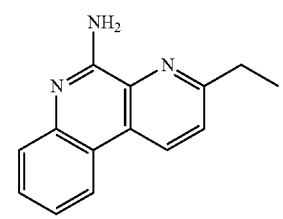 [SMILES: CCc1ccc2c(n1)c(N)nc1ccccc12]

To a solution of 3-vinylbenzo[f][1,7]naphthyridin-5-amine (Example 23) in ethyl acetate/ethanol (1:1, 0.07 M) was added 10% wt palladium on carbon (0.2 eq.). Hydrogen gas was introduced via a balloon, and the reaction was stirred overnight. The mixture was filtered through a pad of celite, washing with dichloromethane. The filtrate was concentrated en vacuo giving 3-ethylbenzo[f][1,7]naphthyridin-5-amine as a white solid. ¹H NMR (acetone d-6): δ 8.93 (d, 1H), 8.41 (d, 1H), 7.76 (d, 1H), 7.61 (d, 1H), 7.51-7.55 (dd, 1H), 7.30-7.34 (dd, 1H), 6.55 (br, 2H), 6.03 (q, 2H), 1.41 (t, 3H). LRMS [M+H]=224.1

Example 25

3-fluorobenzo[f][1,7]naphthyridin-5-amine

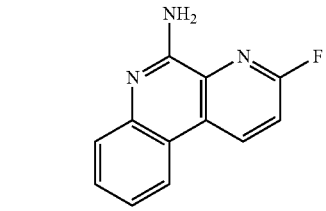 [SMILES: Nc1nc2ccccc2c2ccc(F)nc12]

A solution of 3-chlorobenzo[f][1,7]naphthyridin-5-amine (Example 20) (1.0 eq.), potassium fluoride (3.0 eq.), and 18-crown-6 (0.2 eq.) in N-methylpyrrolidone (NMP) (0.4 M) was heated in a microwave reactor at 210° C. for 80 minutes. After cooling to room temperature, the crude reaction mixture was purified by HPLC using 10-50% acetonitrile in water to give 3-fluorobenzo[f][1,7]naphthyridin-5-amine. ¹H NMR (acetone d-6): δ 11.40 (br, 2H), 9.38-9.42 (dd, 1H), 8.60 (d, 1H), 7.89-7.92 (dd, 1H), 7.81-7.83 (m, 2H), 7.59-7.66 (m, 1H). LRMS [M+H]=214.1

Example 26

2-(trifluoromethyl)benzo[f][1,7]naphthyridin-5-amine

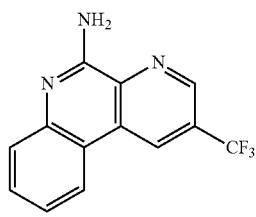 [SMILES: Nc1nc2ccccc2c2cc(C(F)(F)F)cnc12]

Step 1: 3-chloro-5-(trifluoromethyl)picolinaldehyde oxime

A solution of 3-chloro-5-(trifluoromethyl)picolinaldehyde (1.0 eq.), hydroxylamine hydrochloride (5.0 eq.), and pyridine (4.0 eq.) in ethanol was heated to 95° C. and stirred for 1 hour. The reaction was cooled to room temperature and diluted with ethyl acetate and water. The organic layer was washed with brine, water, dried over anhydrous $MgSO_4$, and concentrated en vacuo to give a solid that was carried onto the next step without further purification.

Step 2: 3-chloro-5-(trifluoromethyl)picolinonitrile

A solution of 3-chloro-5-(trifluoromethyl)picolinaldehyde oxime (1.0 eq.) and Burgess reagent (1.5 eq.) in tetrahydrofuran (0.5 M) was heated to 65° C. and stirred for 1 hour. The reaction was cooled to room temperature and diluted with ethyl acetate and water. The organic layer was washed with water, brine, dried over anhydrous $MgSO_4$, and concentrated en vacuo to give a solid that was carried onto the next step without further purification.

Step 3: 2-(trifluoromethyl)benzo[f][1,7]naphthyridin-5-amine

A solution of 2-(tert-butoxycarbonylamino)phenylboronic acid (1.0 eq.) and 3-chloro-5-(trifluoromethyl)picolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane to give 2-(trifluoromethyl)benzo[f][1,7]naphthyridin-5-amine. $^1$H NMR (acetone d-6): δ 9.44 (s, 1H), 9.20 (s, 1H), 8.65-8.63 (d, 1H), 7.70-7.61 (m, 2H), 7.44-7.36 (m, 1H), 6.84 (br, 2H). LRMS [M+H]=264.2

Example 27

2-methoxybenzo[f][1,7]naphthyridin-5-amine

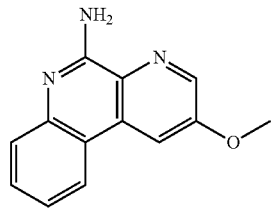

Step 1: 3-chloro-5-methoxypicolinonitrile

To a solution of 3,5-dichloropicolinonitrile (1.0 eq.) in dimethyl formamide (DMF) (0.5 M) was added sodium methoxide (1.5 eq.) and heated to 75° C. After stirring for 14 hours, the reaction was diluted with ethyl acetate and water. The organic layer was washed with saturated aqueous $NaHCO_3$ three times, water twice, dried over anhydrous $MgSO_4$, and concentrated en vacuo. The crude residue was purified by a COMBIFLASH® system (ISCO) using 15% ethyl acetate in hexane to give a mixture of two methoxy regioisomers, one of which was the desired product. The mixture was carried onto the next step without further purification.

Step 2: 2-methoxybenzo[f][1,7]naphthyridin-5-amine

A solution of 2-(tert-butoxycarbonylamino)phenylboronic acid (1.0 eq.) and 3-chloro-5-methoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 50-100% ethyl acetate in hexane to give 2-methoxybenzo[f][1,7]naphthyridin-5-amine.

Example 28

2-(benzyloxy)benzo[f][1,7]naphthyridin-5-amine

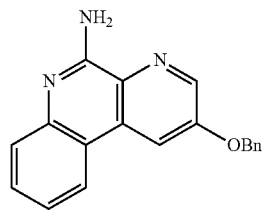 [SMILES: Nc1nc2ccccc2c2cc(OCc3ccccc3)cnc12]

Step 1: 3-(benzyloxy)-5-bromopyridine

A solution of 5-bromopyridin-3-ol (1.0 eq.), benzyl bromide (1.2 eq.), and silver carbonate (1.3 eq.) in toluene (0.1 M) was heated to 50° C. and stirred for 18 hours. After cooling to room temperature, the reaction mixture was filtered, eluting with ethyl acetate. The filtrate was concentrated en vacuo into a residue that was purified by a COMBIFLASH® system (ISCO) using 20% ethyl acetate in hexane to give 3-(benzyloxy)-5-bromopyridine.

Step 2: 3-(benzyloxy)-5-bromopyridine 1-oxide

A solution of 3-(benzyloxy)-5-bromopyridine (from step 1) (1.0 eq.) and meta-chloroperbenzoic acid (mCPBA) (4.0 eq.) in dichloromethane (0.1 M) was stirred at room temperature for 18 hours. The reaction was quenched with saturated aqueous NaHCO$_3$ solution and extracted with dichloromethane three times. The combined organic layers were dried over anhydrous MgSO$_4$ and concentrated en vacuo. The crude residue was purified by a COMBIFLASH® system (ISCO) using 0-100% ethyl acetate in hexane to give 3-(benzyloxy)-5-bromopyridine 1-oxide.

Step 3: 5-(benzyloxy)-3-bromopicolinonitrile

To a solution of 53-(benzyloxy)-5-bromopyridine 1-oxide (from step 2) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-40% ethyl acetate in hexane to give a mixture of two benzoxy regioisomers, one of which was the desired product. The mixture was carried onto the next step without further purification.

Step 4: 2-(benzyloxy)benzo[f][1,7]naphthyridin-5-amine

A solution of 2-(tert-butoxycarbonylamino)phenylboronic acid (1.0 eq.) and 5-(benzyloxy)-3-bromopicolinonitrile (from step 3) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 50-100% ethyl acetate in hexane to give 2-(benzyloxy)benzo[f][1,7]naphthyridin-5-amine. $^1$H NMR (acetone d-6): δ 8.36 (s, 1H), 7.86 (s, 1H), 7.59-7.56 (d, 2H), 7.46-7.42 (dd, 2H), 7.40-7.37 (d, 1H), 7.20-7.15 (dd, 1H), 7.12-7.09 (d, 1H), 6.88-6.86 (d, 1H), 6.77-6.73 (dd, 1H), 5.51 (s, 2H), 4.74 (br, 2H). LRMS [M+H]=302.3.

Example 29

2-vinylbenzo[f][1,7]naphthyridin-5-amine

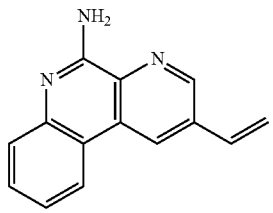 [SMILES: C=Cc1cnc2c(N)nc3ccccc3c2c1]

Step 1: 3-chloro-5-vinylpicolinonitrile

A solution of 3,5-dichloropicolinonitrile (1.0 eq.), 4,4,5,5-tetramethyl-2-vinyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-80% ethyl acetate in hexane to give a white solid.

Step 2: 2-vinylbenzo[f][1,7]naphthyridin-5-amine

A solution of 2-(tert-butoxycarbonylamino)phenylboronic acid (1.0 eq.) and 3-chloro-5-vinylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude material was purified by flash chromatography on a COMBIFLASH® system (ISCO) using 0-80% ethyl acetate in hexane to give 2-vinylbenzo[f][1,7]naphthyridin-5-amine as a yellow solid. $^1$H NMR (methanol-d4-CDCl$_3$): δ 8.87 (d, 1H), 8.69 (d, 1H), 8.28 (d, 1H), 7.49-7.58 (m, 2H), 7.32 (dt, 1H), 6.90 (dd, 1H), 6.09 (d, 1H), 5.54 (d, 1H). LRMS [M+H]=222.1.

Example 30

2-ethylbenzo[f][1,7]naphthyridin-5-amine

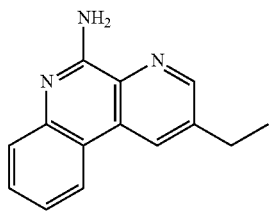 [SMILES: CCc1cnc2c(N)nc3ccccc3c2c1]

To a solution of 2-vinylbenzo[f][1,7]naphthyridin-5-amine (Example 29) in ethyl acetate/methanol (1:4, 0.05 M)

was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and purified by a COMBIFLASH® system (ISCO) using 0-80% ethyl acetate in hexane to give 2-ethylbenzo[f][1,7]naphthyridin-5-amine as a solid. $^1$H NMR (methanol-d4): δ 8.78-8.81 (m, 2H), 8.45 (d, 1H), 7.55-7.63 (m, 2H), 7.35-7.40 (m, 1H), 2.97 (q, 2H), 1.43 (t, 2H). LRMS [M+H]=224.1.

Example 31

2-phenylbenzo[f][1,7]naphthyridin-5-amine

Step 1: 3-chloro-5-phenylpicolinonitrile

A solution of 3,5-dichloropicolinonitrile (1.0 eq.), 4,4,5,5-tetramethyl-2-phenyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-80% ethyl acetate in hexane to give a white solid.

Step 2: 2-phenylbenzo[f][1,7]naphthyridin-5-amine

A solution of 2-(tert-butoxycarbonylamino)phenylboronic acid (1.0 eq.) and 3-chloro-5-phenylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-phenylbenzo[f][1,7]naphthyridin-5-amine as a white solid. $^1$H NMR (dmso-d6): δ 9.13 (d, 1H), 9.03 (d, 1H), 8.56 (d, 1H), 7.98 (d, 2H), 7.43-7.56 (m, 5H), 7.27 (m, 1H), 7.13 (bs, 2H). LRMS [M+H]=272.2.

Example 32

(E)-2-styrylbenzo[f][1,7]naphthyridin-5-amine

Step 1: (E)-3-chloro-5-styrylpicolinonitrile

A solution of 3,5-dichloropicolinonitrile (1.0 eq.), (E)-4,4,5,5-tetramethyl-2-styryl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give a white solid.

Step 2: (E)-2-styrylbenzo[f][1,7]naphthyridin-5-amine

A solution of 2-(tert-butoxycarbonylamino)phenylboronic acid (1.0 eq.) and (E)-3-chloro-5-styrylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-styrylbenzo[f][1,7]naphthyridin-5-amine as a brown solid. $^1$H NMR (dmso-d6): δ 9.22 (d, 1H), 9.06 (d, 1H), 8.51 (d, 1H), 7.78 (d, 1H), 7.66 (d, 2H), 7.46-7.56 (m, 3H), 7.70 (t, 2H), 7.26-7.32 (m, 2H), 7.08 (bs, 2H). LRMS [M+H]=298.2.

Example 33

2-phenethylbenzo[f][1,7]naphthyridin-5-amine

To a solution of (E)-2-styrylbenzo[f][1,7]naphthyridin-5-amine (Example 32) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-phenethylbenzo[f][1,7]naphthyridin-5-amine as a yellow solid. $^1$H NMR (CDCl$_3$): δ 8.54 (d, 1H), 8.32 (d, 1H), 8.10 (dd, 1H), 7.63 (dd, 1H), 7.51 (m, 1H), 7.03-7.32 (m, 6H), 6.16 (bs, 2H), 3.11 (t, 2H), 2.97 (t, 2H). LRMS [M+H]=300.1.

Example 34

(E)-2-(3-methoxyprop-1-enyl)benzo[f][1,7]naphthyridin-5-amine

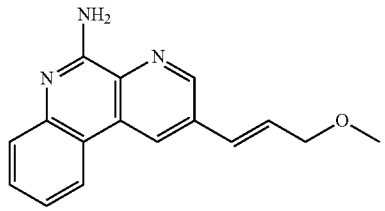 [SMILES: COC/C=C/c1cnc2c(N)nc3ccccc3c2c1]

Step 1: (E)-3-chloro-5-(3-methoxyprop-1-enyl)picolinonitrile

A solution of 3,5-dichloropicolinonitrile (1.0 eq.), (E)-2-(3-methoxyprop-1-enyl)-4,4,5,5-tetramethyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give (E)-3-chloro-5-(3-methoxyprop-1-enyl)picolinonitrile as a white solid.

Step 2: (E)-2-(3-methoxyprop-1-enyl)benzo[f][1,7]naphthyridin-5-amine

A solution of 2-(tert-butoxycarbonylamino)phenylboronic acid (1.0 eq.) and (E)-3-chloro-5-(3-methoxyprop-1-enyl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-(3-methoxyprop-1-enyl)benzo[f][1,7]naphthyridin-5-amine as a yellow solid. $^1$H NMR (dmso-d6): δ 9.24 (d, 1H), 9.18 (d, 1H), 8.54 (d, 1H), 7.52-7.58 (m, 2H), 7.31 (m, 1H), 7.11 (bs, 2H), 6.86-7.00 (m, 2H), 4.18 (d, 2H), 3.36 (s, 3H). LRMS [M+H]=266.2.

Example 35

2-(3-methoxypropyl)benzo[f][1,7]naphthyridin-5-amine

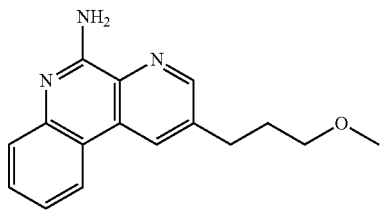 [SMILES: COCCCc1cnc2c(N)nc3ccccc3c2c1]

To a solution of (E)-2-(3-methoxyprop-1-enyl)benzo[f][1,7]naphthyridin-5-amine (Example 34) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-(3-methoxypropyl)benzo[f][1,7]naphthyridin-5-amine as a white solid. $^1$H NMR (CDCl$_3$): δ 8.64 (d, 1H), 8.46 (d, 1H), 8.19 (d, 1H), 7.66 (d, 1H), 7.53 (m, 1H), 7.31 (m, 1H), 6.56 (bs, 2H), 3.37 (t, 2H), 3.31 (s, 3H), 2.91 (t, 2H), 1.93-2.00 (m, 2H). LRMS [M+H]=268.1.

Example 36

2-(prop-1-en-2-yl)benzo[f][1,7]naphthyridin-5-amine

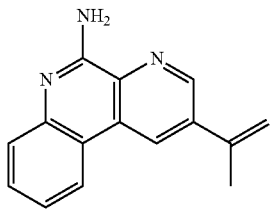 [SMILES: C=C(C)c1cnc2c(N)nc3ccccc3c2c1]

Step 1: 3-chloro-5-(prop-1-en-2-yl)picolinonitrile

A solution of 3,5-dichloropicolinonitrile (1.0 eq.), 4,4,5,5-tetramethyl-2-(prop-1-en-2-yl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give 3-chloro-5-(prop-1-en-2-yl)picolinonitrile as a white solid.

Step 2: 2-(prop-1-en-2-yl)benzo[f][1,7]naphthyridin-5-amine

A solution of 2-(tert-butoxycarbonylamino)phenylboronic acid (1.0 eq.) and 3-chloro-5-(prop-1-en-2-yl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-(prop-1-en-2-yl)benzo[f][1,7]naphthyridin-5-amine as a white solid. $^1$H NMR (dmso-d6): δ 9.03 (d, 1H), 8.96 (d, 1H), 8.55 (d, 1H), 7.47-7.53 (m, 2H), 7.25 (m, 1H), 7.07 (bs, 2H) 5.80 (s, 1H), 5.36 (s, 1H), 2.27 (s, 3H). LRMS [M+H]=236.2.

Example 37

2-isopropylbenzo[f][1,7]naphthyridin-5-amine

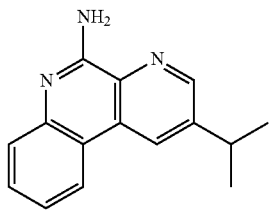 [SMILES: CC(C)c1cnc2c(N)nc3ccccc3c2c1]

To a solution of 2-(prop-1-en-2-yl)benzo[f][1,7]naphthyridin-5-amine (Example 36) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-isopropylbenzo[f][1,7]naphthyridin-5-amine as a yellow solid. $^1$H NMR (CDCl$_3$): δ 8.69 (d, 1H), 8.49 (d, 1H), 8.25 (dd, 1H), 7.65 (dd, 1H), 7.53 (m, 1H), 7.31 (m, 1H), 6.02 (bs, 2H), 3.15 (septet, 1H), 1.37 (d, 6H). LRMS [M+H]=238.2.

Example 38

1-methylbenzo[f][1,7]naphthyridin-5-amine

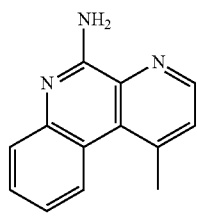 [SMILES: Cc1ccnc2c(N)nc3ccccc3c12]

Step 1: 5-bromo-2-chloro-4-methylpyridine 1-oxide

A solution of 5-bromo-2-chloro-4-methylpyridine (1.0 eq.) and meta-chloroperbenzoic acid (mCPBA) (2.5 eq.) in chloroform (0.1 M) was stirred at 50° C. overnight. After cooling to room temperature, Ca(OH)$_2$ (2.5 eq.) was added to the reaction mixture. The precipitate was filtered and washed with 5% methanol in dichloromethane and ethyl acetate. The filtrate was washed with saturated aqueous Na$_2$S$_2$O$_3$ solution and saturated aqueous NaHCO$_3$ solution. The combined organic layers were washed with brine, dried over anhydrous MgSO$_4$, and concentrated en vacuo into a pale solid that was carried onto the next step without further purification.

Step 2: 3-bromo-6-chloro-4-methylpicolinonitrile

To a solution of 5-bromo-2-chloro-4-methylpyridine 1-oxide (from step 1) (1.0 eq.) in acetonitrile (0.2 M) was added TMSCN (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-50% ethyl acetate in hexane to give 3-bromo-6-chloro-4-methylpicolinonitrile.

Step 3: 3-chloro-1-methylbenzo[f][1,7]naphthyridin-5-amine

A solution of 2-(tert-butoxycarbonylamino)phenylboronic acid (1.0 eq.) and 3-bromo-6-chloro-4-methylpicolinonitrile (from step 2) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 3-chloro-1-methylbenzo[f][1,7]naphthyridin-5-amine as a white solid. $^1$H NMR (dmso-d6): δ 8.44 (d, 1H), 7.83 (s, 1H), 7.50-7.58 (m, 2H), 7.02 (bs, 2H), 2.98 (s, 3H). LRMS [M+H]=244.1.

Step 4: 1-methylbenzo[f][1,7]naphthyridin-5-amine

To a solution of 3-chloro-1-methylbenzo[f][1,7]naphthyridin-5-amine (from step 3) in ethyl acetate/methanol (1:2, 0.03 M) was added 10% wt palladium on carbon (0.2 eq.). The reaction vessel was shaken on a hydrogen Parr apparatus under 50 psi of hydrogen overnight. The mixture was filtered through a pad of celite, washing with dichloromethane. The filtrate was concentrated en vacuo and purified by a COMBIFLASH® system (ISCO) using 0-80% ethyl acetate in hexane to give 1-methylbenzo[f][1,7]naphthyridin-5-amine as a white solid. $^1$H NMR (CDCl$_3$): δ 8.63 (d, 1H), 8.44 (d, 1H), 7.71 (dd, 1H), 7.54 (m, 1H), 7.45 (d, 1H), 7.30 (m, 1H), 6.20 (bs, 2H), 3.01 (s, 3H). LRMS [M+H]=210.1.

Example 40 pyrido[3,2-f][1,7]naphthyridin-6-amine

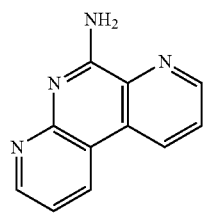 [SMILES: Nc1nc2ncccc2c2cccnc12]

A solution of tert-butyl 3-(4,4,5,5-tetramethyl-1,3,2-dioxaborolan-2-yl)pyridin-2-ylcarbamate (1.0 eq.) and 3-bromopicolinonitrile (1.0 eq.), tetrakis(triphenyl-phosphine) palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give pyrido[3,2-f][1,7]naphthyridin-6-amine as a white solid. $^1$H NMR (dmso-d6): δ 9.14 (dd, 1H), 8.98 (dd, 1H), 8.90 (dd, 1H), 7.93 (dd, 1H), 7.60 (bs, 2H), 7.30 (dd, 1H). LRMS [M+H]=197.

Example 41

2-ethyl-8-methylbenzo[f][1,7]naphthyridin-5-amine

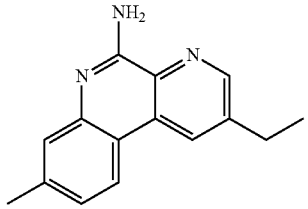 [SMILES: CCc1cnc2c(N)nc3cc(C)ccc3c2c1]

Step 1: 8-methyl-2-vinylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/step 2) (1.0 eq.) and 3-chloro-5-vinylpicolinonitrile (from Example 29/Step 1) (1.0 eq.), tetrakis(triphenyl-phosphine) palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude material was purified by flash chromatography on a COMBIFLASH® system (ISCO) using 0-80% ethyl acetate in hexane to give 8-methyl-2-vinylbenzo[f][1,7]naphthyridin-5-amine as a yellow solid.

Step 2: 2-ethyl-8-methylbenzo[f][1,7]naphthyridin-5-amine

To a solution of 8-methyl-2-vinylbenzo[f][1,7]naphthyridin-5-amine (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite and washed with dichloromethane. The filtrate was concentrated en vaccuo and purified by a COMBIFLASH® system (ISCO) using 0-80% ethyl acetate in hexane to give 2-ethyl-8-methylbenzo[f][1,7]naphthyridin-5-amine as an offwhite solid. $^1$H NMR (CDCl$_3$): δ 8.61 (d, 1H), 8.42 (d, 1H), 8.10 (d, 1H), 7.44 (s, 1H), 7.12 (dd, 1H), 6.00 (bs, 2H), 2.84 (q, 2H), 2.45 (s, 3H), 1.33 (t, 3H). LRMS [M+H]=238.1.

Example 42

(5-amino-8-methylbenzo[f][1,7]naphthyridin-2-yl)methanol

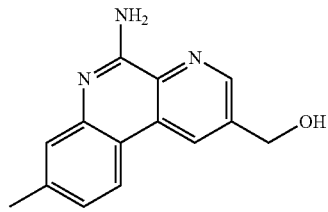 [SMILES: Cc1ccc2c(c1)nc(N)c1ncc(CO)cc12]

Step 1: ethyl 5-chloro-6-cyanonicotinate

A solution of ethyl 5,6-dichloronicotinate (1 eq), zinc cyanide (0.75 eq) and tetrakis(triphenyl-phosphine)palladium (0.10 eq.) in DMF (0.3 M) was degassed and then heated at 100° C. for 3 hours. Solvent was removed en vaccuo to obtain a crude residue. The crude material was purified by flash chromatography on a COMBIFLASH® system (ISCO) using 0-80% ethyl acetate in hexane to give ethyl 5-chloro-6-cyanonicotinate as a white solid.

Step 2: ethyl 5-amino-8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/step 2) (1.0 eq.) and ethyl 5-chloro-6-cyanonicotinate (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give ethyl 5-amino-8-methylbenzo[f][1,7]naphthyridine-2-carboxylate.

Step 3: 2-ethyl-8-methylbenzo[f][1,7]naphthyridin-5-amine

To a stirred solution of ethyl 5-amino-8-methylbenzo[f][1,7]naphthyridine-2-carboxylate (from the previous step) in THF (0.2 M) cooled in an ice-water bath was added 1 N solution of super hydride in THF (10 eq.). Upon completion of the reaction the reaction was quenched with 1 N HCl, and extracted with EtOAc. Combined organic extracts were concentrated en vaccuo to obtain a crude residue. The crude material was purified by flash chromatography on a COMBIFLASH® system (ISCO) using 0-80% ethyl acetate in hexane to give (5-amino-8-methylbenzo[f][1,7]naphthyridin-2-yl)methanol as a white solid. $^1$H NMR (CDCl$_3$): δ 8.68 (d, 1H), 8.52 (d, 1H), 8.04 (d, 1H), 7.44 (s, 1H), 7.12 (dd, 1H), 6.00 (bs, 2H), 4.90 (s, 2H), 2.45 (s, 3H). LRMS [M+H]=240.1

Example 43

8-methyl-2-propylbenzo[f][1,7]naphthyridin-5-amine

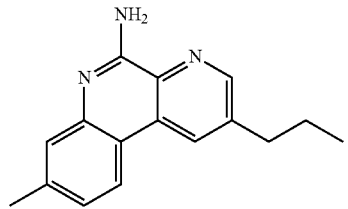 [SMILES: CCCc1cnc2c(N)nc3cc(C)ccc3c2c1]

Step 1: (E)-3-chloro-5-(prop-1-enyl)picolinonitrile

A solution of 3,5-dichloropicolinonitrile (1.0 eq.), (E)-4,4,5,5-tetramethyl-2-(prop-1-enyl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vaccuo to obtain a crude residue. The crude material was purified by flash chromatography on a COMBIFLASH® system (ISCO) using 0-80% ethyl acetate in hexane to give a white solid (E)-3-chloro-5-(prop-1-enyl)picolinonitrile.

Step 2: (E)-8-methyl-2-(prop-1-enyl)benzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/Step 2) (1.0 eq.) and (E)-3-chloro-5-(prop-1-enyl)picolinonitrile (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give (E)-8-methyl-2-(prop-1-enyl)benzo[f][1,7]naphthyridin-5-amine as a yellow solid.

Step 3: 8-methyl-2-propylbenzo[f][1,7]naphthyridin-5-amine

To a solution of (E)-8-methyl-2-(prop-1-enyl)benzo[f][1,7]naphthyridin-5-amine (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give 8-methyl-2-propylbenzo[f][1,7]naphthyridin-5-amine as offwhite solid. $^1$H NMR (CDCl$_3$): δ 8.59 (d, 1H), 8.41 (d, 1H), 8.10 (d, 1H), 7.43 (s, 1H), 7.13 (dd, 1H), 5.94 (bs, 2H), 2.78 (t, 2H), 2.44 (s, 3H), 1.75 (m, 2H), 0.95 (t, 3H). LRMS [M+H]=252.1

Example 44

2-(2-(1H-indol-5-yl)ethyl)-8-methylbenzo[f][1,7]naphthyridin-5-amine

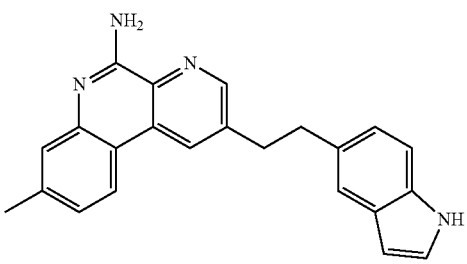 [SMILES: Cc1ccc2c(c1)nc(N)c1ncc(CCc3ccc4[nH]ccc4c3)cc12]

Step 1: 5-((triethylsilyl)ethynyl)-1H-indole

To a scintillation vial was added -iodo-1H-indole (1.1 eq.), triethyl(ethynyl)silane (1 eq.), triethylamine (5 eq.), and anhydrous DMF (0.2 M). Vacuumed and nitrogen flushed for three times. CuI (0.1 eq.) and bis(triphenylphosphine)dichloro-palladium(II) (0.1 eq) were added. The vial was sealed and heated at 60° C. overnight. Upon completion of the reaction as monitored by TLC, the content of the vial was loaded onto a silica gel column pretreated with hexanes. Column was washed with hexanes and diethylether until all eluents containing product were collected. Carefully distill off hexanes and ether using rotary evaporator with minim heating afforded product 5-((triethylsilyl)ethynyl)-1H-indole as colorless oil, which was carried directly on to the next step.

Step 2: 5-ethynyl-1H-indole

To a stirred solution of 5-((triethylsilyl)ethynyl)-1H-indole (from the previous step) in THF (0.2 M) cooled at 0° C. was treated with a solution (0.5 eq.) of tetrabutylammonium fluoride in a dropwise fashion. The reaction mixture turned black and was continued to stir for 30 minutes before warming up to rt. TLC showed full conversion. The reaction was quenched with water and was extracted with diethylether. Combined organic layers were dried over anhydrous Na$_2$SO$_4$ and concentrated using rotary evaporator with minim heating. Chromatography (silica gel, diethylether) afforded the product 5-ethynyl-1H-indole as colorless oil.

Step 3: 5-((1H-indol-5-yl)ethynyl)-3-chloropicolinonitrile

To a round bottom flask capped with septa was added 5-ethynyl-1H-indole (from the previous step) (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine)dichloro-palladium(II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 5-((1H-indol-5-yl)ethynyl)-3-chloropicolinonitrile.

Step 4: 2-((1H-indol-5-ethynyl)-8-methylbenzo[f][1,7]naphthyridin-5-amine

To a round bottom flask with refluxing condenser were added 5-(1H-indol-5-yl)ethynyl)-3-chloropicolinonitrile (from the previous step) (1 eq.), tert-butyl 2-(4,4,5,5-tetramethyl-1,3,2-dioxaborolan-2-yl)phenylcarbamate (from Example 5/Step 2) (1.25 eq.), K₃PO₄ (2 eq.), tris(dibenzylideneacetone)dipalladium(0) (0.05 eq.), and 2-Dicyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried (Na₂SO₄) and concentrated. Flash chromatography (silica gel, 0-50% EtOAc in CH₂Cl₂) afforded the product 2-(1H-indol-5-yl)ethynyl)-8-methylbenzo[f][1,7]naphthyridin-5-amine as a yellow solid.

Step 5: 2-(2-(2,3-dihydrobenzofuran-5-yl)ethyl)-8-methylbenzo[f][1,7]naphthyridin-5-amine To a round bottom flask was added 2-(1H-indol-5-yl)ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The content were vacuumed followed by hydrogen flush for three times. The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in CH₂Cl₂) afforded the product 2-(2-(2,3-Dihydrobenzofuran-5-yl)ethyl)-8-methylbenzo[f][1,7]naphthyridin-5-amine as a yellow solid. ¹H NMR (CDCl₃): δ 8.54 (d, 1H), 8.34 (d, 1H), 8.28 (s, 1H), 7.99 (d, 1H), 7.64-7.56 (m, 1H), 7.50-7.35 (m, 1H), 7.24 (d, 1H), 7.12 (t, 1H), 7.08 (dd, 1H), 6.92 (dd, 1H), 6.41 (s, 1H), 6.01 (bs, 2H), 3.16-3.12 (m, 2H), 3.10-3.05 (m, 2H), 2.43 (s, 3H). LRMS [M+H]=353.2

Example 45

2-(4-ethoxyphenethyl)-8-methylbenzo[f][1,7]naphthyridin-5-amine

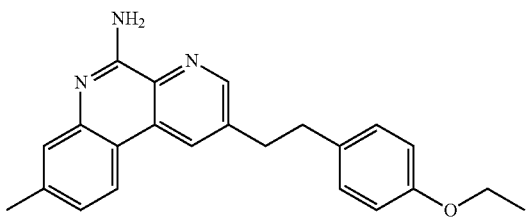 [SMILES: CCOc1ccc(CCc2cnc3c(N)nc4cc(C)ccc4c3c2)cc1]

Step 1: 3-chloro-5-((4-ethoxyphenyl)ethynyl)picolinonitrile

To a round bottom flask capped with septa was added 1-ethoxy-4-ethynylbenzene (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine)dichloro-palladium (II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-chloro-5-((4-ethoxyphenyl)ethynyl)picolinonitrile.

Step 2: 2-((4-ethoxyphenyl)ethynyl)-8-methylbenzo[f][1,7]naphthyridin-5-amine To a round bottom flask with refluxing condenser were added 3-chloro-5-((4-ethoxyphenyl)ethynyl)picolinonitrile (from the previous step) (1 eq.), tert-butyl 5-methyl-2-(4,4,5,5-tetramethyl-1,3,2-dioxaborolan-2-yl)phenylcarbamate (from Example 5/Step 2) (1.25 eq.), K₃PO₄ (2 eq.), tris(dibenzylideneacetone)dipalladium(0) (0.05 eq.), and 2-dicyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried (Na₂SO₄) and concentrated. Flash chromatography (silica gel, 0-50% EtOAc in CH₂Cl₂) afforded the product 2-((4-ethoxyphenyl)ethynyl)-8-methylbenzo[f][1,7]naphthyridin-5-amine.

Step 3: 2-(4-ethoxyphenethyl)-8-methylbenzo[f][1,7]naphthyridin-5-amine

To a round bottom flask was added 2-((4-ethoxyphenyl)ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The contents were degassed under vacuum followed by hydrogen flush (three times). The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in CH$_2$Cl$_2$) afforded the product as a yellow solid. Further recrystalization using toluene afforded product 2-(4-ethoxyphenethyl)-8-methylbenzo[f][1,7]naphthyridin-5-amine as a white fine crystal. $^1$H NMR (CDCl$_3$): δ 8.52 (d, 1H), 8.30 (d, 1H), 8.10 (d, 1H), 7.46 (s, 1H), 7.12 (dd, 1H), 7.06 (d, 2H), 6.75 (d, 2H), 5.95 (bs, 2H), 3.93 (q, 2H), 3.11-3.05 (dd, 2H), 2.95-2.90 (dd, 2H), 2.44 (s, 3H), 1.33 (t, 3H). LRMS [M+H]=358.2

Example 46

8-methyl-2-(4-phenoxyphenethyl)benzo[f][1,7]naphthyridin-5-amine

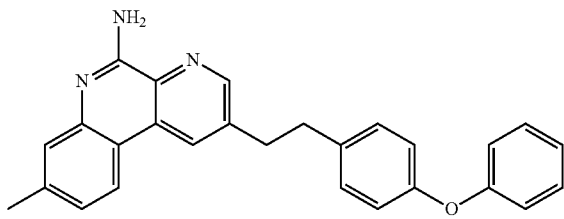 [SMILES: Cc1ccc2c(c1)nc(N)c1ncc(CCc3ccc(Oc4ccccc4)cc3)cc12]

Step 1: 3-chloro-5-((4-phenoxyphenyl)ethynyl)picolinonitrile

3-Chloro-5-((4-phenoxyphenyl)ethynyl)picolinonitrile was prepared from 1-ethynyl-4-phenoxybenzene (commercially available) following the procedures described for Example 45, step 1.

Step 2: 8-methyl-2-((4-phenoxyphenyl)ethynyl)benzo[f][1,7]naphthyridin-5-amine

8-Methyl-2-((4-phenoxyphenyl)ethynyl)benzo[f][1,7]naphthyridin-5-amine was prepared from 3-chloro-5-((4-phenoxyphenyl)ethynyl)picolinonitrile (from the previous step) following the procedures described for Example 45, step 2.

Step 3: 8-methyl-2-(4-phenoxyphenethyl)benzo[f][1,7]naphthyridin-5-amine

8-Methyl-2-(4-phenoxyphenethyl)benzo[f][1,7]naphthyridin-5-amine was prepared from 8-methyl-2-((4-phenoxyphenyl)ethynyl)benzo[f][1,7]naphthyridin-5-amine (from the previous step) following the procedures described for Example 45, step 3. $^1$H NMR (CDCl$_3$): δ 8.54 (d, 1H), 8.30 (d, 1H), 8.01 (d, 1H), 7.45 (s, 1H), 7.25-7.20 (m, 2H), 7.12 (dd, 1H), 7.07-6.84 (m, 8H), 6.00 (bs, 2H), 3.13-3.08 (dd, 2H), 2.99-2.94 (dd, 2H), 2.44 (s, 3H). LRMS [M+H]=406.2

Example 47

2-(2,4-dimethylphenethyl)benzo[f][1,7]naphthyridin-5-amine

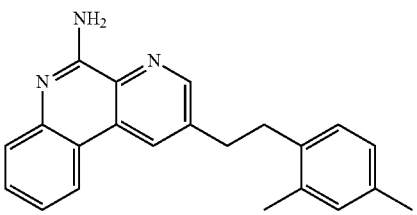 [SMILES: Cc1ccc(CCc2cnc3c(N)nc4ccccc4c3c2)c(C)c1]

Step 1: ((2,4-dimethylphenyl)ethynyl)triethylsilane ((2,4-Dimethylphenyl)ethynyl)triethylsilane was prepared from 1-iodo-2,4-dimethylbenzene (commercially available) following the procedures described for Example 44, step 1.

Step 2: 1-ethynyl-2,4-dimethylbenzene

1-Ethynyl-2,4-dimethylbenzene was prepared from ((2,4-dimethylphenyl)ethynyl)triethylsilane (from the previous step) following the procedures described for Example 44, step 2.

Step 3: 3-chloro-5-((2,4-dimethylphenyl)ethynyl)picolinonitrile

3-Chloro-5-((2,4-dimethylphenyl)ethynyl)picolinonitrile was prepared from 1-ethynyl-2,4-dimethylbenzene (from the previous step) following the procedures described for Example 44, step 3.

Step 4: 2-((2,4-dimethylphenyl)ethynyl)benzo[f][1,7]naphthyridin-5-amine 2-(2,4-Dimethylphenyl)ethynyl)benzo[f][1,7]naphthyridin-5-amine was prepared from 3-chloro-5-((2,4-dimethylphenyl)ethynyl)-picolinonitrile (from the previous step) following the procedures described for Example 44, step 4.

Step 5: 2-(2,4-dimethylphenethyl)benzo[f][1,7]naphthyridin-5-amine 2-(2,4-Dimethylphenethyl)benzo[f][1,7]naphthyridin-5-amine was prepared from 2-(2,4-dimethylphenyl)ethynyl)benzo[f][1,7]naphthyridin-5-amine (from the previous step) following the procedures described for Example 44, step 5. $^1$H NMR (CDCl$_3$): δ 8.60 (d, 1H), 8.33 (d, 1H), 8.14 (d, 1H), 7.67 (d, 1H), 7.54 (t, 1H), 7.31 (t, 1H), 6.96-6.86 (m, 3H), 6.29 (bs, 2H), 3.04-3.10 (dd, 2H), 2.97-2.91 (dd, 2H), 2.24 (s, 3H), 2.20 (s, 3H). LRMS [M+H]=328.2.

Example 48

2-(2,4-dimethylphenethyl)-8-methylbenzo[f][1,7]naphthyridin-5-amine

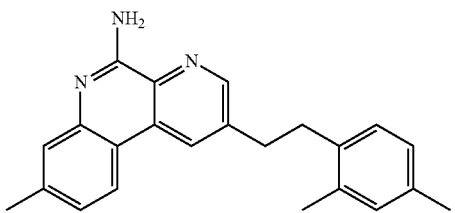

Step 1: 2-((2, 4-dimethylphenyl)ethynyl)-8-methyl-benzo[f][1,7]naphthyridin-5-amine 2-(2,4-Dimethylphenyl)ethynyl)-8-methylbenzo[f][1,7]naphthyridin-5-amine was prepared from 3-chloro-5-((2,4-dimethylphenyl)ethynyl)picolinonitrile (from Example 47/Step 3) and tert-butyl 5-methyl-2-(4,4,5,5-tetramethyl-1,3,2-dioxaborolan-2-yl)phenylcarbamate (from Example 5/Step 2) following the procedures described for Example 44, step 4.

Step 2: 2-(2,4-dimethylphenethyl)-8-methylbenzo[f][1,7]naphthyridin-5-amine 2-(2,4-Dimethylphenethyl)-8-methylbenzo[f][1,7]naphthyridin-5-amine was prepared from 1-ethynyl-4-phenoxybenzene (from the previous step) following the procedures described for Example 44, step 5. $^1$H NMR (CDCl$_3$): δ 8.56 (d, 1H), 8.28 (d, 1H), 8.00 (d, 1H), 7.46 (s, 1H), 7.14 (dd, 1H), 6.95-6.85 (m, 3H), 6.26 (bs, 2H), 3.08-3.02 (dd, 2H), 2.96-2.90 (dd, 2H), 2.45 (s, 3H), 2.23 (s, 3H), 2.19 (s, 3H). LRMS [M+H]=342.2

Example 49

2-(4-methoxy-2-methylphenethyl)-8-methylbenzo[f][1,7]naphthyridin-5-amine

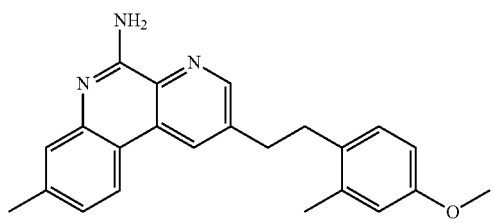

Step 1: 3-chloro-5-((4-methoxy-2-methylphenyl)ethynyl)picolinonitrile

3-Chloro-5-((4-methoxy-2-methylphenyl)ethynyl)picolinonitrile was prepared from 1-ethynyl-4-methoxy-2-methylbenzene (commercially available) following the procedure described for Example 44/Step 3.

Step 2: 2-((4-methoxy-2-methylphenyl)ethynyl)-8-methylbenzo[f][1,7]naphthyridin-5-amine 2-(4-Methoxy-2-methylphenyl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 44, step 4.

Step 3: 2-(4-methoxy-2-methylphenethyl)-8-methyl-benzo[f][1,7]naphthyridin-5-amine 2-(4-Methoxy-2-methylphenethyl)-8-methylbenzo[f][1,7]naphthyridin-5-amine was prepared from 2-(4-methoxy-2-methylphenyl)ethynyl)-8-methylbenzo[f][1,7]naphthyridin-5-amine (from the previous step) following the procedures described for Example 44, step 5. $^1$H NMR (CDCl$_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2

Example 50

4-(2-(5-amino-8-methylbenzo[f][1,7]naphthyridin-2-yl)ethyl)-3-methylphenol

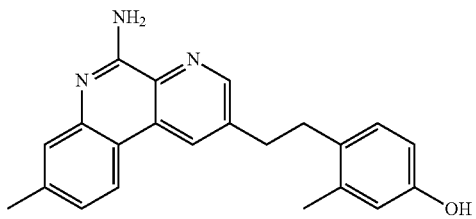 [SMILES: Cc1ccc2c(c1)nc(N)c1ncc(CCc3ccc(O)cc3C)cc12]

To a stirred solution of 2-(4-methoxy-2-methylphenethyl)-8-methylbenzo[f][1,7]naphthyridin-5-amine (Example 49) in methylene chloride (0.2 M) in an ice-water bath was added 1 N solution of BBr$_3$ (2 eq) in CH$_2$Cl$_2$ in a drop-wise fashion. In 30 minutes the reaction was quenched with methanol and was concentrated en vaccuo to obtain a crude residue. The crude material was purified by flash chromatography on a COMBIFLASH® system (ISCO) using 0-20% methanol in dichloromethane to give 4-(2-(5-amino-8-methylbenzo[f][1,7]naphthyridin-2-yl)ethyl)-3-methylphenol as a white solid. $^1$H NMR (DMSO-d$_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]=344.2

Example 51

2-(2-(2,3-dihydrobenzofuran-5-yl)ethyl)-8-methyl-benzo[f][1,7]naphthyridin-5-amine

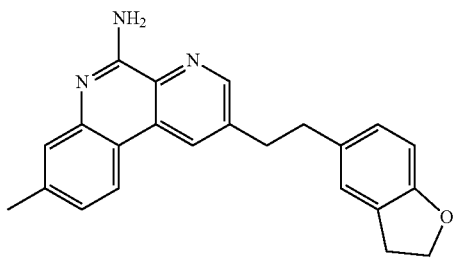 [SMILES: Cc1ccc2c(c1)nc(N)c1ncc(CCc3ccc4c(c3)CCO4)cc12]

Step 1: ((2,3-dihydrobenzofuran-5-yl)ethynyl)triethylsilane ((2,3-Dihydrobenzofuran-5-yl)ethynyl)triethylsilane was prepared from 5-iodo-2,3-dihydrobenzofuran (commercially available) following the procedures described for Example 44, step 1.

Step 2: 5-ethynyl-2,3-dihydrobenzofuran

5-Ethynyl-2,3-dihydrobenzofuran was prepared from ((2,3-dihydrobenzofuran-5-yl)ethynyl)triethylsilane (from the previous step) following the procedures described for Example 44/Step 2.

Step 3: 3-chloro-5-((2,3-dihydrobenzofuran-5-ethynyl)picolinonitrile

3-Chloro-5-((2,3-dihydrobenzofuran-5-yl)ethynyl)picolinonitrile was prepared from 5-ethynyl-2,3-dihydrobenzofuran (from the previous step) following the procedures described for Example 44/Step 3.

Step 4: 2-((2,3-dihydrobenzofuran-5-ethynyl)-8-methylbenzo[f][1,7]naphthyridin-5-amine 2-(2,3-Dihydrobenzofuran-5-yl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 44/Step 4.

Step 5: 2-(2-(2, 3-dihydrobenzofuran-5-yl)ethyl)-8-methylbenzo[f][1,7]naphthyridin-5-amine 2-(2-(2,3-Dihydrobenzofuran-5-yl)ethyl)-8-methylbenzo[f][1,7]naphthyridin-5-amine was prepared from 2-((2,3-dihydrobenzofuran-5-yl)ethynyl)-8-methylbenzo[f][1,7]naphthyridin-5-amine (from the previous step) following the procedures described for Example 44/Step 5. $^1$H NMR (CDCl$_3$): δ 8.62 (d, 1H), 8.40 (d, 1H), 8.11 (d, 1H), 7.53 (s, 1H), 7.21 (dd, 1H), 6.99 (s, 1H), 6.95 (dd, 1H), 6.74 (d, 1H), 6.05 (bs, 2H), 4.57 (t, 2H), 3.19-3.13 (m, 4H), 3.03-2.98 (dd, 2H), 2.54 (s, 3H). LRMS [M+H]=356.2

Example 52

2-(5-amino-8-methylbenzo[f][1,7]naphthyridin-2-yl)ethanol

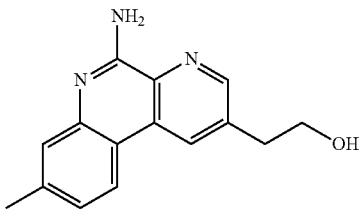 [SMILES: Cc1ccc2c(c1)nc(N)c1ncc(CCO)cc12]

Step 1: (Z)-3-chloro-5-(2-ethoxyvinyl)picolinonitrile (Z)-3-Chloro-5-(2-ethoxyvinyl)picolinonitrile was prepared from (Z)-2-(2-ethoxyvinyl)-4,4,5,5-tetramethyl-1,3,2-dioxaborolane (commercially available) following the procedures described for Example 43/Step 1.

Step 2: (Z)-2-(2-ethoxyvinyl)-8-methylbenzo[f][1,7]naphthyridin-5-amine (Z)-2-(2-Ethoxyvinyl)-8-methylbenzo[f][1,7]naphthyridin-5-amine was prepared from (Z)-3-chloro-5-(2-ethoxyvinyl)picolinonitrile (from the previous step) following the procedures described for Example 43/Step 2.

Step 3: 2-(5-amino-8-methylbenzo[f][1,7]naphthyridin-2-yl)ethanol

A solution of (Z)-2-(2-ethoxyvinyl)-8-methylbenzo[f][1,7]naphthyridin-5-amine (from the previous step) in a mixture of 2:5 conc. HCl and dioxane (0.1 M) was heated at 60° C. overnight. Upon cooling down to rt, the reaction mixture was treated with excess NaHCO$_3$ saturated solution, followed by extraction with EtOAc. Combined organic extracts were concentrated and was taken up in THF (0.2 M), and was treated with 1 N super hydride solution in THF (10 eq.) at 0° C. The reaction mixture was allowed to warm to room temperature and stirred overnight. The reaction was worked up following the procedures described for Example 42/Step 3, to afford 2-(5-amino-8-methylbenzo[f][1,7]naphthyridin-2-yl)ethanol as white solid. $^1$H NMR (CDCl$_3$): δ 8.61 (d, 1H), 8.47 (d, 1H), 8.01 (d, 1H), 7.41 (s, 1H), 7.10 (d, 1H), 6.40 (s, 1H), 6.01 (bs, 2H), 4.01 (t, 2H), 3.06 (t, 2H), 2.43 (s, 3H). LRMS [M+H]=254.1

Example 53

3-methyl-9-phenyl-9,10-dihydrobenzo[f]furo[2,3-b][1,7]naphthyridin-6-amine

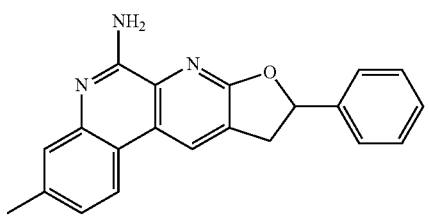 [SMILES: Cc1ccc2c(c1)nc(N)c1nc3c(cc12)CC(c1ccccc1)O3]

Step 1: 5-bromo-2-chloro-3-methylpyridine 1-oxide

5-Bromo-2-chloro-3-methylpyridine 1-oxide was prepared from 5-bromo-2-chloro-3-methylpyridine (commercially available) following the procedures described for Example 19/Step 1.

Step 2: 3-bromo-6-chloro-5-methylpicolinonitrile

3-Bromo-6-chloro-5-methylpicolinonitrile was prepared from (Z)-3-chloro-5-(2-ethoxyvinyl)picolinonitrile (from the previous step) following the procedures described for Example 19/Step 2.

Step 3: 3-bromo-6-chloro-5-(2-hydroxy-2-phenylethyl)picolinonitrile

A solution of 3-bromo-6-chloro-5-methylpicolinonitrile (from the previous step) in THF (0.2 M) was cooled to −78° C. LDA (2N solution, 2 eq) was added dropwise. The reaction was kept stirring at −78° C. for 1 hour, followed by addition of benzaldehyde (1 eq). The reaction was kept stirring at −78° C. for another 30 minutes before allowing it to slowly warm to room temperature. The reaction was quenched with sat. NH$_4$Cl and extracted with EtOAc. Combined organic washes were concentrated. Flash chromatography (silica gel, 20-50% EtOAc in hexanes) afforded the product 3-bromo-6-chloro-5-(2-hydroxy-2-phenylethyl)picolinonitrile as a yellow solid.

Step 4: 3-methyl-9-phenyl-9,10-dihydrobenzo[f]furo[2,3-b][1,7]naphthyridin-6-amine 3-Methyl-9-phenyl-9,10-dihydrobenzo[f]furo[2,3-b][1,7]naphthyridin-6-amine was prepared from 3-bromo-6-chloro-5-methylpicolinonitrile (from the previous step) following the procedures described for Example 44/Step 4. $^1$H NMR (CDCl$_3$): δ 8.45 (s, 1H), 7.98 (d, 1H), 7.45 (s, 1H), 7.40-7.28 (m, 5H), 7.12 (d, 1H), 5.93 (t, 1H), 5.93 (brs, 2H), 3.86 (dd, 1H), 3.40 (dd, 1H), 2.44 (s, 3H). LRMS [M+H]=328.1

Example 54

8-methylbenzo[f][1,7]naphthyridine-2,5-diamine

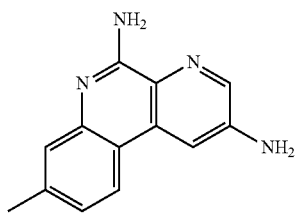 [SMILES: Cc1ccc2c(c1)nc(N)c1ncc(N)cc12]

Step 1: tert-butyl 5,6-dichloropyridin-3-ylcarbamate

To a solution of 5,6-dichloropyridin-3-amine (commercially available) in THF (0.2 M) stirred at 0° C. was added (BOC)$_2$O (1.2 eq). The reaction mixture was heated at 40° C. until full conversion as monitored by TLC. The reaction mixture was then concentrated. Flash chromatography (silica gel, 20-50% EtOAc in hexanes) of the crude afforded tert-butyl 5,6-dichloropyridin-3-ylcarbamate.

Step 2: tert-butyl 5-chloro-6-cyanopyridin-3-ylcarbamate

Tert-butyl 5-chloro-6-cyanopyridin-3-ylcarbamate was prepared from tert-butyl 5,6-dichloropyridin-3-ylcarbamate (from the previous step) following the procedures described for Example 42/Step 1.

Step 3: 8-methylbenzo[f][1,7]naphthyridin-5-amine 8-methylbenzo[f][1,7]naphthyridine-2,5-diamine was prepared (as minor product) together with tert-butyl 5-amino-8-methylbenzo[f][1,7]naphthyridin-2-ylcarbamate (as major product) from tert-butyl 5-chloro-6-cyanopyridin-3-ylcarbamate (from the previous step) following the procedures described for Example 5/Step 2. $^1$H NMR (DMSO-d$_6$): δ 10.11 (s, 1H), 9.02 (s, 1H), 8.82 (d, 1H), 8.06 (d, 1H), 7.34 (s, 1H), 7.15 (dd, 1H), 6.99 (s, 2H), 2.44 (s, 3H). LRMS [M+H]=225.1

Example 55

1-(5-amino-8-methylbenzo[f][1,7]naphthyridin-2-yl)propan-2-ol

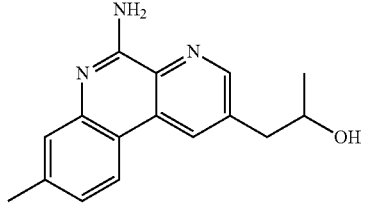 [SMILES: Cc1ccc2c(c1)nc(N)c1ncc(CC(C)O)cc12]

Step 1: 3-bromo-5-methylpicolinonitrile

3-Bromo-5-methylpicolinonitrile was prepared from 2,3-dibromo-5-methylpyridine (commercially available) following the procedures described for Example 42/Step 1.

Step 2: 3-bromo-5-(2-hydroxypropyl)picolinonitrile

3-Bromo-5-(2-hydroxypropyl)picolinonitrile was prepared from 3-bromo-5-methylpicolinonitrile (from the previous step) and acetaldehyde following the procedures described for Example 53/Step 3.

Step 3: 1-(5-amino-8-methylbenzo[f][1,7]naphthyridin-2-yl)propan-2-ol 1-(5-Amino-8-methylbenzo[f][1,7]naphthyridin-2-yl)propan-2-ol was prepared from 3-bromo-5-(2-hydroxypropyl)picolinonitrile (from the previous step) following the procedures described for Example 53, step 4. $^1$H NMR (methanol-d$_4$): δ 8.72 (d, 1H), 8.68 (d, 1H), 8.24 (d, 1H), 7.38 (s, 1H), 7.18 (dd, 1H), 4.16-4.07 (m, 1H), 3.05-2.99 (m, 2H), 2.97-2.90 (m, 2H), 2.47 (s, 3H), 1.28 (d, 3H). LRMS [M+H]=268.1

Example 56

2-(5-amino-8-methylbenzo[f][1,7]naphthyridin-2-yl)acetonitrile

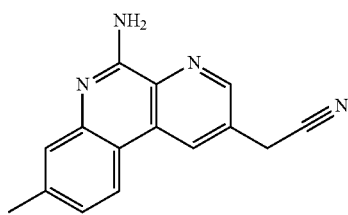 [SMILES: Cc1ccc2c(c1)nc(N)c1ncc(CC#N)cc12]

Step 1: 2,3-dichloro-5-((methoxymethoxy)methyl)pyridine

To a stirred solution of (5,6-dichloropyridin-3-yl)methanol (commercially available) in $CH_2Cl_2$ (0.2 M) at 0° C. was added triethylamine (3 eq.) and chloro(methoxy)methane (2 eq.). After stirring at 0° C. for 3 hours the reaction mixture was concentrated and the crude was purified by chromatography (silica gel, 20-50% EtOAc in hexanes) to afford 2,3-dichloro-5-((methoxymethoxy)methyl)pyridine as a colorless oil.

Step 2: 3-chloro-5-((methoxymethoxy)methyl)picolinonitrile

3-Chloro-5-((methoxymethoxy)methyl)picolinonitrile was prepared from 2,3-dichloro-5-((methoxymethoxy)methyl)pyridine (from the previous step) following the procedures described for Example 42/Step 1.

Step 3: 3-chloro-5-(hydroxymethyl)picolinonitrile

To a stirred solution of 2,3-dichloro-5-((methoxymethoxy)methyl)pyridine (from the previous step) in methanol (0.2 M) was added conc. HCl (10 eq). After stirring at room temperature overnight the reaction mixture was concentrated under vacuum and the resulting crude was purified by chromatography (silica gel, 20-50% EtOAc in hexanes) to afford 3-chloro-5-(hydroxymethyl)picolinonitrile.

Step 4: 3-chloro-5-(chloromethyl)picolinonitrile

To a stirred solution of 3-chloro-5-(hydroxymethyl)picolinonitrile (from the previous step) in $CH_2Cl_2$ (0.2 M) at 0° C. was added thionyl chloride (10 eq). After stirring at room temperature overnight the reaction mixture was concentrated under vacuum and the resulting crude was purified by chromatography (silica gel, 20-50% EtOAc in hexanes) to afford 3-chloro-5-(chloromethyl)picolinonitrile as a colorless oil.

Step 5: 3-chloro-5-(cyanomethyl)picolinonitrile

To a solution of 3-chloro-5-(chloromethyl)picolinonitrile (from the previous step) in DMSO (0.2 M) was added sodium cyanide (1.25 eq). The reaction mixture was heated at 130° C. under microwave irradiation. The reaction mixture taken up in water and EtOAc, and extracted with EtOAc. Organic phases were dried over anhydrous $Na_2SO_4$, and concentrated. Flash chromatography (silica gel, 20-50% EtOAc in hexanes) of the crude afforded 3-chloro-5-(cyanomethyl)picolinonitrile.

Step 6: 2-(5-amino-8-methylbenzo[f][1,7]naphthyridin-2-yl)acetonitrile 2-(5-amino-8-methylbenzo[f][1,7]naphthyridin-2-yl)acetonitrile was prepared from 3-chloro-5-(cyanomethyl)picolinonitrile (from the previous step) following the procedures described for Example 44/Step 4. $^1$H NMR (methanol-$d_4$): δ 8.79 (d, 1H), 8.78 (d, 1H), 8.20 (d, 1H), 7.66 (s, 2H), 7.36 (s, 1H), 7.18 (dd, 1H), 4.15 (d, 2H), 2.43 (s, 3H). LRMS [M+H]=249.1

Example 57

N-(5-amino-8-methylbenzo[f][1,7]naphthyridin-2-yl)acetamide

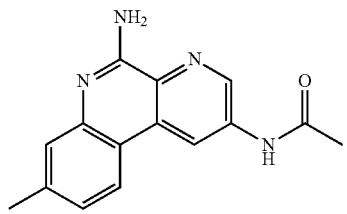 [SMILES: CC(=O)Nc1cnc2c(N)nc3cc(C)ccc3c2c1]

Step 1: N-(5,6-dichloropyridin-3-yl)acetamide

To a stirred solution of 5,6-dichloropyridin-3-amine (commercially available) and triethyl amine (3 eq) in $CH_2Cl_2$ (0.2 M) at 0° C. was added acetyl chloride (2 eq). After stirring at room temperature overnight the reaction mixture was concentrated under vacuum and the resulting crude residue was purified by chromatography (silica gel, 20-50% EtOAc in hexanes) to afford N-(5,6-dichloropyridin-3-yl)acetamide.

Step 2: N-(5-chloro-6-cyanopyridin-3-yl)acetamide

N-(5-chloro-6-cyanopyridin-3-yl)acetamide was prepared from N-(5,6-dichloropyridin-3-yl)acetamide (from the previous step) following the procedures described for Example 42/Step 1.

Step 3: N-(5-amino-8-methylbenzo[f][1,7]naphthyridin-2-yl)acetamide

N-(5-amino-8-methylbenzo[f][1,7]naphthyridin-2-yl)acetamide was prepared from N-(5-chloro-6-cyanopyridin-3-yl)acetamide (from the previous step) following the procedures described for Example 44/Step 4. $^1$H NMR (DMSO-$d_6$): δ 10.99 (s, 1H), 8.18 (d, 1H), 8.95 (d, 1H), 8.12 (d, 1H), 7.44 (s, 1H), 7.35 (dd, 1H), 2.43 (s, 3H), 2.16 (s, 3H). LRMS [M+H]=267.1

Example 58

2-(5-amino-8-methylbenzo[f][1,7]naphthyridin-2-yl)-1-(2,4-dimethylphenyl)ethanol

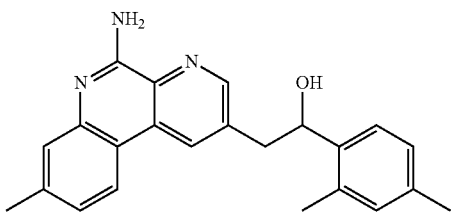

Step 1: 3-bromo-5-(2-(2,4-dimethylphenyl)-2-hydroxyethyl)picolinonitrile 3-bromo-5-(2-(2,4-dimethylphenyl)-2-hydroxyethyl)picolinonitrile was prepared from 3-bromo-5-methylpicolinonitrile (Example 55/Step 1) and 2,4-dimethylbenzaldehyde following the procedures described for Example 53/Step 3.

Step 2: 2-(5-amino-8-methylbenzo[f][1,7]naphthyridin-2-yl)-1-(2,4-dimethylphenyl)ethanol 2-(5-Amino-8-methylbenzo[f][1,7]naphthyridin-2-yl)-1-(2,4-dimethylphenyl)ethanol was prepared from 3-bromo-5-(2-(2,4-dimethylphenyl)-2-hydroxyethyl)picolinonitrile (from the previous step) following the procedures described for Example 53/Step 4. $^1$H NMR (CDCl$_3$): δ 8.67 (d, 1H), 8.45 (d, 1H), 8.06 (d, 1H), 7.57 (s, 1H), 7.42 (d, 1H), 7.23 (d, 1H), 7.11 (d, 1H), 7.01 (s, 1H), 5.31 (dd, 1H), 3.28-3.25 (m, 2H), 2.53 (s, 3H), 2.35 (s, 3H), 2.33 (s, 3H). LRMS [M+H]=358.2

Example 59

2-(2-(6-methoxy-4-methylpyridin-3-yl)ethyl)-8-methylbenzo[f][1,7]naphthyridin-5-amine

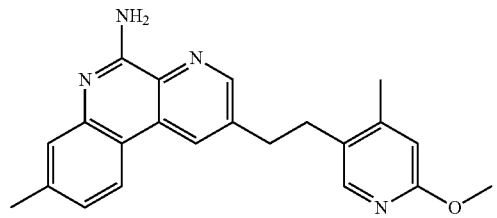

Step 1: 2-methoxy-4-methyl-5-((triethylsilyl)ethynyl)pyridine

2-Methoxy-4-methyl-5-((triethylsilyl)ethynyl)pyridine was prepared from 5-bromo-2-methoxy-4-methylpyridine (commercially available) following the procedures described for Example 44/Step 1.

Step 2: 5-ethynyl-2-methoxy-4-methylpyridine

5-Ethynyl-2-methoxy-4-methylpyridine was prepared from 2-methoxy-4-methyl-5-((triethylsilyl)ethynyl)pyridine (from the previous step) following the procedures described for Example 44/Step 2.

Step 3: 3-chloro-5-((6-methoxy-4-methylpyridin-3-yl)ethynyl)picolinonitrile

3-Chloro-5-((6-methoxy-4-methylpyridin-3-yl)ethynyl)picolinonitrile was prepared from 5-ethynyl-2-methoxy-4-methylpyridine (from the previous step) following the procedures described for Example 44/Step 3.

Step 4: 2-((6-methoxy-4-methylpyridin-3-yl)ethynyl)-8-methylbenzo[f][1,7]naphthyridin-5-amine 2-(6-Methoxy-4-methylpyridin-3-yl)ethynyl)-8-methylbenzo[f][1,7]naphthyridin-5-amine was prepared from 3-chloro-5-((6-methoxy-4-methylpyridin-3-yl)ethynyl)picolinonitrile (from the previous step) following the procedures described for Example 44/Step 4.

Step 4: 2-((6-methoxy-4-methylpyridin-3-yl)ethynyl)-8-methylbenzo[f][1,7]naphthyridin-5-amine 2-(2-(6-Methoxy-4-methylpyridin-3-yl)ethyl)-8-methylbenzo[f][1,7]naphthyridin-5-amine was prepared from 2-(6-methoxy-4-methylpyridin-3-yl)ethynyl)-8-methylbenzo[f][1,7]naphthyridin-5-amine (from the previous step) following the procedures described for Example 44/Step 5. $^1$H NMR (CDCl$_3$): δ 8.65 (d, 1H), 8.43 (d, 1H), 8.13 (d, 1H), 7.87 (s, 1H), 7.57 (s, 1H), 7.24 (dd, 1H), 6.60 (s, 1H), 6.39 (bs, 2H), 3.91 (s, 3H), 3.17-3.11 (dd, 2H), 3.03-2.98 (dd, 2H), 2.54 (s, 3H), 2.28 (s, 3H). LRMS [M+H]=359.2

Example 60

4-(4-(2-(5-amino-8-methylbenzo[f][1,7]naphthyridin-2-yl)ethyl)phenyl)butan-1-ol

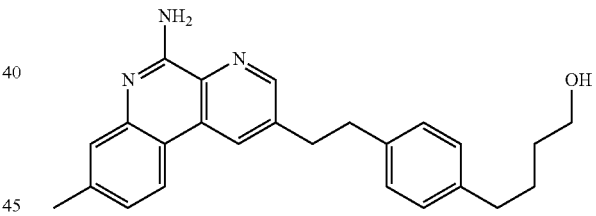

Step 1: 4-(4-((trimethylsilyl)ethynyl)phenyl)but-3-yn-1-ol 4-(4-((trimethylsilyl)ethynyl)phenyl)but-3-yn-1-ol was prepared from ((4-bromophenyl)ethynyl)trimethylsilane (commercially available) and but-3-yn-1-ol (commercially available) following the procedures described for Example 44/Step 1.

Step 2: 4-(4-ethynylphenyl)but-3-yn-1-ol 4-(4-ethynylphenyl)but-3-yn-1-ol was prepared from 4-(4-((trimethylsilyl)ethynyl)phenyl)but-3-yn-1-ol following the procedures described for Example 44/Step 2.

Step 3: 5-((4-(4-hydroxybut-1-ynyl)phenyl)ethynyl)-3-methylpicolinonitrile 5-((4-(4-hydroxybut-1-ynyl)phenyl)ethynyl)-3-methylpicolinonitrile was prepared from 4-(4-ethynylphenyl)but-3- yn-1-ol (from the previous step) following the procedures described for Example 44/Step 3.

Step 4: 4-(4-((5-amino-8-methylbenzo[f][1,7]naphthyridin-2-yl)ethynyl)phenyl)but-2-yn-1-ol 4-(4-((5-amino-8-methylbenzo[f][1,7]naphthyridin-2-yl)ethynyl)phenyl)but-2-yn-1-ol was prepared from 5-((4-(4-hydroxybut-1-ynyl)phenyl)ethynyl)-3-methylpicolinonitrile (from the previous step) following the procedures described for Example 44/Step 4.

Step 5: 4-(4-(2-(5-amino-8-methylbenzo[f][1,7]naphthyridin-2-yl)ethyl)phenyl)butan-1-ol 4-(4-(2-(5-amino-8-methylbenzo[f][1,7]naphthyridin-2-yl)ethyl)phenyl)butan-1-ol was prepared from 4-(4-((5-amino-8-methylbenzo[f][1,7]naphthyridin-2-yl)ethynyl)phenyl)but-2-yn-1-ol (from the previous step) following the procedures described for Example 44/Step 5. $^1$H NMR (CDCl$_3$): δ 8.58 (d, 1H), 8.36 (d, 1H), 8.07 (d, 1H), 7.53 (s, 1H), 7.20 (dd, 1H), 7.10 (dd, 4H), 6.20 (bs, 2H), 3.68 (t, 2H), 3.20-3.15 (dd, 2H), 3.06-3.01 (dd, 2H), 2.64 (t, 2H), 2.52 (s, 3H), 1.75-1.57 (m, 4H). LRMS [M+H]=386.2

Example 61 methyl 3-(4-(2-(5-amino-8-methylbenzo[f][1,7]naphthyridin-2-yl)ethyl)phenyl)propanoate

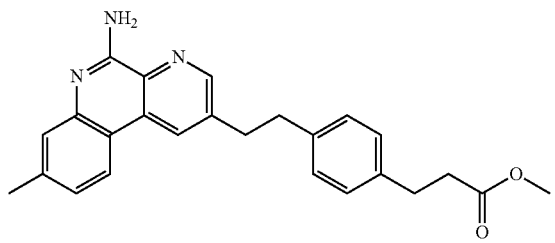

Step 1: methyl 3-(4-iodophenyl)propanoate

To a stirred solution of 3-(4-iodophenyl)propanoic acid (commercially available) in toluene and methanol (9:1, 0.2 M) 0° C. was added (diazomethyl)trimethylsilane (1 N solution in Et$_2$O, 2 eq). After stirring at room temperature overnight the reaction mixture was concentrated under vacuum and the resulting crude residue was purified by chromatography (silica gel, 20-50% EtOAc in hexanes) to afford methyl 3-(4-iodophenyl)propanoate.

Step 2: methyl 3-(4-ethynylphenyl)propanoate

Methyl 3-(4-ethynylphenyl)propanoate was prepared from methyl 3-(4-iodophenyl)propanoate (from the previous step) following the procedures described for Example 44/Steps 1 and 2.

Step 3: methyl 3-(4-((5-chloro-6-cyanopyridin-3-yl)ethynyl)phenyl)propanoate

Methyl 3-(4-((5-chloro-6-cyanopyridin-3-yl)ethynyl)phenyl)propanoate was prepared from methyl 3-(4-ethynylphenyl)propanoate (from the previous step) following the procedures described for Example 44/Step 3.

Step 4: methyl 3-(4-((5-amino-8-methylbenzo[f][1,7]naphthyridin-2-yl)ethynyl)phenyl)propanoate Methyl 3-(4-((5-amino-8-methylbenzo[f][1,7]naphthyridin-2-yl)ethynyl)phenyl)propanoate was prepared from methyl 3-(4-((5-chloro-6-cyanopyridin-3-yl)ethynyl)phenyl)propanoate (from the previous step) following the procedures described for Example 44/Step 4.

Step 5: methyl 3-(4-(2-(5-amino-8-methylbenzo[f][1,7]naphthyridin-2-yl)ethyl)phenyl)propanoate Methyl 3-(4-(2-(5-amino-8-methylbenzo[f][1,7]naphthyridin-2-yl)ethyl)phenyl)propanoate was prepared from methyl 3-(4-((5-amino-8-methylbenzo[f][1,7]naphthyridin-2-yl)ethynyl)phenyl)propanoate (from the previous step) following the procedures described for Example 44/Step 5. $^1$H NMR (DMSO-d$_6$): δ 8.83 (d, 1H), 8.72 (d, 1H), 8.32 (d, 1H), 7.35 (s, 1H), 7.21-7.12 (m, 5H), 7.05 (br s, 2H), 7.05 (dd, 2H), 3.57 (s, 3H), 3.19-3.13 (dd, 2H), 3.06-3.00 (dd, 2H), 2.81 (t, 2H), 2.60 (t, 2H), 2.45 (s, 3H). LRMS [M+H]=400.2

Example 62

3-(4-(2-(5-amino-8-methylbenzo[f][1,7]naphthyridin-2-yl)ethyl)phenyl)propan-1-ol

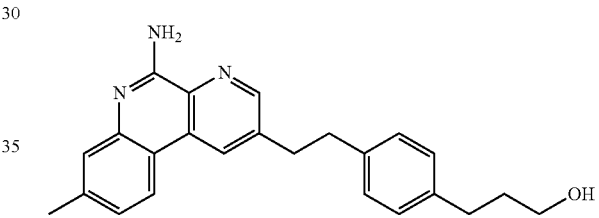

3-(4-(2-(5-amino-8-methylbenzo[f][1,7]naphthyridin-2-yl)ethyl)phenyl)propan-1-ol was prepared from methyl 3-(4-(2-(5-amino-8-methylbenzo[f][1,7]naphthyridin-2-yl)ethyl)phenyl)propanoate (from Example 61) following the procedures described for Example 42/Step 3. $^1$H NMR of the TFA salt: (DMSO-d$_6$): δ 9.56 (s, 1H), 9.24 (s, 1H), 8.92 (d, 1H), 8.81 (d, 1H), 8.43 (d, 1H), 7.44 (d, 1H), 7.35 (d, 1H), 7.13 (dd, 2H), 7.05 (dd, 2H), 3.32 (t, 2H), 3.18-3.12 (dd, 2H), 3.02-2.95 (dd, 2H), 2.50 (t, 2H), 2.44 (s, 3H), 1.65-1.57 (m, 2H). LRMS [M+H]=372.2

Example 63

4-(4-(2-(5-amino-8-methylbenzo[f][1,7]naphthyridin-2-yl)ethyl)phenyl)-2-methylbutan-2-ol

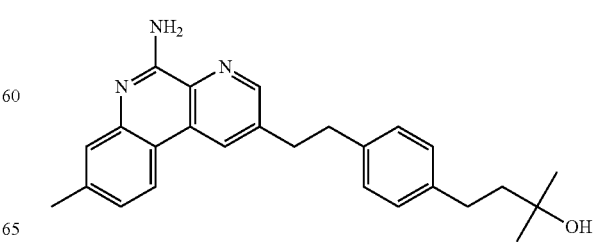

To a solution of methyl 3-(4-(2-(5-amino-8-methylbenzo[f][1,7]naphthyridin-2-yl)ethyl)phenyl)propanoate (from Example 61) in THF (0.2 M) at 0° C. was added in a dropwise fashion a solution of methylmagnesium bromide in THF (1.0 μM, 2 eq). After stirring at room temperature overnight the reaction mixture was concentrated under vacuum and the resulting crude residue was purified by chromatography (silica gel, 50-100% EtOAc in hexanes) to afford 4-(4-(2-(5-amino-8-methylbenzo[f][1,7]naphthyridin-2-yl)ethyl)phenyl)-2-methylbutan-2-ol. ¹H NMR (CDCl₃): δ 8.64 (d, 1H), 8.34 (d, 1H), 8.06 (t, 1H), 7.57 (d, 1H), 7.30-7.20 (m, 2H), 7.18-7.07 (m, 4H), 6.67 (bs, 2H), 3.24-3.16 (dd, 2H), 3.08-3.01 (dd, 2H), 2.73-2.66 (m, 2H), 2.53 (s, 3H), 1.82-1.75 (m, 2H), 1.31 (s, 3H), 1.29 (s, 3H). LRMS [M+H]=400.2

Example 64

2-(4-(aminomethyl)phenethyl)-8-methylbenzo[f][1,7]naphthyridin-5-amine

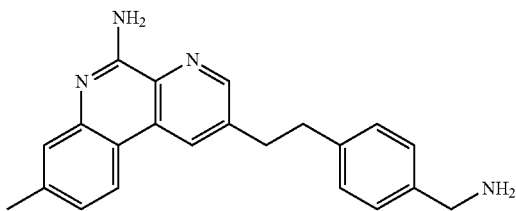 [SMILES: Cc1ccc2c(c1)nc(N)c1ncc(CCc3ccc(CN)cc3)cc12]

Step 1: 4-(2-(5-amino-8-methylbenzo[f][1,7]naphthyridin-2-yl)ethyl)benzonitrile 4-(2-(5-amino-8-methylbenzo[f][1,7]naphthyridin-2-yl)ethyl)benzonitrile was prepared from 4-ethynylbenzonitrile (commercially available) following the procedures described for Example 44/Steps 3 to 5.

Step 2: 2-(4-(aminomethyl)phenethyl)-8-methylbenzo[f][1,7]naphthyridin-5-amine

To a solution of 4-(2-(5-amino-8-methylbenzo[f][1,7]naphthyridin-2-yl)ethyl)benzonitrile (from the previous step) in ethanol and ammonium hydroxide (4:1, 0.2 M) stirred at room temperature was added raney nickel (10 eq). The reaction mixture was stirred under hydrogen atmosphere until the conversion was complete as shown by TLC. The reaction mixture was filtered through a short celite pad. The celite pad was washed with EtOAc. Combined organic extracts were concentrated under vacuum and the resulting crude residue was purified by chromatography (silica gel, 50-100% EtOAc in hexanes) to afford product 2-(4-(aminomethyl)phenethyl)-8-methylbenzo[f][1,7]naphthyridin-5-amine. ¹H NMR of the TFA salt: (methanol-d₄): δ 8.81 (d, 1H), 8.79 (d, 1H), 8.38 (d, 1H), 7.51 (s, 1H), 7.44 (dd, 1H), 7.36 (dd, 4H), 4.07 (s, 2H), 3.29 (s, 2H), 3.20-3.14 (dd, 2H), 2.55 (s, 3H). LRMS [M+H]=343.2

Example 65

(E)-ethyl 3-(4-(2-(5-amino-8-methylbenzo[f][1,7]naphthyridin-2-yl)ethyl)-3-methylphenyl)acrylate

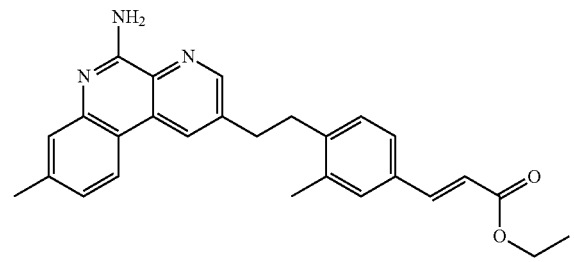 [SMILES: CCOC(=O)/C=C/c1ccc(CCc2cnc3c(N)nc4cc(C)ccc4c3c2)c(C)c1]

Step 1: (4-(2-(5-amino-8-methylbenzo[f][1,7]naphthyridin-2-yl)ethyl)-3-methylphenyl)methanol (4-(2-(5-amino-8-methylbenzo[f][1,7]naphthyridin-2-yl)ethyl)-3-methylphenyl)methanol was prepared from methyl 4-(2-(5-amino-8-methylbenzo[f][1,7]naphthyridin-2-yl)ethyl)-3-methylbenzoate (Example 115) following the procedures described for Example 42/Step 3.

Step 2: 4-(2-(5-amino-8-methylbenzo[f][1,7]naphthyridin-2-yl)ethyl)-3-methylbenzaldehyde To a solution of (4-(2-(5-amino-8-methylbenzo[f][1,7]naphthyridin-2-yl)ethyl)-3-methylphenyl)methanol (from the previous step) in DMSO was added 2-iodoxybenzoic acid (IBX, 2.5 eq). The reaction was stirred at room temperature for 3 hours before being diluted with water. Extraction with EtOAc followed by concentration gave a crude residue which was purified by chromatography (silica gel, 50-100% EtOAc in hexanes) to afford 4-(2-(5-amino-8-methylbenzo[f][1,7]naphthyridin-2-yl)ethyl)-3-methylbenzaldehyde.

Step 3: (E)-ethyl 3-(4-(2-(5-amino-8-methylbenzo[f][1,7]naphthyridin-2-yl)ethyl)-3-methylphenyl)acrylate To a suspension of NaH (3 eq) in THF (0.2 M) stirred at 0° C. was added ethyl 2-(diethoxyphosphoryl)acetate (commercially available) (3 eq). After stirring for 30 minutes, a solution of 4-(2-(5-amino-8-methylbenzo[f][1,7]naphthyridin-2-yl)ethyl)-3-methylbenzaldehyde (from the previous step) in THF (0.2 M) was added dropwise. The reaction was allowed to warm to room temperature and stirred overnight. The reaction was quenched with sat. NH4Cl solution, and was extracted with EtOAc. Combined organic extracts were dried and concentrated to give a crude residue which was purified by chromatography (silica gel, 50-100% EtOAc in hexanes) to afford (E)-ethyl 3-(4-(2-(5-amino-8-methylbenzo[f][1,7]naphthyridin-2-yl)ethyl)-3-methylphenyl)acrylate as a white solid. ¹H NMR: (CDCl₃): δ 8.54 (d, 1H), 8.29 (d, 1H), 7.99 (d, 1H), 7.57 (d, 1H), 7.44 (s, 1H), 7.23 (dd, 1H), 7.11 (dd, 1H), 7.05 (d, 1H), 6.33 (d, 1H), 5.93 (s, 2H), 4.19 (q, 2H), 3.10-2.95 (m, 4H), 2.44 (s, 3H), 2.23 (s, 3H), 1.26 (t, 3H). LRMS [M+H]=426.2

Example 66 ethyl 3-(4-(2-(5-amino-8-methylbenzo[f][1,7]naphthyridin-2-yl)ethyl)-3-methylphenyl)propanoate

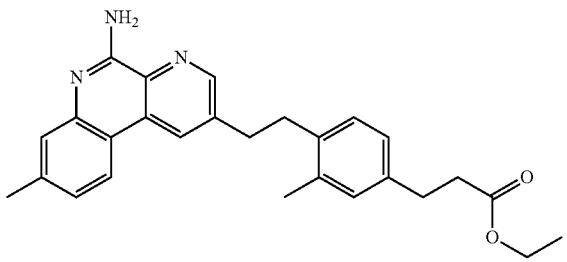 [SMILES: CCOC(=O)CCc1ccc(CCc2cnc3c(N)nc4cc(C)ccc4c3c2)c(C)c1]

Ethyl 3-(4-(2-(5-amino-8-methylbenzo[f][1,7]naphthyridin-2-yl)ethyl)-3-methylphenyl)propanoate was prepared from (E)-ethyl 3-(4-(2-(5-amino-8-methylbenzo[f][1,7]naphthyridin-2-yl)ethyl)-3-methylphenyl)acrylate (from Example 65) following the procedures described for Example 44/Step 5. $^1$H NMR: (CDCl$_3$): δ 8.55 (d, 1H), 8.26 (d, 1H), 7.99 (d, 1H), 7.45 (s, 1H), 7.12 (dd, 1H), 6.98-6.88 (m, 3H), 6.02 (s, 2H), 4.06 (q, 2H), 3.04 (dd, 2H), 2.93 (dd, 2H), 2.83 (t, 2H), 2.53 (t, 2H), 2.44 (s, 3H), 2.19 (s, 3H), 1.17 (t, 3H). LRMS [M+H]=428.2

Example 67

2-(4-(2-(5-amino-8-methylbenzo[f][1,7]naphthyridin-2-yl)ethyl)-3-methylbenzyl)propane-1,3-diol

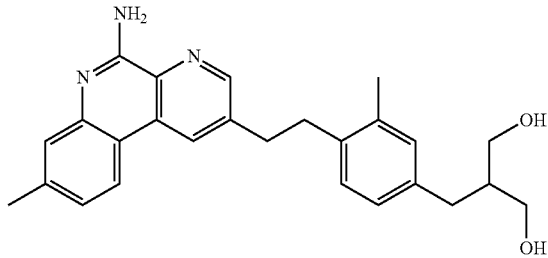 [SMILES: Cc1ccc2c(c1)nc(N)c1ncc(CCc3ccc(CC(CO)CO)cc3C)cc12]

Step 1: diethyl 2-(4-(2-(5-amino-8-methylbenzo[f][1,7]naphthyridin-2-yl)ethyl)-3-methylbenzyl)malonate To a stirred solution of (4-(2-(5-amino-8-methylbenzo[f][1,7]naphthyridin-2-yl)ethyl)-3-methylphenyl)methanol (from Example 65/Step 1) (0.2 M) and diethyl malonate (2 eq) in dry toluene was added tributylphosphine (2 eq) and N$^1$,N$^1$,N$^2$,N$^2$-tetramethyldiazene-1,2-dicarboxamide (2 eq). The reaction mixture was stirred at 120° C. overnight. Upon completion of the reaction, the reaction mixture was concentrated under vacuum and the resulting crude residue was purified by chromatography (silica gel, 50-100% EtOAc in hexanes) to afford diethyl 2-(4-(2-(5-amino-8-methylbenzo[f][1,7]naphthyridin-2-yl)ethyl)-3-methylbenzyl)malonate as a white solid.

Step 2: 2-(4-(2-(5-amino-8-methylbenzo[f][1,7]naphthyridin-2-yl)ethyl)-3-methylbenzyl)propane-1,3-diol 2-(4-(2-(5-Amino-8-methylbenzo[f][1,7]naphthyridin-2-yl)ethyl)-3-methylbenzyl)propane-1,3-diol was prepared from diethyl 2-(4-(2-(5-amino-8-methylbenzo[f][1,7]naphthyridin-2-yl)ethyl)-3-methylbenzyl)malonate (from the previous step) following the procedures described for Example 42/Step 3. $^1$H NMR: (methanol-d$_4$): δ 8.51 (d, 1H), 8.39 (d, 1H), 8.05 (d, 1H), 7.45 (s, 1H), 7.10 (dd, 1H), 6.91-6.87 (m, 2H), 6.83 (dd, 1H), 3.42 (d, 4H), 3.08-3.02 (m, 2H), 2.96-2.91 (m, 2H), 2.47 (d, 2H), 2.38 (s, 3H), 2.13 (s, 3H). LRMS [M+H]=416.2

Example 68

3-(4-(2-(5-amino-8-methylbenzo[f][1,7]naphthyridin-2-yl)ethyl)-3-methylphenyl)propanoic acid

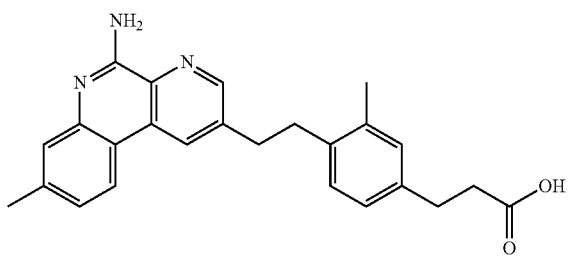 [SMILES: Cc1ccc2c(c1)nc(N)c1ncc(CCc3ccc(CCC(=O)O)cc3C)cc12]

A solution of ethyl 3-(4-(2-(5-amino-8-methylbenzo[f][1,7]naphthyridin-2-yl)ethyl)-3-methylphenyl)propanoate (from Example 66) in 1 N NaOH, THF and methanol (1:5:2, 0.1 N) was heated at 60° C. for 3 hours. After cooling to room temperature the reaction mixture was neutralized with 1 N HCl to pH 7, and was concentrated to give a crude residue which was purified by chromatography (silica gel, 0-20% methanol in dichloromethane) to afford (E)-ethyl 3-(4-(2-(5-amino-8-methylbenzo[f][1,7]naphthyridin-2-yl)ethyl)-3-methylphenyl)acrylate as a white solid. $^1$H NMR: (methanol-d$_4$): δ 8.73 (d, 1H), 8.54 (d, 1H), 8.20 (d, 1H), 7.45 (s, 1H), 7.37 (d, 1H), 7.00-6.97 (m, 2H), 6.92 (d, 1H), 3.19 (t, 2H), 3.04 (t, 2H), 2.81 (t, 2H), 2.53 (t, 2H), 2.50 (s, 3H), 2.25 (s, 3H). LRMS [M+H]=400.2

Example 69

5-amino-2-(4-methoxy-2-methylphenethyl)benzo[f][1,7]naphthyridine-8-carbaldehyde

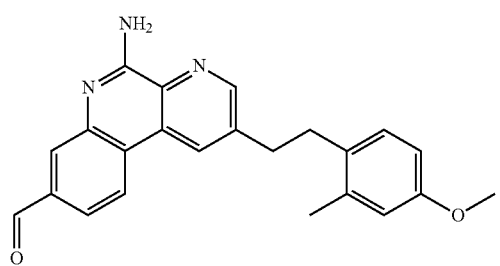 [SMILES: COc1ccc(CCc2cnc3c(N)nc4cc(C=O)ccc4c3c2)c(C)c1]

5-amino-2-(4-methoxy-2-methylphenethyl)benzo[f][1,7]naphthyridine-8-carbaldehyde was prepared from (5-amino-2-(4-methoxy-2-methylphenethyl)benzo[f][1,7]naphthyridin-8-yl)methanol (from Example 108) following the procedures described for Example 65/Step 2. $^1$H NMR: (CDCl$_3$): δ 10.19 (s, 1H), 8.74 (d, 1H), 8.43 (d, 1H), 8.32 (d, 1H), 8.18 (d, 1H), 7.88 (dd, 1H), 7.00 (d, 1H), 6.76 (d, 1H), 6.70 (dd, 1H), 6.30 (s, 2H), 3.80 (s, 3H), 3.16 (dd, 2H), 3.02 (dd, 2H), 2.29 (s, 3H). LRMS [M+H]=372.2

Example 70 ethyl 4-(2-(5-amino-8-methylbenzo[f][1,7]naphthyridin-2-yl)ethyl)benzoate

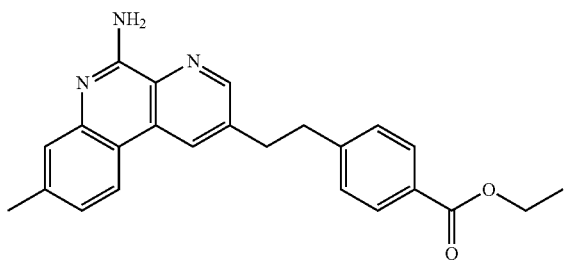 [SMILES: CCOC(=O)c1ccc(CCc2cnc3c(N)nc4cc(C)ccc4c3c2)cc1]

Step 1: ethyl 4-((5-chloro-6-cyanopyridin-3-yl)ethynyl)benzoate

A solution of 3,5-dichloropicolinonitrile (commercially available) (1.0 eq.), ethyl 4-ethynylbenzoate (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-20% ethyl acetate in hexane to give ethyl 4-((5-chloro-6-cyanopyridin-3-yl)ethynyl)benzoate as a white solid.

Step 2: ethyl 4-((5-amino-8-methylbenzo[f][1,7]naphthyridin-2-yl)ethynyl) benzoate A solution of ethyl 4-((5-chloro-6-cyanopyridin-3-yl)ethynyl)benzoate (from the previous step) (1.0 eq.), tert-butyl 5-methyl-2-(4,4,5,5-tetramethyl-1,3,2-dioxaborolan-2-yl)phenylcarbamate (from Example 5/Step 2) (2.6 eq.), tetrakis(triphenylphosphine)palladium (10 mol %), and potassium carbonate (5.3 eq.) in toluene/ethanol (2:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7]naphthyridin-2-yl)ethynyl)benzoate.

Step 3: ethyl 4-(2-(5-amino-8-methylbenzo[f][1,7]naphthyridin-2-yl)ethyl)benzoate A solution of ethyl 4-((5-amino-8-methylbenzo[f][1,7]naphthyridin-2-yl)ethynyl)benzoate (from the previous step) (1.0 eq.) in THF/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give ethyl 4-(2-(5-amino-8-methylbenzo[f][1,7]naphthyridin-2-yl)ethyl)benzoate. $^1$H NMR (Acetone-d$_6$): δ 8.80 (s, 1H), 8.69 (s, 1H), 8.25 (d, 1H), 7.90 (d, 2H), 7.40-7.42 (m, 3H), 7.12 (d, 1H), 6.55 (br, 2H), 4.28 (q, 2H), 3.2-3.3 (m, 4H), 2.44 (s, 3H), 1.31 (t, 3H). LRMS [M+H]=386.2

Example 71

8-methyl-2-(4-methylphenethyl)benzo[f][1,7]naphthyridin-5-amine

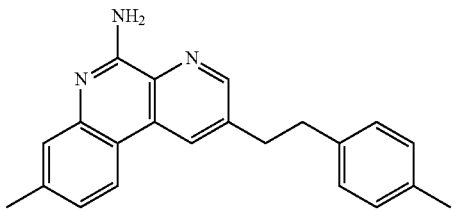

Step 1: 3-chloro-5-(p-tolylethynyl)picolinonitrile

A solution of 3,5-dichloropicolinonitrile (commercially available) (1.0 eq.), 1-ethynyl-4-methylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by stirring in hot ether/hexane mixtures and filtered to give 3-chloro-5-(p-tolylethynyl)picolinonitrile.

Step 2: 8-methyl-2-(p-tolylethynyl)benzo[f][1,7]naphthyridin-5-amine

A solution of 3-chloro-5-(p-tolylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.2 eq.), tetrakis(triphenylphosphine)palladium (10 mol %), and 2N sodium carbonate aqueous solution (4.0 eq.) in toluene/ethanol (2:1, 0.2 M) was stirred at 100° C. overnight. After cooling to ambient temperature, the reaction mixture was diluted with 2% MeOH in DCM. The two phases were separated, and the aqueous layer was extracted with 2% MeOH in DCM twice. The combined organic layers were washed with brine, dried over anhydrous MgSO₄, and concentrated en vaccuo. The crude material was purified by flash chromatography on a COMBIFLASH® system (ISCO) using 0-40% ethyl acetate in toluene to give 8-methyl-2-(p-tolylethynyl)benzo[f][1,7]naphthyridin-5-amine.

Step 3: 8-methyl-2-(4-methylphenethyl)benzo[f][1,7]naphthyridin-5-amine

A solution of 8-methyl-2-(p-tolylethynyl)benzo[f][1,7]naphthyridin-5-amine (from the previous step) (1.0 eq.) in EtOH/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give 8-methyl-2-(4-methylphenethyl)benzo[f][1,7]naphthyridin-5-amine. $^1$H NMR (Acetone-d₆): δ 8.74 (s, 1H), 8.68 (s, 1H), 8.24 (d, 1H), 7.41 (s, 1H), 7.13-7.15 (m, 3H), 7.06 (d, 2H), 6.6 (br, 2H), 3.19 (t, 2H), 3.06 (t, 2H), 2.44 (s, 3H), 2.25 (s, 3H). LRMS [M+H]=328.1

Example 72

2-(4-(2-(5-amino-8-methylbenzo[f][1,7]naphthyridin-2-yl)ethyl)phenyl)propan-2-ol

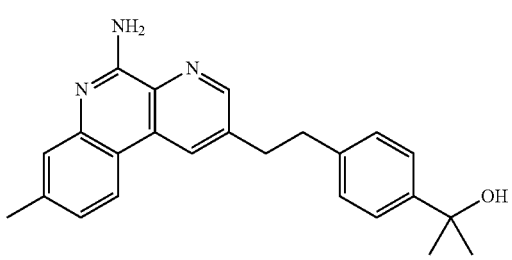 [SMILES: Cc1ccc2c(c1)nc(N)c1ncc(CCc3ccc(C(C)(C)O)cc3)cc12]

To a solution of ethyl 4-(2-(5-amino-8-methylbenzo[f][1,7]naphthyridin-2-yl)ethyl)benzoate (from Example 70) (1.0 eq.) in DCM at 0° C. was added 3.0 M methyl magnesium iodide (10 eq.) in ether and warmed to room temperature overnight. The reaction was cooled to 0° C. and quenched with 1N HCl aqueous solution and ether. After stirring for 15 minutes, the reaction mixture was neutralized with saturated aqueous sodium bicarbonate solution. The two phases were separated, and the aqueous layer was extracted with ether. The combined organic layers were washed with brine, dried over anhydrous MgSO₄, and concentrated en vaccuo. The crude material was purified by RP-HPLC using a 10-50% MeCN in water gradient followed by extraction in DCM to give 2-(4-(2-(5-amino-8 methylbenzo[f][1,7]naphthyridin-2-yl)ethyl)phenyl)propan-2-ol. $^1$H NMR (Acetone-d₆): δ 8.73 (m, 2H), 8.22 (d, 1H), 7.40-7.44 (m, 3H), 7.20 (d, 2H), 7.12 (d, 1H), 6.5 (br, 2H), 3.94 (s, 1H), 3.21 (t, 2H), 3.08 (t, 2H), 2.44 (s, 3H), 1.47 (s, 6H). LRMS [M+H]=372.2

Example 73

(4-(2-(5-amino-8-methylbenzo[f][1,7]naphthyridin-2-yl)ethyl)phenyl)methanol

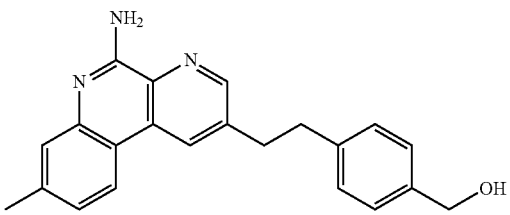 [SMILES: Cc1ccc2c(c1)nc(N)c1ncc(CCc3ccc(CO)cc3)cc12]

To a solution of ethyl 4-(2-(5-amino-8-methylbenzo[f][1,7]naphthyridin-2-yl)ethyl)benzoate (Example 70) (1.0 eq.) in THF (0.1 M) at 0° C. was added 1.0 M lithium triethylborohydride in THF (10 eq.) and warmed to room temperature over 2 hours. 1N HCl aqueous solution was added slowly to quench the reaction, and the mixture was heated to reflux for 30 minutes. The reaction mixture was neutralized with saturated aqueous sodium bicarbonate solution. The two phases were separated, and the aqueous layer was extracted with ethyl acetate (EA). The combined organic layers were washed with brine, dried over anhydrous MgSO₄, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)phenyl)methanol. $^1$H NMR (Acetone-d₆): δ 8.77 (s, 1H), 8.69 (s, 1H), 8.26 (d, 1H), 7.40 (s, 1H), 7.21-7.28 (m, 4H), 7.13 (d, 1H), 6.5 (br, 2H), 4.56 (s, 2H), 4.1 (br t, 1H), 3.10-3.23 (m, 4H), 2.44 (s, 3H). LRMS [M+H]=344.2

Example 74 ethyl 4-(2-(5-amino-8-methylbenzo[f][1,7]naphthyridin-2-yl)ethyl)-3-methylbenzoate

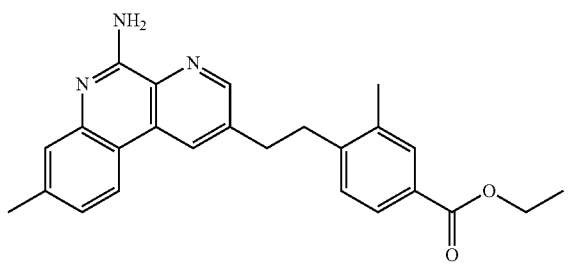 [SMILES: CCOC(=O)c1ccc(CCc2cnc3c(N)nc4cc(C)ccc4c3c2)c(C)c1]

Step 1: ethyl 4-bromo-3-methylbenzoate

To a solution of 4-bromo-3-methylbenzoic acid (commercially available) (1.0 eq.) in EtOH (0.3 M) was added thionyl chloride (1.5 eq.) and heated to reflux for 2 hours. The solvent was concentrated en vaccuo, and the residue was diluted in ether and neutralized with saturated aqueous sodium bicarbonate solution. The two phases were separated, and the aqueous layer was extracted with ether. The combined organic layers were washed with brine, dried over anhydrous MgSO₄, and concentrated en vaccuo to give ethyl 4-bromo-3-methylbenzoate.

Step 2: ethyl 3-methyl-4-((triethylsilyl)ethynyl)benzoate

A solution of ethyl 4-bromo-3-methylbenzoate (from the previous step) (1.0 eq.), triethyl(ethynyl)silane (1.1 eq.), trans-dichlororbis(triphenylphosphine)palladium (II) (10 mol %), copper (I) iodide (20 mol %), and triethylamine (5.0 eq.) in DMF (0.3 M) was stirred at 60° C. overnight. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-5% ethyl acetate in hexane to give ethyl 3-methyl-4-((triethylsilyl)ethynyl)benzoate as a yellow oil.

Step 3: ethyl 4-ethynyl-3-methylbenzoate

To a solution of ethyl 3-methyl-4-((triethylsilyl)ethynyl)benzoate (from the previous step) (1.0 eq.) in THF (0.3 M) at 0° C. was added dropwise 1.0 M TBAF in THF (1.2 eq.). After stirring for 10 minutes at 0° C., the reaction was quenched with saturated aqueous sodium bicarbonate solution. The two phases were separated, and the aqueous layer was extracted with ether. The combined organic layers were washed with brine, dried over anhydrous MgSO$_4$, and concentrated en vaccuo. The crude material was purified by flash chromatography on a COMBIFLASH® system (ISCO) using 0-5% ethyl acetate in hexane to give ethyl 4-ethynyl-3-methylbenzoate as a white solid.

Step 4: ethyl 4-((5-chloro-6-cyanopyridin-3-yl)ethynyl)-3-methylbenzoate

A solution of 3,5-dichloropicolinonitrile (1.0 eq.), ethyl 4-ethynyl-3-methylbenzoate (from the previous step) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-10% ethyl acetate in hexane to give ethyl 4-((5-chloro-6-cyanopyridin-3-yl)ethynyl)-3-methylbenzoate as a white solid.

Step 5: ethyl 4-((5-amino-8-methylbenzo[f][1,7] naphthyridin-2-yl)ethynyl)-3-methylbenzoate A solution of ethyl 4-((5-chloro-6-cyanopyridin-3-yl)ethynyl)-3-methylbenzoate (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and potassium carbonate (3.0 eq.) in toluene/ethanol (9:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7] naphthyridin-2-yl)ethynyl)-3-methylbenzoate.

Step 6: ethyl 4-(2-(5-amino-8-methylbenzo[f][1,7] naphthyridin-2-yl)ethyl)-3-methylbenzoate A solution of ethyl 4-((5-amino-8-methylbenzo[f][1,7] naphthyridin-2-yl)ethynyl)-3-methylbenzoate (from the previous step) (1.0 eq.) in THF/ethyl acetate (1:1, 0.05M) was flushed with nitrogen and added 10% palladium on carbon (10 wt %). The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 30-100% EA in hexane to give ethyl 4-(2-(5-amino-8-methylbenzo[f][1,7]naphthyridin-2-yl)ethyl)-3-methylbenzoate. $^1$H NMR (Acetone-d$_6$): δ 8.79 (s, 1H), 8.71 (s, 1H), 8.24 (d, 1H), 7.80 (s, 1H), 7.73 (d, 1H), 7.40 (s, 1H), 7.31 (d, 1H), 7.12 (d, 1H), 6.5 (br, 2H), 4.29 (q, 2H), 3.19-3.22 (m, 4H), 2.44 (s, 3H), 2.39 (s, 3H), 1.31 (t, 3H). LRMS [M+H]=400.2

Example 75

4-(2-(5-amino-8-methylbenzo[f][1,7]naphthyridin-2-yl)ethyl)-3-methylbenzoic acid

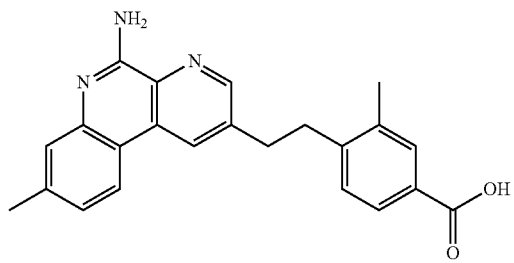 [SMILES: Cc1ccc2c(c1)nc(N)c1ncc(CCc3ccc(C(=O)O)cc3C)cc12]

To a solution of ethyl 4-(2-(5-amino-8-methylbenzo[f][1,7]naphthyridin-2-yl)ethyl)-3-methylbenzoate (from Example 74) (1.0 eq.) in EtOH was added 1N aqueous sodium hydroxide (1.5 eq.) and heated to 80° C. for 5 hours. The reaction mixture was neutralized by adding 1N aqueous HCl (1.5 eq.) and concentrated en vaccuo. The crude material was purified by RP-HPLC using a 10-50% MeCN in water gradient followed by concentration en vaccuo to give the TFA salt. $^1$H NMR (DMSO-d$_6$) of the TFA salt: δ 7.94-7.96 (m, 2H), 7.55 (d, 1H), 7.00 (s, 1H), 6.91 (d, 1H), 6.62-6.66 (m, 2H), 6.39 (d, 1H), 2.36-2.5 (m, 4H), 1.73 (s, 3H), 1.54 (s, 3H). LRMS [M+H]=372.2

Example 76

(4-(2-(5-amino-8-methylbenzo[f][1,7]naphthyridin-2-yl)ethyl)-3-methylphenyl)methanol

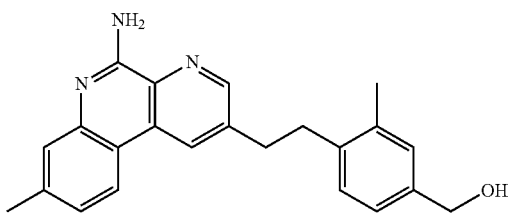 [SMILES: Cc1ccc2c(c1)nc(N)c1ncc(CCc3ccc(CO)cc3C)cc12]

To a solution of ethyl 4-(2-(5-amino-8-methylbenzo[f][1,7]naphthyridin-2-yl)ethyl)-3-methylbenzoate (from Example 74) (1.0 eq.) in THF (0.1M) at −78° C. was added 1.0 M DIBAL-H in toluene (10 eq.) and warmed to room temperature over 2 hours. 1.5 M Rochelle salt aqueous solution was added slowly to quench the reaction followed by addition of EA, and the mixture was stirred for 45 minutes. The two phases were separated, and the aqueous layer was extracted twice with EA. The combined organic layers were washed with brine, dried over anhydrous MgSO$_4$, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)-3-methylphenyl)methanol. $^1$H NMR (Acetone-d$_6$): δ 8.77 (s, 1H), 8.71 (s, 1H), 8.25 (d, 1H), 7.41 (s, 1H), 7.10-7.15 (m, 4H), 6.5 (br, 2H), 4.54 (s, 2H), 4.05 (br, 1H), 3.08-3.18 (m, 4H), 2.44 (s, 3H), 2.31 (s, 3H). LRMS [M+H]=358.2

Example 77

8-methyl-2-(2,4,6-trimethylphenethyl)benzo[f][1,7]naphthyridin-5-amine

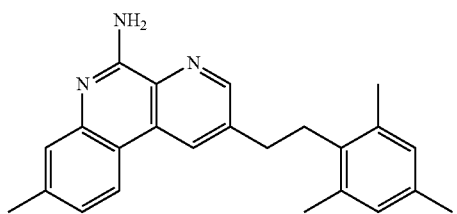

Step 1: 3-chloro-5-(mesitylethynyl)picolinonitrile

A solution of 3,5-dichloropicolinonitrile (1.0 eq.), 2-ethynyl-1,3,5-trimethylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-10% ethyl acetate in hexane to give 3-chloro-5-(mesitylethynyl)picolinonitrile a as white solid.

Step 2: 2-(mesitylethynyl)-8-methylbenzo[f][1,7]naphthyridin-5-amine

A solution of 3-chloro-5-(mesitylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and 2N aqueous sodium carbonate solution (3.0 eq.) in toluene/ethanol (4:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give 2-(mesitylethynyl)-8-methylbenzo[f][1,7]naphthyridin-5-amine.

Step 3: 8-methyl-2-(2,4,6-trimethylphenethyl)benzo[f][1,7]naphthyridin-5-amine A solution of 2-(mesitylethynyl)-8-methylbenzo[f][1,7]naphthyridin-5-amine (from the previous step) (1.0 eq.) in EtOH (0.05M) was flushed with nitrogen and added palladium on carbon (10 wt %). The reaction vessel was evacuated, flushed with hydrogen, and stirred overnight at rt. The reaction mixture was filtered through celite, washed with 2% MeOH in DCM, and concentrated en vaccuo. The crude material was purified by flash chromatography on a COMBIFLASH® system (ISCO) using 0-50% ethyl acetate in hexane to give 8-methyl-2-(2,4,6-trimethylphenethyl)benzo[f][1,7]naphthyridin-5-amine. $^1$H NMR (Acetone-d$_6$): δ 8.73-8.74 (m, 2H), 8.25 (d, 1H), 7.42 (s, 1H), 7.14 (d, 1H), 6.83 (s, 2H), 6.55 (br, 2H), 3.07 (m, 4H), 2.47 (s, 3H), 2.29 (s, 6H), 2.22 (s, 3H). LRMS [M+H]=356.2

Example 78

2-(4-(2-(5-amino-8-methylbenzo[f][1,7]naphthyridin-2-yl)ethyl)-3-methylphenyl)propan-2-ol

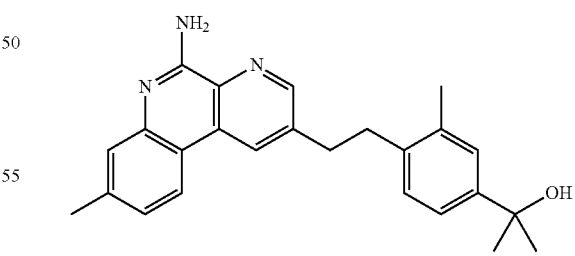

To a solution of ethyl 4-(2-(5-amino-8-methylbenzo[f][1,7]naphthyridin-2-yl)ethyl)-3-methylbenzoate (from Example 74) (1.0 eq.) in DCM at 0° C. was added 3.0 M methyl magnesium iodide (10 eq.) in ether and warmed to room temperature overnight. The reaction was cooled to 0° C. and quenched with water. After stirring for 15 min, the reaction mixture was neutralized with saturated aqueous sodium bicarbonate solution and added EA. The two phases were separated, and the aqueous layer was extracted three times with EA. The combined organic layers were washed with brine, dried over anhydrous MgSO$_4$, and concentrated en vaccuo. The crude material was purified by flash chromatography on a COMBIFLASH® system (ISCO) using 0-5% MeOH in DCM to give a 2-(4-(2-(5-amino-8-methyl-benzo[f][1,7]naphthyridin-2-yl)ethyl)-3-methylphenyl)propan-2-ol. $^1$H NMR (Acetone-d$_6$): δ 8.72-8.75 (m, 2H), 8.23 (d, 1H), 7.41 (s, 1H), 7.32 (s, 1H), 7.25 (d, 1H), 7.12-7.14 (m, 2H), 6.6 (br, 2H), 3.91 (s, 1H), 3.07-3.18 (m, 4H), 2.44 (s, 3H), 2.31 (s, 3H), 1.48 (s, 6H). LRMS [M+H]=386.2

Example 79

8-methyl-2-(4-propoxyphenethyl)benzo[f][1,7]naphthyridin-5-amine

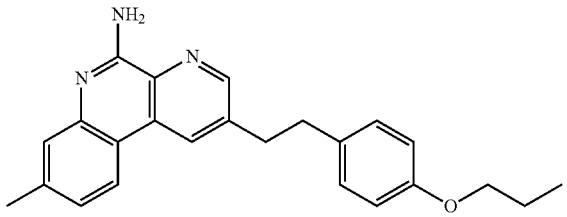 [SMILES: CCCOc1ccc(CCc2cnc3c(N)nc4cc(C)ccc4c3c2)cc1]

Step 1: 3-chloro-5-((4-propoxyphenyl)ethynyl)picolinonitrile

A solution of 3,5-dichloropicolinonitrile (1.0 eq.), 1-ethynyl-4-propoxybenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-10% ethyl acetate in hexane to give 3-chloro-5-((4-propoxyphenyl)ethynyl)picolinonitrile as a white solid.

Step 2: 3-chloro-5-(4-propoxyphenethyl)picolinonitrile

A solution of 3-chloro-5-((4-propoxyphenyl)ethynyl)picolinonitrile (from the previous step) (1.0 eq.) in EtOH (0.05M) was flushed with nitrogen and added platinum (VI) oxide (0.5 eq.). The reaction vessel was evacuated, flushed with hydrogen, and stirred for 5 hours at room temperature. The reaction mixture was filtered through celite, washed with 2% MeOH in DCM, and concentrated en vaccuo. The crude material was purified by flash chromatography on a COMBIFLASH® system (ISCO) using 0-15% ethyl acetate in hexane to give 3-chloro-5-(4-propoxyphenethyl)picolinonitrile.

Step 3: 8-methyl-2-(4-propoxyphenethyl)benzo[f][1,7]naphthyridin-5-amine

A solution of 3-chloro-5-(4-propoxyphenethyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and 2N aqueous sodium carbonate solution (3.0 eq.) in toluene (0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give 8-methyl-2-(4-propoxyphenethyl)benzo[f][1,7]naphthyridin-5-amine. $^1$H NMR (Acetone-d$_6$): δ 8.74 (s, 1H), 8.67 (s, 1H), 8.24 (d, 1H), 7.41 (s, 1H), 7.15-7.17 (m, 3H), 6.81 (d, 2H), 6.5 (br, 2H), 3.87 (t, 2H), 3.18 (t, 2H), 3.04 (t, 2H), 2.44 (s, 3H), 1.73 (m, 2H), 0.99 (t, 3H). LRMS [M+H]=372.2

Example 80

(E)-ethyl 3-(5-amino-2-(4-methoxy-2-methylphenethyl)benzo[f][1,7]naphthyridin-8-yl)acrylate

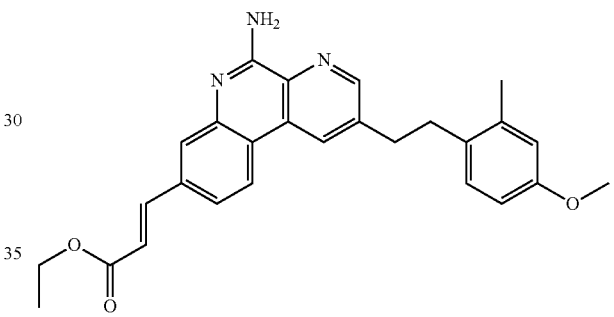

(E)-ethyl 3-(5-amino-2-(4-methoxy-2-methylphenethyl)benzo[f][1,7]naphthyridin-8-yl)acrylate was prepared from 5-amino-2-(4-methoxy-2-methylphenethyl)benzo[f][1,7]naphthyridine-8-carbaldehyde (from Example 69) and ethyl 2-(diethoxyphosphoryl)acetate (commercially available) following the procedures described for Example 65/Step 3. LRMS [M+H]=442.2

Example 81

(E)-3-(5-amino-2-(4-methoxy-2-methylphenethyl)benzo[f][1,7]naphthyridin-8-yl)acrylic acid

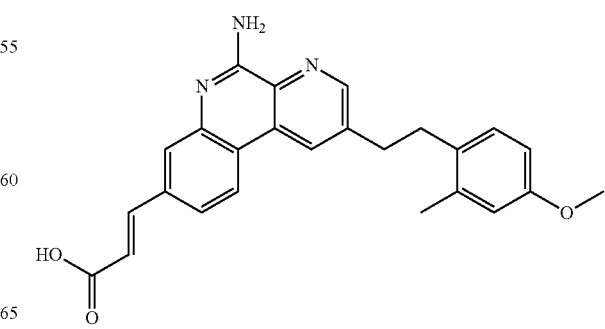

(E)-3-(5-amino-2-(4-methoxy-2-methylphenethyl)benzo[f][1,7]naphthyridin-8-yl)acrylic acid was prepared from (E)-ethyl 3-(5-amino-2-(4-methoxy-2-methylphenethyl)benzo[f][1,7]naphthyridin-8-yl)acrylate (from Example 80) following the procedures described for Example 68. ¹H NMR of TFA salt (DMSO-d₆): δ 12.66 (s, 1H), 9.09 (s, 1H), 8.88 (s, 1H), 8.66 (d, 1H), 7.95 (d, 1H), 7.91 (s, 1H), 7.75 (d, 1H), 7.10 (d, 1H), 6.77-6.71 (m, 2H), 6.68 (dd, 1H), 3.70 (s, 3H), 3.16 (t, 2H), 3.00 (t, 2H), 2.30 (s, 3H). LRMS [M+H]=414.2

Example 82 ethyl 3-(5-amino-2-(4-methoxy-2-methylphenethyl)benzo[f][1,7]naphthyridin-8-yl)propanoate

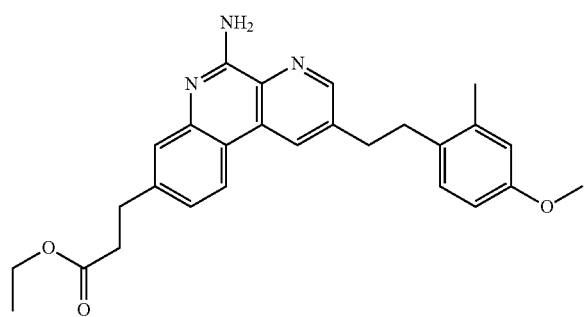 [SMILES: CCOC(=O)CCc1ccc2c(c1)nc(N)c1ncc(CCc3ccc(OC)cc3C)cc12]

Ethyl 3-(5-amino-2-(4-methoxy-2-methylphenethyl)benzo[f][1,7]naphthyridin-8-yl)propanoate was prepared from (E)-ethyl 3-(5-amino-2-(4-methoxy-2-methylphenethyl)benzo[f][1,7]naphthyridin-8-yl)acrylate (from Example 80) following the procedures described for Example 44/Step 5. ¹H NMR (CDCl₃): δ 8.63 (d, 1H), 8.37 (d, 1H), 8.13 (d, 1H), 7.56 (d, 1H), 7.24 (dd, 1H), 7.02 (d, 1H), 6.75 (d, 1H), 6.69 (dd, 1H), 6.15 (br s, 2H), 4.17 (q, 2H), 3.79 (s, 3H), 3.12 (dd, 4H), 2.99 (dd, 2H), 2.75 (t, 2H), 2.29 (s, 3H), 1.27 (t, 2H), 0.99 (t, 3H). LRMS [M+H]=444.2

Example 83

3-(5-amino-2-(4-methoxy-2-methylphenethyl)benzo[f][1,7]naphthyridin-8-yl)propanoic acid

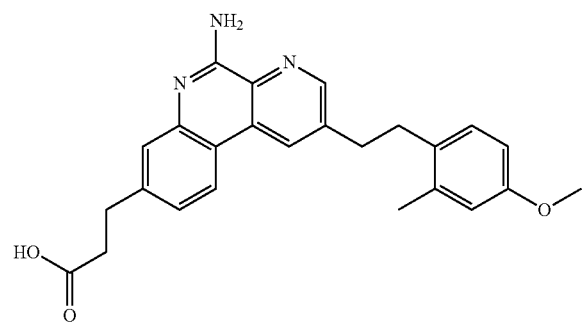 [SMILES: COc1ccc(CCc2cnc3c(N)nc4cc(CCC(=O)O)ccc4c3c2)c(C)c1]

3-(5-Amino-2-(4-methoxy-2-methylphenethyl)benzo[f][1,7]naphthyridin-8-yl)propanoic acid was prepared from ethyl 3-(5-amino-2-(4-methoxy-2-methylphenethyl)benzo[f][1,7]naphthyridin-8-yl)propanoate (from Example 82) following the procedures described for Example 68. ¹H NMR (DMSO-d₆): δ 12.18 (s, 1H), 8.84 (d, 1H), 8.70 (d, 1H), 8.36 (d, 1H), 7.39 (d, 1H), 7.20 (dd, 1H), 7.09 (m, 2H), 6.74 (d, 1H), 6.68 (dd, 1H), 3.70 (s, 3H), 3.09 (dd, 2H), 2.96 (dd, 4H), 2.63 (t, 2H), 2.27 (s, 3H). LRMS [M+H]=416.2

Example 84

3-(5-amino-2-(4-methoxy-2-methylphenethyl)benzo[f][1,7]naphthyridin-8-yl)propan-1-ol

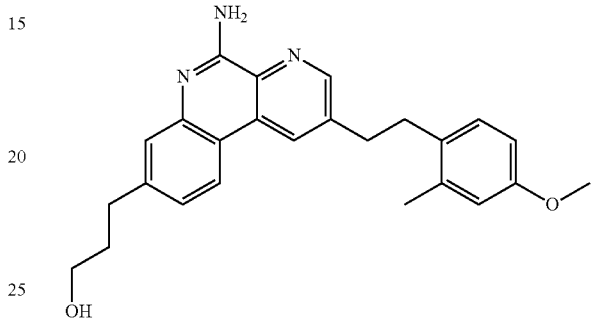

3-(5-Amino-2-(4-methoxy-2-methylphenethyl)benzo[f][1,7]naphthyridin-8-yl)propan-1-ol was prepared from ethyl 3-(5-amino-2-(4-methoxy-2-methylphenethyl)benzo[f][1,7]naphthyridin-8-yl)propanoate (from Example 82) following the procedures described for Example 42/Step 3. ¹H NMR (CDCl₃): δ 8.54 (d, 1H), 8.30 (d, 1H), 8.05 (d, 1H), 7.48 (d, 1H), 7.15 (dd, 1H), 6.93 (d, 1H), 6.66 (d, 1H), 6.61 (dd, 1H), 5.98 (br s, 2H), 3.71 (s, 3H), 3.66 (t, 2H), 3.03 (dd, 2H), 2.91 (dd, 2H), 2.81 (t, 2H), 2.20 (s, 3H), 1.98-1.90 (m, 2H). LRMS [M+H]=402.2

Example 85

(5-aminobenzo[f][1,7]naphthyridin-8-yl)methanol

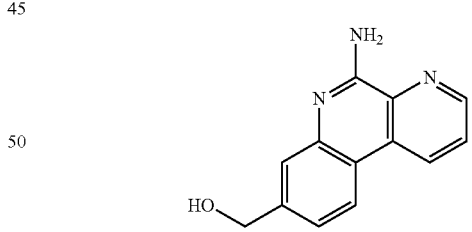

Step 1: 2-(tert-butoxycarbonylamino)-4-(methoxycarbonyl)phenylboronic acid

A solution of 2-amino-4-(methoxycarbonyl)phenylboronic acid hydrochloride (commercially available) (1.0 eq.), triethylamine (3.0 eq.), di-tert-butyl dicarbonate (1.1 eq.), and DMAP (0.1 eq.) in CH₃CN (0.3 M) was stirred at 40° C. overnight. After cooling to ambient temperature, the reaction mixture was concentrated en vaccuo to obtain a crude residue. The crude material was purified by flash chromatography on a COMBIFLASH® system (ISCO)

using 0-30% MeOH/DCM to give 2-(tert-butoxycarbonylamino)-4-(methoxycarbonyl)phenylboronic acid as a brown solid.

Step 2: methyl 5-aminobenzo[f][1,7]naphthyridine-8-carboxylate

A solution of 2-(tert-butoxycarbonylamino)-4-(methoxycarbonyl) phenylboronic acid (from the previous step) (1.0 eq.) and 3-bromopicolinonitrile (1.0 eq.), tetrakis(triphenylphosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was filtered to collect the precipitate. The precipitate was rinsed with EtOAc to give methyl 5-aminobenzo[f][1,7]naphthyridine-8-carboxylate as a pale brown solid.

Step 3: (5-aminobenzo[f][1,7]naphthyridin-8-yl)methanol

To a solution of methyl 5-aminobenzo[f][1,7]naphthyridine-8-carboxylate (from the previous step) (1.0 eq.) in EtOH (0.03M) was added NaBH$_4$ (10 eq.) at 25° C. The solution was heated to 80° C. for 5 hours. After cooling to ambient temperature, the reaction mixture was concentrated en vaccuo. The residue was portionized between saturated NaHCO$_3$ and EtOAc. The layers were separated and aqueous layer was extracted with EtOAc twice. The combined organic layer was washed with brine, dried over MgSO$_4$ and concentrated en vaccuo to obtain a crude residue. The crude material was purified by flash chromatography on a COMBIFLASH® system (ISCO) using 0-10% MeOH/DCM to give (5-aminobenzo[f][1,7]naphthyridin-8-yl)methanol as an off white solid: $^1$H NMR (methanol-d$_4$): δ 8.82 (dd, 1H), 8.77 (dd, 1H), 7.26 (d, 1H), 7.70 (dd, 1H), 7.50 (d, 1H), 7.27 (dd, 1H), 4.66 (s, 2H). LRMS [M+H]=226.1.

Example 86

5-aminobenzo[f][1,7]naphthyridin-8-ol

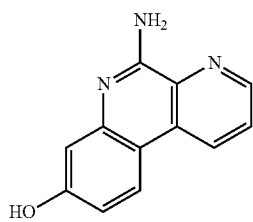 [SMILES: Nc1nc2cc(O)ccc2c2cccnc12]

To a solution of 8-methoxybenzo[f][1,7]naphthyridin-5-amine (from Example 10) (1.0 eq.) in DCM (0.04 M) was added BBr$_3$ (2.5 eq.) dropwise under N$_2$ at -20° C. The reaction was allowed to warm to ambient temperature over 30 minutes. The reaction was then stirred overnight. The reaction was quenched with saturated NaHCO$_3$ and extracted with EtOAc. The combined organic layer was washed with brine, dried over MgSO$_4$ and concentrated en vaccuo to obtain a crude residue. The crude material was purified by flash chromatography on a COMBIFLASH® system (ISCO) using 0-20% MeOH/DCM to give 5-aminobenzo[f][1,7]naphthyridin-8-ol as a yellow solid: $^1$H NMR (acetone-d$_6$): δ 8.90 (dd, 1H), 8.83 (dd, 1H), 8.32 (d, 1H), 7.83 (dd, 1H), 7.11 (br s, 2H), 7.10 (d, 1H), 6.96 (dd, 1H), 5.86 (br s, 1H). LRMS [M+H]=212.1.

Example 87

5-aminobenzo[f][1,7]naphthyridine-8-carbaldehyde

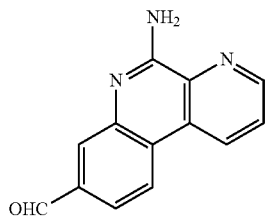 [SMILES: Nc1nc2cc(C=O)ccc2c2cccnc12]

A solution of (5-aminobenzo[f][1,7]naphthyridin-8-yl)methanol (from Example 85) (1.0 eq.) and activated MnO$_2$ (20 eq.) in DCM (0.1 M) was stirred at ambient temperature overnight. The reaction mixture was diluted with DCM. The MnO$_2$ was filtered off, and the filtrate was concentrated en vaccuo to obtain a crude residue. The crude material was purified by flash chromatography on a COMBIFLASH® system (ISCO) using 0-10% MeOH/DCM to give 5-aminobenzo[f][1,7]naphthyridine-8-carbaldehyde as a yellow solid: $^1$H NMR (acetone-d$_6$): δ 10.19 (s, 1H), 9.14 (dd, 1H), 9.01 (dd, 1H), 8.63 (d, 1H), 8.14 (d, 1H), 7.93 (dd, 1H), 7.81 (dd, 1H), 6.96 (br s, 2H). LRMS [M+H]=224.1

Example 88

1-(5-aminobenzo[f][1,7]naphthyridin-8-yl)ethanol

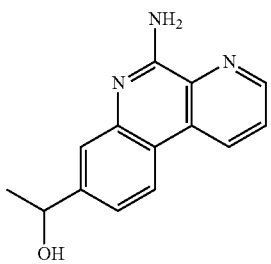 [SMILES: CC(O)c1ccc2c(c1)nc(N)c1ncccc12]

To a solution of 5-aminobenzo[f][1,7]naphthyridine-8-carbaldehyde (from Example 87) (1.0 eq.) in THF (0.02M) was added MeLi (2.5 eq.) at -78° C. The reaction was allowed to warm to ambient temperature overnight. The reaction was quenched by saturated NH$_4$Cl and extracted with EtOAc. The combined organic layer was washed with brine, dried over MgSO$_4$ and concentrated en vaccuo to obtain a crude residue. The crude material was purified by flash chromatography on a COMBIFLASH® system (ISCO) using 0-5% MeOH/DCM to give 1-(5-aminobenzo[f][1,7]naphthyridin-8-yl)ethanol as a yellow solid: $^1$H NMR (methanol-d$_4$): δ 8.94 (dd, 1H), 8.88 (dd, 1H), 8.38 (d, 1H), 7.81 (dd, 1H), 7.62 (d, 1H), 7.41 (dd, 1H), 4.97 (q, 1H), 1.53 (d, 3H). LRMS [M+H]=240.1.

Example 89

1-(5-aminobenzo[f][1,7]naphthyridin-8-yl)ethanone

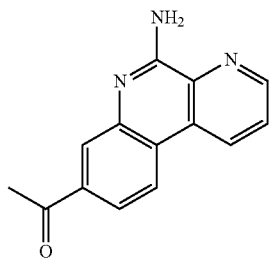 [SMILES: CC(=O)c1ccc2c(c1)nc(N)c1ncccc12]

A solution 1-(5-aminobenzo[f][1,7]naphthyridin-8-yl)ethanol (from Example 88) (1.0 eq.) and activated $MnO_2$ (20 eq.) in DCM (0.1 M) was stirred at ambient temperature overnight. The reaction mixture was diluted with DCM. The $MnO_2$ was filtered off, and the filtrate was concentrated en vaccuo to obtain a crude residue. The crude material was purified by flash chromatography on a COMBIFLASH® system (ISCO) using 0-5% MeOH/DCM to give 1-(5-aminobenzo[f][1,7]naphthyridin-8-yl)ethanone as a yellow solid: $^1$H NMR (acetone-$d_6$): δ 9.11 (dd, 1H), 8.99 (dd, 1H), 8.56 (d, 1H), 8.20 (d, 1H), 7.94-7.88 (m, 2H), 6.90 (br s, 2H), 2.70 (s, 3H). LRMS [M+H]=238.1.

Example 90

8-isopropylbenzo[f][1,7]naphthyridin-5-amine

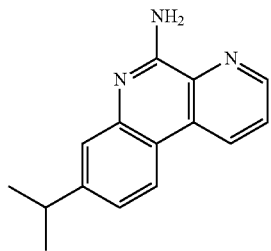 [SMILES: CC(C)c1ccc2c(c1)nc(N)c1ncccc12]

Step 1: 2-(5-aminobenzo[f][1,7]naphthyridin-8-yl)propan-2-ol

To a solution of methyl 5-aminobenzo[f][1,7]naphthyridine-8-carboxylate (from Example 85/Step 2) (1.0 eq.) in THF (0.02M) was added MeLi (10 eq.) at −78° C. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-10% MeOH/DCM to give 2-(5-aminobenzo[f][1,7]naphthyridin-8-yl)propan-2-ol as a yellow oil.

Step 2: 8-(prop-1-en-2-yl)benzo[f][1,7]naphthyridin-5-amine

A solution of 2-(5-aminobenzo[f][1,7]naphthyridin-8-yl)propan-2-ol (from the previous step) (1.0 eq.) and p-TsOH (2 eq.) in toluene (0.01 M) was stirred at 90° C. for 6 hours. The reaction was quenched by saturated $NaHCO_3$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-5% MeOH/DCM to give 8-(prop-1-en-2-yl)benzo[f][1,7]naphthyridin-5-amine as a yellow solid.

Step 3: 8-isopropylbenzo[f][1,7]naphthyridin-5-amine

A mixture of 8-(prop-1-en-2-yl)benzo[f][1,7]naphthyridin-5-amine (from the previous step) (1.0 eq) and Pd/C (wet, 10% wt) in EtOH was stirred under $H_2$ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-isopropylbenzo[f][1,7]naphthyridin-5-amine as a yellow solid: $^1$H NMR (acetone-$d_6$): δ 8.98 (dd, 1H), 8.88 (dd, 1H), 8.37 (d, 1H), 7.83 (dd, 1H), 7.49 (d, 1H), 7.27 (dd, 1H), 6.66 (br s, 2H), 3.10-3.00 (m, 1H), 1.33 (d, 6H). LRMS [M+H]=238.1.

Example 91

8-vinylbenzo[f][1,7]naphthyridin-5-amine

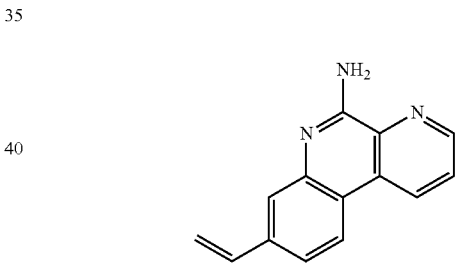

To a solution of methyl triphenyl phosphonium iodide (6.0 eq.) was added nBuLi (7.0 eq.) at −78° C. The reaction mixture was allowed to warm to 0° C. and stirred for 30 minutes (deep orange color). The reaction was again cooled down to −78° C. and 5-aminobenzo[f][1,7]naphthyridine-8-carbaldehyde (from Example 87) (1.0 eq.) in THF was introduced dropwise to the reaction. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-50% EtOAc/Hexanes to give 8-vinylbenzo[f][1,7]naphthyridin-5-amine as a white solid: $^1$H NMR (acetone-$d_6$): $^1$H NMR (acetone-$d_6$): δ 9.00 (dd, 1H), 8.90 (dd, 1H), 8.41 (d, 1H), 7.84 (dd, 1H), 7.65 (d, 1H), 7.52 (dd, 1H), 6.91 (dd, 1H), 6.77 (br s, 2H), 5.97 (dd, 1H), 5.34 (dd, 1H). LRMS [M+H]=222.1.

Example 92

8-ethylbenzo[f][1,7]naphthyridin-5-amine

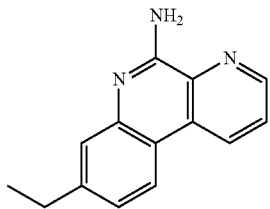 [SMILES: CCc1ccc2c(c1)nc(N)c1ncccc12]

A mixture of 8-vinylbenzo[f][1,7]naphthyridin-5-amine (1.0 eq) (from Example 91) and Pd/C (wet, 10% wt) in EtOH was stirred under $H_2$ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-ethylbenzo[f][1,7]naphthyridin-5-amine as a white foam: $^1$H NMR (acetone-$d_6$): δ 8.98 (dd, 1H), 8.88 (dd, 1H), 8.35 (d, 1H), 7.82 (dd, 1H), 7.46 (d, 1H), 7.22 (dd, 1H), 6.63 (br s, 2H), 2.78 (q, 2H), 1.30 (t, 3H). LRMS [M+H]=224.1.

Example 93

8-(methoxymethyl)benzo[f][1,7]naphthyridin-5-amine

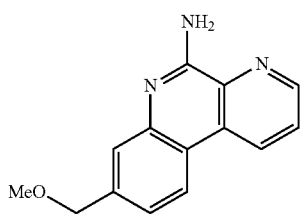

Step 1: tert-butyl 2-chloro-5-(methoxymethyl)phenylcarbamate

To a solution of 2-chloro-5-(methoxymethyl)aniline (commercially available) (1.0 eq.) in THF (0.2M) at 0° C. under $N_2$ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous $MgSO_4$, and concentrated en vaccuo. The crude material was purified by flash chromatography on a COMBIFLASH® system (ISCO) using 0-30% EtOAc/Hexanes to give tert-butyl 2-chloro-5-(methoxymethyl)phenylcarbamate as a colorless oil.

Step 2: tert-butyl 5-(methoxymethyl)-2-(4,4,5,5-tetramethyl-1,3,2-dioxaborolan-2-yl)phenylcarbamate Tert-butyl 2-chloro-5-(methoxymethyl)phenylcarbamate (from the previous step) (1.0 eq.), 4,4,4',4',5,5,5',5'-octamethyl-2,2'-bi(1,3,2-dioxaborolane) (3.0 eq.), $Pd_2dba_3$ (2.5%), XPhos (10%), and KOAc (3 eq.) were mixed in dioxane (0.2 M) under $N_2$ atmosphere. The reaction was heated to 110° C. and stirred overnight. The resulting suspension was cooled to ambient temperature, diluted with ether, filtered through celite, and the filtrate was concentrated en vaccuo. The combined organic layers were washed with brine, dried over anhydrous $MgSO_4$, and concentrated en vaccuo. The crude material was purified by flash chromatography on a COMBIFLASH® system (ISCO) using 0-20% EtOAc/Hexanes to give tert-butyl 5-(methoxymethyl)-2-(4,4,5,5-tetramethyl-1,3,2-dioxaborolan-2-yl)phenylcarbamate as a white foam.

Step 3: 8-(methoxymethyl)benzo[f][1,7]naphthyridin-5-amine

A solution of tert-butyl 5-(methoxymethyl)-2-(4,4,5,5-tetramethyl-1,3,2-dioxaborolan-2-yl)phenylcarbamate (from the previous step) (1.0 eq.) and 3-bromopicolinonitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction mixture was diluted with 2% MeOH in DCM and water. The two phases were separated, and the aqueous layer was extracted twice with 2% MeOH in DCM. The combined organic layers were washed with brine, dried over anhydrous $MgSO_4$, and concentrated en vaccuo. The crude material was purified by flash chromatography on a COMBIFLASH® system (ISCO) using 0-100% EtOAc/Hexanes to give 8-(methoxymethyl)benzo[f][1,7]naphthyridin-5-amine as a white solid: $^1$H NMR (methanol-$d_4$): δ 8.97 (dd, 1H), 8.91 (dd, 1H), 8.41 (dd, 1H), 7.83 (dd, 1H), 7.59 (d, 1H), 7.37 (dd, 1H), 4.62 (s, 2H), 3.45 (s, 3H). LRMS [M+H]=240.1.

Example 94

(5-amino-2-phenethylbenzo[f][1,7]naphthyridin-8-yl)methanol

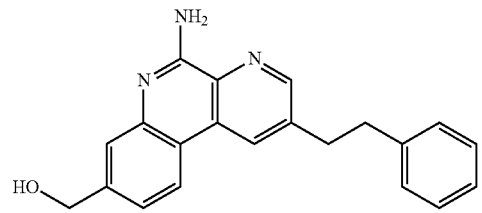 [SMILES: Nc1nc2cc(CO)ccc2c2cc(CCc3ccccc3)cnc12]

Step 1: methyl 5-amino-2-phenethylbenzo[f][1,7]naphthyridin-8-carboxylate

A solution of 2-(tert-butoxycarbonylamino)-4-(methoxycarbonyl) phenylboronic acid (from Example 85/Step 1) (1.0 eq.) and 2-chloro-6-phenethylnicotinonitrile (prepared from (E)-3-chloro-5-styrylpicolinonitrile (from Example 32/Step 1) following the procedure described in Example 114/Step 3) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-60% EtOAc/Hexanes to give methyl 5-amino-2-phenethylbenzo[f][1,7]naphthyridine-8-carboxylate as a white solid.

Step 2: (5-amino-2 phenethylbenzo[f][1,7]naphthyridin-8-yl)methanol

To a solution of methyl 5-amino-2-phenethylbenzo[f][1,7]naphthyridine-8-carboxylate (from the previous step) (1.0 eq.) in THF (0.03M) was added Super-H (10 eq.) at 0° C. The solution was allowed to warm to ambient temperature over 30 min. The reaction was quenched by water until no bubbling. The layers were separated and aqueous layer was extracted with EtOAc. The combined organic layer was washed with brine, dried over MgSO$_4$ and concentrated en vaccuo to obtain a crude residue. The crude material was purified by flash chromatography on a COMBIFLASH® system (ISCO) using 0-10% MeOH/DCM to give (5-amino-2-phenethylbenzo[f][1,7]naphthyridin-8-yl)methanol as an off white solid: $^1$H NMR (methanol-d$_4$): δ 8.63 (dd, 1H), 8.56 (dd, 1H), 8.24 (d, 1H), 7.57 (d, 1H), 7.35 (dd, 1H), 7.27-7.15 (m, 5H), 4.75 (s, 2H), 3.20 (t, 2H), 3.06 (t, 2H). LRMS [M+H]=330.1.

Example 95

(5-amino-2-(4-methoxyphenethyl)benzo[f][1,7]naphthyridin-8-yl)methanol

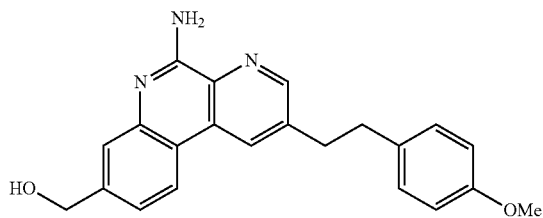 [SMILES: COc1ccc(CCc2cnc3c(N)nc4cc(CO)ccc4c3c2)cc1]

Step 1: methyl 5-amino-2-(4-methoxyphenethyl)benzo[f][1,7]naphthyridin-8-carboxylate A solution of 2-(tert-butoxycarbonylamino)-4-(methoxycarbonyl) phenylboronic acid (from Example 85/Step 1) (1.0 eq.) and 2-chloro-6-(4-methoxyphenethyl)nicotinonitrile (prepared from reaction of 3,5-dichloropicolinonitrile with 1-ethynyl-4-methoxybenzene following the procedure described in Example 44/Step 3 and reduction of the product following the procedure described in Example 114/Step 3) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-80% EtOAc/Hexanes to give methyl 5-amino-2-(4-methoxyphenethyl)benzo[f][1,7]naphthyridine-8-carboxylate as a white solid.

Step 2: (5-amino-2-(4-methoxyphenethyl)benzo[f][1,7]naphthyridin-8-yl)methanol

To a solution of methyl 5-amino-2-(4-methoxyphenethyl)benzo[f][1,7]naphthyridine-8-carboxylate (from the previous step) (1.0 eq.) in THF (0.03M) was added Super-H (10 eq.) at 0° C. The solution was allowed to warm to ambient temperature over 30 minutes. The reaction was quenched by water until no bubbling. The layers were separated and aqueous layer was extracted with EtOAc. The combined organic layer was washed with brine, dried over MgSO$_4$ and concentrated en vaccuo to obtain a crude residue. The crude material was purified by flash chromatography on a COMBIFLASH® system (ISCO) using 0-100% EtOAc/Hexanes to give (5-amino-2-(4-methoxyphenethyl)benzo[f][1,7]naphthyridin-8-yl)methanol as an off white solid (31%): $^1$H NMR (acetone-d$_6$): δ 8.79 (d, 1H), 8.70 (d, 1H), 8.35 (d, 1H), 7.61 (d, 1H), 7.33 (dd, 1H), 7.13 (d, 2H), 6.83 (d, 2H), 6.62 (br s, 2H), 4.47 (s, 2H), 4.40 (br s, 1H), 3.75 (s, 3H), 3.22 (t, 2H), 3.06 (t, 2H). LRMS [M+H]=360.2.

Example 96 benzo[f][1,7]naphthyridine-5,8-diamine

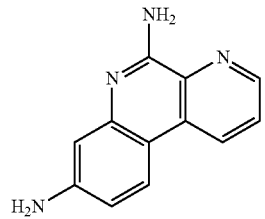 [SMILES: Nc1ccc2c(c1)nc(N)c1ncccc12]

Step 1: tert-butyl 2-bromo-5-nitrophenylcarbamate

To a solution of 2-bromo-5-nitroaniline (commercially available) (1.0 eq.) in THF (0.2M) at 0° C. under N$_2$ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-30% EtOAc/Hexanes to give tert-butyl 2-bromo-5-nitrophenylcarbamate as a colorless oil.

Step 2: tert-butyl 5-nitro-2-(4,4,5,5-tetramethyl-1,3,2-dioxaborolan-2-yl)phenyl carbamate Tert-butyl 2-bromo-5-nitrophenylcarbamate (from the previous step) (1.0 eq.), 4,4,4',4',5,5,5',5'-octamethyl-2,2'-bi(1,3,2-dioxaborolane) (1.8 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vaccuo. The residue was purified by flash chromatography on a COMBIFLASH® system (ISCO) using 0-30% EtOAc/Hexanes to give tert-butyl 5-nitro-2-(4,4,5,5-tetramethyl-1,3,2-dioxaborolan-2-yl)phenyl carbamate as a white foam.

Step 3: 8-nitrobenzo[f][1,7]naphthyridin-5-amine

A solution of tert-butyl 5-nitro-2-(4,4,5,5-tetramethyl-1,3,2-dioxaborolan-2-yl)phenylcarbamate (from the previous step) (1.0 eq.) and 3-bromopicolinonitrile (1.0 eq.) in toluene (0.44 M) was mixed with tetrakis(triphenyl-phosphine) palladium (5 mol %) and 2N aqueous potassium carbonate solution (2.0 eq.). The reaction was heated to 100° C. and stirred overnight. After cooling to ambient temperature, the reaction mixture was filtered to collect the precipitate. The precipitate was rinsed with EtOAc to give 8-nitrobenzo[f][1,7]naphthyridin-5-amine as a yellow solid.

Step 4: benzo[f][1,7]naphthyridin-5,8-diamine

A mixture of 8-nitrobenzo[f][1,7]naphthyridin-5-amine (from the previous step) (1.0 eq) and Pd/C (wet, 10% wt) in EtOH was stirred under $H_2$ balloon overnight. The reaction mixture was diluted with DCM. The insoluble solid was filtered off through celite, and the filtrate was concentrated en vaccuo to obtain a crude residue. The crude material was washed with acetone to give benzo[f][1,7]naphthyridine-5,8-diamine as an off white solid: $^1$H NMR (methanol-$d_4$): δ 8.73 (dd, 1H), 8.71 (dd, 1H), 8.11 (d, 1H), 7.69 (dd, 1H), 6.86 (d, 1H), 6.82 (dd, 1H). LRMS [M+H]=211.1.

Example 97

8-(aminomethyl)benzo[f][1,7]naphthyridin-5-amine

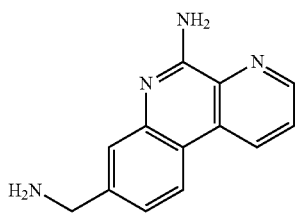 [SMILES: NCc1ccc2c(c1)nc(N)c1ncccc12]

Step 1:
2-(tert-butoxycarbonylamino)-4-cyanophenylboronic acid

The titled compound was prepared according to the procedure described in Example 85/Step 1, but using 2-amino-4-cyanophenylboronic acid hydrochloride (commercially available) as the starting material. The crude material was purified by flash chromatography on a COMBIFLASH® system (ISCO) using 0-30% MeOH/DCM to give 2-(tert-butoxycarbonylamino)-4-cyanophenylboronic acid as an off white solid.

Step 2: 5-aminobenzo[f][1,7]naphthyridine-8-carbonitrile

The titled compound was prepared according to the procedure described in Example 96/Step 3, but using 2-(tert-butoxycarbonylamino)-4-cyanophenylboronic acid (from the previous step) as the starting material. The crude material was rinsed with 1:1 EtOAc/Hexanes to give 5-aminobenzo[f][1,7]naphthyridine-8-carbonitrile as a pale yellow solid.

Step 4: benzo[f][1,7]naphthyridin-5,8-diamine

A mixture of 8-nitrobenzo[f][1,7]naphthyridin-5-amine (from the previous step) (1.0 eq) and Raney Nickel (wet, 10% wt) in EtOH/ammonia (2:1) was stirred under $H_2$ balloon overnight. The reaction mixture was diluted with DCM. The insoluble solid was filtered off through celite, and the filtrate was concentrated en vaccuo to obtain a crude residue. The crude material was washed with 10% MeOH/DCM and 70% EtOAc/Hexanes to give benzo[f][1,7]naphthyridine-5,8-diamine as an off white solid: $^1$H NMR (methanol-$d_4$): δ 8.97 (dd, 1H), 8.90 (dd, 1H), 8.41 (d, 1H), 7.83 (dd, 1H), 7.57 (d, 1H), 7.39 (dd, 1H), 3.96 (s, 2). LRMS [M+H]=229.1.

Example 98

3-fluoro-8-methylbenzo[f][1,7]naphthyridin-5-amine

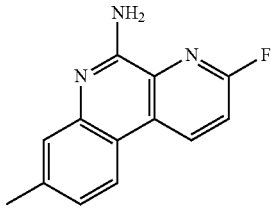 [SMILES: Cc1ccc2c(c1)nc(N)c1nc(F)ccc12]

A solution of tert-butyl 5-methyl-2-(4,4,5,5-tetramethyl-1,3,2-dioxaborolan-2-yl)phenylcarbamate (from Example 5/Step 2) (1.0 eq.) and 3-bromo-6-chloropicolinonitrile (from Example 20/Step 2) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous $MgSO_4$, and concentrated en vaccuo. The crude material was purified by flash chromatography on a COMBIFLASH® system (ISCO) using 0-40% EtOAc/Hexanes to give 3-chloro-8-methylbenzo[f][1,7]naphthyridin-5-amine as a pale yellow solid.

Step 2: 3-fluoro-8-methylbenzo[f][1,7]naphthyridin-5-amine

A mixture of 3-chloro-8-methylbenzo[f][1,7]naphthyridin-5-amine (from the previous step) (1.0 eq.) potassium fluoride (4.0 eq.), and 18-crown-6 (0.4 eq.) in NMP (0.1M) was heated in microwave reactor at 210° C. for 2 hours. After cooling to ambient temperature, the reaction residue was purified by flash chromatography on a COMBI- FLASH® system (ISCO) using 0-30% EtOAc/Hexanes to give 3-fluoro-8-methylbenzo[f][1,7]naphthyridin-5-amine as a white solid. ¹H NMR (acetone-d₆): δ 9.20 (dd, 1H), 8.32 (d, 1H), 7.58 (dd, 1H), 7.46 (d, 1H), 7.21 (dd, 1H), 6.51 (br s, 2H), 2.47 (s, 3H). LRMS [M+H]=228.1.

Example 99

(5-amino-3-fluorobenzo[f][1,7]naphthyridin-8-yl)methanol

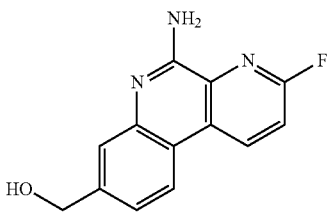 [SMILES: Nc1nc2cc(CO)ccc2c2ccc(F)nc12]

Step 1: tert-butyl 5-((tert-butyldimethylsilyloxy)methyl)-2-(4,4,5,5-tetramethyl-1,3,2-dioxaborolan-2-yl)phenylcarbamate The titled compound was prepared according to the procedure described in Example 93/Step 1 and 2, but using 5-((tert-butyldimethylsilyloxy)methyl)-2-chloroaniline (commercially available) as the starting material. The crude material was purified by flash chromatography on a COMBIFLASH® system (ISCO) using 0-20% EtOAc/Hexanes to give tert-butyl 5-((tert-butyldimethylsilyloxy)methyl)-2-(4,4,5,5-tetramethyl-1,3,2-dioxaborolan-2-yl)phenylcarbamate as a white foam.

Step 2: 8-((tert-butyldimethylsilyloxy)methyl)-3-chlorobenzo[f][1,7]naphthyridin-5-amine The titled compound was prepared according to the procedure described in Example 98/Step 1, but using tert-butyl 5-((tert-butyldimethylsilyloxy)methyl)-2-(4,4,5,5-tetramethyl-1,3,2-dioxaborolan-2-yl)phenylcarbamate (from the previous step) as the starting material. The crude material was purified by flash chromatography on a COMBIFLASH® system (ISCO) using 0-15% EtOAc/Hexanes to give 8-((tert-butyldimethylsilyloxy)methyl)-3-chlorobenzo[f][1,7]naphthyridin-5-amine as a pale yellow solid.

Step 3: (5-amino-3-chlorobenzo[f][1,7]naphthyridin-8-yl)methanol

A solution of 8-((tert-butyldimethylsilyloxy)methyl)-3-chlorobenzo[f][1,7]naphthyridin-5-amine (from the previous step) (1.0 eq.) and TBAF (1.1 eq.) in THF was stirred at ambient temperature overnight. The reaction was quenched with saturated NaHCO₃. The two phases were separated, and the aqueous layer was extracted twice with Et₂O. The combined organic layers were washed with brine, dried over anhydrous MgSO₄, and concentrated en vaccuo. The crude material was purified by flash chromatography on a COMBIFLASH® system (ISCO) using 0-5% MeOH/DCM to give (5-amino-3-chlorobenzo[f][1,7]naphthyridin-8-yl)methanol as a white solid.

Step 4: (5-amino-3-fluorobenzo[f][1,7]naphthyridin-8-yl)methanol

The titled compound was prepared according to the procedure described in Example 98/Step 2, but using (5-amino-3-chlorobenzo[f][1,7]naphthyridin-8-yl)methanol (from the previous step) as the starting material. The crude material was purified by flash chromatography on a COMBIFLASH® system (ISCO) using 0-40% EtOAc/Hexanes to give (5-amino-3-fluorobenzo[f][1,7]naphthyridin-8-yl)methanol as a white solid. ¹H NMR (methanol-d₄): δ 9.15 (dd, 1H), 8.38 (d, 1H), 7.64 (d, 1H), 7.55 (dd, 1H), 7.41 (dd, 1H), 4.77 (s, 2H). LRMS [M+H]=244.1.

Example 100

3-chlorobenzo[f][1,7]naphthyridine-5,8-diamine

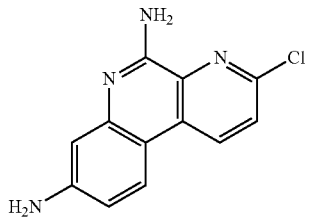 [SMILES: Nc1ccc2c(c1)nc(N)c1nc(Cl)ccc12]

Step 1: 3-chloro-8-nitrobenzo[f][1,7]naphthyridin-5-amine

The titled compound was prepared according to the procedure described in Example 98/Step 1, but using tert-butyl 5-nitro-2-(4,4,5,5-tetramethyl-1,3,2-dioxaborolan-2-yl)phenylcarbamate (commercially available) as the starting material. The crude material was purified by flash chromatography on a COMBIFLASH® system (ISCO) using 0-40% EtOAc/Hexanes to give 3-chloro-8-nitrobenzo[f][1,7]naphthyridin-5-amine as a pale yellow solid.

Step 2: 3-chlorobenzo[f][1,7]naphthyridine-5,8-diamine

A mixture of 8-nitrobenzo[f][1,7]naphthyridin-5-amine (from the previous step) (1.0 eq) and Raney Nickel (wet, 10% wt) in EtOH was stirred under H₂ balloon overnight. The reaction mixture was diluted with DCM. The insoluble solid was filtered off through celite, and the filtrate was concentrated en vaccuo to obtain a crude residue. The crude material was purified by flash chromatography on a COMBIFLASH® system (ISCO) using 0-100% EtOAc/Hexanes to give 3-chlorobenzo[f][1,7]naphthyridine-5,8-diamine as a white solid. ¹H NMR (methanol-d₄): δ 8.75 (d, 1H), 8.08 (dd, 1H), 7.70 (d, 1H), 6.84-6.81 (m, 2H). LRMS [M+H]=245.1.

Example 101

3-fluorobenzo[f][1,7]naphthyridine-5,8-diamine

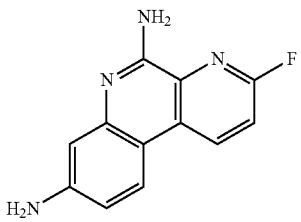 [SMILES: Nc1ccc2c(c1)nc(N)c1nc(F)ccc12]

The titled compound was prepared according to the procedure described in Example 98/Step 2, but using 3-chlorobenzo[f][1,7]naphthyridine-5,8-diamine (from Example 100) as the starting material. The crude material was purified by flash chromatography on a COMBIFLASH® system (ISCO) using 0-7% MeOH/DCM to give 3-fluorobenzo[f][1,7]naphthyridine-5,8-diamine as a white solid. $^1$H NMR (methanol-$d_4$): δ 8.93 (dd, 1H), 8.09 (d, 1H), 7.44 (dd, 1H), 6.86-6.83 (m, 2H). LRMS [M+H]=229.1.

Example 102

8-isobutylbenzo[f][1,7]naphthyridin-5-amine

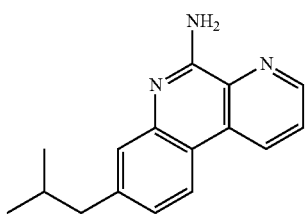 [SMILES: CC(C)Cc1ccc2c(c1)nc(N)c1ncccc12]

8-Isobutylbenzo[f][1,7]naphthyridin-5-amine was prepared from 5-aminobenzo[f][1,7]naphthyridine-8-carbaldehyde (from Example 87) with isopropyl(triphenyl)phosphonium bromide following the procedures described for Example 91 (wittig reaction) and Example 92 (reduction). $^1$H NMR (acetone-$d_6$): δ 8.98 (dd, 1H), 8.88 (dd, 1H), 8.35 (d, 1H), 7.82 (dd, 1H), 7.44 (d, 1H), 7.18 (dd, 1H), 6.73 (br s, 2H), 2.63 (d, 2H), 2.04-1.94 (m, 1H), 0.94 (d, 6H). LRMS [M+H]=252.1.

Example 103

(E)-8-(prop-1-enyl)benzo[f][1,7]naphthyridin-5-amine

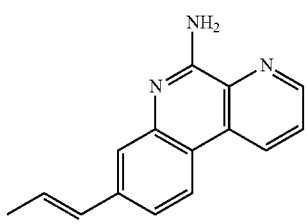 [SMILES: C/C=C/c1ccc2c(c1)nc(N)c1ncccc12]

(E)-8-(prop-1-enyl)benzo[f][1,7]naphthyridin-5-amine was prepared from 5-aminobenzo[f][1,7]naphthyridine-8-carbaldehyde (from Example 87) with ethyl(triphenyl)phosphonium bromide following the procedures described for Example 91. $^1$H NMR (acetone-$d_6$): δ 8.98 (dd, 1H), 8.88 (dd, 1H), 8.36 (d, 1H), 7.83 (dd, 1H), 7.54 (d, 1H), 7.43 (dd, 1H), 6.67 (br s, 2H), 6.60-6.42 (m, 2H), 1.92 (dd, 3H). LRMS [M+H]=236.1.

Example 104

8-propylbenzo[f][1,7]naphthyridin-5-amine

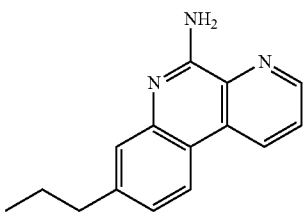 [SMILES: CCCc1ccc2c(c1)nc(N)c1ncccc12]

8-Propylbenzo[f][1,7]naphthyridin-5-amine was prepared from (E)-8-(prop-1-enyl)benzo[f][1,7]naphthyridin-5-amine (from Example 103) following the procedures described for Example 92. $^1$H NMR (acetone-$d_6$): δ 8.99 (dd, 1H), 8.88 (dd, 1H), 8.35 (d, 1H), 7.83 (dd, 1H), 7.45 (d, 1H), 7.21 (dd, 1H), 6.64 (br s, 2H), 2.74 (t, 2H), 1.74 (qt, 2H), 0.98 (t, 3H). LRMS [M+H]=238.1.

Example 105

8-(2-cyclopropylethyl)benzo[f][1,7]naphthyridin-5-amine

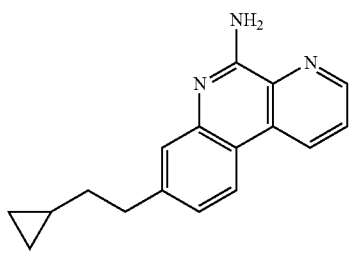 [SMILES: Nc1nc2cc(CCC3CC3)ccc2c2cccnc12]

8-(2-Cyclopropylethyl)benzo[f][1,7]naphthyridin-5-amine was prepared from 5-aminobenzo[f][1,7]naphthyridine-8-carbaldehyde (from Example 87) with (cyclopropylmethyl)triphenylphosphonium bromide following the procedures described for Example 91 (wittig reaction) and Example 92 (reduction). $^1$H NMR (acetone-$d_6$): δ 8.99 (dd, 1H), 8.88 (dd, 1H), 8.35 (d, 1H), 7.83 (dd, 1H), 7.47 (d, 1H), 7.23 (dd, 1H), 6.64 (br s, 2H), 1.60 (q, 2H), 1.34-1.25 (m, 1H), 0.91-0.72 (m, 2H), 0.45-0.41 (m, 2H), 0.11-0.07 (m, 2H). LRMS [M+H]=264.1.

Example 106

8-phenethylbenzo[f][1,7]naphthyridin-5-amine

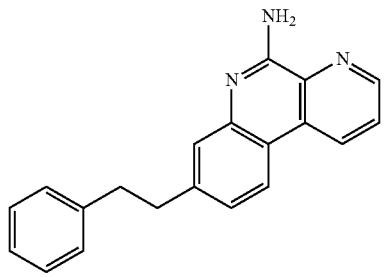 [SMILES: Nc1nc2cc(CCc3ccccc3)ccc2c2cccnc12]

8-Phenethylbenzo[f][1,7]naphthyridin-5-amine was prepared from 5-aminobenzo[f][1,7]naphthyridine-8-carbaldehyde (from Example 87) with benzyltriphenylphosphonium bromide following the procedures described for Example 91 (wittig reaction) and Example 92 (reduction). $^1$H NMR (acetone-$d_6$): δ 8.99 (dd, 1H), 8.88 (dd, 1H), 8.35 (d, 1H), 7.83 (dd, 1H), 7.49 (d, 1H), 7.29-7.15 (dd, 6H), 6.70 (br s, 2H), 3.10-3.00 (m, 4H). LRMS [M+H]=300.1.

Example 107

(5-amino-2-(4-bromophenethyl)benzo[f][1,7]naphthyridin-8-yl)methanol

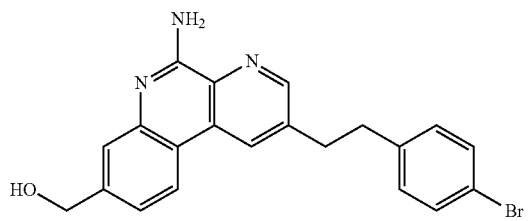 [SMILES: Nc1nc2cc(CO)ccc2c2cc(CCc3ccc(Br)cc3)cnc12]

(5-Amino-2-(4-bromophenethyl)benzo[f][1,7]naphthyridin-8-yl)methanol was prepared from (5-amino-2-(4-methoxyphenethyl)benzo[f][1,7]naphthyridin-8-yl)methanol (from Example 95) following the procedures described for Example 86. $^1$H NMR (acetone-$d_6$): δ 8.81 (d, 1H), 8.72 (d, 1H), 8.40 (d, 1H), 7.68 (d, 1H), 7.39 (dd, 1H), 7.08 (d, 2H), 6.74 (d, 2H), 6.66 (br s, 2H), 4.49 (s, 2H), 3.21 (t, 2H), 3.03 (t, 2H). LRMS [M+H]=408.1.

Example 108

(5-amino-2-(4-methoxy-2-methylphenethyl)benzo[f][1,7]naphthyridin-8-yl)methanol

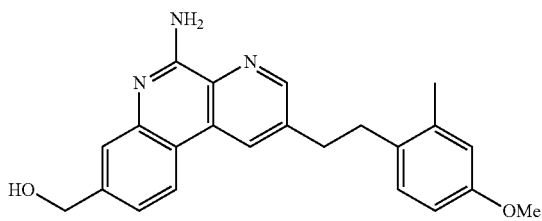 [SMILES: COc1ccc(CCc2cnc3c(N)nc4cc(CO)ccc4c3c2)c(C)c1]

(5-Amino-2-(4-methoxy-2-methylphenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (Example 99/Step 1) and 3-chloro-5-((4-methoxy-2-methylphenyl)ethynyl)picolinonitrile (from Example 49/Step 1) following the procedures described for Example 44/Step 4 and deprotection of TBS group following the procedure describes from Example 99/Step 3. $^1$H NMR (acetone-$d_6$): δ 8.79 (s, 1H), 8.73 (s, 1H), 8.35 (d, 1H), 7.61 (s, 1H), 7.33 (d, 1H), 7.09 (d, 1H), 6.75 (d, 1H), 6.68 (dd, 1H), 6.57 (br s, 2H), 4.47 (d, 2H), 4.32 (t, 1H), 3.58 (s, 3H), 3.17 (t, 2H), 3.04 (t, 2H), 2.30 (s, 3H). LRMS [M+H]=374.2.

Example 109

2-(4-methoxy-2-methylphenethyl)-8-pentylbenzo[f][1,7]naphthyridin-5-amine

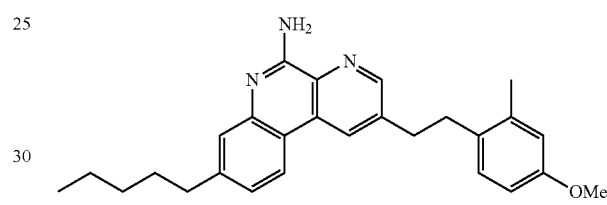

and

Example 110

8-(2-cyclopropylethyl)-2-(4-methoxy-2-methylphenethyl)benzo[f][1,7]naphthyridin-5-amine

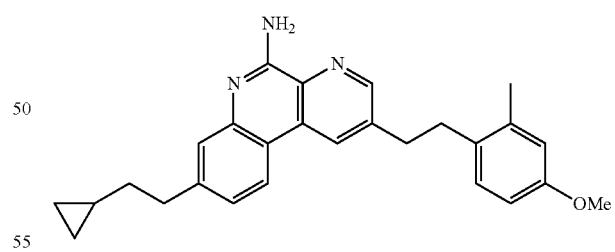

Step 1: tert-butyl 5-bromo-2-chlorophenylcarbamate

The titled compound was prepared according to the procedure described in Example 5/Step 1, but using 5-bromo-2-chloroaniline (commercially available) as the starting material. The crude material was purified by flash chromatography on a COMBIFLASH® system (ISCO) using 0-40% EtOAc/Hexanes to give tert-butyl 5-bromo-2-chlorophenylcarbamate as a pale yellow solid.

Step 2: (E)-tert-butyl 2-chloro-5-(2-cyclopropylvinyl)phenylcarbamate

A solution of tert-butyl 5-bromo-2-chlorophenylcarbamate (from the previous step) (1.0 eq.) and (E)-2-(2-cyclopropylvinyl)-4,4,5,5-tetramethyl-1,3,2-dioxaborolane (commercially available) (1.0 eq.) in toluene (0.2 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction mixture was diluted with EtOAc and water. The two phases were separated, and the aqueous layer was extracted twice with EtOAc. The combined organic layers were washed with brine, dried over anhydrous $MgSO_4$, and concentrated en vaccuo. The crude product was purified by flash chromatography on a COMBIFLASH® system (ISCO) using 0-5% EtOAc/Hexanes to give (E)-tert-butyl 2-chloro-5-(2-cyclopropylvinyl)phenylcarbamate as a pale yellow solid.

Step 3: (E)-tert-butyl 5-(2-cyclopropylvinyl)-2-(4,4,5,5-tetramethyl-1,3,2-dioxaborolan-2-yl)phenylcarbamate The titled compound was prepared according to the procedure described in Example 93/Step 2, but using (E)-tert-butyl 2-chloro-5-(2-cyclopropylvinyl) phenylcarbamate (from previous step) as the starting material. The crude product was purified by flash chromatography on a COMBIFLASH® system (ISCO) using 0-10% EtOAc/Hexanes to give (E)-tert-butyl 5-(2-cyclopropylvinyl)-2-(4,4,5,5-tetramethyl-1,3,2-dioxaborolan-2-yl)phenylcarbamate as a pale yellow solid.

Step 4: 2-(4-methoxy-2-methylphenethyl)-8-pentyl-benzo[f][1,7]naphthyridin-5-amine and 8-(2-cyclopropylethyl)-2-(4-methoxy-2-methylphenethyl)benzo[f][1,7]naphthyridin-5-amine The titled compounds were prepared according to the procedure described in Example 44/Step 4 (Suzuki coupling) and 5 (reduction), but using (E)-tert-butyl 5-(2-cyclopropylvinyl)-2-(4,4,5,5-tetramethyl-1,3,2-dioxaborolan-2-yl)phenylcarbamate (from previous step) and 3-chloro-5-((4-methoxy-2-methylphenyl)ethynyl) picolinonitrile (from Example 49/Step 1) as the starting material. The crude product was purified by flash chromatography on a COMBIFLASH® system (ISCO) using 0-40% EtOAc/Hexanes to give Example 109 as a white solid: $^1$H NMR (acetone-$d_6$): δ 8.76 (d, 1H), 8.70 (d, 1H), 8.29 (d, 1H), 7.44 (d, 1H), 7.18 (dd, 1H), 7.08 (d, 1H), 6.74 (d, 1H), 6.68 (dd, 1H), 6.59 (br s, 2H), 3.74 (s, 3H), 3.18 (t, 2H), 3.04 (t, 2H), 2.75 (t, 2H), 2.29 (s, 3H), 1.75-1.68 (m, 2H), 1.40-1.35 (m, 4H), 0.90 (s, 3H); LRMS [M+H]=414.3; and Example 110 as an off white solid: $^1$H NMR (acetone-$d_6$): δ 8.76 (d, 1H), 8.70 (d, 1H), 8.28 (d, 1H), 7.45 (d, 1H), 7.19 (dd, 1H), 7.08 (d, 1H), 6.74 (d, 1H), 6.67 (dd, 1H), 6.55 (br s, 2H), 3.73 (s, 3H), 3.16 (t, 2H), 3.03 (t, 2H), 2.29 (s, 3H), 1.60 (q, 2H), 1.29-1.28 (m, 1H), 0.89-0.74 (m, 2H), 0.44-0.41 (m, 2H), 0.10-0.07 (m, 2H). LRMS [M+H]=412.3.

Example 111

(5-amino-2-(2,4,6-trimethylphenethyl)benzo[f][1,7]naphthyridin-8-yl)methanol

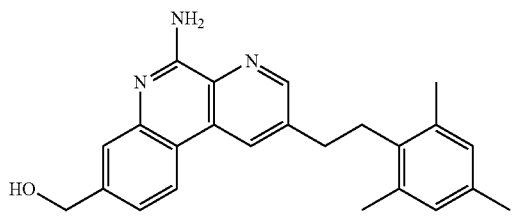 [SMILES: Cc1cc(C)c(CCc2cnc3c(N)nc4cc(CO)ccc4c3c2)c(C)c1]

(5-Amino-2-(2,4,6-trimethylphenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 99/step 1), 2-ethynyl-1,3,5-trimethylbenzene (commercially available) and 3-chloro-5-(mesitylethynyl) picolinonitrile (from Example 77/step 1) following the procedures described for Example 44/Step 4, Example 99/step 3 (deprotecion of TBS) and Example 77/step 3 (reduction). $^1$H NMR (acetone-$d_6$): δ 8.77 (s, 2H), 8.34 (d, 1H), 7.61 (s, 1H), 7.33 (d, 1H), 6.84 (s, 2H), 6.60 (br s, 2H), 4.77 (d, 2H), 4.35 (t, 1H), 3.08 (s, 3H), 2.84 (s, 6H), 2.30-2.29 (m, 4H). LRMS [M+H]=372.2.

Example 112

(5-amino-2-(4-propoxyphenethyl)benzo[f][1,7]naphthyridin-8-yl)methanol

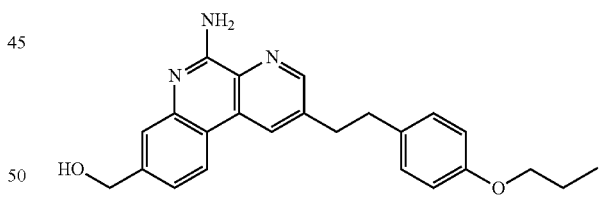

(5-Amino-2-(4-propoxyphenethyl)benzo[f][1,7]naphthyridin-8-yl)methanol was prepared from 8-((tert-butyldimethylsilyloxy)methyl)-3-chlorobenzo[f][1,7]naphthyridin-5-amine (from Example 99/step 1) and 3-chloro-5-(4-propoxyphenethyl) picolinonitrile (from Example 79/step 2) following the procedures described for Example 44/Step 4 and Example 99/step 3 (deprotecion of TBS). $^1$H NMR (acetone-$d_6$): δ 8.79 (d, 1H), 8.70 (d, 1H), 8.35 (d, 1H), 7.61 (d, 1H), 7.33 (dd, 1H), 7.17 (d, 2H), 6.83 (d, 2H), 6.57 (br s, 2H), 4.77 (d, 2H), 4.34 (t, 1H), 3.89 (t, 2H), 3.22 (t, 2H), 3.06 (t, 2H), 1.83-1.70 (m, 2H), 1.00 (t, 3H). LRMS [M+H]=388.2.

Example 113

(2-(2-(1H-indol-5-yl)ethyl)-5-aminobenzo[f][1,7]naphthyridin-8-yl)methanol

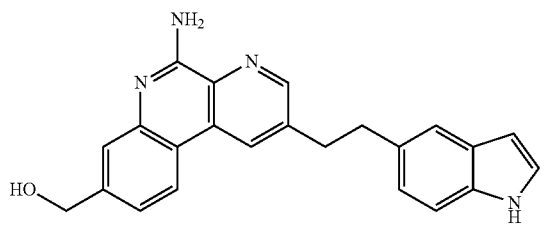 [SMILES: Nc1nc2cc(CO)ccc2c2cc(CCc3ccc4[nH]ccc4c3)cnc12]

(2-(2-(1H-indol-5-yl)ethyl)-5-aminobenzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 99/step 1) and 5-((1H-indol-5-yl)ethynyl)-3-chloropicolinonitrile (from Example 44/step 3) following the procedures described for Example 44/Step 4 and Example 99/step 3 (deprotecion of TBS). $^1$H NMR (acetone-d$_6$): δ 10.19 (t, 1H), 8.83 (d, 1H), 8.71 (d, 1H), 8.35 (d, 1H), 7.60 (d, 1H), 7.46 (d, 1H), 7.36-7.27 (m, 3H), 7.04 (dd, 1H), 6.57 (br s, 2H), 6.38 (dt, 1H), 4.77 (d, 2H), 4.36 (t, 1H), 3.29 (t, 2H), 3.19 (t, 2H). LRMS [M+H]=369.2.

Example 114

N-(4-(2-(5-amino-8-methylbenzo[f][1,7]naphthyridin-2-yl)ethyl)phenyl)acetamide

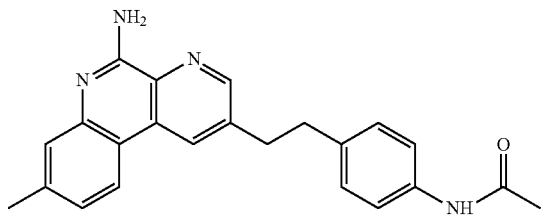 [SMILES: CC(=O)Nc1ccc(CCc2cnc3c(N)nc4cc(C)ccc4c3c2)cc1]

Step 1: N-(4-ethynylphenyl)acetamide

To a solution of 4-ethynylaniline (commercially available) (1.0 eq.), and triethylamine (1.0 eq.) in methylene chloride (0.04 M), acetyl chloride (1.5 eq.) was added slowly. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(4-ethynylphenyl)acetamide as a white solid.

Step 2: N-(4-((5-chloro-6-cyanopyridin-3-yl)ethynyl)phenyl)acetamide

A solution of 3,5-dichloropicolinonitrile (1.0 eq.), N-(4-ethynylphenyl)acetamide (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-80% ethyl acetate in hexane to give N-(4-((5-chloro-6-cyanopyridin-3-yl)ethynyl)phenyl)acetamide as a white solid.

Step 3: N-(4-(2-(5-chloro-6-cyanopyridin-3-yl)ethyl)phenyl)acetamide

To a solution of N-(4-((5-chloro-6-cyanopyridin-3-yl)ethynyl)phenyl)acetamide (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give N-(4-(2-(5-chloro-6-cyanopyridin-3-yl)ethyl)phenyl)acetamide.

Step 4: N-(4-(2-(5-amino-8-methylbenzo[f][1,7]naphthyridin-2-yl)ethyl)phenyl)acetamide A solution of N-(4-(2-(5-chloro-6-cyanopyridin-3-yl)ethyl)phenyl)acetamide (from the previous step) (1.0 eq.), tert-butyl 4-methyl-2-(4,4,5,5-tetramethyl-1,3,2-dioxaborolan-2-yl)phenylcarbamate (from Example 5/Step 2) (1.5 eq.), Tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/H$_2$O (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(4-(2-(5-amino-8-methylbenzo[f][1,7]naphthyridin-2-yl)ethyl)phenyl)acetamide as a white solid. $^1$H NMR (CDCl$_3$): δ 8.51 (s, 1H), 8.32 (s, 1H), 8.01 (d, 1H), 7.44 (s, 1H), 7.33-7.36 (m, 2H), 7.03-7.19 (m, 3H), 5.98 (br, 2H), 3.07-3.11 (m, 2H), 2.94-2.98 (m, 2H), 2.44 (s, 3H), 2.10 (s, 3H). LRMS [M+H]=371.2.

Example 115 methyl 4-(2-(5-amino-8-methylbenzo[f][1,7]naphthyridin-2-yl)ethyl)-3-methylbenzoate

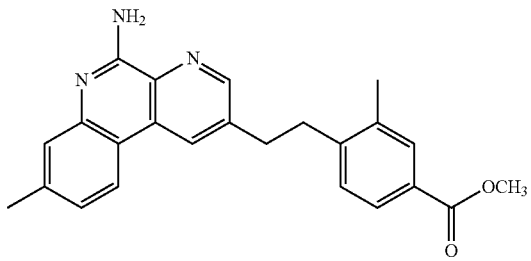 [SMILES: COC(=O)c1ccc(CCc2cnc3c(N)nc4cc(C)ccc4c3c2)c(C)c1]

Step 1: methyl 3-methyl-4-((triethylsilyl)ethynyl)benzoate

A solution of methyl 4-bromo-3-methylbenzoate (1.0 eq.), triethyl(ethynyl)silane (1.0 eq.), bis(triphenyl-phosphine) palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-50% ethyl acetate in hexane to give methyl 3-methyl-4-((triethylsilyl)ethynyl)benzoate as a white solid.

Step 2: methyl 4-ethynyl-3-methylbenzoate

To a solution of methyl 3-methyl-4-((triethylsilyl)ethynyl)benzoate (from the previous step) (1.0 eq.) in THF (0.2 M), was added TBAF (0.2 eq.) slowly at 0° C. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give methyl 4-ethynyl-3-methylbenzoate as a white solid.

Step 3: methyl 4-((5-chloro-6-cyanopyridin-3-yl)ethynyl)-3-methylbenzoate

A solution of 3,5-dichloropicolinonitrile (1.0 eq.), methyl 4-ethynyl-3-methylbenzoate (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-80% ethyl acetate in hexane to give methyl 4-((5-chloro-6-cyanopyridin-3-yl)ethynyl)-3-methylbenzoate as a white solid.

Step 4: methyl methyl 4-((5-amino-8-methylbenzo[f][1,7]naphthyridin-2-yl)ethynyl)-3-methylbenzoate A solution of methyl 4-((5-chloro-6-cyanopyridin-3-yl)ethynyl)-3-methylbenzoate (from the previous step) (1.0 eq.), tert-butyl 4-methyl-2-(4,4,5,5-tetramethyl-1,3,2-dioxaborolan-2-yl)phenylcarbamate (From Example 5/Step 2) (1.5 eq.), tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/H$_2$O (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give methyl methyl-4-((5-amino-8-methylbenzo[f][1,7]naphthyridin-2-yl)ethynyl)-3-methylbenzoate as a white solid.

Step 5: methyl 4-(2-(5-amino-8-methylbenzo[f][1,7]naphthyridin-2-yl)ethyl)-3-methylbenzoate To a solution of methyl methyl 4-((5-amino-8-methylbenzo[f][1,7]naphthyridin-2-yl)ethynyl)-3-methylbenzoate (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give methyl 4-(2-(5-amino-8-methylbenzo[f][1,7]naphthyridin-2-yl)ethyl)-3-methylbenzoate. $^1$H NMR (CDCl$_3$): δ 8.61 (s, 1H), 8.40 (s, 1H), 8.09 (d, 1H), 7.83 (s, 1H), 7.81 (d, 1H), 7.54 (s, 1H), 7.18-7.20 (m, 2H), 6.17 (br, 2H), 3.92 (s, 3H), 3.10-3.16 (m, 4H), 2.53 (s, 3H), 2.36 (s, 3H). LRMS [M+H]=386.2.

Example 116

4-(2-(5-amino-8-methylbenzo[f][1,7]naphthyridin-2-yl)ethyl)-N,3-dimethylbenzamide

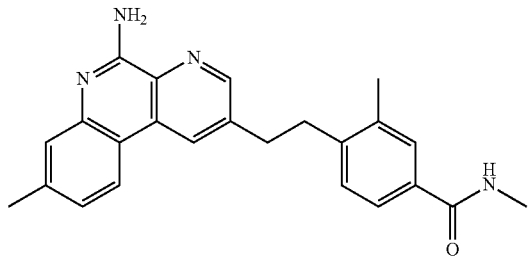

Step 1: 4-(2-(5-amino-8-methylbenzo[f][1,7]naphthyridin-2-yl)ethyl)-3-methylbenzoic acid A solution of methyl 4-(2-(5-amino-8-methylbenzo[f][1,7]naphthyridin-2-yl)ethyl)-3-methylbenzoate (from Example 115) (1.0 eq.), and 1N sodium hydroxide (1.5 eq.) in methanol (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-50% ethyl acetate in hexane to give 4-(2-(5-amino-8-methylbenzo[f][1,7]naphthyridin-2-yl)ethyl)-3-methylbenzoic acid as a white solid.

Step 2: 4-(2-(5-amino-8-methylbenzo[f][1,7]naphthyridin-2-yl)ethyl)-3-methylbenzoyl chloride A solution of 4-(2-(5-amino-8-methylbenzo[f][1,7]naphthyridin-2-yl)ethyl)-3-methylbenzoic acid (from the previous step) in thionyl chloride was stirred at 60° C. for 3 hour. After cooling to ambient temperature, the reaction mixture was concentrated en vaccuo. The crude material was used for next step without purification.

Step 3: 4-(2-(5-amino-8-methylbenzo[f][1,7]naphthyridin-2-yl)ethyl)-N,3-dimethylbenzamide To a solution of 4-(2-(5-amino-8-methylbenzo[f][1,7]naphthyridin-2-yl)ethyl)-3-methylbenzoyl chloride (from the previous step) (Example 5) and triethylamine (2.5 eq.) in ether (0.05 M) was added methanamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give 4-(2-(5-amino-8-methylbenzo[f][1,7]naphthyridin-2-yl)ethyl)-N,3-dimethylbenzamide as a white solid. $^1$H NMR (CDCl$_3$): δ 8.62 (s, 1H), 8.32 (s, 1H), 8.04 (d, 1H), 7.60 (s, 1H), 7.46-7.52 (m, 2H), 7.09-7.11 (m, 2H), 6.05 (br, 2H), 3.09-3.17 (m, 4H), 3.00 (d, 3H), 2.52 (s, 3H), 2.33 (s, 3H). LRMS [M+H]=385.2.

Example 117

4-(2-(5-amino-8-methylbenzo[f][1,7]naphthyridin-2-yl)ethyl)-N-(2-(dimethylamino)ethyl)-N,3-dimethylbenzamide

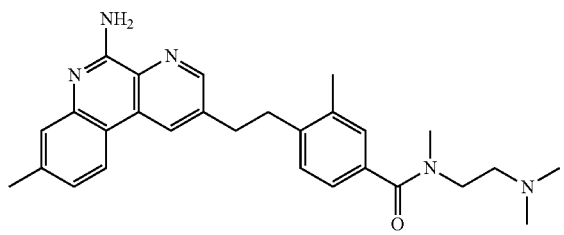

To a solution of 4-(2-(5-amino-8-methylbenzo[f][1,7]naphthyridin-2-yl)ethyl)-3-methylbenzoyl chloride (Example 116/Step 2) and triethylamine (2.5 eq.) in ether (0.05 M) was added N$^1$,N$^1$,N$^2$-trimethylethane-1,2-diamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give 4-(2-(5-amino-8-methylbenzo[f][1,7]naphthyridin-2-yl)ethyl)-N-(2-(dimethylamino)ethyl)-N,3-dimethylbenzamide as a white solid. $^1$H NMR (CDCl$_3$): δ 8.66 (s, 1H), 8.37 (s, 1H), 8.07 (d, 1H), 7.63 (s, 1H), 7.09-7.30 (m, 4H), 3.90 (br, 2H), 3.01-3.19 (m, 4H), 3.08 (s, 6H), 2.72 (br, 5H), 2.52 (s, 3H), 2.33 (s, 3H). LRMS [M+H]=456.3.

Example 118

2-(4-methoxyphenethyl)benzo[f][1,7]naphthyridin-5-amine

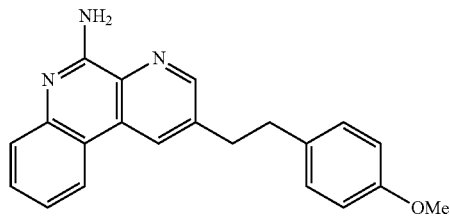 [SMILES: COc1ccc(CCc2cnc3c(N)nc4ccccc4c3c2)cc1]

2-(4-Methoxyphenethyl)benzo[f][1,7]naphthyridin-5-amine was prepared from 1-ethynyl-4-methoxybenzene (Example 116/Step 2) following the procedures described for Example 45/Steps 1 to 3. $^1$H NMR (CDCl$_3$): δ 8.69 (s, 1H), 8.47 (s, 1H), 8.27 (d, 1H), 7.80 (d, 2H), 7.58-7.66 (m, 1H), 7.33-7.42 (m, 1H), 7.15 (d, 2H), 6.90 (d, 2H), 6.25 (br, 2H), 3.86 (s, 3H), 3.13-3.23 (m, 2H), 2.97-3.10 (m, 2H). LRMS [M+H]=330.2.

Example 119

2-(4-methoxy-2-methylphenethyl)benzo[f][1,7]naphthyridin-5-amine

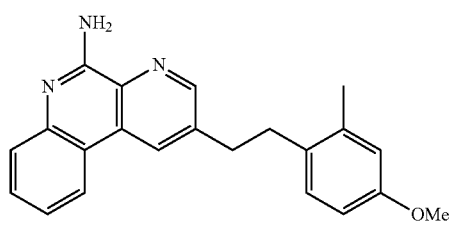 [SMILES: COc1ccc(CCc2cnc3c(N)nc4ccccc4c3c2)c(C)c1]

2-(4-Methoxy-2-methylphenethyl)benzo[f][1,7]naphthyridin-5-amine was prepared from 1-ethynyl-4-methoxy-2-methylbenzene (commercially available) following the procedures described for Example 45/Step 1 to 3. 1H NMR (CDCl$_3$): δ 8.60 (s, 1H), 8.37 (s, 1H), 8.18 (d, 1H), 7.69 (d, 1H), 7.49-7.57 (m, 1H), 7.24-7.34 (m, 1H), 6.98 (d, 1H), 6.56-6.70 (m, 2H), 6.00 (br, 2H), 3.70 (s, 3H), 3.00-3.09 (m, 2H), 2.83-2.96 (m, 2H), 2.20 (s, 3H). LRMS [M+H]=344.2.

Example 120

4-(2-(5-amino-8-methylbenzo[f][1,7]naphthyridin-2-yl)ethyl)-3-methylbenzamide

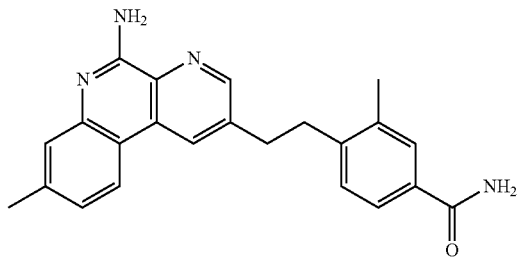 [SMILES: Cc1ccc2c(c1)nc(N)c1ncc(CCc3ccc(C(N)=O)cc3C)cc12]

4-(2-(5-Amino-8-methylbenzo[f][1,7]naphthyridin-2-yl)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and ammonia following the procedures described for Example 117. $^1$H NMR (CDCl$_3$): δ 8.60 (s, 1H), 8.35 (s, 1H), 8.05 (d, 1H), 7.65 (s, 1H), 7.51-7.53 (m, 2H), 7.13-7.21 (m, 2H), 3.09-3.16 (m, 4H), 2.51 (s, 3H), 2.34 (s, 3H). LRMS [M+H]=371.2

Example 121

4-(2-(5-amino-8-methylbenzo[f][1,7]naphthyridin-2-yl)ethyl)-N,N,3-trimethylbenzamide

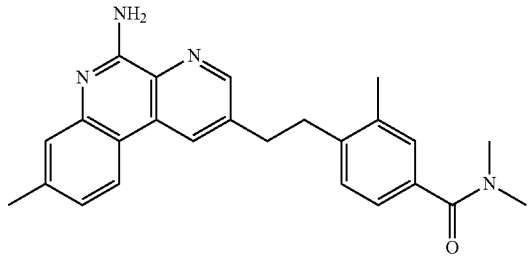

4-(2-(5-Amino-8-methylbenzo[f][1,7]naphthyridin-2-yl)ethyl)-N,N,3-trimethylbenzamide was prepared from 4-(2-(5-amino-8-methylbenzo[f][1,7]naphthyridin-2-yl)ethyl)-3-methylbenzoyl chloride (Example 116/Step 2) and dimethylamine following the procedures described for Example 117. $^1$H NMR (CDCl$_3$): δ 8.68 (s, 1H), 8.32 (s, 1H), 8.04 (d, 1H), 7.66 (s, 1H), 7.31 (d, 1H), 7.06-7.18 (m, 3H), 3.08-3.19 (m, 4H), 2.96 (d, 3H), 2.54 (s, 3H), 2.33 (s, 3H), 2.05 (s, 3H). LRMS [M+H]=399.2

Example 122

4-(2-(5-amino-8-methylbenzo[f][1,7]naphthyridin-2-yl)ethyl)-N-(2-hydroxyethyl)-3-methylbenzamide

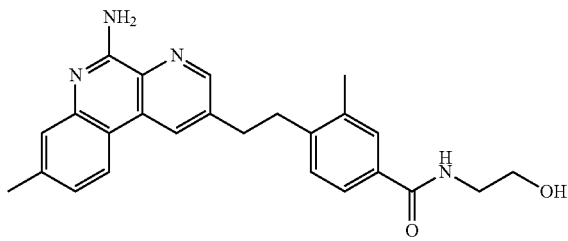 [SMILES: Cc1ccc2c(c1)nc(N)c1ncc(CCc3ccc(C(=O)NCCO)cc3C)cc12]

4-(2-(5-Amino-8-methylbenzo[f][1,7]naphthyridin-2-yl)ethyl)-N-(2-hydroxyethyl)-3-methylbenzamide was prepared from 4-(2-(5-amino-8-methylbenzo[f][1,7]naphthyridin-2-yl)ethyl)-3-methylbenzoyl chloride (Example 116/Step 2) and 2-aminoethanol following the procedures described for Example 117. $^1$H NMR (CDCl$_3$): δ 8.59 (s, 1H), 8.34 (s, 1H), 8.04 (d, 1H), 7.50-7.62 (m, 3H), 7.08-7.25 (m, 2H), 3.80 (t, 2H), 3.63 (t, 2H), 3.07-3.16 (m, 4H), 2.51 (s, 3H), 2.32 (s, 3H). LRMS [M+H]=415.2

Example 123

4-(2-(5-amino-8-methylbenzo[f][1,7]naphthyridin-2-yl)ethyl)-N-(2-(dimethylamino)ethyl)-3-methylbenzamide

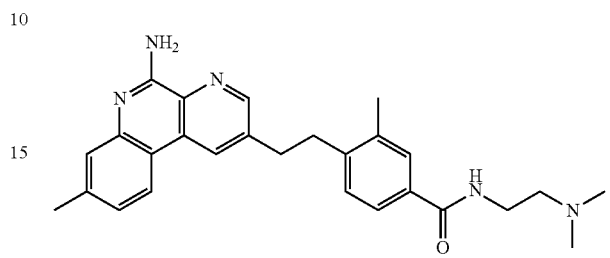

4-(2-(5-Amino-8-methylbenzo[f][1,7]naphthyridin-2-yl)ethyl)-N-(2-(dimethylamino)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and N$^1$,N$^1$-dimethylethane-1,2-diamine following the procedures described for Example 117. $^1$H NMR (methanol-d$_4$): δ 8.60 (s, 1H), 8.39 (s, 1H), 8.08 (d, 1H), 7.68 (s, 1H), 7.57-7.59 (m, 2H), 7.19-7.22 (m, 2H), 3.57-3.61 (m, 2H), 3.07-3.16 (m, 4H), 2.64-2.67 (m, 2H), 2.52 (s, 3H), 2.38 (s, 6H), 2.35 (s, 3H). LRMS [M+H]=442.3

Example 124

(4-(2-(5-amino-8-methylbenzo[f][1,7]naphthyridin-2-yl)ethyl)-3-methylphenyl)(pyrrolidin-1-yl)methanone

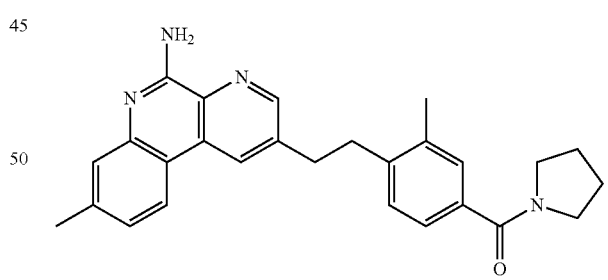

(4-(2-(5-Amino-8-methylbenzo[f][1,7]naphthyridin-2-yl)ethyl)-3-methylphenyl)(pyrrolidin-1-yl)methanone was prepared from 4-(2-(5-amino-8-methylbenzo[f][1,7]naphthyridin-2-yl)ethyl)-3-methylbenzoyl chloride (Example 116/Step 2) and pyrrolidine following the procedures described for Example 117. $^1$H NMR (methanol-d$_4$): δ 8.60 (s, 1H), 8.42 (s, 1H), 8.09 (d, 1H), 7.34 (s, 1H), 7.23 (s, 1H), 7.05-7.15 (m, 3H), 3.49 (t, 2H), 3.27 (t, 2H), 3.05-3.17 (m, 4H), 2.42 (s, 3H), 2.26 (s, 3H), 1.88-1.91 (m, 2H), 1.73-1.77 (m, 2H). LRMS [M+H]=425.2

Example 125

4-(2-(5-amino-8-methylbenzo[f][1,7]naphthyridin-2-yl)ethyl)-N-(2-(diethylamino)ethyl)-3-methylbenzamide

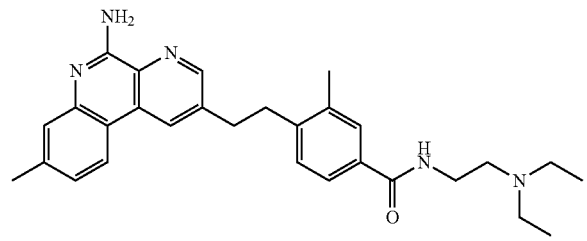 [SMILES: CCN(CC)CCNC(=O)c1ccc(CCc2cnc3c(N)nc4cc(C)ccc4c3c2)c(C)c1]

4-(2-(5-Amino-8-methylbenzo[f][1,7]naphthyridin-2-yl)ethyl)-N-(2-(diethylamino)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and $N^1,N^1$-diethylethane-1,2-diamine following the procedures described for Example 117. $^1$H NMR (methanol-$d_4$): δ 8.55 (s, 1H), 8.48 (s, 1H), 8.10 (d, 1H), 7.56 (s, 1H), 7.47-7.50 (m, 1H), 7.33 (s, 1H), 7.10-7.14 (m, 2H), 3.44 (t, 2H), 3.25 (t, 2H), 3.08-3.14 (m, 4H), 2.62-2.72 (m, 4H), 2.42 (s, 3H), 2.27 (s, 3H), 1.05 (t, 6H). LRMS [M+H]=470.3

Example 126

(4-(2-(5-amino-8-methylbenzo[f][1,7]naphthyridin-2-yl)ethyl)-3-methylphenyl)(4-ethylpiperazin-1-yl)methanone

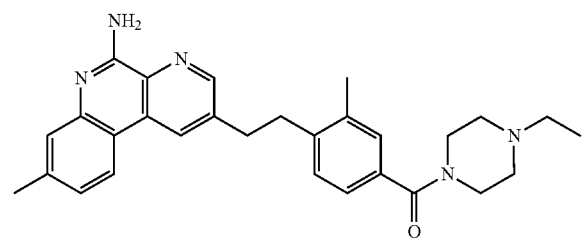 [SMILES: CCN1CCN(C(=O)c2ccc(CCc3cnc4c(N)nc5cc(C)ccc5c4c3)c(C)c2)CC1]

(4-(2-(5-Amino-8-methylbenzo[f][1,7]naphthyridin-2-yl)ethyl)-3-methylphenyl)(4-ethylpiperazin-1-yl)methanone was prepared from 4-(2-(5-amino-8-methylbenzo[f][1,7]naphthyridin-2-yl)ethyl)-3-methylbenzoyl chloride (Example 116/Step 2) and 1-ethylpiperazine following the procedures described for Example 117. $^1$H NMR (Methanol-$d_4$): δ 8.59 (s, 1H), 8.37 (s, 1H), 8.06 (d, 1H), 7.32 (s, 1H), 7.00-7.12 (m, 4H), 3.67 (br, 2H), 3.06-3.13 (m, 4H), 2.45 (br, 4H), 2.37 (q, 2H), 2.41 (s, 3H), 2.26 (s, 3H), 2.19 (br, 2H), 1.04 (t, 3H). LRMS [M+H]=468.3

Example 127

(4-(2-(5-amino-8-methylbenzo[f][1,7]naphthyridin-2-yl)ethyl)-3-methylphenyl)(piperazin-1-yl)methanone

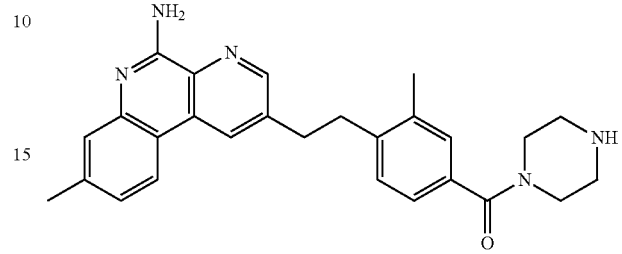

(4-(2-(5-Amino-8-methylbenzo[f][1,7]naphthyridin-2-yl)ethyl)-3-methylphenyl)(piperazin-1-yl)methanone was prepared from 4-(2-(5-amino-8-methylbenzo[f][1,7]naphthyridin-2-yl)ethyl)-3-methylbenzoyl chloride (Example 116/Step 2) and piperazine following the procedures described for Example 117. $^1$H NMR (methanol-$d_4$): δ 8.66 (s, 1H), 8.55 (s, 1H), 8.19 (d, 1H), 7.38 (s, 1H), 7.21-7.23 (m, 2H), 7.10-7.15 (m, 2H), 3.66 (br, 6H), 3.08-3.18 (m, 6H), 2.45 (s, 3H), 2.30 (s, 3H). LRMS [M+H]=440.2

Example 128

4-(2-(5-amino-8-methylbenzo[f][1,7]naphthyridin-2-yl)ethyl)-3-methyl-N-(2-(pyrrolidin-1-yl)ethyl)benzamide

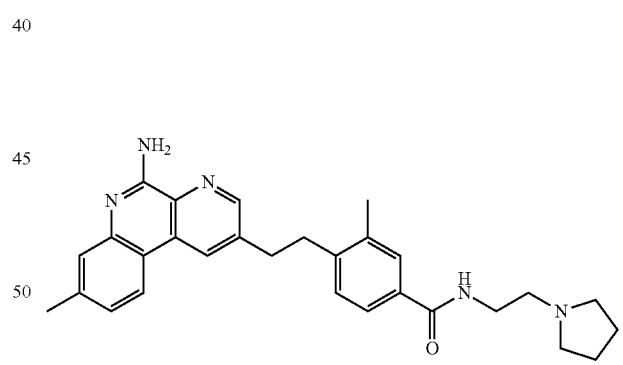

4-(2-(5-Amino-8-methylbenzo[f][1,7]naphthyridin-2-yl)ethyl)-3-methyl-N-(2-(pyrrolidin-1-yl)ethyl)benzamide was prepared from 4-(2-(5-amino-8-methylbenzo[f][1,7]naphthyridin-2-yl)ethyl)-3-methylbenzoyl chloride (Example 116/Step 2) and 2-(pyrrolidin-1-yl)ethanamine following the procedures described for Example 117. $^1$H NMR (CDCl$_3$): δ 8.58 (s, 1H), 8.38 (s, 1H), 8.07 (d, 1H), 7.64 (s, 1H), 7.51-7.55 (m, 2H), 7.12-7.20 (m, 2H), 6.26 (br, 2H), 3.61 (dd, 2H), 3.05-3.12 (m, 4H), 2.81 (t, 2H), 2.69 (br, 4H), 2.50 (s, 3H), 2.33 (s, 3H), 1.83-1.85 (m, 4H). LRMS [M+H]=468.3

Example 129

4-(2-(5-amino-8-methylbenzo[f][1,7]naphthyridin-2-yl)ethyl)-N-(2-aminoethyl)-3-methylbenzamide

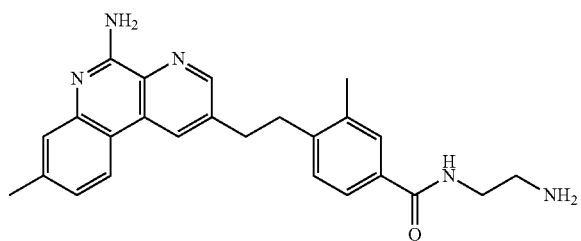 [SMILES: Cc1ccc2c(c1)nc(N)c1ncc(CCc3ccc(C(=O)NCCN)cc3C)cc12]

4-(2-(5-Amino-8-methylbenzo[f][1,7]naphthyridin-2-yl)ethyl)-N-(2-aminoethyl)-3-methylbenzamide was prepared from 4-(2-(5-amino-8-methylbenzo[f][1,7]naphthyridin-2-yl)ethyl)-3-methylbenzoyl chloride (Example 116/Step 2) and ethane-1,2-diamine following the procedures described for Example 117. $^1$H NMR (CDCl$_3$): δ 8.59 (s, 1H), 8.37 (s, 1H), 8.07 (d, 1H), 7.63 (s, 1H), 7.51 (br, 2H), 7.12-7.21 (m, 2H), 6.25 (br, 2H), 3.48-3.52 (m, 2H), 3.08-3.15 (m, 4H), 2.94 (t, 2H), 2.51 (s, 3H), 2.34 (s, 3H). LRMS [M+H]=414.2

Example 130

4-(2-(5-aminobenzo[f][1,7]naphthyridin-2-yl)ethyl)-N-(2-(dimethylamino)ethyl)-N,3-dimethylbenzamide

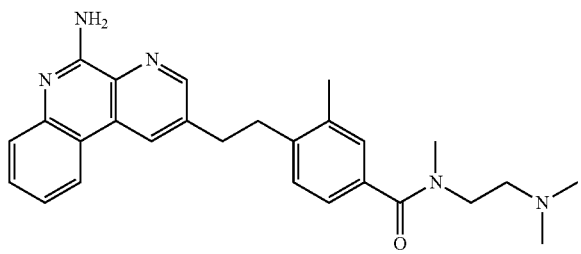 [SMILES: Cc1cc(C(=O)N(C)CCN(C)C)ccc1CCc1cnc2c(N)nc3ccccc3c2c1]

4-(2-(5-Aminobenzo[f][1,7]naphthyridin-2-yl)ethyl)-N-(2-(dimethylamino)ethyl)-N,3-dimethylbenzamide was prepared from 44245-aminobenzo[f][1,7]naphthyridin-2-yl)ethyl)-3-methylbenzoyl chloride (Example 116/Step 2) and N$^1$,N$^1$,N$^2$-trimethylethane-1,2-diamine following the procedures described for Example 117. $^1$H NMR (methanol-d$_4$): δ 8.84 (s, 1H), 8.63 (s, 1H), 8.39 (d, 1H), 7.76-7.83 (m, 2H), 7.60-7.64 (m, 1H), 7.37 (s, 1H), 7.19-7.29 (m, 2H), 3.96 (t, 2H), 3.48 (t, 2H), 3.32 (t, 2H), 3.20 (t, 2H), 3.09 (s, 3H), 3.06 (s, 6H), 2.42 (s, 3H). LRMS [M+H]=442.3

Example 131

4-(2-(5-amino-8-methylbenzo[f][1,7]naphthyridin-2-yl)ethyl)-N-(2-(dimethylamino)ethyl)-N-methylbenzamide

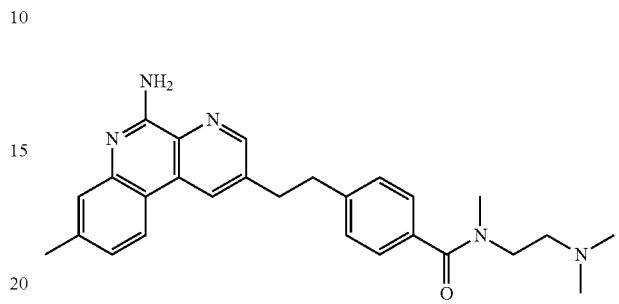

4-(2-(5-Amino-8-methylbenzo[f][1,7]naphthyridin-2-yl)ethyl)-N-(2-(dimethylamino)ethyl)-N-methylbenzamide was prepared from 4-(2-(5-amino-8-methylbenzo[f][1,7]naphthyridin-2-yl)ethyl)-3-methylbenzoyl chloride (Example 116/Step 2) and N$^1$,N$^1$,N$^2$-trimethylethane-1,2-diamine following the procedures described for Example 117. $^1$H NMR (CDCl$_3$): δ 8.64 (s, 1H), 8.36 (s, 1H), 8.05 (d, 1H), 7.60 (s, 1H), 7.41 (d, 2H), 7.31 (d, 1H), 7.21 (d, 2H), 3.91 (t, 2H), 3.44 (t, 2H), 3.25 (t, 2H), 3.12 (t, 2H), 3.03 (s, 3H), 3.01 (s, 6H), 2.53 (s, 3H). LRMS [M+H]=442.3

Example 132

2-(4-(2-(5-aminobenzo[f][1,7]naphthyridin-2-yl)ethyl)-3-methylphenyl)propan-2-ol

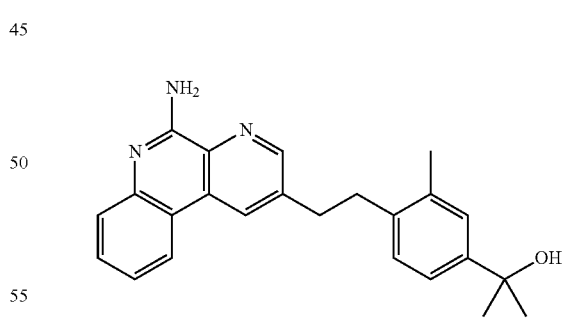

2-(4-(2-(5-Aminobenzo[f][1,7]naphthyridin-2-yl)ethyl)-3-methylphenyl)propan-2-ol was prepared following the procedures described for Example 78, but using methyl 4-(2-(5-aminobenzo[f][1,7]naphthyridin-2-yl)ethyl)-3-methylbenzoate which was prepared analogous to Example 115 but using tert-butyl 2-(4,4,5,5-tetramethyl-1,3,2-dioxaborolan-2-yl)phenylcarbamate in Step 4. LRMS [M+H]=372.2

Example 133

2-(4-butoxyphenethyl)-8-methylbenzo[f][1,7]naphthyridin-5-amine

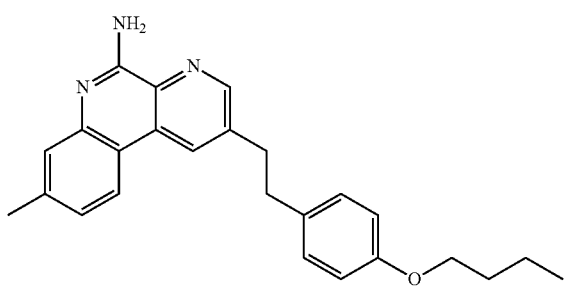 [SMILES: CCCCOc1ccc(CCc2cnc3c(N)nc4cc(C)ccc4c3c2)cc1]

2-(4-Butoxyphenethyl)-8-methylbenzo[f][1,7]naphthyridin-5-amine was prepared following the procedures described for Example 45/Steps 1 to 3, but using 1-butoxy-4-ethynylbenzene (commercially available) with 3,5-dichloropicolinonitrile (commercially available) in step 1. $^1$H NMR (Acetone-d$_6$): δ 8.75 (s, 1H), 8.68 (s, 1H), 8.28 (d, 1H), 7.42 (s, 1H), 7.10-7.18 (m, 3H), 6.84 (d, 2H), 6.58 (br, 2H), 3.94 (t, 2H), 3.21 (t, 2H), 3.05 (t, 2H), 2.46 (s, 3H), 1.65-1.75 (m, 2H), 1.41-1.58 (m, 2H), 0.94 (s, 3H). LRMS [M+H]=386.2.

Example 134

2-(2-(biphenyl-4-yl)ethyl)-8-methylbenzo[f][1,7]naphthyridin-5-amine

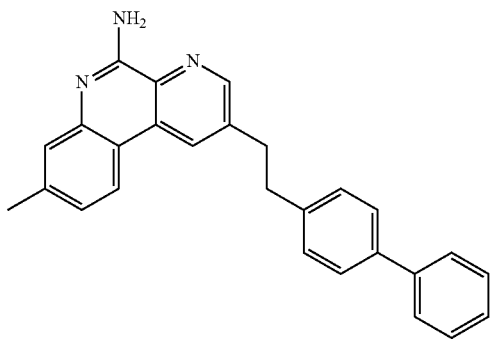 [SMILES: Cc1ccc2c(c1)nc(N)c1ncc(CCc3ccc(-c4ccccc4)cc3)cc12]

2-(2-(Biphenyl-4-yl)ethyl)-8-methylbenzo[f][1,7]naphthyridin-5-amine was prepared following the procedures described for Example 45/Steps 1 to 3, but using 4-ethynylbiphenyl (commercially available) with 3,5-dichloropicolinonitrile (commercially available) in Step 1. $^1$H NMR (Acetone-d$_6$): δ 8.80 (s, 1H), 8.75 (s, 1H), 8.26 (d, 2H), 7.55-7.69 (m, 4H), 7.30-7.46 (m, 4H), 7.13 (d, 2H), 6.58 (br, 2H), 3.30 (t, 2H), 3.18 (t, 2H), 2.45 (s, 3H). LRMS [M+H]=390.2

Example 135

2-((1,3-dihydroisobenzofuran-1-yl)methyl)-8-methylbenzo[f][1,7]naphthyridin-5-amine

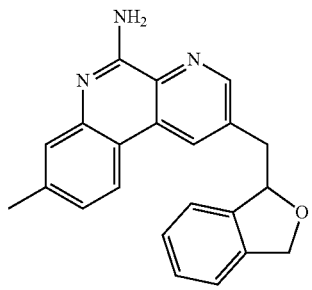 [SMILES: Cc1ccc2c(c1)nc(N)c1ncc(CC3OCc4ccccc43)cc12]

Step 1: 2-((5-amino-8-methylbenzo[f][1,7]naphthyridin-2-yl)ethynyl)phenyl)methanol 2-((5-Amino-8-methylbenzo[f][1,7]naphthyridin-2-yl)ethynyl)phenyl)methanol was prepared following the procedures described for Example 45/Steps 1 to 2, but using (2-ethynylphenyl)methanol (commercially available) with 3,5-dichloropicolinonitrile (commercially available) in Step 1.

Step 2: 2-((1,3-dihydroisobenzofuran-1-yl)methyl)-8-methylbenzo[f][1,7]naphthyridin-5-amine To a solution of 2-((5-amino-8-methylbenzo[f][1,7]naphthyridin-2-yl)ethynyl)phenyl)methanol (1.0 equiv.) (from the previous step) in ethanol (0.05 M) was added 10% wt palladium on carbon (0.2 equiv. by weight). Hydrogen gas was then introduced via a balloon, and the reaction was allowed to stir for 18 hours. At this point, the mixture was filtered through a pad of celite, washing with methanol. The volatiles were removed in vacuo and the resulting residue was purified by a COMBIFLASH® system (ISCO) using 0-60% ethyl acetate in hexanes to give 2-((1,3-dihydroisobenzofuran-1-yl)methyl)-8-methylbenzo[f][1,7]naphthyridin-5-amine as a solid. $^1$H NMR (Acetone-d$_6$): δ 8.78 (s, 1H), 8.74 (s, 1H), 8.24 (d, 2H), 7.40-7.44 (m, 2H), 7.20-7.34 (m, 3H), 6.61 (br, 2H), 5.63-5.69 (m, 1H), 4.89-5.00 (dd, 2H), 3.51-3.56 (dd, 1H), 3.28-3.34 (dd, 1H), 2.46 (s, 3H). LRMS [M+H]=342.1

Example 136

8-methyl-2-(4-(2-methylallyloxy)phenethyl)benzo[f][1,7]naphthyridin-5-amine

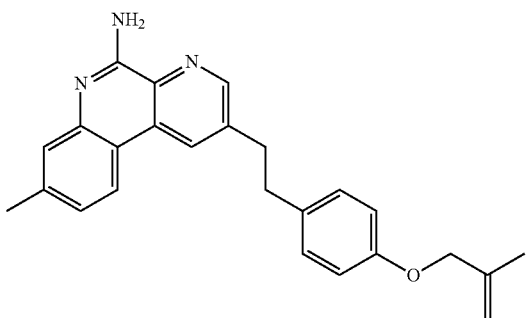 [SMILES: C=C(C)COc1ccc(CCc2cnc3c(N)nc4cc(C)ccc4c3c2)cc1]

To a solution of 4-(2-(5-amino-8-methylbenzo[f][1,7] naphthyridin-2-yl)ethyl)phenol (from Example 170) (1.0 equiv.) in dimethylformamide (0.10 M) was added anhydrous potassium carbonate (1.5 euiv.) followed by methallyl bromide (1.2 equiv.). The resulting mixture was allowed to stir for 18 hours at 100° C. After cooling to ambient temperature, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-60% ethyl acetate in hexanes to provide 8-methyl-2-(4-(2-methylallyloxy)phenethyl)benzo[f][1,7]naphthyridin-5-amine as a solid. $^1$H NMR (Acetone-$d_6$): δ 8.75 (s, 1H), 8.68 (s, 1H), 8.27 (d, 1H), 7.41 (s, 1H), 7.12-7.19 (m, 3H), 6.87 (d, 2H), 6.60 (br, 2H), 5.06 (s, 1H), 4.93 (s, 1H), 4.43 (s, 2H), 3.20 (t, 2H), 3.05 (t, 2H), 2.45 (s, 3H), 1.79 (s, 3H). LRMS [M+H]=384.2

Example 137

2-(4-(isopentyloxy)phenethyl)-8-methylbenzo[f][1,7]naphthyridin-5-amine

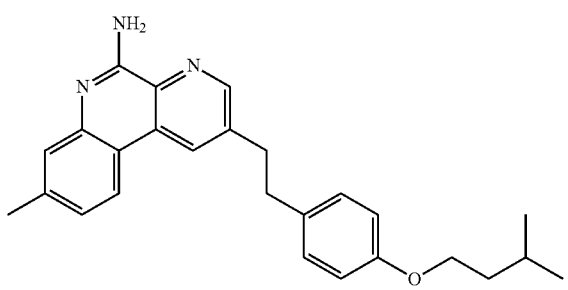 [SMILES: Cc1ccc2c(c1)nc(N)c1ncc(CCc3ccc(OCCC(C)C)cc3)cc12]

2-(4-(Isopentyloxy)phenethyl)-8-methylbenzo[f][1,7] naphthyridin-5-amine was prepared from 4-(2-(5-amino-8-methylbenzo[f][1,7]naphthyridin-2-yl)ethyl)phenol (from Example 170) following the procedure described for Example 136, but using 1-bromo-3-methylbutane. $^1$H NMR (Acetone-$d_6$): δ 8.72 (s, 1H), 8.69 (s, 1H), 8.26 (d, 1H), 7.43 (s, 1H), 7.12-7.18 (m, 3H), 6.84 (d, 2H), 6.50 (br, 2H), 3.98 (t, 2H), 3.21 (t, 2H), 3.06 (t, 2H), 2.46 (s, 3H), 1.78-1.87 (m, 1H), 1.61-1.67 (dd, 2H), 0.96 (s, 3H), 0.95 (3H). LRMS [M+H]=400.2

Example 138

4-(2-(5-amino-8-methylbenzo[f][1,7]naphthyridin-2-yl)ethyl)phenyl propyl carbonate

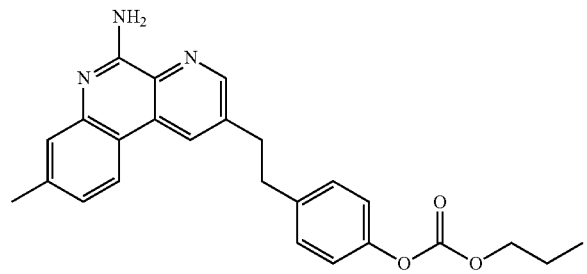 [SMILES: CCCOC(=O)Oc1ccc(CCc2cnc3c(N)nc4cc(C)ccc4c3c2)cc1]

To a solution of 4-(2-(5-amino-8-methylbenzo[f][1,7] naphthyridin-2-yl)ethyl)phenol (from Example 170) (1.0 equiv.) and triethyl amine (2 equiv.) in dichloromethane (0.10 M) at 0° C. was added ethyl chloroformate (1.2 equiv.). The resulting mixture was allowed to stir for 30 minutes at 0° C., after which it was diluted with water and dichloromethane. The biphasic layers were separated and the aqueous layer was washed twice with dichloromethane. The combined organic layers were dried over anhydrous $Na_2SO_4$ and the volatiles were removed in vacuo. The resulting residue was purified by a COMBIFLASH® system (ISCO) using 0-50% ethyl acetate in hexanes to provide 4-(2-(5-amino-8-methylbenzo[f][1,7]naphthyridin-2-yl) ethyl)phenyl ethyl carbonate as a solid. $^1$H NMR (Acetone-$d_6$): δ 8.78 (s, 1H), 8.73 (s, 1H), 8.28 (d, 1H), 7.43 (s, 1H), 7.33 (d, 2H), 7.10-7.17 (m, 3H), 6.64 (br, 2H), 4.18 (t, 2H), 3.25 (t, 2H), 3.14 (t, 2H), 2.45 (s, 3H), 1.68-1.77 (m, 2H), 0.97 (t, 3H). LRMS [M+H]=416.2

Example 139 ethyl 5-(4-(2-(5-amino-8-methylbenzo[f][1,7]naphthyridin-2-yl)ethyl)phenoxy)pentanoate

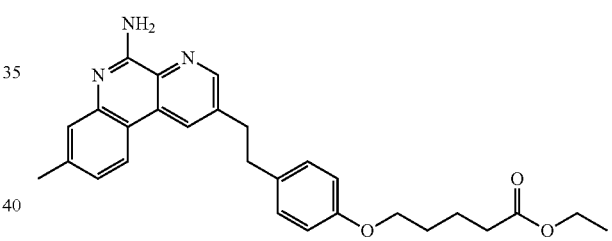

To a solution of 4-(2-(5-amino-8-methylbenzo[f][1,7] naphthyridin-2-yl)ethyl)phenol (from Example 170) (1.0 equiv.) in dimethylformamide (0.10 M) 22° C. was added 60% dispersion of sodium hydride in mineral oil (1.5 euiv.) and the resulting mixture was allowed to stir for 30 min. At this point, ethyl 5-bromopentanoate (1.2 equiv.) was added to this mixture. The reaction mixture was then allowed to stir for 18 hours. after which it was diluted with ethyl acetate and water. The biphasic layers were separated and the organic layer was washed twice with water. The organic layer was dried over anhydrous $Na_2SO_4$ and the volatiles were removed in vacuo. The resulting residue was purified by RP-HPLC using a 10-50% MeCN in water gradient. The resulting trifluoroacetate salt was then converted to the free base form by utilizing a StratoSpheres™ PL-SO3H SPE ion exchange resin, delivering ethyl 5-(4-(2-(5-amino-8-methylbenzo[f][1,7]naphthyridin-2-yl)ethyl)phenoxy)pentanoate as a solid. $^1$H NMR (Acetone-$d_6$): δ 8.80 (s, 1H), 8.74 (s, 1H), 8.33 (d, 1H), 7.47 (s, 1H), 7.24 (d, 1H), 7.17 (d, 2H), 6.85 (d, 2H), 4.10 (q, 2H), 3.97 (t, 2H), 3.25 (t, 2H), 3.07 (t, 2), 2.50 (s, 3H), 2.37 (t, 3H), 1.74-1.84 (m, 4H), 1.21 (t, 3H). LRMS [M+H]=458.2

Example 140

2-(4-(cyclopentyloxy)phenethyl)-8-methylbenzo[f][1,7]naphthyridin-5-amine

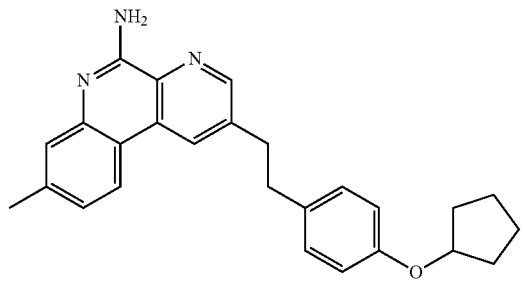 [SMILES: Cc1ccc2c(c1)nc(N)c1ncc(CCc3ccc(OC4CCCC4)cc3)cc12]

2-(4-(Cyclopentyloxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using bromocyclopentane. $^1$H NMR (Acetone-d$_6$): δ 8.75 (d, 2H), 8.30 (d, 1H), 7.45 (s, 1H), 7.20 (d, 1H), 7.14 (d, 2H), 6.79 (d, 2H), 4.73-4.81 (m, 1H), 3.22 (t, 2H), 3.05 (t, 2H), 2.47 (s, 3H), 1.85-1.96 (m, 2H), 1.70-1.79 (m, 4H), 1.56-1.64 (m, 2H). LRMS [M+H]=398.2

Example 141

2-(4-(cyclobutylmethoxy)phenethyl)-8-methylbenzo[f][1,7]naphthyridin-5-amine

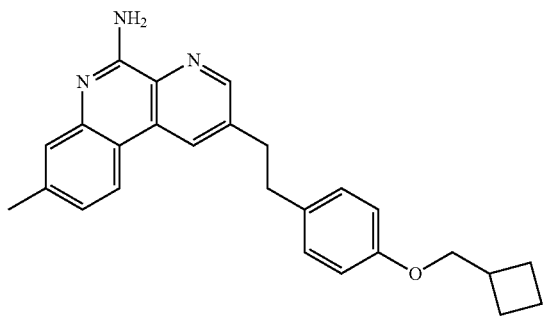 [SMILES: Cc1ccc2c(c1)nc(N)c1ncc(CCc3ccc(OCC4CCC4)cc3)cc12]

2-(4-(Cyclobutylmethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using (bromomethyl)cyclobutane. $^1$H NMR (Acetone-d$_6$): δ 8.79 (s, 1H), 8.73 (s, 1H), 8.33 (d, 1H), 7.47 (s, 1H), 7.26 (d, 1H), 7.16 (d, 2H), 6.82 (d, 2H), 3.90 (d, 2H), 3.23 (t, 2H), 3.06 (t, 2H), 2.68-2.79 (m, 1H), 2.49 (s, 3H), 2.05-2.14 (m, 2H), 1.80-1.98 (m, 4H). LRMS [M+H]=398.2

Example 142

8-methyl-2-(4-(2-morpholinoethoxy)phenethyl)benzo[f][1,7]naphthyridin-5-amine

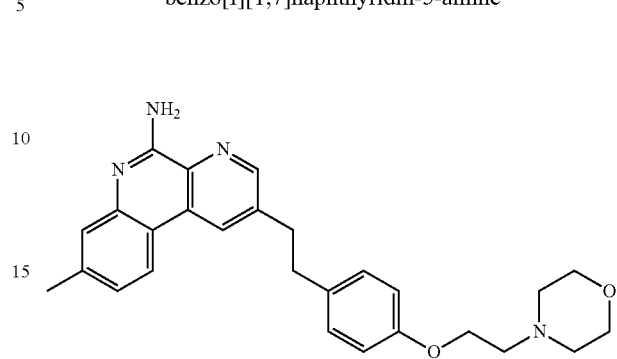

8-Methyl-2-(4-(2-morpholinoethoxy)phenethyl)benzo[f][1,7]naphthyridin-5-amine was prepared from 4-(2-(5-amino-8-methylbenzo[f][1,7]naphthyridin-2-yl)ethyl)phenol (from Example 170) following the procedure described for Example 139, but using 4-(2-bromoethyl)morpholine. $^1$H NMR (Acetone-d$_6$): δ 8.78 (s, 1H), 8.72 (s, 1H), 8.30 (d, 1H), 7.46 (s, 1H), 7.17-7.24 (m, 3H), 6.85 (d, 2H), 4.08 (t, 2H), 3.56-3.62 (m, 4H), 3.45-3.53 (m, 2H), 3.24 (t, 2H), 3.07 (t, 2H), 2.73 (t, 2H), 2.52-2.56 (m, 2H), 2.49 (s, 3H). LRMS [M+H]=443.2

Example 143

2-(4-(2-(5-amino-8-methylbenzo[f][1,7]naphthyridin-2-yl)ethyl)phenoxy)-1-phenylethanone

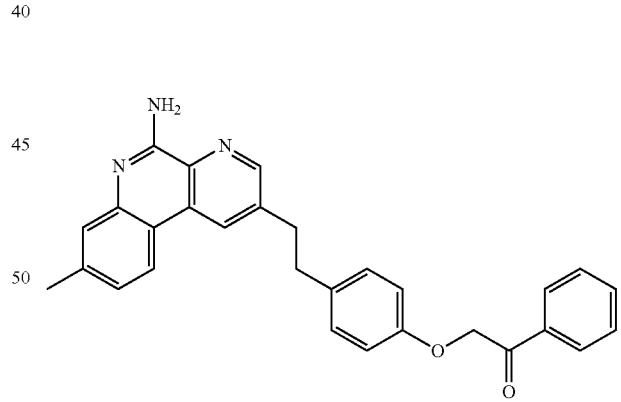

2-(4-(2-(5-Amino-8-methylbenzo[f][1,7]naphthyridin-2-yl)ethyl)phenoxy)-1-phenylethanone was prepared from 4-(2-(5-amino-8-methylbenzo[f][1,7]naphthyridin-2-yl)ethyl)phenol (from Example 170) following the procedure described for Example 139, but using 2-bromo-1-phenylethanone. $^1$H NMR (Acetone-d$_6$): δ 8.76 (s, 1H), 8.71 (s, 1H), 8.27 (d, 1H), 8.06 (d, 2H), 7.67 (t, 1H), 7.57 (t, 2H), 7.43 (s, 1H), 7.17 (d, 3H), 6.90 (d, 2H), 5.45 (s, 2H), 3.21 (t, 2H), 3.06 (t, 2H), 2.45 (s, 3H). LRMS [M+H]=448.2

Example 144

5-(4-(2-(5-amino-8-methylbenzo[f][1,7]naphthyridin-2-yl)ethyl)phenoxy)pentanoic acid

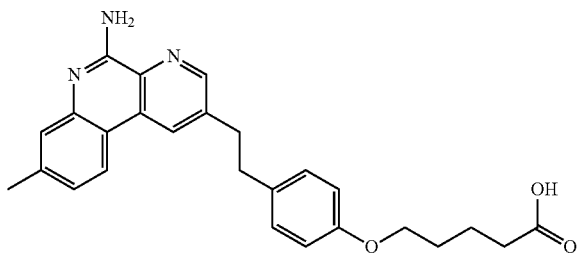 [SMILES: Cc1ccc2c(c1)nc(N)c1ncc(CCc3ccc(OCCCCC(=O)O)cc3)cc12]

To a solution of ethyl 5-(4-(2-(5-amino-8-methylbenzo[f][1,7]naphthyridin-2-yl)ethyl)phenoxy)pentanoate (1.0 equiv.) (from Example 139) in ethanol (0.10 M) was added anhydrous sodium hydroxide (2.0 equiv.) and the resulting mixture was allowed to stir at 80° C. for 2 hours. After cooling to ambient temperature, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 5-(4-(2-(5-amino-8-methylbenzo[f][1,7]naphthyridin-2-yl)ethyl)phenoxy)pentanoic acid as a solid. $^1$H NMR (Methanol-$d_4$): δ 8.61 (s, 1H), 8.57 (s, 1H), 8.20 (d, 1H), 7.40 (s, 1H), 7.20 (d, 1H), 7.07 (d, 2H), 6.81 (d, 2H), 3.93 (t, 2H), 3.18 (t, 2H), 3.00 (t, 2H), 2.48 (s, 3H), 2.25 (t, 2H), 1.74-1.81 (m, 2H), 0.86-0.96 (m, 2H). LRMS [M+H]=430.2

Example 145

2-(4-(2-(5-amino-8-methylbenzo[f][1,7]naphthyridin-2-yl)ethyl)phenoxy)ethanol

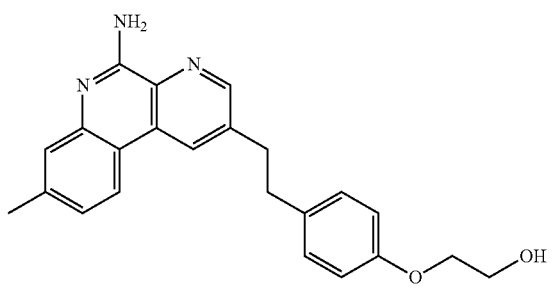 [SMILES: Cc1ccc2c(c1)nc(N)c1ncc(CCc3ccc(OCCO)cc3)cc12]

Step 1: 2-(4-(2-(tert-butyldimethylsilyloxy)ethoxy)phenethyl)-8-methylbenzo[f][1,7]naphthyridin-5-amine 2-(4-(2-(Tert-butyldimethylsilyloxy)ethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 139, but using (2-bromoethoxy)(tert-butyl)dimethylsilane.

Step 2: 2-(4-(2-(5-amino-8-methylbenzo[f][1,7]naphthyridin-2-yl)ethyl)phenoxy)ethanol To a solution of 2-(4-(2-(tert-butyldimethylsilyloxy)ethoxy)phenethyl)-8-methylbenzo[f][1,7]naphthyridin-5-amine (from the previous step) (1.0 equiv.) in tetrahydrofuran (0.10 M) was added a 1.0 M solution of tetrabutylammonium fluoride (5 equiv.) in THF and the resulting mixture was allowed to stir at 22° C. for 2 hours. At this point, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 2-(4-(2-(5-amino-8-methylbenzo[f][1,7]naphthyridin-2-yl)ethyl)phenoxy)ethanol as a solid. $^1$H NMR (Acetone-$d_6$): δ 8.76 (s, 1H), 8.67 (s, 1H), 8.28 (d, 1H), 7.40 (s, 1H), 7.15 (t, 3H), 6.84 (d, 2H), 6.54 (br, 2H), 4.00 (t, 2H), 3.83 (t, 2H), 3.21 (t, 2H), 3.05 (t, 2H), 2.45 (s, 3H). LRMS [M+H]=374.2

Example 146

2-(4-(2-(5-amino-8-methylbenzo[f][1,7]naphthyridin-2-yl)ethyl)phenoxy)-N,N-dimethylacetamide

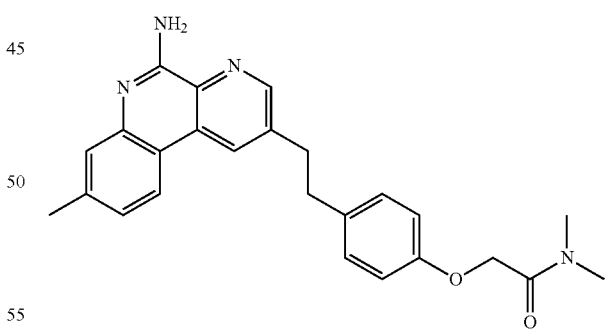

2-(4-(2-(5-Amino-8-methylbenzo[f][1,7]naphthyridin-2-yl)ethyl)phenoxy)-N,N-dimethylacetamide was prepared from 4-(2-(5-amino-8-methylbenzo[f][1,7]naphthyridin-2-yl)ethyl)phenol (from Example 170) and following the procedure described for Example 139, but using 2-bromo-N,N-dimethylacetamide. $^1$H NMR (Acetone-$d_6$): δ 8.75 (s, 1H), 8.70 (s, 1H), 8.28 (d, 1H), 7.40 (s, 1H), 7.18 (t, 3H), 6.87 (d, 2H), 6.56 (br, 2H), 4.72 (s, 2H), 3.20 (t, 2H), 3.07 (s, 3H), 3.05 (t, 2H), 2.87 (s, 3H), 2.45 (s, 3H). LRMS [M+H]=415.2

Example 147

8-methyl-2-(2-methyl-4-(2-morpholinoethoxy)phenethyl)benzo[f][1,7]naphthyridin-5-amine

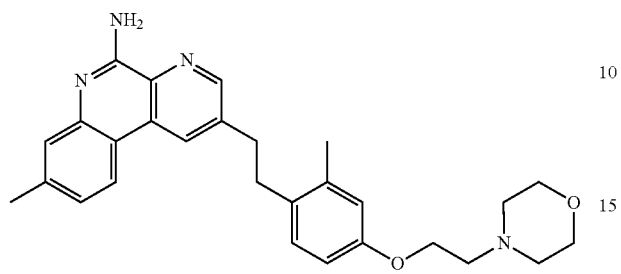

8-Methyl-2-(2-methyl-4-(2-morpholinoethoxy)phenethyl)benzo[f][1,7]naphthyridin-5-amine was prepared following an analogous procedure to the preparation described for Example 139, but using 4-(2-(5-amino-8-methylbenzo[f][1,7]naphthyridin-2-yl)ethyl)-3-methylphenol (from Example 50) and 4-(2-bromoethyl)morpholine. $^1$H NMR (Acetone-d$_6$): δ 8.73 (d, 2H), 8.26 (d, 1H), 7.44 (s, 1H), 7.17 (d, 1H), 7.05 (d, 1H), 6.76 (s, 1H), 6.67 (d, 1), 4.04-4.08 (m, 3H), 3.60-3.62 (m, 4H), 3.30 (s, 1H), 3.16 (t, 2H), 3.04 (t, 2H), 2.71 (t, 2H), 2.50-2.52 (m, 2H), 2.47 (s, 3H), 2.28 (s, 3H). LRMS [M+H]=457.3

Example 148

2-(2-(4-(2-(5-amino-8-methylbenzo[f][1,7]naphthyridin-2-yl)ethyl)-3-methylphenoxy)ethoxy)ethanol

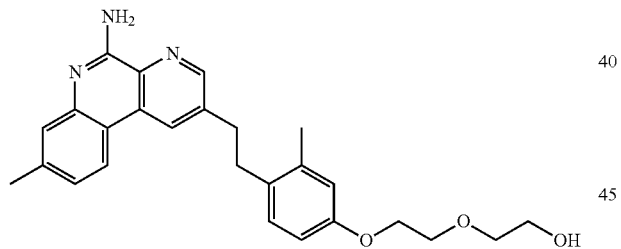

Step 1: 2-(4-(2-(2-(tert-butyldimethylsilyloxy)ethoxy)ethoxy)-2-methylphenethyl)-8-methylbenzo[f][1,7]naphthyridin-5-amine 2-(4-(2-(2-(Tert-butyldimethylsilyloxy)ethoxy)ethoxy)-2-methylphenethyl)-8-methylbenzo[f][1,7]naphthyridin-5-amine was prepared following an analogous procedure to the preparation described for Example 145/Step 1, but using 4-(2-(5-amino-8-methylbenzo[f][1,7]naphthyridin-2-yl)ethyl)-3-methylphenol (from Example 50) with tert-butyl (2-(2-chloroethoxy)ethoxy)dimethylsilane.

Step 2: 2-(2-(4-(2-(5-Amino-8-methylbenzo[f][1,7]naphthyridin-2-yl)ethyl)-3-methylphenoxy)ethoxy)ethanol 2-(2-(4-(2-(5-Amino-8-methylbenzo[f][1,7]naphthyridin-2-yl)ethyl)-3-methylphenoxy)ethoxy)ethanol was prepared from 2-(4-(2-(2-(tert-butyldimethylsilyloxy)ethoxy)ethoxy)-2-methylphenethyl)-8-methylbenzo[f][1,7]naphthyridin-5-amine (from the previous step) following the procedures described for Example 145/Step 2. $^1$H NMR (Acetone-d$_6$): δ 8.74 (s, 1H), 8.69 (s, 1H), 8.27 (d, 1H), 7.41 (s, 1H), 7.14 (d, 1H), 7.06 (d, 1H), 6.75 (s, 1H), 6.69 (d, 1), 6.54 (br, 2H), 4.07 (t, 2H), 3.79 (t, 2H), 3.64 (t, 2H), 3.59 (t, 2H), 3.16 (t, 2H), 3.03 (t, 2H), 2.45 (s, 3H), 2.29 (s, 3H). LRMS [M+H]=432.2

Example 149 diethyl 3-(4-(2-(5-amino-8-methylbenzo[f][1,7]naphthyridin-2-yl)ethyl)-3-methylphenoxy)propylphosphonate

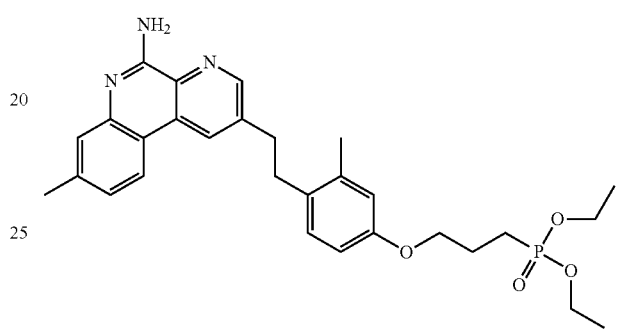

Diethyl 3-(4-(2-(5-amino-8-methylbenzo[f][1,7]naphthyridin-2-yl)ethyl)-3-methylphenoxy)propylphosphonate was prepared following an analogous procedure to the preparation described for Example 139, but using 4-(2-(5-amino-8-methylbenzo[f][1,7]naphthyridin-2-yl)ethyl)-3-methylphenol (from Example 50) with diethyl 3-bromopropylphosphonate. $^1$H NMR (Acetone-d$_6$): δ 9.52 (s, 1H), 9.47 (s, 1H), 9.03 (d, 1H), 8.21 (s, 1H), 7.93 (d, 1H), 7.84 (d, 1H), 7.60 (br, 2H), 7.53 (s, 1), 7.45 (d, 1H), 4.76-4.91 (m, 6H), 3.93 (t, 2H), 3.81 (t, 2H), 3.24 (s, 3H), 3.06 (s, 3H), 2.76-2.86 (m, 2H), 2.61-2.72 (m, 2H), 2.07 (t, 6H). LRMS [M+H]=522.2

Example 150

3-(4-(2-(5-amino-8-methylbenzo[f][1,7]naphthyridin-2-yl)ethyl)-3-methylphenoxy)propylphosphonic acid

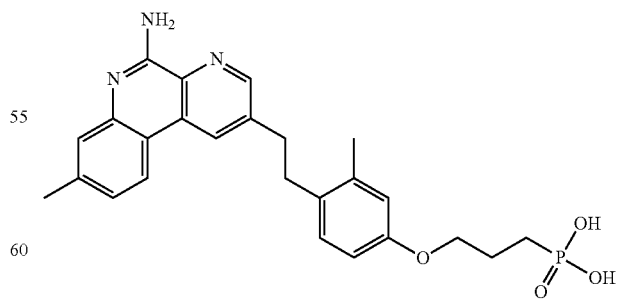

A 12 N solution of hycrochloric acid (0.10 M) was added to diethyl 3-(4-(2-(5-amino-8-methylbenzo[f][1,7]naphthyridin-2-yl)ethyl)-3-methylphenoxy)propylphosphonate (from Example 149) and the resulting mixture was allowed to stir at 100° C. for 18 hours. At this point, hydrochloric acid was removed under reduced pressure and the resulting residue was purified by RP-HPLC using a 10-50% MeCN in water gradient. The resulting trifluoroacetate salt was then converted to the free base form by the addition of a saturated aqueous solution of sodium bicarbonate, followed by washing three times with ethyl acetate. The combined organic layers were dried with anhydrous $Na_2SO_4$, and the volatiles were removed in vacuo to deliver 3-(4-(2-(5-amino-8-methylbenzo[f][1,7]naphthyridin-2-yl)ethyl)-3-methylphenoxy)propylphosphonic acid as a solid. $^1H$ NMR (Dimethylsulfoxide-$d_6$): δ 9.72 (br, 1H), 9.01 (s, 1H), 8.96 (br, 1H), 8.85 (s, 1H), 8.54 (d, 1H), 7.54 (s, 1H), 7.42 (d, 1H), 7.08 (d, 1), 6.74 (s, 1H), 6.66 (d, 1H), 3.95 (t, 2H), 3.14 (t, 2H), 2.97 (t, 2H), 2.50 (s, 3H), 2.27 (s, 3H), 1.81-1.91 (m, 2H), 1.56-1.67 (m, 2H). LRMS [M+H]=466.2

Example 151

2-(4-butoxy-2-methylphenethyl)-8-methylbenzo[f][1,7]naphthyridin-5-amine

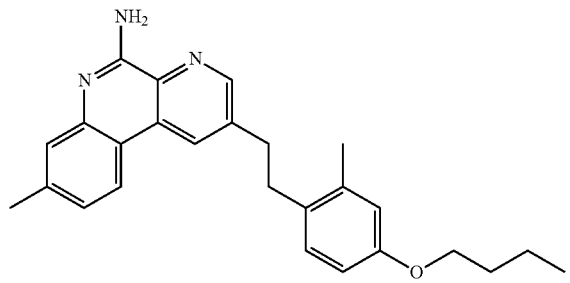 [SMILES: CCCCOc1ccc(CCc2cnc3c(N)nc4cc(C)ccc4c3c2)c(C)c1]

2-(4-Butoxy-2-methylphenethyl)-8-methylbenzo[f][1,7]naphthyridin-5-amine was prepared following an analogous procedure to the preparation described for Example 139, but using 4-(2-(5-amino-8-methylbenzo[f][1,7]naphthyridin-2-yl)ethyl)-3-methylphenol (from Example 50) with 1-bromobutane. $^1H$ NMR (Acetone-$d_6$): δ 8.75 (s, 1H), 8.71 (s, 1H), 8.28 (d, 1H), 7.43 (s, 1H), 7.15 (d, 1H), 7.07 (d, 1H), 6.75 (s, 1H), 6.69 (d, 1H), 6.54 (br, 2H) 3.95 (t, 2H), 3.16 (t, 2H), 3.04 (t, 2H), 2.47 (s, 3H), 2.30 (s, 3H), 1.69-1.77 (m, 2H), 1.43-1.54 (m, 2H), 0.97 (t, 3H). LRMS [M+H]=400.2

Example 152

2-(4-(2-(5-aminobenzo[f][1,7]naphthyridin-2-yl)ethyl)-3-methylphenoxy)ethanol

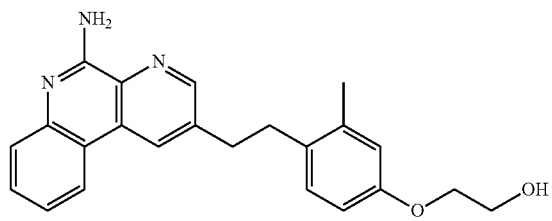 [SMILES: Cc1cc(OCCO)ccc1CCc1cnc2c(N)nc3ccccc3c2c1]

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 145, but using 2-(4-Methoxy-2-methylphenethyl)benzo[f][1,7]naphthyridin-5-amine (from Example 119).

Step 2: 2-(4-(2-(5-Aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared from 4-(2-(5-aminobenzo[f][1,7]naphthyridin-2-yl)ethyl)-3-methylphenol (from the previous step) following the procedures described for Example 145/Steps 1 to 2. LRMS [M+H]=374.2

Example 153

2-(4-(2-(5-aminobenzo[f][1,7]naphthyridin-2-yl)ethyl)-3-methylphenoxy)ethanol

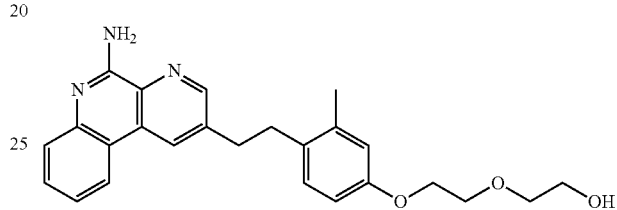

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 50, but using 2-(4-Methoxy-2-methylphenethyl)benzo[f][1,7]naphthyridin-5-amine (from Example 119).

Step 2: 2-(4-(2-(5-Aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared following the procedures described for Example 148/Steps 1 to 2. LRMS [M+H]=418.2

Example 154 ethyl 5-(4-(2-(5-amino-8-methylbenzo[f][1,7]naphthyridin-2-yl)ethyl)-3-methylphenoxy)pentanoate

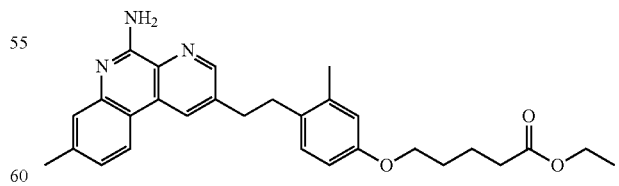

Ethyl 5-(4-(2-(5-amino-8-methylbenzo[f][1,7]naphthyridin-2-yl)ethyl)-3-methylphenoxy)pentanoate was prepared from 4-(2-(5-amino-8-methylbenzo[f][1,7]naphthyridin-2-yl)ethyl)-3-methylphenol (from Example 50) following the procedure described for Example 139, but using ethyl 5-bromopentanoate. $^1H$ NMR (CDCl3): δ 8.64 (s, 1H), 8.27 (s, 1H), 8.02 (d, 1H), 7.66 (s, 1H), 7.32 (d, 1H), 6.91 (d, 1H), 6.66 (s, 1H), 6.63 (d, 1H), 4.13 (q, 2H), 3.93 (t, 2H), 3.14 (t, 2H), 2.99 (t, 2H), 2.54 (s, 3H), 2.38 (t, 2H), 2.25 (s, 3H), 1.79-1.83 (m, 4H), 1.26 (t, 3H). LRMS [M+H]=472.3

Example 155

5-(4-(2-(5-amino-8-methylbenzo[f][1,7]naphthyridin-2-yl)ethyl)-3-methylphenoxy)pentanoic acid

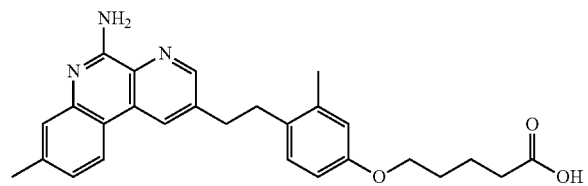 [SMILES: Cc1ccc2c(c1)nc(N)c1ncc(CCc3ccc(OCCCCC(=O)O)cc3C)cc12]

5-(4-(2-(5-Amino-8-methylbenzo[f][1,7]naphthyridin-2-yl)ethyl)-3-methylphenoxy)pentanoic acid was prepared from ethyl 5-(4-(2-(5-amino-8-methylbenzo[f][1,7]naphthyridin-2-yl)ethyl)-3-methylphenoxy)pentanoate (from the previous step) following the procedure described for Example 144. $^1$H NMR (CDCl3): δ 8.52 (s, 1H), 8.27 (s, 1H), 8.02 (d, 1H), 7.65 (s, 1H), 7.32 (d, 1H), 6.86 (d, 1H), 6.72 (s, 1H), 6.63 (d, 1H), 3.95 (t, 2H), 3.15 (t, 2H), 2.99 (t, 2H), 2.54 (s, 3H), 2.45 (t, 2H), 2.23 (s, 3H), 1.79-1.83 (m, 4H). LRMS [M+H]=444.2

Example 156

2-(4-(2-(5-amino-8-methylbenzo[f][1,7]naphthyridin-2-yl)ethyl)-3-methylphenoxy)ethanol

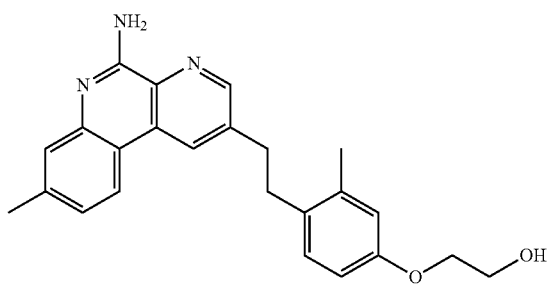 [SMILES: Cc1ccc2c(c1)nc(N)c1ncc(CCc3ccc(OCCO)cc3C)cc12]

2-(4-(2-(5-Amino-8-methylbenzo[f][1,7]naphthyridin-2-yl)ethyl)-3-methylphenoxy)ethanol was prepared following the procedures described for Example 145/Steps 1 to 2, but using 4-(2-(5-amino-8-methylbenzo[f][1,7]naphthyridin-2-yl)ethyl)-3-methylphenol (from Example 50). $^1$H NMR (Acetone-d$_6$): δ 8.76 (s, 1H), 8.69 (s, 1H), 8.28 (d, 1H), 7.40 (s, 1H), 7.15 (d, 1H), 7.09 (d, 1H), 6.75 (s, 1H), 6.68 (d, 1H), 6.57 (br, 2H), 4.00 (t, 2H), 3.79-3.88 (m, 2H), 3.17 (t, 2H), 3.04 (t, 2H), 2.46 (s, 2H), 2.29 (s, 2H). LRMS [M+H]=388.5.

Example 157

4-(2-(5-amino-8-methylbenzo[f][1,7]naphthyridin-2-yl)ethyl)phenyl ethyl carbonate

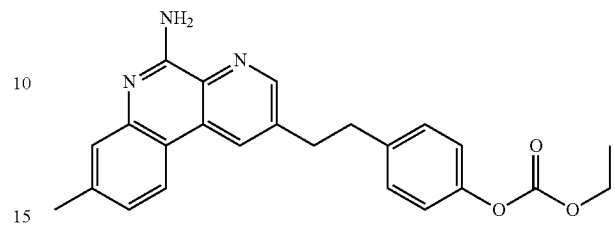

4-(2-(5-Amino-8-methylbenzo[f][1,7]naphthyridin-2-yl)ethyl)phenyl ethyl carbonate was prepared from 4-(2-(5-amino-8-methylbenzo[f][1,7]naphthyridin-2-yl)ethyl)phenol (from Example 170) following the procedure described for Example 138, but using ethyl carbonochloridate. LRMS [M+H]=402.2

Example 158 methyl 4-(4-(2-(5-amino-8-methylbenzo[f][1,7]naphthyridin-2-yl)ethyl)phenoxy)butanoate

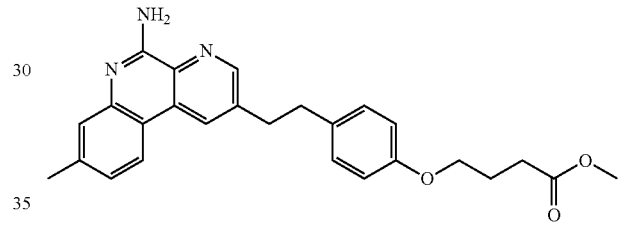

Methyl 4-(4-(2-(5-amino-8-methylbenzo[f][1,7]naphthyridin-2-yl)ethyl)phenoxy)butanoate was prepared from 4-(2-(5-amino-8-methylbenzo[f][1,7]naphthyridin-2-yl)ethyl)phenol (from Example 170) following the procedure described for the preparation of Example 139, but using methyl 4-bromobutanoate. $^1$H NMR (Acetone-d$_6$): δ 8.74 (s, 1H), 8.67 (s, 1H), 8.24 (d, 1H), 7.39 (s, 1H), 7.09-7.19 (m, 3H), 6.82 (d, 2H), 6.53 (br, 2H), 3.97 (t, 2H), 3.60 (s, 3H), 3.19 (t, 2H), 3.04 (t, 2H), 2.48 (t, 2H), 2.44 (s, 3H), 0.84-0.91 (m, 2H). LRMS [M+H]=430.2.

Example 159

4-(4-(2-(5-amino-8-methylbenzo[f][1,7]naphthyridin-2-yl)ethyl)phenoxy)butanoic acid

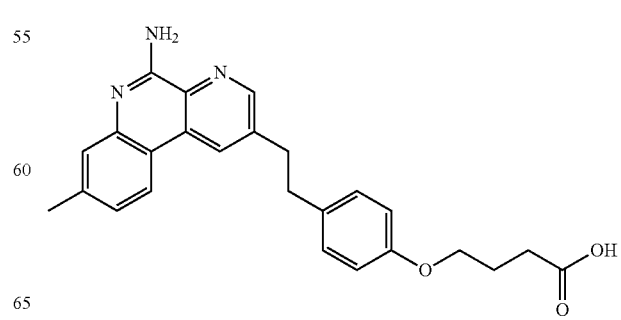

4-(4-(2-(5-Amino-8-methylbenzo[f][1,7]naphthyridin-2-yl)ethyl)phenoxy)butanoic acid was prepared from methyl 4-(4-(2-(5-amino-8-methylbenzo[f][1,7]naphthyridin-2-yl)ethyl)phenoxy)butanoate (from the previous step) following the procedure described for Example 144. $^1$H NMR (Acetone-$d_6$): δ 7.47 (s, 1H), 7.41 (s, 1H), 7.09 (d, 1H), 6.21 (s, 1H), 6.18 (d, 1H), 5.82 (d, 2H), 5.52 (d, 2H), 2.66 (t, 2H), 1.99 (t, 2H), 1.77 (t, 2H), 1.28 (s, 3H), 1.17 (t, 2H), 0.70-0.79 (m, 2H). LRMS [M+H]=416.2.

Example 160

4-(4-(2-(5-amino-8-methylbenzo[f][1,7]naphthyridin-2-yl)ethyl)-3-methylphenoxy)butanoic acid

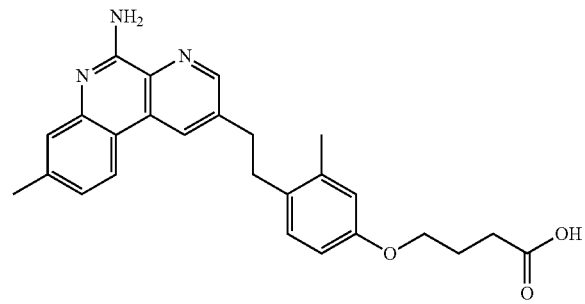 [SMILES: Cc1ccc2c(c1)nc(N)c1ncc(CCc3ccc(OCCCC(=O)O)cc3C)cc12]

Step 1: methyl 4-(4-(2-(5-amino-8-methylbenzo[f][1,7]naphthyridin-2-yl)ethyl)-3-methylphenoxy)butanoate Methyl 4-(4-(2-(5-amino-8-methylbenzo[f][1,7]naphthyridin-2-yl)ethyl)-3-methylphenoxy)butanoate was prepared following the same procedure described for the preparation of Example 158, but using 4-(2-(5-amino-8-methylbenzo[f][1,7]naphthyridin-2-yl)ethyl)-3-methylphenol (from Example 50).

Step 2: 4-(4-(2-(5-Amino-8-methylbenzo[f][1,7]naphthyridin-2-yl)ethyl)-3-methylphenoxy)butanoic acid 4-(4-(2-(5-Amino-8-methylbenzo[f][1,7]naphthyridin-2-yl)ethyl)-3-methylphenoxy)butanoic acid was prepared from methyl 4-(4-(2-(5-amino-8-methylbenzo[f][1,7]naphthyridin-2-yl)ethyl)-3-methylphenoxy)butanoate (from the previous step) following the procedure described for Example 144. $^1$H NMR (Acetone-$d_6$): δ 8.38 (s, 1H), 8.24 (s, 1H), 7.90 (d, 1H), 6.90 (s, 1H), 6.68 (d, 1H), 6.54-6.63 (m, 2H), 6.27 (d, 1H), 6.20 (d, 1H), 3.40 (t, 2H), 2.62 (t, 2H), 2.47 (t, 2H), 1.99 (s, 3H), 1.80 (s, 2H), 1.45 (t, 2H), 1.27-1.39 (m, 2H). LRMS [M+H]=430.2.

Example 161

2-(4-(isopentyloxy)-2-methylphenethyl)-8-methylbenzo[f][1,7]naphthyridin-5-amine

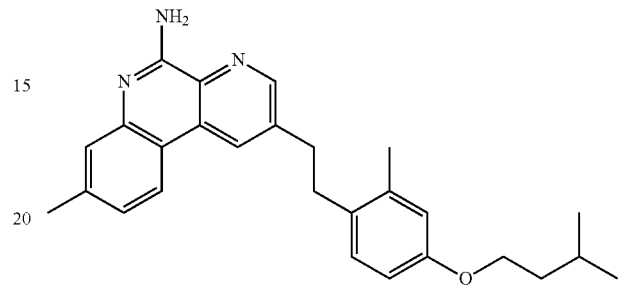

2-(4-(Isopentyloxy)-2-methylphenethyl)-8-methylbenzo[f][1,7]naphthyridin-5-amine was prepared from 4-(2-(5-amino-8-methylbenzo[f][1,7]naphthyridin-2-yl)ethyl)-3-methylphenol (from Example 50) following the procedure described for Example 136, but using 1-bromo-3-methylbutane. $^1$H NMR (Acetone-$d_6$): δ 8.75 (s, 1H), 8.72 (s, 1H), 8.29 (d, 1H), 7.43 (s, 1H), 7.17 (D, 1H), 7.10 (d, 1H), 6.76 (d, 1H), 6.68 (d, 1H), 6.56 (br, 2H), 4.00 (t, 2H), 3.17 (t, 2H), 3.07 (t, 2H), 2.48 (s, 3H), 1.76-1.91 (m, 1H), 1.60-1.71 (m, 2H), 0.96 (s, 6H). LRMS [M+H]=414.2.

Example 162

4-(2-(5-amino-8-methylbenzo[f][1,7]naphthyridin-2-yl)ethyl)phenyl hexyl carbonate

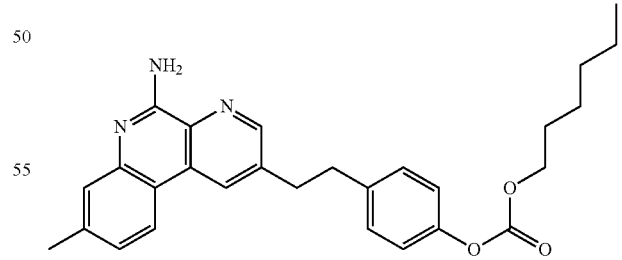

4-(2-(5-Amino-8-methylbenzo[f][1,7]naphthyridin-2-yl)ethyl)phenyl hexyl carbonate was prepared from 4-(2-(5-amino-8-methylbenzo[f][1,7]naphthyridin-2-yl)phenol (from Example 170) following the procedures described for Example 138, but using hexyl carbonochloridate. LRMS [M+H]=458.2.

Example 163

2-(2,4,6-trimethylphenethyl)benzo[f][1,7]naphthyridin-5-amine

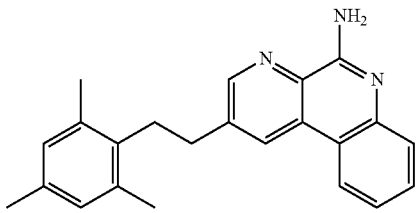 [SMILES: Cc1cc(C)c(CCc2cnc3c(N)nc4ccccc4c3c2)c(C)c1]

Step 1: 2-(mesitylethynyl)benzo[f][1,7]naphthyridin-5-amine 2-(Mesitylethynyl)benzo[f][1,7]naphthyridin-5-amine was prepared from 3-chloro-5-(mesitylethynyl)picolinonitrile (Example 77/Step 1) and tert-butyl 2-(4,4,5,5-tetramethyl-1,3,2-dioxaborolan-2-yl)phenylcarbamate (commercially available) following the procedures described for Example 45/Step 1.

Step 2: 2-(2,4,6-Trimethylphenethyl)benzo[f][1,7]naphthyridin-5-amine 2-(2,4,6-Trimethylphenethyl)benzo[f][1,7]naphthyridin-5-amine was prepared from 2-(mesitylethynyl)benzo[f][1,7]naphthyridin-5-amine (from the previous step) following the procedures described for Example 45/Step 2 to 3. $^1$H NMR (Acetone-$d_6$): δ 8.80 (s, 2H), 8.38 (d, 1H), 7.60 (d, 2H), 7.54 (d, 2H), 7.31 (t, 1H), 6.84 (s, 2H), 6.61 (br, 2H), 3.08 (s, 2H), 2.30 (s, 6H), 2.23 (s, 3H). LRMS [M+H]=342.2.

Example 164

(5-amino-2-(2,4-dimethylphenethyl)benzo[f][1,7]naphthyridin-8-yl)methanol

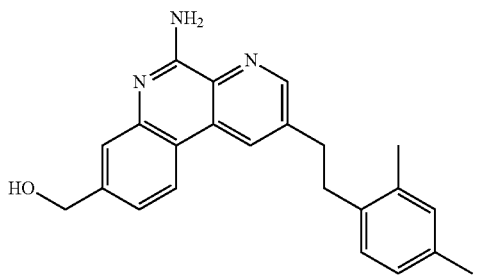 [SMILES: Cc1ccc(CCc2cnc3c(N)nc4cc(CO)ccc4c3c2)c(C)c1]

Step 1: methyl 5-amino-2-((2,4-dimethylphenyl)ethynyl)benzo[f][1,7]naphthyridine-8-carboxylate Methyl 5-amino-2-((2,4-dimethylphenyl)ethynyl)benzo[f][1,7]naphthyridine-8-carboxylate was prepared from 3-chloro-5-((2,4-d methylphenyl) ethynyl)picolinonitrile (from Example 47/Step 3) and 2-(tert-butoxycarbonylamino)-4-(methoxycarbonyl) phenylboronic acid (from Example 85/Step 1) following the procedures described in Example 95/step 1.

Step 2: methyl 5-amino-2-(2,4-dimethylphenethyl)benzo[f][1,7]naphthyridin-8-carboxylate Methyl 5-amino-2-(2,4-dimethylphenethyl)benzo[f][1,7]naphthyridine-8-carboxylate was prepared from methyl 5-amino-2-((2,4-dimethylphenyl)ethynyl) benzo[f][1,7]naphthyridine-8-carboxylate (from the previous step) following the procedures described in Example 44/Step 5.

Step 3: (5-amino-2-(2,4-dimethylphenethyl)benzo[f][1,7]naphthyridin-8-yl)methanol (5-Amino-2-(2,4-dimethylphenethyl)benzo[f][1,7]naphthyridin-8-yl)methanol was prepared from methyl 5-amino-2-(2,4-dimethylphenethyl)benzo[f][1,7]naphthyridine-8-carboxylate (from the previous step) following the procedures described in Example 95/Step 2. $^1$H NMR (Acetone-$d_6$): δ 8.79 (s, 1H), 8.73 (s, 1H), 8.35 (d, 1H), 7.61 (s, 1H), 7.34 (d, 1H), 7.08 (d, 1H), 6.97 (s, 1H), 6.91 (d, 1H), 6.51 (br. 2H), 4.77 (s, 2H), 3.16-3.20 (m, 2H), 3.04-3.10 (m, 2H), 2.28 (s, 3H), 2.25 (s, 3H). LRMS [M+H]=358.2.

Example 165 diethyl 3-(2-(4-(2-(5-amino-8-methylbenzo[f][1,7]naphthyridin-2-yl)ethyl)-3-methylphenoxy)ethoxy)propylphosphonate

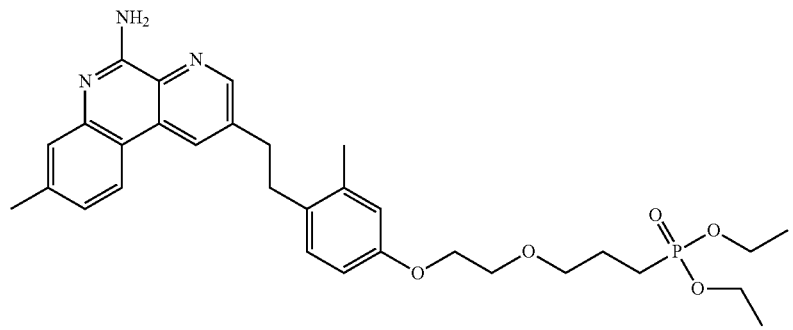 [SMILES: CCOP(=O)(CCCOCCOc1ccc(CCc2cnc3c(N)nc4cc(C)ccc4c3c2)c(C)c1)OCC]

Diethyl 3-(2-(4-(2-(5-amino-8-methylbenzo[f][1,7]naphthyridin-2-yl)ethyl)-3-methylphenoxy)ethoxy)propylphosphonate was prepared following the procedure described for Example 139, but using 4-(2-(5-amino-8-methylbenzo[f][1,7]naphthyridin-2-yl)ethyl)-3-methylphenol (from Example 156) and diethyl 3-(2-bromoethoxy)propylphosphonate. LRMS [M+H]=566.3.

Example 166 diethyl 3-(2-(2-(4-(2-(5-amino-8-methylbenzo[f][1,7]naphthyridin-2-yl)ethyl)-3-methylphenoxy)ethoxy)ethoxy)propylphosphonate

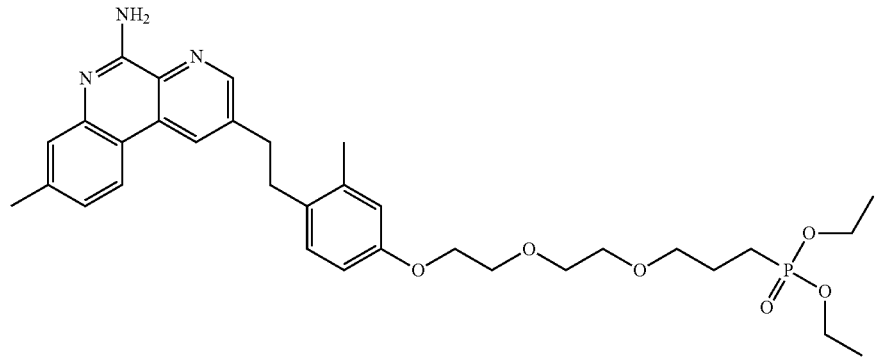 [SMILES: CCOP(=O)(CCCOCCOCCOc1ccc(CCc2cnc3c(N)nc4cc(C)ccc4c3c2)c(C)c1)OCC]

Diethyl 3-(2-(2-(4-(2-(5-amino-8-methylbenzo[f][1,7]naphthyridin-2-yl)ethyl)-3-methylphenoxy)ethoxy)ethoxy)propylphosphonate was prepared from following the procedure described for Example 139, but using 4-(2-(5-amino-8-methylbenzo[f][1,7]naphthyridin-2-yl)ethyl)-3-methylphenol (from Example 148) and diethyl 3-(2-(2-bromoethoxy)ethoxy)propylphosphonate. $^1$H NMR (Acetone-d$_6$): δ 8.75 (s, 1H), 8.70 (s, 1H), 8.26 (d, 1H), 7.42 (s, 1H), 7.16 (d, 1H), 7.09 (d, 1H), 6.77 (s, 1H), 6.71 (d, 1H), 6.58 (br, 2H), 3.95-4.11 (m, 6H), 3.76-3.80 (m, 2H), 3.63-3.67 (m, 2H), 3.55-3.58 (m, 2H), 3.57-3.51 (m, 2H), 3.14-3.18 (m, 2H), 3.04-3.05 (m, 2H), 2.46 (s, 3H), 2.29 (s, 3H), 1.71-1.87 (m, 4H), 1.22-1.29 (m, 8H). LRMS [M+H]=610.3.

Example 167

4-(2-(5-amino-8-methylbenzo[f][1,7]naphthyridin-2-yl)ethyl)-3-methylphenyl dimethylsulfamate

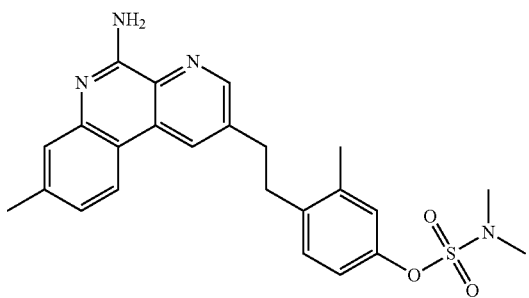

4-(2-(5-Amino-8-methylbenzo[f][1,7]naphthyridin-2-yl)ethyl)-3-methylphenyl dimethylsulfamate was prepared from 4-(2-(5-amino-8-methylbenzo[f][1,7]naphthyridin-2-yl)ethyl)-3-methylphenol (from Example 50) following the procedure described for Example 138, but using dimethylsulfamoyl chloride. $^1$H NMR (Acetone-d$_6$): δ 8.79 (s, 1H), 8.72 (s, 1H), 8.28 (d, 1H), 7.42 (s, 1H), 7.27 (d, 1H), 7.17 (s, 1H), 7.14 (t, 1H), 7.05-7.10 (d, 1H), 3.19-3.25 (m, 2H), 3.11-3.17 (m, 2H), 2.92 (s, 6H), 2.46 (s, 3H), 2.37 (s, 3H). LRMS [M+H]=451.2.

Example 168

(5-amino-2-(4-(dimethylamino)phenethyl)benzo[f][1,7]naphthyridin-8-yl)methanol

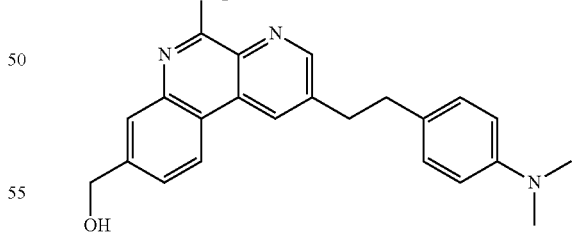

(5-Amino-2-(4-(dimethylamino)phenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 99/step 1) and 4-ethynyl-N,N-dimethylaniline (commercially available) following the procedures described in Example 45/Step 1 to 4 followed by deprotection of TBS group as in Example 99/Step 3. $^1$H NMR (Acetone-d$_6$): δ 8.78 (s, 1H), 8.73 (s, 1H), 8.35 (d, 1H), 7.61

(s, 1H), 7.31-7.35 (d, 1H), 7.08 (d, 1H), 6.68 (d, 2H), 6.50 (br, 2H), 4.78 (s, 2H), 4.34 (s, 1H), 3.16-3.20 (m, 2H), 3.03-3.10 (m, 2H), 2.83 (s, 3H), 2.80 (s, 3H). LRMS [M+H]=373.2.

Example 169

2-(4-(dimethylamino)phenethyl)-8-methylbenzo[f][1,7]naphthyridin-5-amine

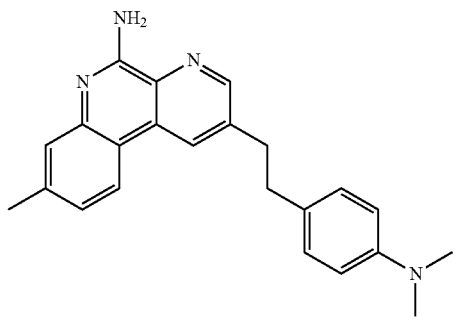

2-(4-(Dimethylamino)phenethyl)-8-methylbenzo[f][1,7]naphthyridin-5-amine was prepared following the procedures described for Example 45/Steps 1 to 3, but using 4-ethynyl-N,N-dimethylaniline in step 1. $^1$H NMR (Acetone-$d_6$) Free base: δ 8.60 (s, 1H), 8.55 (s, 1H), 8.15 (d, 1H), 7.28 (s, 1H), 7.03 (d, 1H), 6.96 (d, 2H), 6.56 (d, 2H), 6.55 (br s, 2H), 3.05 (t, 2H), 2.88 (t, 2H), 2.75 (s, 6H), 2.33 (s, 3H). LRMS [M+H]=357.2

Example 170

4-(2-(5-amino-8-methylbenzo[f][1,7]naphthyridin-2-yl)ethyl)phenol

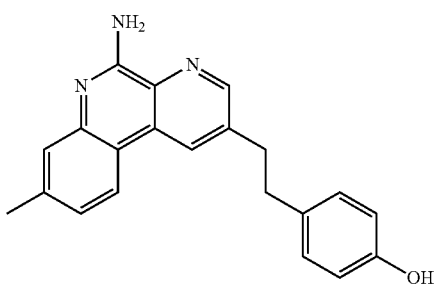 [SMILES: Cc1ccc2c(c1)nc(N)c1ncc(CCc3ccc(O)cc3)cc12]

Step 1: 2-(4-methoxyphenethyl)-8-methylbenzo[f][1,7]naphthyridin-5-amine 2-(4-methoxyphenethyl)-8-methylbenzo[f][1,7]naphthyridin-5-amine was prepared following the procedures described for Example 79/Steps 1 to 3, but using 1-ethynyl-4-methoxybenzene in Step 1.

Step 2: 4-(2-(5-Amino-8-methylbenzo[f][1,7]naphthyridin-2-yl)ethyl)phenol 4-(2-(5-Amino-8-methylbenzo[f][1,7]naphthyridin-2-yl)ethyl)phenol was prepared from 2-(4-methoxyphenethyl)-8-methylbenzo[f][1,7]naphthyridin-5-amine (from the previous step) following the procedure described for Example 50. $^1$H NMR (Methanol-$d_4$): δ 8.59

Example 171

1-(4-(2-(5-amino-8-methylbenzo[f][1,7]naphthyridin-2-yl)ethyl)phenyl)ethanone

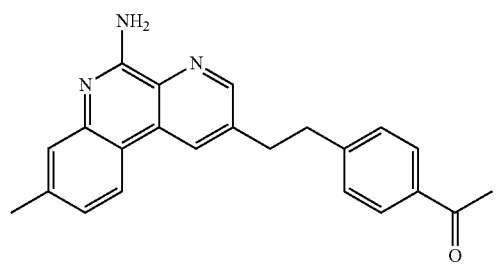 [SMILES: CC(=O)c1ccc(CCc2cnc3c(N)nc4cc(C)ccc4c3c2)cc1]

Step 1: 5-((4-acetylphenyl)ethynyl)-3-chloropicolinonitrile

To a solution of 1-(4-ethynylphenyl)ethanone (commercially available) (1 eq) 3,5-dichloropicolinonitrile (1 eq), dichlorobis(triphenylphosphine)-palladium (II) (20 mol %), copper iodide (10 mol %) and DMF: Triethylamine (10:1) (0.13 M) was stirred at ambient temperature overnight. The reaction mixture was then diluted with ethyl acetate and sodium bicarbonate solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 5-((4-acetylphenyl)ethynyl)-3-chloropicolinonitrile was isolated as a yellow solid Step 2: 5-(4-acetylphenethyl)-3-chloropicolinonitrile To a solution of 5-((4-acetylphenyl)ethynyl)-3-chloropicolinonitrile (from the previous step) (1 eq) in ethanol (0.1 M) was added Platinum Oxide (30 mol %). Hydrogen gas was introduced via a balloon, and the reaction was stirred for 0.5 hour. The mixture was filtered through a pad of celite, washing with dichloromethane. The filtrate was concentrated en vaccuo and purified by flash chromatography on a COMBIFLASH® system (ISCO) using 0-100% ethyl acetate in hexane to give 5-(4-acetylphenethyl)-3-chloropicolinonitrile as an off-white solid.

To a solution of 5-(4-acetylphenethyl)-3-chloropicolinonitrile (from the previous step) (1 eq) and tert-butyl 5-methyl-2-(4,4,5,5-tetramethyl-1,3,2-dioxaborolan-2-yl)phenylcarbamate (1.0 eq.), tetrakis(triphenyl-phosphine)palladium (10 mol %), and 2N aqueous sodium carbonate solution (2.0 eq.) in toluene/ethanol (1:1, 0.09 M) was heated under microwave condition using a BIOTAGE INITIATOR 2.0 at 150° C. for 20 minutes. After cooling to ambient temperature, the reaction mixture was diluted with ethanol/water. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 1-(4-(2-(5-amino-8-methylbenzo

[f][1,7]naphthyridin-2-yl)ethyl)phenyl)ethanone as a yellow solid. $^1$H NMR (Methanol-d$_4$) TFA Salt: δ 8.69 (d, 2H), 8.30 (d, 1H), 7.80 (d, 2H), 7.38 (s, 1H), 7.36 (d, 1H), 7.28 (d, 2H), 3.25 (t, 2H), 3.13 (t, 2H), 2.47 (s, 3H), 2.45 (s, 3H). LRMS [M+H]=356.2

Example 172

2-(4-((dimethylamino)methyl)phenethyl)-8-methyl-benzo[f][1,7]naphthyridin-5-amine

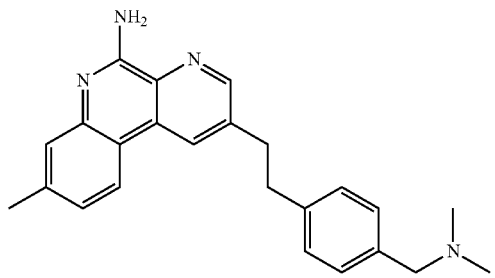

Step 1: 4-(2-(5-amino-8-methylbenzo[f][1,7]naphthyridin-2-yl)ethyl)benzaldehyde 4-(2-(5-Amino-8-methylbenzo[f][1,7]naphthyridin-2-yl)ethyl)benzaldehyde was prepared from 4-ethynylbenzaldehyde (commercially available) following the procedures described for Example 171/Steps 1 to 3.

Step 2: 2-(4-((dimethylamino)methyl)phenethyl)-8-methylbenzo[f][1,7]naphthyridin-5-amine A solution of 4-(2-(5-amino-8-methylbenzo[f][1,7]naphthyridin-2-yl)ethyl)benzaldehyde (from the previous step) (1 eq), sodium acetate (3.5 eq) and N, N'-dimethyl amine hydrochloride (3.5 eq) dissolved in 1-2, dichloroethane (0.04 M) was heated at 80° C. for 2 hours in a sealed vial. After cooling to ambient temperature, the reaction mixture was further cooled down to 0° C. and sodium tri-acetoxy borohydride (1.25 eq) was added. The reaction mixture was stirred at room temperature for one hour. The mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by preparative HPLC using 10-90% acetonitrile/water as the gradient and 2-(4-((dimethylamino)methyl)phenethyl)-8-methylbenzo[f][1,7]naphthyridin-5-amine was isolated as a off-white powder as a TFA salt. $^1$H NMR (Methanol-d$_4$) TFA Salt: δ 8.83 (s, 1H), 8.81 (s, 1H), 8.41 (d, 1H), 7.52 (s, 1H), 7.45 (d, 1H), 7.43 (s, 1H), 7.40 (m, 3H), 4.29 (s, 2H), 3.30-3.24 (m, 4H), 2.79 (s, 6H), 2.60 (s, 3H). LRMS [M+H]=371.2

Example 173

2-(4-(1-(dimethylamino)ethyl)phenethyl)-8-methyl-benzo[f][1,7]naphthyridin-5-amine

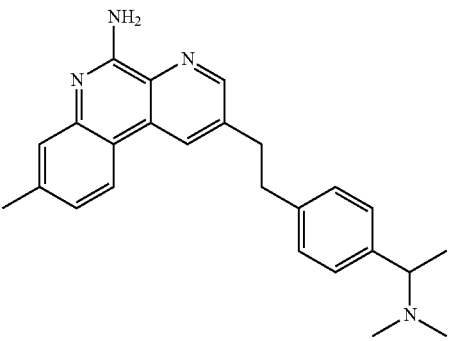

2-(4-(1-(Dimethylamino)ethyl)phenethyl)-8-methyl-benzo[f][1,7]naphthyridin-5-amine was prepared from 1-(4-(2-(5-amino-8-methylbenzo[f][1,7]naphthyridin-2-yl)ethyl)phenyl)ethanone (from Example 171) following the procedures described for Example 172/Step 2. $^1$H NMR (Methanol-d$_4$) TFA Salt: δ 8.84 (s, 1H), 8.79 (s, 1H), 8.40 (d, 1H), 7.52 (s, 1H), 7.44-7.46 (m, 2H), 7.38-7.42 (m, 3H), 4.45 (m, 1H), 3.31 (t, 2H), 3.19 (t, 2H), 2.83 (s, 3H), 2.66 (s, 3H), 2.56 (s, 3H), 1.70 (d, 3H). LRMS [M+H]=385.2

Example 174

1-(4-(2-(5-amino-8-methylbenzo[f][1,7]naphthyridin-2-yl)ethyl)phenyl)ethanone oxime

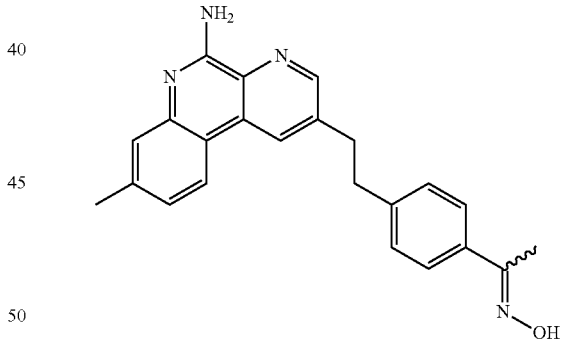

A solution of 1-(4-(2-(5-amino-8-methylbenzo[f][1,7]naphthyridin-2-yl)ethyl)phenyl)ethanone (from Example 171) (1 eq), hydroxylamine hydrochloride (2 eq) and 1 drop of HOAc, dissolved in absolute ethanol (0.028M) was stirred at room temperature for 1.5 hours. The mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 10-80% ethyl acetate in hexane to give 1-(4-(2-(5-amino-8-methylbenzo[f][1,7]naphthyridin-2-yl)ethyl)phenyl)ethanone oxime as a white solid. $^1$H NMR (Methanol-d$_4$): δ 8.56 (s, 1H), 8.52 (s, 1H), 8.12 (d, 1H), 7.45 (d, 2H), 7.31 (s, 1H), 7.12 (m, 3H), 4.51 (s, OH), 3.15 (t, 2H), 3.01 (t, 2H), 2.39 (s, 3H), 2.09 (s, 3H). LRMS [M+H]=371.2

Example 175

8-methyl-2-(4-((methylamino)methyl)phenethyl) benzo[f][1,7]naphthyridin-5-amine

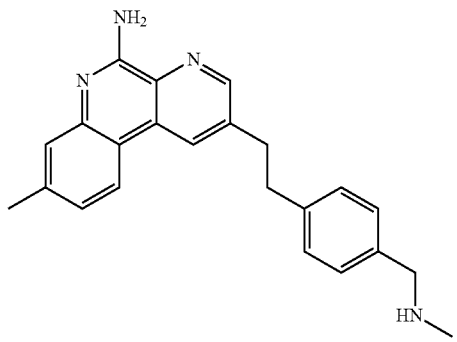

8-Methyl-2-(4-((methylamino)methyl)phenethyl)benzo[f][1,7]naphthyridin-5-amine was prepared from 4-(2-(5-Amino-8-methylbenzo[f][1,7]naphthyridin-2-yl)ethyl)benzaldehyde (from Example 172/Step 1) and methylamine following the procedures described for Example 172, step 2. $^1$H NMR (Acetone-$d_6$) TFA Salt: δ 8.95 (s, 1H), 8.88 (s, 1H), 8.43 (d, 1H), 7.58 (s, 1H), 7.54 (d, 2H), 7.42 (d, 1H), 7.37 (d, 2H), 4.30 (s, 2H), 3.32-3.37 (m, 4H), 2.75 (s, 3H), 2.55 (s, 3H). LRMS [M+H]=357.2

Example 176

(4-(2-(5-amino-8-methylbenzo[f][1,7]naphthyridin-2-yl)ethyl)benzylamino)ethanol

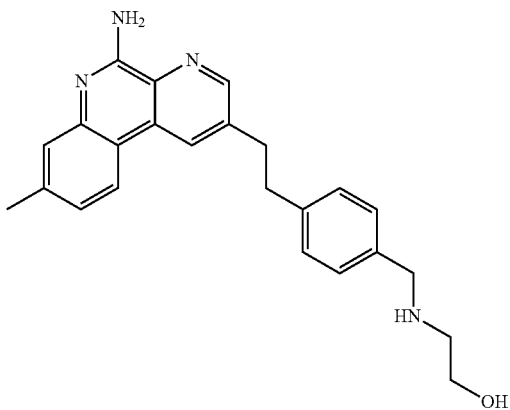 [SMILES: Cc1ccc2c(c1)nc(N)c1ncc(CCc3ccc(CNCCO)cc3)cc12]

A solution of 4-(2-(5-amino-8-methylbenzo[f][1,7]naphthyridin-2-yl)ethyl)benzaldehyde (from Example 172/Step 1) (1 eq), ethanol amine (8 eq) and 1 drop of HOAc, dissolved in absolute ethanol (0.018M) was stirred at 80° C. for 2 hours. The mixture was cooled down to 0° C. and NaBH$_4$ (3.5 eq) was added and the reaction mixture was stirred for another one hour at room temperature. The mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give a light yellow solid as a TFA salt. $^1$H NMR (Acetone-$d_6$) TFA Salt: δ 8.82 (s, 1H), 8.75 (s, 1H), 8.30 (d, 1H), 7.44 (m, 3H), 7.28 (d, 1H), 7.21 (d, 2H), 4.22 (s, 2H), 3.72 (t, 2H), 3.22 (t, 2H), 3.09 (m, 2H), 3.07 (t, 2H), 3.01 (bs, OH), 2.41 (s, 3H), LRMS [M+H]=387.2

Example 177

8-methyl-2-(4-(pyrrolidin-1-ylmethyl)phenethyl) benzo[f][1,7]naphthyridin-5-amine

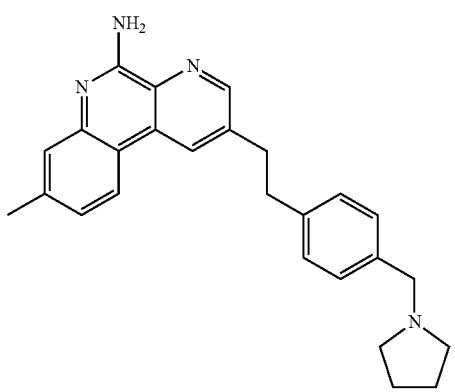 [SMILES: Cc1ccc2c(c1)nc(N)c1ncc(CCc3ccc(CN4CCCC4)cc3)cc12]

8-Methyl-2-(4-(pyrrolidin-1-ylmethyl)phenethyl)benzo[f][1,7]naphthyridin-5-amine was prepared from 4-(2-(5-Amino-8-methylbenzo[f][1,7]naphthyridin-2-yl)ethyl)benzaldehyde (from Example 172/Step 1) and pyrrolidine following the procedures described for Example 172, step 2. $^1$H NMR (Acetone-$d_6$) TFA Salt: δ 8.88 (s, 1H), 8.82 (s, 1H), 8.82 (s, 1H), 8.43 (d, 1H), 8.38 (d, 1H), 7.58 (s, 1H), 7.51 (m, 1H), 7.33 (d, 2H), 4.16 (s, 2H), 3.32-3.38 (m, 4H), 2.55 (s, 3H), 2.20-2.32 (m, 4H), 1.90-1.99 (m, 4H). LRMS [M+H]=397.2

Example 178

2-(3,4-dimethoxyphenethyl)-8-methylbenzo[f][1,7] naphthyridin-5-amine

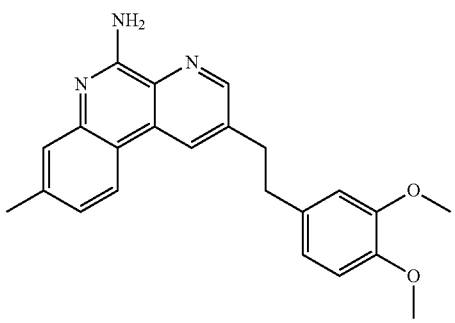

2-(3,4-Dimethoxyphenethyl)-8-methylbenzo[f][1,7]naphthyridin-5-amine was prepared from 4-ethynyl-1,2-dimethoxybenzene (commercially available) following the procedures described for Example 45/Steps 1 to 3. $^1$H NMR (Acetone-d$_6$): δ 8.64 (s, 1H), 8.56 (s, 1H), 8.14 (d, 1H), 7.29 (s, 1H), 7.03 (d, 1H), 6.77 (s, 1H), 6.71 (s, 1H), 6.62 (d, 1H), 6.45 (bs, 2H), 3.62 (s, 6H), 3.12 (t, 2H), 2.94 (t, 2H), 2.33 (s, 3H). LRMS [M+H]=374.2

Example 179

2-(1-(4-(2-(5-amino-8-methylbenzo[f][1,7]naphthyridin-2-yl)ethyl)phenyl)ethylamino)ethanol

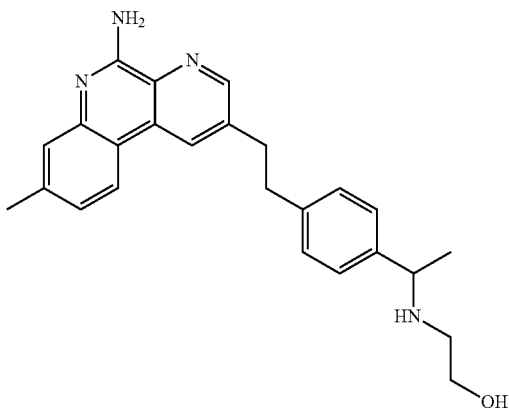

2-(1-(4-(2-(5-Amino-8-methylbenzo[f][1,7]naphthyridin-2-yl)ethyl)phenyl)ethylamino)ethanol (from Example 171) was prepared from 1-(4-(2-(5-amino-8-methylbenzo[f][1,7]naphthyridin-2-yl)ethyl)phenyl)ethanone and ethanol amine (commercially available) following the procedures described for Example 176. $^1$H NMR (Acetone-d$_6$) of TFA Salt: δ 8.78 (d, 1H), 8.29 (d, 1H), 7.83 (s, 1H), 7.45 (m, 3H), 7.28 (m, 3H), 4.22 (m, 1H), 3.52 (m, 2H), 3.23 (t, 2H), 3.09 (t, 2H), 2.85 (m, 1H), 2.65 (m, 1H), 2.41 (s, 3H), 1.61 (d, 3H). LRMS [M+H]=401.2

Example 180

1-(4-(2-(5-amino-8-methylbenzo[f][1,7]naphthyridin-2-yl)ethyl)phenyl)ethanol

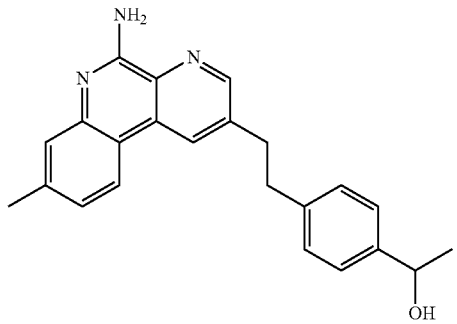 [SMILES: Cc1ccc2c(c1)nc(N)c1ncc(CCc3ccc(C(C)O)cc3)cc12]

1-(4-(2-(5-Amino-8-methylbenzo[f][1,7]naphthyridin-2-yl)ethyl)phenyl)ethanol (from Example 171) was isolated as a side product during the reductive amination as shown in Example 173. $^1$H NMR (Acetone-d$_6$) of TFA Salt: δ 8.90 (s, 1H), 8.88 (s, 1H), 8.42 (d, 1H), 7.57 (s, 1H), 7.43 (d, 1H), 7.33 (d, 2H), 7.26 (d, 2H), 4.82 (q, 1H), 3.32 (t, 2H), 3.17 (t, 2H), 3.01-2.55 (s, 3H), 1.41 (s, 3H). LRMS [M+H]=358.2

Example 181

8-methyl-2-(4-(oxazol-5-yl)phenethyl)benzo[f][1,7]naphthyridin-5-amine

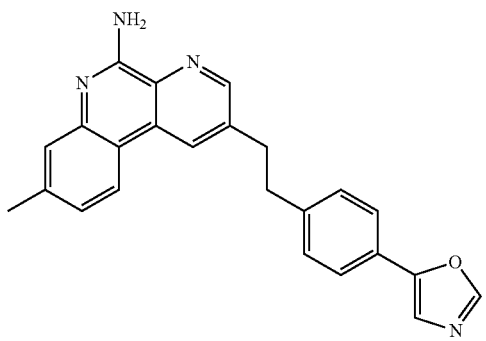 [SMILES: Cc1ccc2c(c1)nc(N)c1ncc(CCc3ccc(-c4cnco4)cc3)cc12]

8-Methyl-2-(4-(oxazol-5-yl)phenethyl)benzo[f][1,7]naphthyridin-5-amine was prepared from 5-(4-ethynylphenyl)oxazole (commercially available) following the procedures described for Example 45/Steps 1 to 3. $^1$H NMR (Acetone-d$_6$) of TFA Salt: 8.69 (s, 1H), 8.59 (s, 1H), 8.16 (d, 1H), 8.04 (s, 1H), 7.55 (m, 2H), 7.38 (s, 1H), 7.28 (m, 2H), 7.01 (m, 2H), 3.16 (t, 2H), 3.07 (t, 2H), 2.33 (s, 3H). LRMS [M+H]=381.2

Example 182

3-(1-(4-(2-(5-amino-8-methylbenzo[f][1,7]naphthyridin-2-yl)ethyl)phenyl)ethylamino)propanenitrile

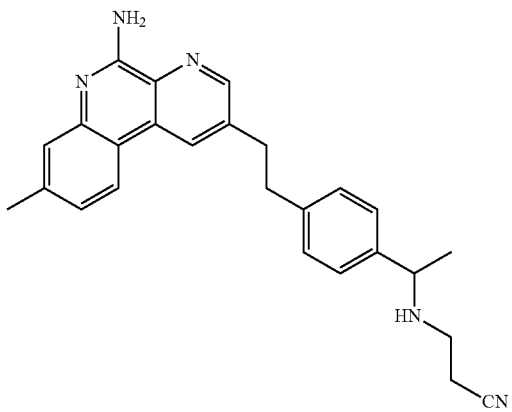 [SMILES: Cc1ccc2c(c1)nc(N)c1ncc(CCc3ccc(C(C)NCCC#N)cc3)cc12]

A solution of 1-(4-(2-(5-amino-8-methylbenzo[f][1,7]naphthyridin-2-yl)ethyl)phenyl)ethanone (from Example 171) (1 eq), 3-aminopropane nitrile (commercially available) (2.5 eq) dissolved in absolute ethanol (0.014M) was stirred at 80° C. for 2 hours. The mixture was cooled to 0° C. and NaCNBH$_3$ (2 eq) was added and the reaction mixture was stirred for another hour at room temperature. The mixture was diluted with ethyl acetate and ammonium chloride. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLAN-TIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanenitrile as a light yellow solid as a TFA salt. $^1$H NMR (Acetone-d$_6$): δ 8.60 (s, 1H), 8.59 (s, 1H), 8.11 (d, 1H), 7.29 (s, 1H), 7.16 (d, 2H), 7.09 (d, 2H), 7.03 (d, 1H), 6.43 (bs, 2H), 3.65 (m, 1H), 3.12 (t, 2H), 2.99 (t, 2H), 2.56 (m, 2H), 2.35 (m, 2H), 2.32 (s, 3H), 1.16 (d, 3H). LRMS [M+H]=410.2

Example 183

(2R)-2-(1-(4-(2-(5-amino-8-methylbenzo[f][1,7]naphthyridin-2-yl)ethyl)phenyl)ethylamino)propan-1-ol (2R)-2-(1-(4-(2-(5-amino-8-methylbenzo[f][1,7]naphthyridin-2-yl)ethyl)phenyl)ethylamino)propan-1-ol was prepared from 1-(4-(2-(5-amino-8-methylbenzo[f][1,7]naphthyridin-2-yl)ethyl)phenyl)ethanone (from Example 171) and (R)-2-aminopropan-1-ol (commercially available) following the procedures described for Example 182. $^1$H NMR (Acetone-d$_6$): δ: 8.94 (m, 2H), 8.45 (m, 1H), 7.64 (d, 2H), 7.59 (s, 1H), 7.55 (br s, 2H), 7.41 (m, 3H), 4.65 (m, 1H), 3.81 (m, 1H), 3.35 (t, 2H), 3.25 (t, 2H), 2.56 (s, 3H), 1.73 (m, 3H), 1.29 (d, 3H), 1.23 (d, 3H). LRMS [M+H]=415.2

Example 184

8-methyl-2-(4-(1-(piperazin-1-yl)ethyl)phenethyl)benzo[f][1,7]naphthyridin-5-amine

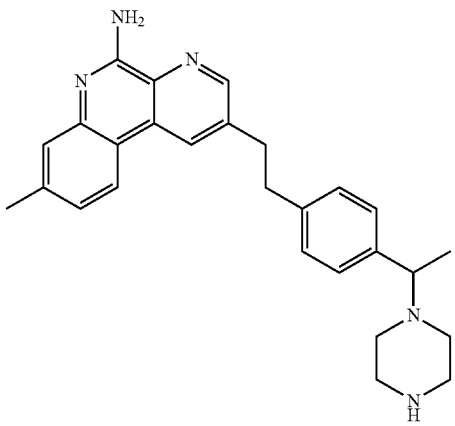 [SMILES: Cc1ccc2c(c1)nc(N)c1ncc(CCc3ccc(C(C)N4CCNCC4)cc3)cc12]

8-Methyl-2-(4-(1-(piperazin-1-yl)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and piperazine (commercially available) following the procedures described for Example 182. $^1$H NMR (Methanol-d$_4$) TFA Salt: δ 8.83 (s, 1H), 8.75 (s, 1H), 8.39 (d, 1H), 7.51 (s, 1H), 7.46 (d, 1H), 7.26 (m, 4H), 3.62 (m, 1H), 3.25 (t, 2H), 3.12 (t, 2H), 2.80 (m, 4H), 2.69 (m, 4H), 2.56 (s, 3H), 1.42 (d, 3H). LRMS [M+H]=426.2

Example 185

((2S)-1-(1-(4-(2-(5-amino-8-methylbenzo[f][1,7]naphthyridin-2-yl)ethyl)phenyl)ethyl)pyrrolidin-2-yl)methanol

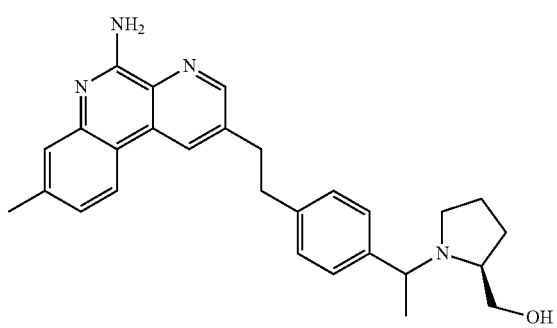 [SMILES: Cc1ccc2c(c1)nc(N)c1ncc(CCc3ccc(C(C)N4CCC[C@H]4CO)cc3)cc12]

((2S)-1-(1-(4-(2-(5-Amino-8-methylbenzo[f][1,7]naphthyridin-2-yl)ethyl)phenyl)ethyl)pyrrolidin-2-yl)methanol was prepared from 1-(4-(2-(5-amino-8-methylbenzo[f][1,7]naphthyridin-2-yl)ethyl)phenyl)ethanone (from Example 171) and (S)-pyrrolidin-2-ylmethanol (commercially available) following the procedures described for Example 182. $^1$H NMR (Acetone-d$_6$) TFA Salt: δ 8.83 (s, 1H), 8.80 (s, 1H), 8.43 (d, 1H), 7.36-7.53 (m, 6H), 4.68 (m, 1H), 3.69 (m, 2H), 3.19-3.21 (m, 4H), 2.55 (m, 4H), 1.75-1.78 (m, 6H), 1.74 (d, 3H). LRMS [M+H]=441.2

Example 186

N[1]-(1-(4-(2-(5-amino-8-methylbenzo[f][1,7]naph-thyridin-2-yl)ethyl)phenyl)ethyl)-N[2],N[2]-dimethyl-ethane-1,2-diamine

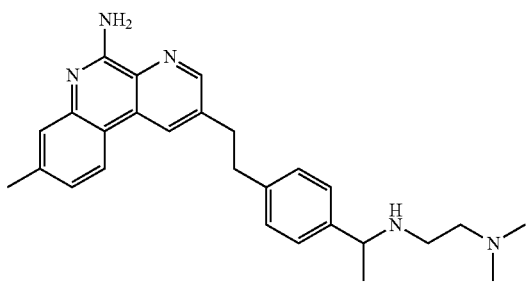

N[1]-(1-(4-(2-(5-amino-8-methylbenzo[f][1,7]naphthyridin-2-yl)ethyl)phenyl)ethyl)-N[2],N[2]-dimethylethane-1,2-diamine was prepared from 1-(4-(2-(5-amino-8-methylbenzo[f][1,7]naphthyridin-2-yl)ethyl)phenyl)ethanone (from Example 171) and N[1],N[1]-dimethylethane-1,2-diamine (commercially available) following the procedures described for Example 182. $^1$H NMR (Acetone-$d_6$) TFA Salt: δ 8.85 (m, 2H), 8.43 (d, 1H), 7.52 (s, 1H), 7.48 (m, 2H), 7.40 (m, 2H), 6.69 (m, 1H), 4.39 (m, 1H), 3.42 (m, 2H), 3.18-3.25 (m, 6H), 2.87 (s, 6H), 2.56 (s, 3H), 1.69 (d, 3H). LRMS [M+H]=428.2

Example 187

3-(1-(4-(2-(5-amino-8-methylbenzo[f][1,7]naphthyridin-2-yl)ethyl)phenyl)ethylamino)propanoic acid

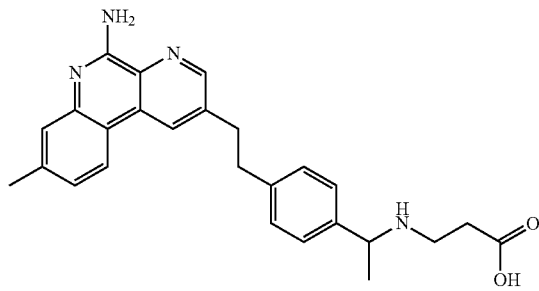 [SMILES: Cc1ccc2c(c1)nc(N)c1ncc(CCc3ccc(C(C)NCCC(=O)O)cc3)cc12]

A solution of 1-(4-(2-(5-amino-8-methylbenzo[f][1,7]naphthyridin-2-yl)ethyl)phenyl)ethanone (from Example 171) (1 eq), 3-aminopropanoic acid (commercially available) (5 eq), triethylamine (3 eq) dissolved in absolute ethanol (0.042M) was stirred at 50° C. for 3 hours. The mixture was cooled to 0° C. and NaCNBH$_3$ (1 eq) was added and the reaction mixture was stirred for another six hours at room temperature. Then another equivalent of NaCNBH$_3$ was added and the reaction mixture was stirred at 50° C. for another hour. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanoic acid a white solid as a TFA salt. $^1$H NMR (Methanol-$d_4$) TFA Salt: δ 8.74 (s, 1H), 8.42 (d, 1H), 7.66 (m, 2H), 7.50 (m, 1H), 7.31 (d, 2H), 7.23 (m, 2H), 4.24 (m, 1H), 3.21 (t, 2H), 3.14 (t, 2H), 2.75-3.10 (m, 2H), 2.51 (t, 2H), 2.10 (s, 3H), 1.55 (d, 3H). LRMS [M+H]=429.2

Example 188

8-methyl-2-(4-(1-(4-methylpiperazin-1-yl)ethyl)phenethyl)benzo[f][1,7]naphthyridin-5-amine

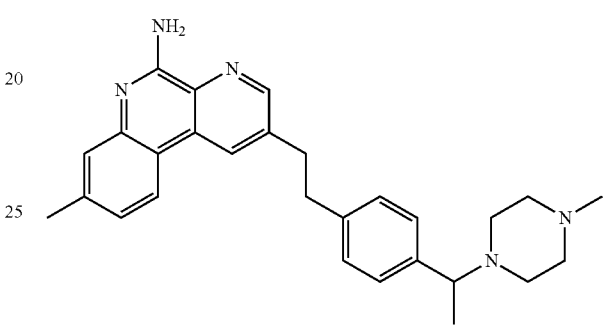

8-Methyl-2-(4-(1-(4-methylpiperazin-1-yl)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and 1-methylpiperazine (commercially available) following the procedures described for Example 182. $^1$H NMR (Acetone-$d_6$) TFA Salt: δ 8.84 (s, 1H), 8.80 (s, 1H), 8.41 (d, 1H), 7.52 (s, 1H), 7.42-7.46 (m, 3H), 7.36-7.38 (m, 2H), 3.53 (m, 1H), 3.18 (m, 2H), 3.12 (m, 2H), 2.92 (s, 2H), 2.66 (s, 2H), 2.56 (s, 2H), 2.16 (s, 3H), 1.99 (m, 2H), 1.69 (d, 3H), 1.30 (s, 3H). LRMS [M+H]=440.2

Example 189

N[2]-(1-(4-(2-(5-amino-8-methylbenzo[f][1,7]naphthyridin-2-yl)ethyl)phenyl)ethyl)-N[1],N[1]-dimethyl-propane-1,2-diamine

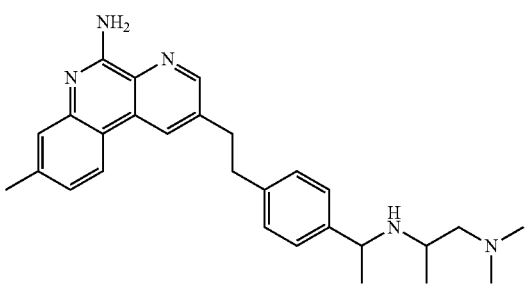

N[2]-(1-(4-(2-(5-amino-8-methylbenzo[f][1,7]naphthyridin-2-yl)ethyl)phenyl)ethyl)-N[1],N[1]-dimethylpropane-1,2-diamine was prepared from 1-(4-(2-(5-amino-8-methylbenzo[f][1,7]naphthyridin-2-yl)ethyl)phenyl)ethanone (from Example 171) and N[1],N[1]-dimethylpropane-1,2-diamine (commercially available) following the procedures described for Example 182. ¹H NMR (Acetone-$d_6$) TFA Salt: δ 8.83 (m, 2H), 8.40 (d, 1H), 7.46-7.51 (m, 3H), 7.43 (m, 1H), 7.37 (d, 2H), 4.54 (m, 1H), 3.74 (m, 1H), 3.19 (m, 4H), 2.90 (s, 3H), 2.77 (s, 3H), 2.55 (s, 3H), 2.41 (d, 2H), 1.66 (d, 3H), 1.39 (d, 3H). LRMS [M+H]=442.2

Example 190

8-methyl-2-(4-(1-(2-(pyridin-4-yl)ethylamino)ethyl)phenethyl)benzo[f][1,7]naphthyridin-5-amine

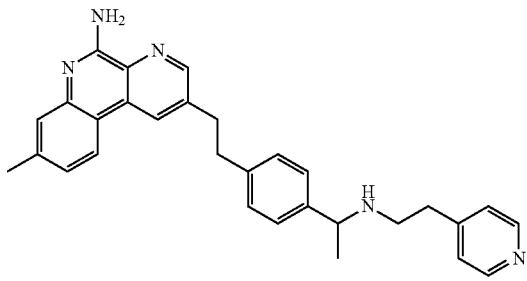 [SMILES: Cc1ccc2c(c1)nc(N)c1ncc(CCc3ccc(C(C)NCCc4ccncc4)cc3)cc12]

8-Methyl-2-(4-(1-(2-(pyridin-4-yl)ethylamino)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and 2-(pyridin-4-yl)ethanamine (commercially available) following the procedures described for Example 182. ¹H NMR (Acetone-$d_6$) TFA Salt: δ 8.94 (m, 2H), 8.92 (d, 2H), 8.73 (s, 1H), 8.43 (d, 1H), 7.60 (m, 2H), 7.40 (m, 2H), 7.16-7.26 (m, 3H), 4.55 (m, 1H), 3.55 (m, 4H), 2.56 (m, 4H), 2.12 (s, 3H), 1.73 (d, 3H) LRMS [M+H]=462.2

Example 191

$N^1$-(1-(4-(2-(5-amino-8-methylbenzo[f][1,7]naphthyridin-2-yl)ethyl)phenyl)ethyl)-$N^2$,$N^2$-diethylethane-1,2-diamine

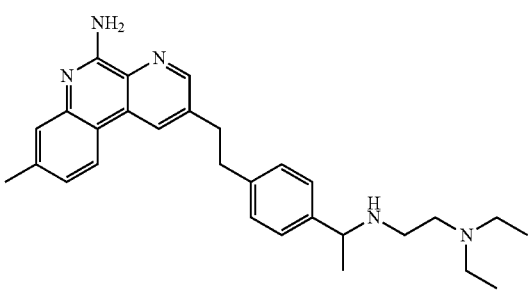 [SMILES: CCN(CC)CCNC(C)c1ccc(CCc2cnc3c(N)nc4cc(C)ccc4c3c2)cc1]

$N^1$-(1-(4-(2-(5-amino-8-methylbenzo[f][1,7]naphthyridin-2-yl)ethyl)phenyl)ethyl)-$N^2$,$N^2$-diethylethane-1,2-diamine was prepared from 1-(4-(2-(5-amino-8-methylbenzo[f][1,7]naphthyridin-2-yl)ethyl)phenyl)ethanone (from Example 171) and $N^1$,$N^1$-diethylethane-1,2-diamine (commercially available) following the procedures described for Example 182. ¹H NMR (Acetone-$d_6$) TFA Salt: δ: 8.81 (s, 1H), 8.75 (s, 1H), 8.23 (d, 1H), 7.60 (d, 2H), 7.39 (d, 2H), 7.28 (m, 2H), 4.51 (m, 1H), 3.82 (m, 1H), 3.62 (m, 1H), 3.34 (m, 4H), 3.20 (t, 2H), 2.46 (s, 3H), 2.10 (m, 4H), 1.74 (d, 3H), 1.34 (t, 6H). LRMS [M+H]=456.2

Example 192

2-(4-(dimethylamino)-2-methylphenethyl)-8-methylbenzo[f][1,7]naphthyridin-5-amine

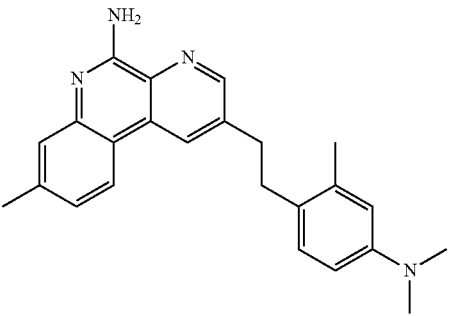

Step 1: 4-iodo-N,N,3-trimethylaniline

To a solution of 4-iodo-3-methylaniline (commercially available) (1 eq), NaHCO₃ (2.5 eq), and iodomethane (2.5 eq), in DMF ((0.2M) was stirred at ambient temperature overnight. The reaction mixture was then diluted with ethyl acetate and water. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-80% ethyl acetate in hexane and 4-iodo-N,N,3-trimethylaniline was isolated as a yellow solid.

Step 2: Syntheswas of N,N,3-trimethyl-4-((trimethylsilyl)ethynyl)aniline

To a solution of 4-iodo-N,N-3-trimethylaniline (from the previous step) (1 eq), ethynyltrimethylsilane (1.5 eq), dichlorobis(triphenylphosphine)-palladium (II) (20 mol %), copper iodide (20 mol %) and triethylamine (0.4 M) was stirred at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and N,N,3-trimethyl-4-((trimethylsilyl)ethynyl)aniline was isolated as a yellow solid.

Step 3: 4-ethynyl-N,N,3-trimethylaniline

To a solution of N,N-3-trimethyl-4-((trimethylsilyl)ethynyl)aniline (from the previous step) (1 eq), K₂CO₃ (2.5 eq), in MeOH ((0.15M) was stirred at ambient temperature for six hours. The solids were filtered out, and the liquid was concentrated en vaccuo. The crude material was purified by flash chromatography on a COMBIFLASH® system (ISCO) using 0-80% ethyl acetate in hexane and 4-ethynyl-N,N-3-trimethylaniline was isolated as a yellow solid.

Step 4: 3-chloro-5-((4-(dimethylamino)-2-methylphenyl)ethynyl) picolinonitrile To a solution of 4-ethynyl-N,N-3-trimethylaniline (from the previous step) (1 eq) 3,5-dichloropicolinonitrile (1.2 eq), dichlorobis(triphenylphosphine)-palladium (II) (10 mol %), copper iodide (10 mol %) and DMF: triethylamine (0.28 M) was stirred at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 3-chloro-5-((4-(dimethylamino)-2-methylphenyl)ethynyl) picolinonitrile was isolated as a off-yellow solid.

Step 5: 2-((4-(dimethylamino)-2-methylphenyl)ethynyl)-8-methylbenzo[f][1,7]naphthyridin-5-amine A solution of tert-butyl 5-methyl-2-(4,4,5,5-tetramethyl-1,3,2-dioxaborolan-2-yl)phenylcarbamate (1.3 eq.) and 3-chloro-5-((4-(dimethylamino)-2-methylphenyl)ethynyl) picolinonitrile (from the previous step) (1.0 eq.), tetrakis(triphenyl-phosphine)palladium (10 mol %), and 2N aqueous sodium carbonate solution (2.0 eq.) in toluene/ethanol (2:1, 0.17 M) was stirred at 100° C. overnight. After cooling to ambient temperature, the reaction mixture was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 2-((4-(dimethylamino)-2-methylphenyl)ethynyl)-8-methylbenzo[f][1,7]naphthyridin-5-amine as a yellow solid.

Step 6: 2-(4-(dimethylamino)-2-methylphenethyl)-8-methylbenzo[f][1,7]naphthyridin-5-amine To a solution of 2-((4-(dimethylamino)-2-methylphenyl)ethynyl)-8-methylbenzo[f][1,7]naphthyridin-5-amine (1 eq), (from the previous step) in ethyl acetate/ethanol (1:5, 0.035 M) was added 10% wt palladium on carbon (0.2 eq.). Hydrogen gas was introduced via a balloon, and the reaction was stirred for 3.5 hours. The mixture was filtered through a pad of celite, washing with dichloromethane. The filtrate was concentrated en vaccuo and purified by preparative HPLC on a 19×50 mm ATLANTIS® 10 micron C18 (Waters Corp.) system using 10-90% Acetonitrile (0.035% TFA) in Water (0.05% TFA) to give 2-(4-(dimethylamino)-2-methylphenethyl)-8-methylbenzo[f][1,7]naphthyridin-5-amine as a white solid as a TFA salt. $^1$H NMR (Acetone-$d_6$) TFA Salt: δ 8.81 (s, 1H), 8.74 (s, 1H), 8.34 (d, 1H), 7.89 (s, 1H), 7.47 (m, 2H), 7.38 (m, 2H), 3.34 (s, 6H), 3.32 (t, 2H), 3.28 (t, 2H), 2.57 (s, 3H), 2.34 (s, 3H). LRMS [M+H]=371.2

Example 193

1-(1-(4-(2-(5-amino-8-methylbenzo[f][1,7]naphthyridin-2-yl)ethyl)phenyl)ethyl)pyrrolidine-3-carboxylic acid

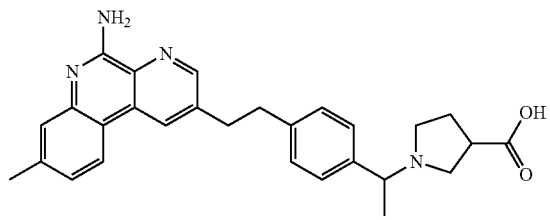 [SMILES: Cc1ccc2c(c1)nc(N)c1ncc(CCc3ccc(C(C)N4CCC(C(=O)O)C4)cc3)cc12]

1-(1-(4-(2-(5-Amino-8-methylbenzo[f][1,7]naphthyridin-2-yl)ethyl)phenyl)ethyl)pyrrolidine-3-carboxylic acid was prepared from 1-(4-(2-(5-amino-8-methylbenzo[f][1,7]naphthyridin-2-yl)ethyl)phenyl)ethanone (from Example 171) and pyrrolidine-3-carboxylic acid (commercially available) following the procedures described for Example 187, except that in this case, acetic acid was used instead of triethylamine (30%). $^1$H NMR (Acetone-$d_6$) TFA Salt: δ 8.81 (s, 1H), 8.75 (s, 1H), 8.70 (s, 1H), 8.28 (d, 1H), 7.59 (d, 2H), 7.37 (m, 3H), 4.46 (m, 1H), 4.21 (m 1H), 3.45 (m, 2H), 3.32 (m, 2H), 3.21 (m, 2H), 3.17 (m, 2H), 2.27 (m, 2H), 2.07 (s, 3H) 1.77 (d, 3H). LRMS [M+H]=455.2

Example 194

4-(1-(4-(2-(5-amino-8-methylbenzo[f][1,7]naphthyridin-2-yl)ethyl)phenyl)ethylamino)phenol

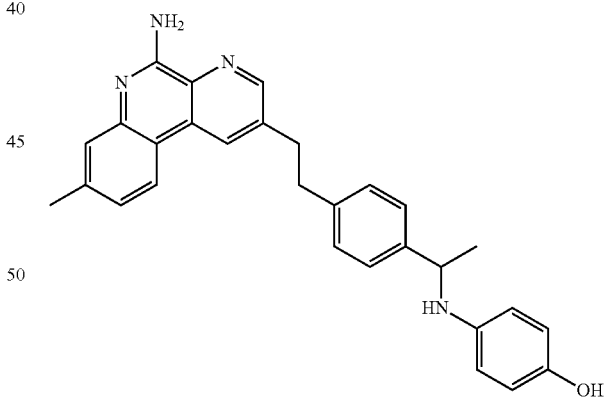

4-(1-(4-(2-(5-Amino-8-methylbenzo[f][1,7]naphthyridin-2-yl)ethyl)phenyl)ethylamino)phenol was prepared from 1-(4-(2-(5-amino-8-methylbenzo[f][1,7]naphthyridin-2-yl)ethyl)phenyl)ethanone (from Example 171) and 4-aminophenol following the procedures described for Example 187, except that in this case, acetic acid was used instead of triethylamine (28%). $^1$H NMR (Acetone-$d_6$) TFA Salt: δ 8.83 (s, 1H), 8.73 (s, 1H), 8.33 (d, 1H), 7.44 (s, 1H), 7.40 (d, 2H), 7.36 (d, 1H), 7.24 (d, 2H), 7.10 (d, 2H), 6.76 (d, 2H), 4.72 (m, 1H) 3.27 (t, 2H), 3.12 (t, 2H), 2.50 (s, 3H), 2.06 (d, 3H). LRMS [M+H]=449.2

Example 195

1-(1-(4-(2-(5-amino-8-methylbenzo[f][1,7]naphthyridin-2 yl)ethyl)phenyl)ethyl)pyrrolidin-3-ol

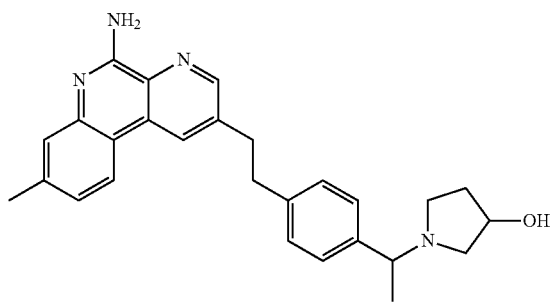 [SMILES: Cc1ccc2c(c1)nc(N)c1ncc(CCc3ccc(C(C)N4CCC(O)C4)cc3)cc12]

1-(1-(4-(2-(5-Amino-8-methylbenzo[f][1,7]naphthyridin-2 yl)ethyl)phenyl)ethyl)pyrrolidin-3-ol was prepared from 1-(4-(2-(5-amino-8-methylbenzo[f][1,7]naphthyridin-2-yl)ethyl)phenyl)ethanone (from Example 171) and pyrrolidin-3-ol following the procedures described for Example 187, except that in this case, acetic acid was used instead of triethylamine (20%). $^1$H NMR (Acetone-$d_6$) TFA Salt: δ 8.83 (s, 1H), 8.76 (s, 1H), 8.72 (s, 1H), 8.29 (d, 1H), 7.57 (s, 1H), 7.42 (s, 1H), 7.33-7.38 (m, 3H), 4.41 (m, 2H), 3.77 (m, 2H), 3.33 (t, 2H), 3.21 (t, 2H), 3.19 (m, 2H), 3.10 (m, 2H), 2.10 (s, 3H), 1.75 (d, 3H). LRMS [M+H]=427.2

Example 196

2-(4-(2-aminopropan-2-yl)phenethyl)-8-methylbenzo[f][1,7]naphthyridin-5-amine

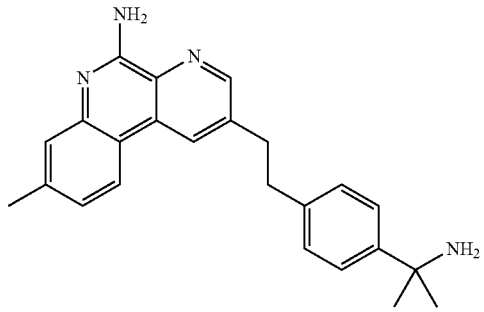 [SMILES: Cc1ccc2c(c1)nc(N)c1ncc(CCc3ccc(C(C)(C)N)cc3)cc12]

To a solution of 4-(2-(5-amino-8-methylbenzo[f][1,7]naphthyridin-2-yl)ethyl)benzonitrile (from Example 64, step 1) (1 eq), dissolved in dry THF (0.029M) was added very slowly methyl magnesium bromide (6 eq) and the reaction mixture was stirred at room temperature for half hour. Then was added to the reaction flask titanium tetra-isopropoxide (3 eq) over ten minutes. The reaction mixture was refluxed for 16 hours. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 2-(4-(2-aminopropan-2-yl)phenethyl)-8-methylbenzo[f][1,7]naphthyridin-5-amine as a white solid of TFA salt. $^1$H NMR (Methanol-$d_4$) TFA Salt δ: 9.01 (s, 2H), 8.92 (s, 1H), 8.42 (s, 1H), 7.65 (d, 2H), 7.56 (s, 1H), 7.39 (m, 2H), 3.19 (m, 4H), 2.54 (s, 3H), 1.82 (6H). LRMS [M+H]=371.2.

Example 197

N-(2-acetamidoethyl)-4-(2-(5-amino-8-methylbenzo[f][1,7]naphthyridin-2-yl)ethyl)-3-methylbenzamide

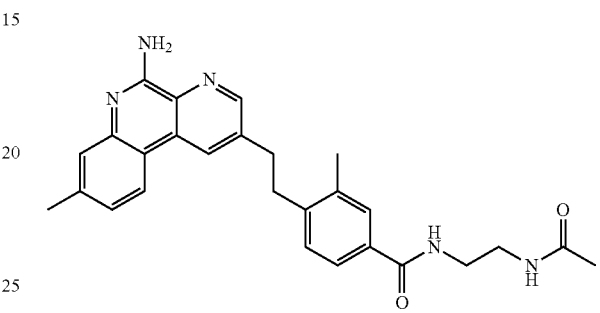

To a solution of 4-(2-(5-amino-8-methylbenzo[f][1,7]naphthyridin-2-yl)ethyl)-3-methylbenzoyl chloride (Example 116/Step 2) and triethylamine (2.5 eq.) in ether (0.05 M) was added N-(2-aminoethyl)acetamide (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(2-acetamidoethyl)-4-(2-(5-amino-8-methylbenzo[f][1,7]naphthyridin-2-yl)ethyl)-3-methylbenzamide as a white solid. $^1$H NMR (CDCl$_3$): δ 8.61 (s, 1H), 8.38 (s, 1H), 8.07 (d, 1H), 7.65 (s, 1H), 7.51-7.56 (m, 2H), 7.10-7.16 (m, 2H), 6.25 (br, 2H), 3.50-3.59 (m, 4H), 3.08-3.16 (m, 4H), 2.62 (s, 3H), 2.52 (s, 3H), 2.35 (s, 3H). LRMS [M+H]=455.2.

Other compounds for carrying out the present invention include: 2-methylbenzo[f][1,7]naphthyridin-5-amine; 2-propylbenzo[f][1,7]naphthyridin-5-amine; 2-(3-methoxyphenethyl)benzo[f][1,7]naphthyridin-5-amine; 8-methyl-2-phenethylbenzo[f][1,7]naphthyridin-5-amine; methyl-5-aminobenzo[f][1,7]naphthyridine-3-carboxylate; (5-aminobenzo[f][1,7]naphthyridin-3-yl)methanol; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine, 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(4-butylphenethyl)benzo[f][1,7]naphthyridin-5-amine; 2-(4-butylphenethyl)-8-methylbenzo f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; 2-(4-isobutoxyphenethyl)-8-methylbenzo[f][1,7]naphthyridin-5-amine; 2-(4-(2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; $N^2$,8-dimethylbenzo[f][1,7]naphthyridine-2,5-diamine; 2-(5-amino-8-methylbenzo[f][1,7]naphthyridin-2-yl)-1-phenylethanol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)

ethyl)pyrrolidine-3-carboxylic acid, and 8-methyl-2-(4-(1-(phenylamino)ethyl)phenethyl)benzo[f][1,7]naphthyridin-5-amine.

Example (II): Development of a Homogeneous Suspension of Example 47

Formulations of small molecule immune potentiators (SMIPs) were evaluated for stability and activity as vaccine adjuvants or immunomodulatory agents against bacterial and viral infections.

Example 47 is a highly crystalline drug substance with very good chemical stability. Due to its extremely low aqueous solubility across full pH range (<0.5 μg/ml) and its high hydrophobic core structure, formulation with Alum (the only vaccine adjuvant licensed in the U.S.) is challenging. However, TLR7 agonist-Alum based vaccines could provide advantages, for example, induction of Th1 polarized response, and enhanced Serum Bactericidal Activity (SBA) and breath of coverage (e.g., MenB).

This example describes the development of a stable and reproducible homogeneous suspension of Example 47 as a vehicle to deliver the molecule in vivo, with particle sizes in the micron range.

Evaluation of Surfactants, Suspension Agents and Homogenization Methods

A number of homogenization methods were evaluated, including vortexing, sonication, and mortar and pestle method.

For vortexing, Example 47 was suspended at 2.5 mg/mL in 0.1% Tween 80 and 0.5% carboxymethyl cellulose (CMC), followed by vortexing. The average particle size was ~100 μm.

For sonication, Example 47 was suspended at 2.5 mg/mL in 0.1% Tween 80 and 0.5% CMC followed by vortexing. The mixture was then subject to probe sonication for 5 minutes (with ice at 3 W, maximum power based on vial size). Finally, the mixture was homogenized by a handheld homogenizer for a few minutes. The average particle size was ~80 μm.

In mortar and pestle method, 10 mg of Example 47 was ground for 5 minutes using mortar and pestle, then suspended in 0.5% Tween 80. Two particle size peaks were observed with particle sizes of 0.1 μm and ~8 μm. Size range for the larger peak was 1-100 μm.

A number of surfactants and suspension agents were also evaluated. The matrix of surfactants and suspending agents, and the corresponding sizes distributions of the suspension particles are shown in the Table 1 below (D50, D90 (μm)).

TABLE 1

|  | 0.1% Tween 80 | 0.5% Tween 80 | 0.5% Pluronic F-68 | 0.5% Sodium Lauryl Sulfate |
| --- | --- | --- | --- | --- |
| 0.5% CMC | 76.2, 144.7 | 75.8, 149.1 | 49.1, 104.4 | 28.0, 53.3 |
| 0.5% HPMC | 25.8, 53.5 | 27.5, 49.7 | 19.4, 33.5 | 26.8, 59.3 |
| 0.5% HPC | 43.6, 68.0 | 35.4, 53.5 | 35.8, 54.9 | 38.9, 53.1 |

In each experiment, 10 mg of Example 47 was mixed with 2 mL surfactant and 2 mL suspending agent. The mixtures were vortexed for 5 minutes, and probe sonicated at 3 W and homogenized for 2-4 minutes. The size distributions of the samples were measured using Mastersizer.

All samples were observed to settle quickly even during the course of probe sonication. No visual size reduction was observed after sonication. Some size reduction was noticed visually after homogenization.

High Pressure Homogenization

Evaluation of a number of surfactants and suspension agents identified a stable homogeneous suspension after high pressure homogenization of Example 47 with the surfactant Tween-80 and the suspension agent carboxymethyl cellulose (CMC). Homogenization was carried out at high pressure on ice for up to 30 minutes.

1% CMC (carboxymethyl cellulose, sodium salt; sigma 419273, M5013) stock solution in milliQ water, and 1% Tween 80 solution in MilliQ water were prepared. Crystalline Example 47 (80 mg) was mixed with equal volumes (10 mL each) of 1% CMC and 1% Tween 80 to a final compound concentration of 4 mg/ml (in 0.5% CMC and 0.5% Tween 80). The mixture was first vortex thoroughly and homogenized for 1 min at 24000 rpm using IKA T-25 homogenizer, then processed through a high pressure homogenizer (Avestin Emulsifex—C3) at high pressure (15,000-20,000 psi) on ice for 20-30 minutes. The size distributions of samples were measured. The homogenization procedure was considered complete once the size distribution of at least about 50% of the suspension particles had a diameter (D50) of about 2 micrometers or less, and at least about 90% of the suspension particles had a diameter (D90) of about 10 micrometers or less, preferably about 5 micrometer or less. The homogenized suspension was stored at 4° C.

Homogeneous suspensions of Example 47 were independently reproduced at two separate locations ("Suspension S" and "Suspension C") using the same protocols. The homogeneous suspensions of Example 47 (created under high pressure) had particle sizes in the μm range, as measured by a Horiba particle sizer. The particle size distributions of the two suspensions are very similar. Further, the suspensions showed good stability over time—size distribution of the particles, as represented by D50 and D90, had not changed significantly after 30 days and 56 days. Table 2 shows that Suspension S was stable over 4 weeks at 4° C. (measured by Beckman coulter particle sizer).

TABLE 2

Example 47 suspension was stable over 4 weeks at 4° C.

| Time after preparation | D50 (μm) | D90 (μm) |
| --- | --- | --- |
| Day 1 | 1.25 | 3.37 |
| Day 30 | 1.46 | 5.92 |
| Day 56 | 1.45 | 7.3 |

Table 3 shows that the homogeneous suspension of Example 47 was stable over 12 months at 4° C., as measured by size distribution.

Table 3: Example 47 suspension was stable over 12 months at 4° C.

TABLE 3

Example 47 suspension was stable over 12 months at 4° C.

| Time after preparation | D50 (μm) | D90 (μm) | Mean (μm) |
| --- | --- | --- | --- |
| 0 | 0.5 (0.5243) | 0.9 (0.9236) | 0.6 (0.5828) |
| 1 | 0.6 (0.5860) | 1.1 (1.1114) | 0.7 (0.6676) |
| 6 | 0.7 (0.6830) | 1.4 (1.3556) | 0.8 (0.7882) |
| 9 | 0.6 (0.6493) | 1.3 (1.2869) | 0.8 (0.7540) |
| 12 | 0.7 (0.6566) | 1.4 (1.3736) | 0.8 (0.7821) |

Example (III): Formulation of Example 47 Homogeneous Suspension with Alum Based Vaccines: Effect on Antigen Adsorption Meningococcus B Giuliani et al. (*Proc. Natl. Acad. Sci. USA* 103:10834-10839 (2006)) discloses a vaccine for serogroup B meningococcus ("MenB") made from three separate polypeptides ("5CVMB"). These polypeptides can adsorb to aluminium hydroxide ("Al—H"), and SDS-PAGE is used to check if this adsorption occurs.

In this study, effects of formulating different doses of Example 47 suspension with the MenB antigens ("5CVMB") plus Al—H (3 mg/ml) ("Alum/3MenB") were evaluated. As shown in FIGS. 1A and 1B, when no (0 μg/dose) suspension was added, the three antigens tested were completely adsorbed on to Al—H. As the dose of the suspension was increased, small amount of antigens were de-adsorbed from Al—H in a time-dependent manner. FIG. 1B is a table showing the percentage of antigen adsorption onto aluminium hydroxide. Although some dose-dependant desorption of the MenB antigens was observed after formulation with the Example 47 suspension, each of the three antigen remained >60% adsorbed after 2 hours at 4° C.

Extraintestinal Pathogenic *E. coli* ("ExPEC")

Figure 2:
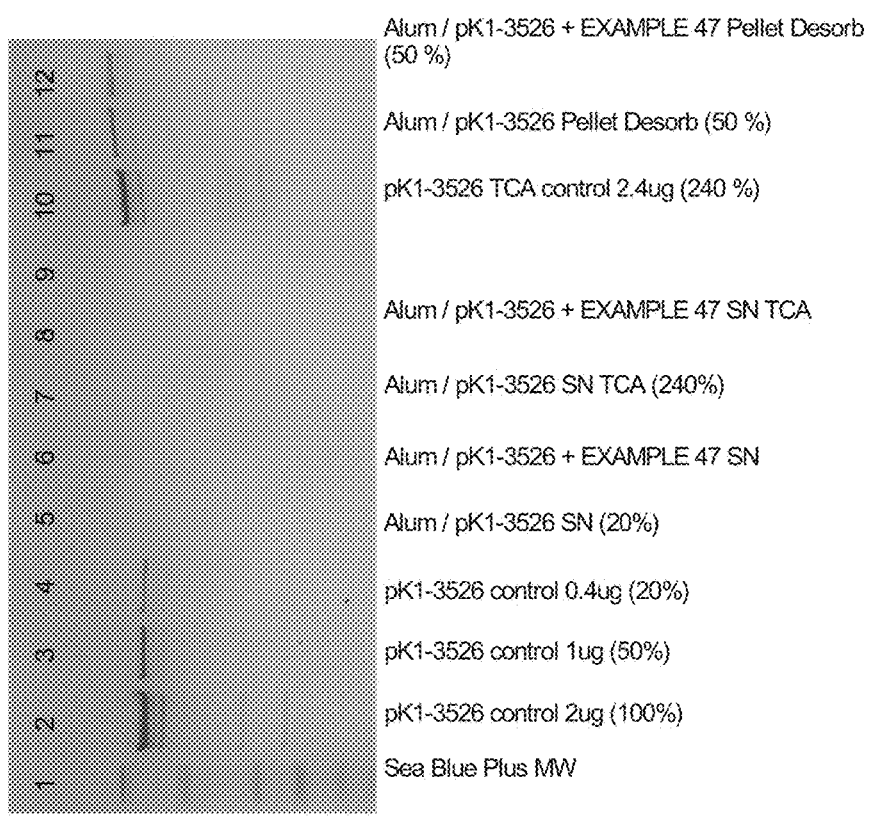
FIG. 2 shows that homogeneous suspension of Example 47 had no impact on the adsorption of the extra-intestinal pathogenic *E. coli* (ExPEC) antigen PK1-3526. Key: 1. Sea Blue Plus MW Marker; 2. pK1-3526 control 2 ug (100%); 3. pK1-3526 control 1 ug (50%); 4. pK1-3526 control 0.4 ug (20%); 5. Alum/pK1-3526 SN (20%); 6. Alum/pK1-3526+Example 47 SN (20%); 7. Alum/pK1-3526 SN TCA (240%); 8. Alum/pK1-3526+Example 47 SN TCA (240%); 9. –; 10. pK1-3526 TCA control 2.4 ug (240%); 11. Alum/pK1-3526 Pellet Desorb (50%); 12. Alum/pK1-3526+Example 47 Pellet Desorb (50%). % values indicate proportions of single dose formulation.

In this study, effects of formulating different doses of Example 47 with ExPEC antigen pK1-3526 plus Al—H were evaluated. Example 47 suspensions were stored at 4° C. for 16 hours, and then added to various pK1-3526 formulations. As shown in FIG. 2, pK1-3526 antigen remained adsorbed with high efficiency (over 90%) and changes in antigen integrity upon desorption were not detected.

Studies have also been conducted with respiratory syncytial virus (RSV) antigens with similar results.

The MenB, ExPEC and RSV studies show that the combination of the Example 47 suspension with antigen/Al—H formulations had no impact on adsorption of MenB, ExPEC and RSV antigens. Some desorption of MenB antigens from Al—H was observed with high doses of Example 47 suspension, but this effect was time dependent and was reduced when the suspension was mixed with the vaccine just prior to immunization.

Example (IV): Pharmacokinetic and Pharmacodynamic Parameters of the Homogeneous Suspension of Example 47

Figure 3C:
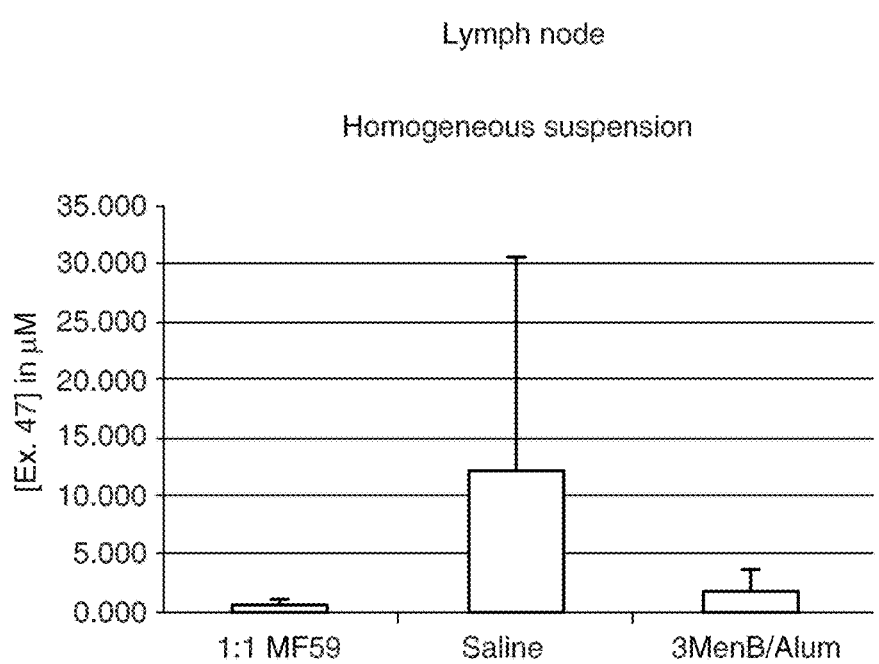
FIG. 3C shows inguinal lymph node level of Example 47 (homogeneous suspension) in mice 24 hours after intramuscular injection at 4 mpk in the vehicles indicated with 3MenB/Alum.
Figure 4:
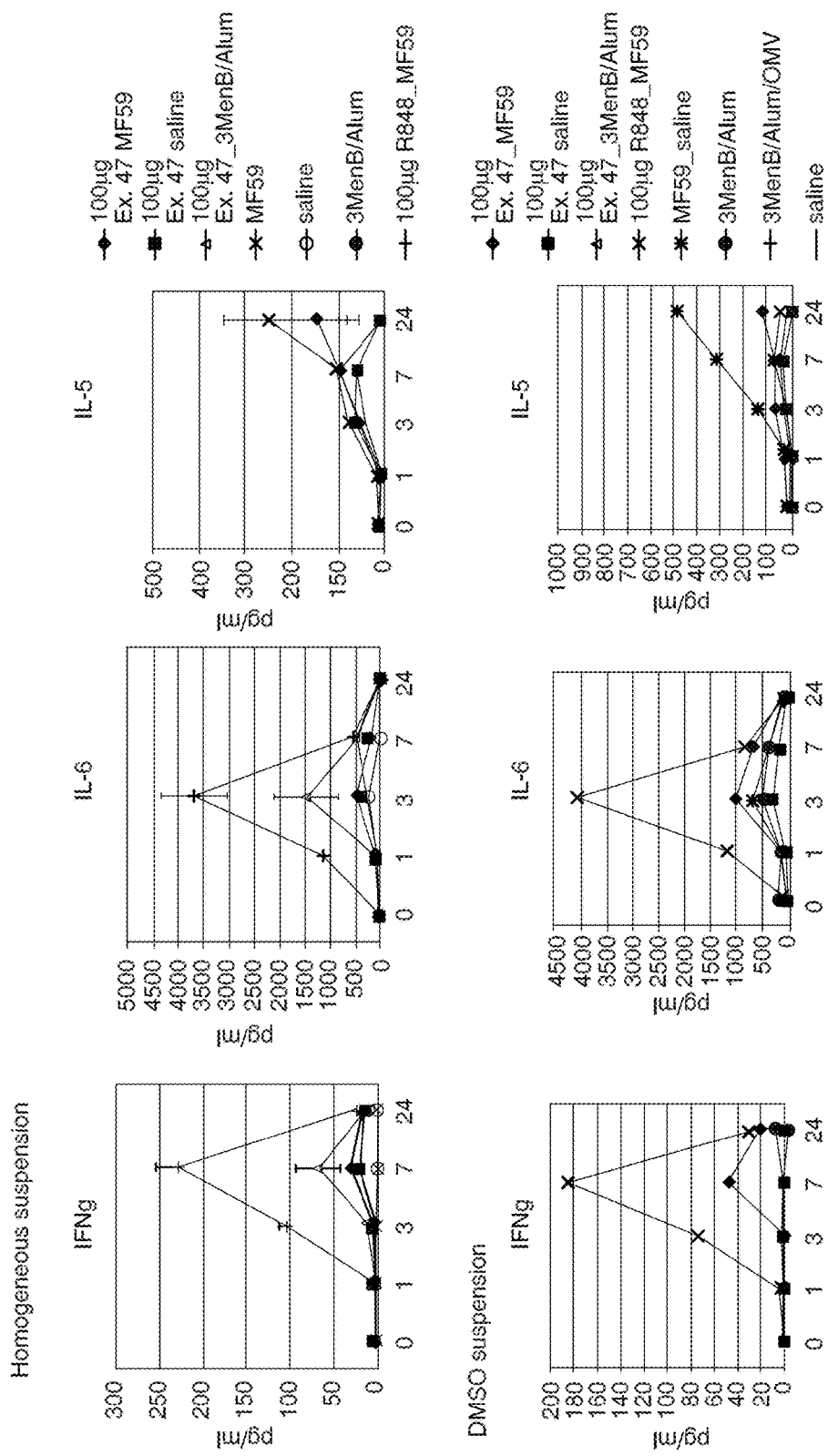
FIG. 4 shows that cytokine release profiles of non-homogeneous/DMSO suspension plus 3MenB/Alum and homogeneous suspension of Example 47 plus 3MenB/Alum were similar. Cytokine releases were minimal as compared to adjuvant R848 after exposure of homogeneous suspensions or DMSO formulated Example 47.

In this study, pharmacokinetic (PK) and pharmacodynamic (PD) parameters of the homogeneous suspension of Example 47 plus Alum/3MenB were studied, and were found to be similar to Example 47 prepared as a non-homogeneous suspension in DMSO/saline (FIGS. 3A, 3B and 4). A slight increase in detectable systemic levels of Example 47 formulated in the homogeneous suspension was identified (FIG. 3A). PK studies demonstrate local exposure of Example 47 in both DMSO (non-homogeneous) and homogeneous suspensions, but low systemic exposure. Homogeneous suspension reduced variability in the local muscle exposure and improves exposure in the local draining lymph node (FIGS. 3B and 3C).

FIG. 4 shows the pharmacodynamic comparison of non-homogeneous/DMSO suspension and homogeneous suspension of Example 47 plus Alum/3MenB. The cytokine release profiles of non-homogeneous/DMSO suspension and homogeneous suspension of Example 47 were similar. Cytokine releases were minimal as compared to cytokine release induced by the adjuvant R848 after exposure of homogeneous suspensions or DMSO formulated Example 47.

Figure 5A:
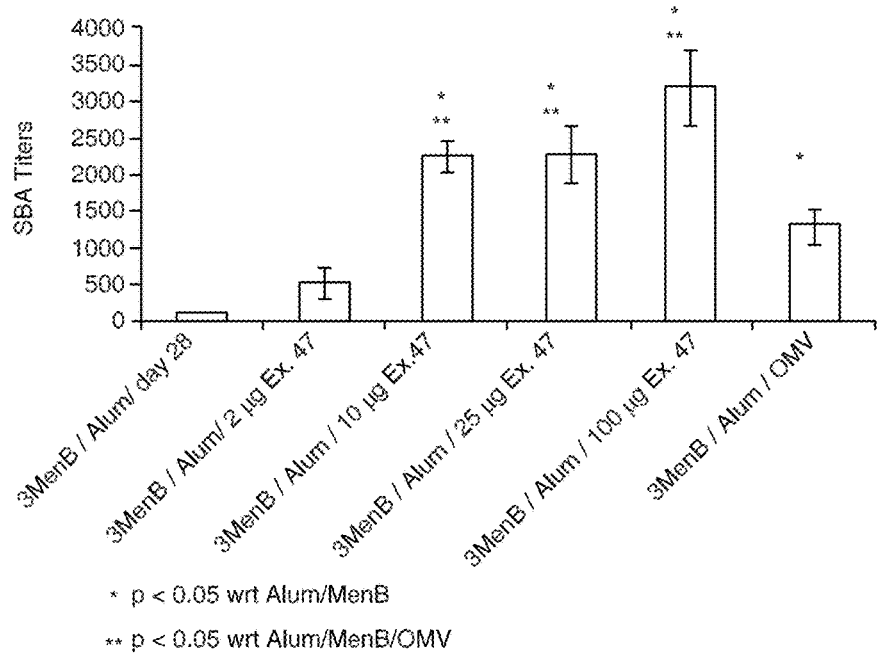
FIG. 5A shows the serum bactericidal antibody (SBA) titers for Alum/3MenB formulated with specified doses of Example 47 homogeneous suspension ranging from 2 to 100 microgram per mouse.
Figure 5B:
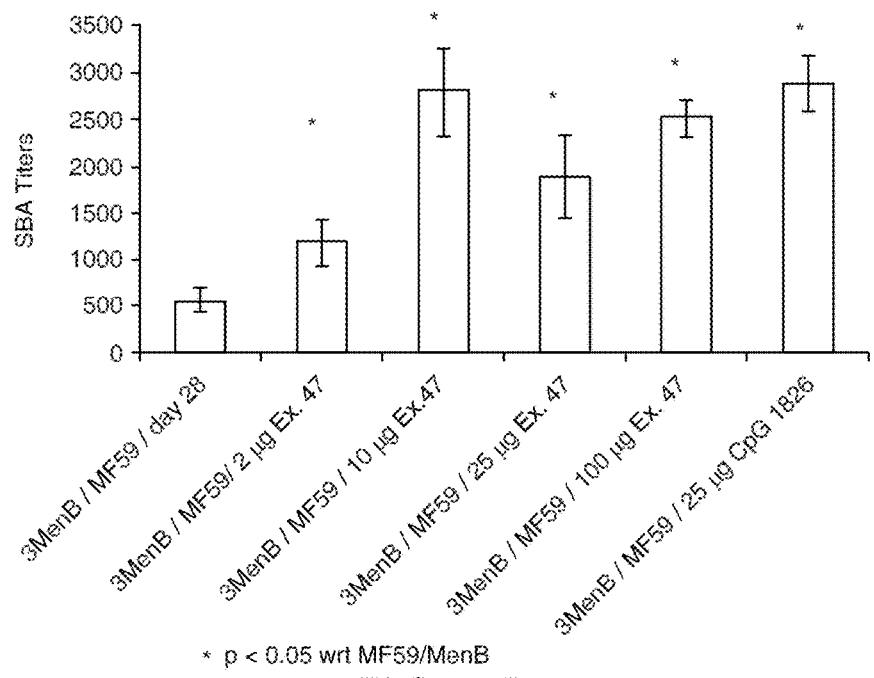
FIG. 5B shows the SBA titers for MF59/3MenB formulated with specified doses of Example 47 homogeneous suspension ranging from 2 to 100 microgram per mouse.

Example (V): Efficacy of Homogeneous Suspension of Example 47 in In Vivo MenB Model 1. Example 47 Homogeneous Suspension Enhanced Immune Responses to *Neisseria* Meningitis In this study, the in vivo efficacy of Example 47, delivered as homogeneous suspension at doses ranging between 2 and 100 μg/mouse, was evaluated using a MenB mouse model. The evaluation was carried out with the three MenB polypeptides ("5CVMB") either adsorbed on Al—H ("Alum/3MenB") or delivered with MF59 ("MF59/3MenB"). The MenB antigens were tested for in vivo immunogenic potency using a serum bactericidal antibody (SBA) assay. FIG. 5A shows bactericidal titers against strain NZ98 of sera obtained after immunization with 5CVMB combined with (a) Al—H alone, (b) Al—H+2 μg Example 47, (c) Al—H+10 μg Example 47, (c) Al—H+25 μg Example 47, (d) Al—H+100 μg Example 47 or (e) Al—H and MenB outer membrane vesicles. FIG. 5B shows bactericidal titers against strain NZ98 of sera obtained after immunization with 5CVMB combined with (a) MF59 alone, (b) MF59+2 μg Example 47, (c) MF59+10 μg Example 47, (c) MF59+25 μg Example 47, (d) MF59+100 μg Example 47 or (e) MF59 and 25 μg CpG1826.

The Alum/3MenB formulations (FIG. 5A) were prepared at 75% volume, and Example 47 homogeneous suspension (4 mg/mL) was added at doses 0, 2, 10, 25 and 100 μg, respectively, within 2 hours prior to immunization. CD1 mice were immunized intramuscularly on days 0 and 14 with 100 μL immunization volume (50 μg/leg) containing 10 μg of each MenB antigen and the specified Example 47 homogenous suspension doses. Mice were bled retro-orbitally on day 28 and SBA titers were measured using Alamar Blue assay.

Alum/3MenB/OMV was used as a benchmark.

The MF59/3MenB formulations (FIG. 5B) were prepared by adding the MenB antigens (5CVMB) (100 μg/mL each) and MF59 to the Example 47 homogeneous suspension (4 mg/mL) at concentrations of 0, 20, 100, 250 and 1,000 μg/mL, respectively. CD1 mice were immunized intramuscularly on days 0 and 14 with 100 uL immunization volume (50 μL/leg) containing 10 μg of each MenB antigen and the specified Example 47 homogeneous suspension doses. Mice were bled retro-orbitally on day 28 and SBA titers were measured using Alamar Blue assay. MF59/3MenB+25 μg CpG1826 was used as a benchmark.

As shown in FIG. 5A, Alum/3MenB plus Example 47 homogeneous suspension at 10 μg, 25 μg and 100 μg gave titers that were significantly enhanced relative to the SBA titers seen with Alum/3MenB alone, and SBA titers that were comparable to, or better than, SBA titers obtained using Alum/3MenB/OMV. Similar results were obtained using MF59/3MenB formulations.

2. Homogeneous Suspension of Example 47 Improved Strain Coverage Compared to Al—H Alone Strain coverage of sera obtained after intramuscular immunization of mice with 5CVMB combined with (a) Al—H alone, (b) Al—H+100 μg Example 47 (DMSO), (c) Al—H+25 μg Example 47 homogeneous suspension, (c) Al—H+100 μg Example 47 homogenous suspension and (d) Al—H and MenB outer membrane vesicles, and intraperitoneal immunization of mice with 5CVMB combined with (e) Al—H and MenB outer membrane vesicles, was evaluated. Alum/3MenB/OMV was used as a benchmark. Efficacy readout is expressed as the % of strains reaching a defined threshold of killing in the SBA assay in the MenB mouse model.

Table 4 shows the sixteen (16) different strains of Neisseria meningitides that were used in these studies. The 16 strains were selected to represent (1) specific target for only one of the antigenic components of 5CVMB; and (2) historically low or negative SBA titers with Alum/3MenB. SBA titers of >1084 was used as a cut off to indicate coverage against a particular strain.

TABLE 4

|  | cpx | ST | ET | YEAR | TYPING | 741 | 961 |
|---|---|---|---|---|---|---|---|
| NZ98/254 | 41/44 | 42 | lin3 | 1998 | NZ B:4:P1.4 | 1.10/++ | − |
| H44/76 | 32 | 32 | ET5 | 1976 | N B:15:P1.7,16 | 1.1/+++ | − |
| M01-240185 | 11 | 11 | ET37 | 2001 | UK B:2a:P1.5,10 | 1.9/+++ | − |
| M2937 | 35 | new | other | 1996 | USA B:4,7:P1.23,14 | 1.7/+++ | − |
| 2996 | 8 | 540 | A4 | 1975 | UK B:2b:P1.5,2 | 2.1/+ | + |
| 961-5945 | 8 | 153 | A4 | 1996 | AUS B:2b:P1.21,16 | 2.1/++ | + |
| B3937 | 18 | new | other | 1995 | D B:22:P1.16 | 2.2/+++ | + |
| M2552 | — | 103 | other | 1996 | USA B:NT:NT | 2.10/+ | − |
| M4407 | 41/44 | new | lin.3 | 1996 | USA B:NT:P1.15 | 2.4/++ | − |
| M0579 | 41/44 | 43 | lin.3 | 1993 | USA B:NT:P1.5,2 | 2.5/+ | − |
| M986 | 11 | 11 | ET37 | 1963 | USA B:2a:P1.5,2 | 2.7/− | + |
| 5/99 | 8 | 1349 | A4 | 1999 | N B:2b:P1.5,2 | 2.8/+ | + |
| M4458 | 22 | new | other | 1998 | USA B:NT:P1.3 | 2.10/+ | + |
| NGP165 | 11 | 11 | ET37 | 1974 | N B:NT:P1.2 | 3.2/+++ | + |
| M01-0240364 | 11 | 11 | ET37 | 2001 | UK B:2a:P1.5,2 | 3.4/+ | + |
| M3369 | — | 1576 | other | 1997 | USA B:10:P1.19,15 | 3.4/++ | − |

CD1 mice were immunized following an immunization schedule of 1 and 14 days. At each immunization, 0.1 ml dose of each formulation was delivered via intramuscular route of 0.05 ml to each of two legs. The mice were bled at 28 days and sera analyzed using SBA assay. An additional control group was included consisting of 0.2 ml Alum/3MenB plus OMV delivered via intraperitoneal route at 1 and 14 days. Two studies, with comparable immunization schemes, were conducted ("MenB Study 1" and "MenB Study 2"), with both giving comparable data.

Table 5 shows SBA titers against strain NZ98/254 in two separate studies.

TABLE 5

| Group | Antigens | Route | NZ |
|---|---|---|---|
| | Study 1: MenB + Example 47 | | |
| 1 | Alum/PBS | IM | <16 |
| 2 | Alum/3MenB | IM | 128 |
| 3 | Alum/3MenB + 100 µg Ex. 47 (DMSO) | IM | 8192 |
| 4 | Alum/3 MenB + 25 µg Ex. 47 homo. suspension | IM | 2048 |
| 5 | Alum/3 MenB + 100 µg Ex. 47 homo. suspension | IM | 1024 |
| 6 | Alum/3MenB + OMV | IM | 128 |
| 7 | Alum/3MenB + OMV | IP | 16384 |
| | Study 2: MenB + Example 47 | | |
| 1 | Alum/PBS | IM | <16 |
| 2 | Alum/3MenB | IM | 128 |
| 3 | Alum/3MenB + 100 µg Ex. 47 (DMSO) | IM | 4096 |
| 4 | Alum/3 MenB + 25 µg Ex. 47 homo. suspension | IM | 4096 |
| 5 | Alum/3 MenB + 100 µg Ex. 47 homo. suspension | IM | 2048 |
| 6 | Alum/3MenB + OMV | IM | 1024 |
| 7 | Alum/3MenB + OMV | IP | 8192 |

Figure 6:
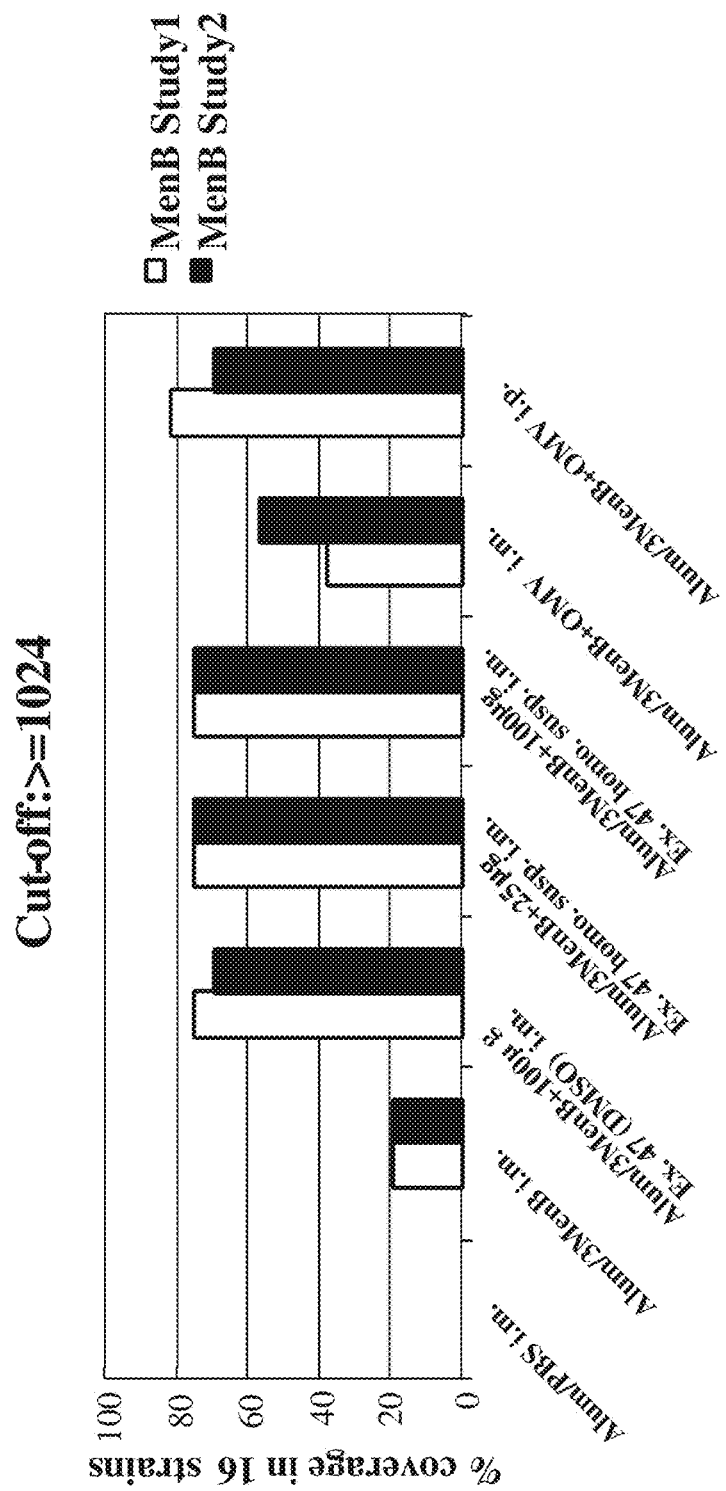
FIG. 6 shows the ability of the Example 47 suspension (when formulated with Alum/3MenB vaccine) to elicit a SBA titer for pooled sera against a panel of 16 stains of *N. meningitides* (all of which had typically low titers with Alum/3MenB formulations). The graph depicts the percentage of coverage against these 16 strains. Cut-off refers to the lowest titers considered to show bactericidal activity.

As shown in FIG. 6, Alum/3MenB formulated with Example 47 homogenous suspension (intramuscular, i.m.) was able to cover 75% of strains used in this experiment, while Alum/3MenB alone was able to cover only 19%. Alum/3MenB/OMV was able to cover ~50% of strains when formulated in Al—H and delivered i.m., and 80% of strains when via delivered intraperitoneal (i.p.) route. The dose-dependent effect was not evident. Thus, Alum/3MenB plus Example 47 homogeneous suspension at 25 µg and 100 µg improved strain coverage compared to Alum/3MenB alone.

Figure 7A:
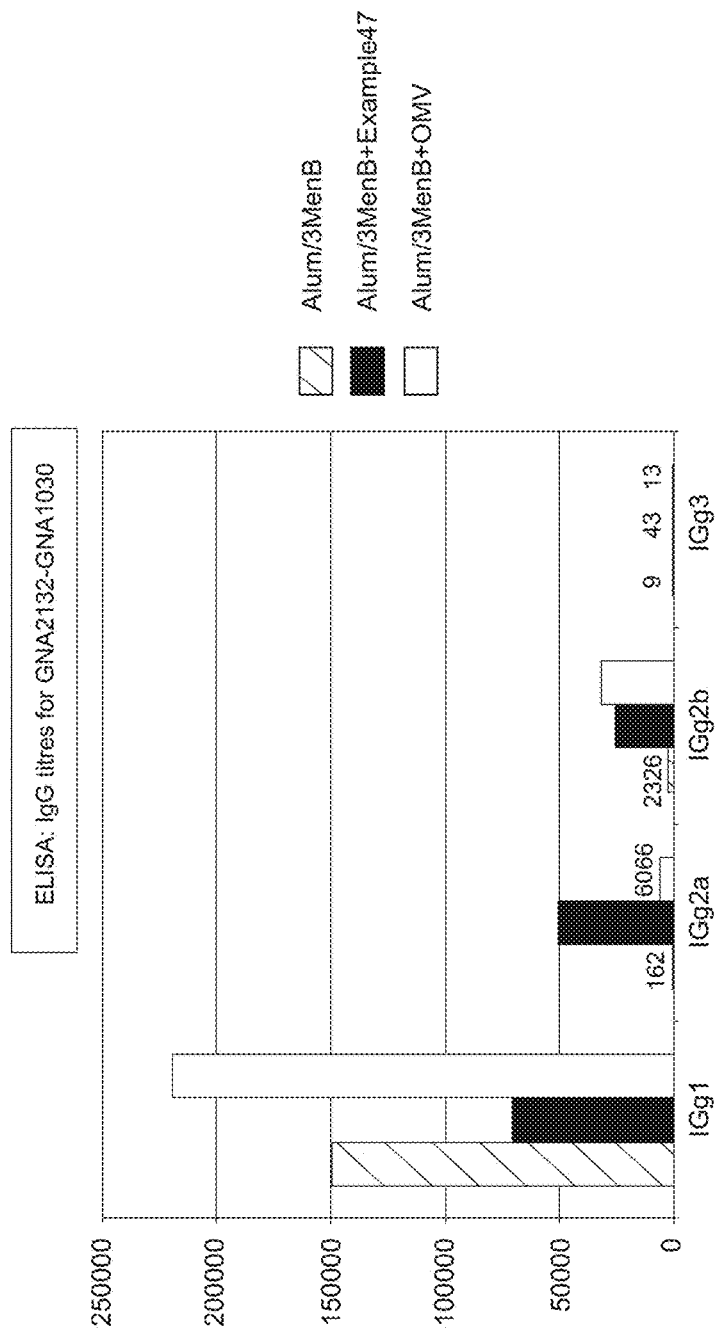
FIGS. 7A-7C show the result of evaluation of IgG1/IgG2a ratios in the MenB mouse model in vivo.
Figure 7B:
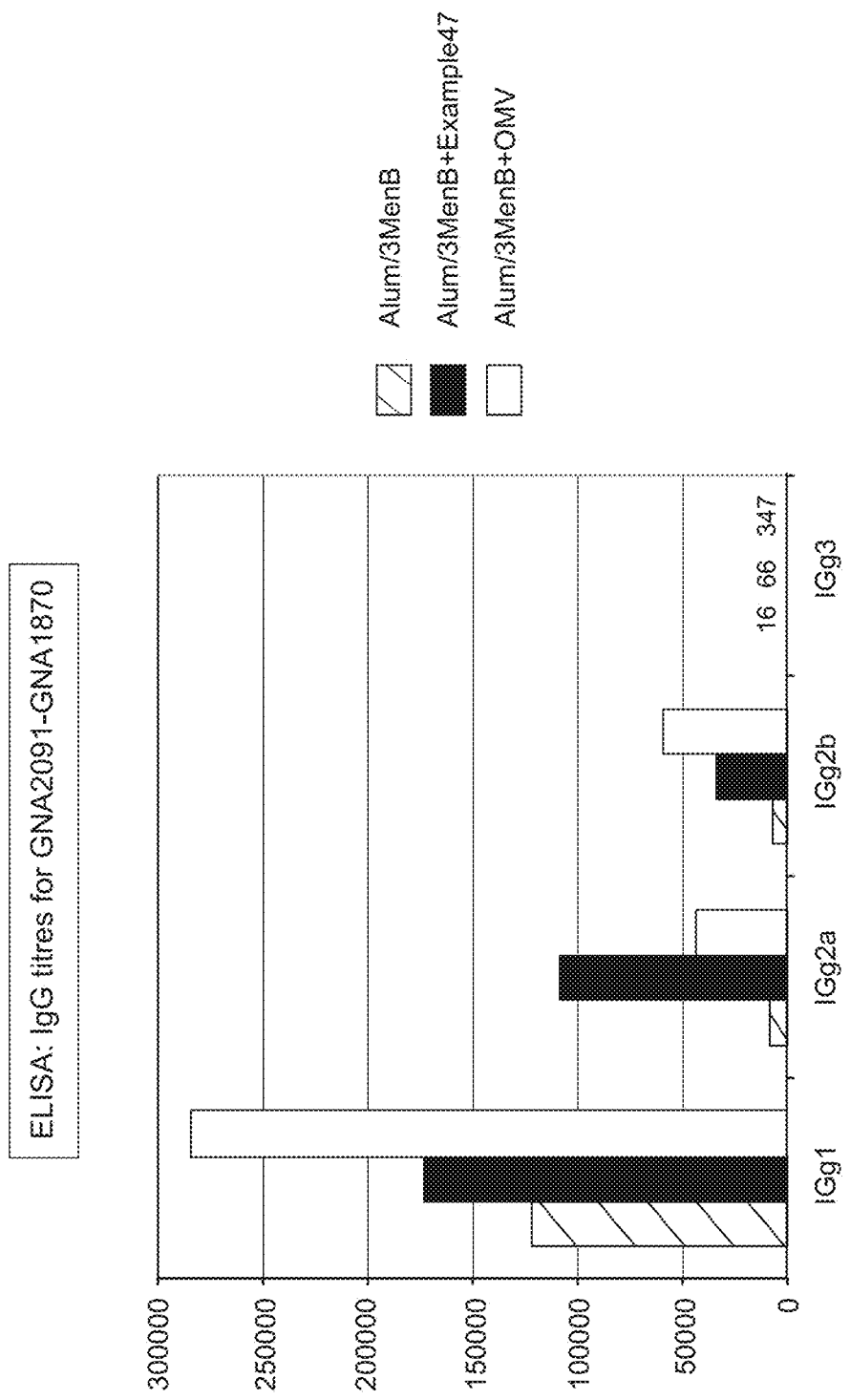
Figure 7C:
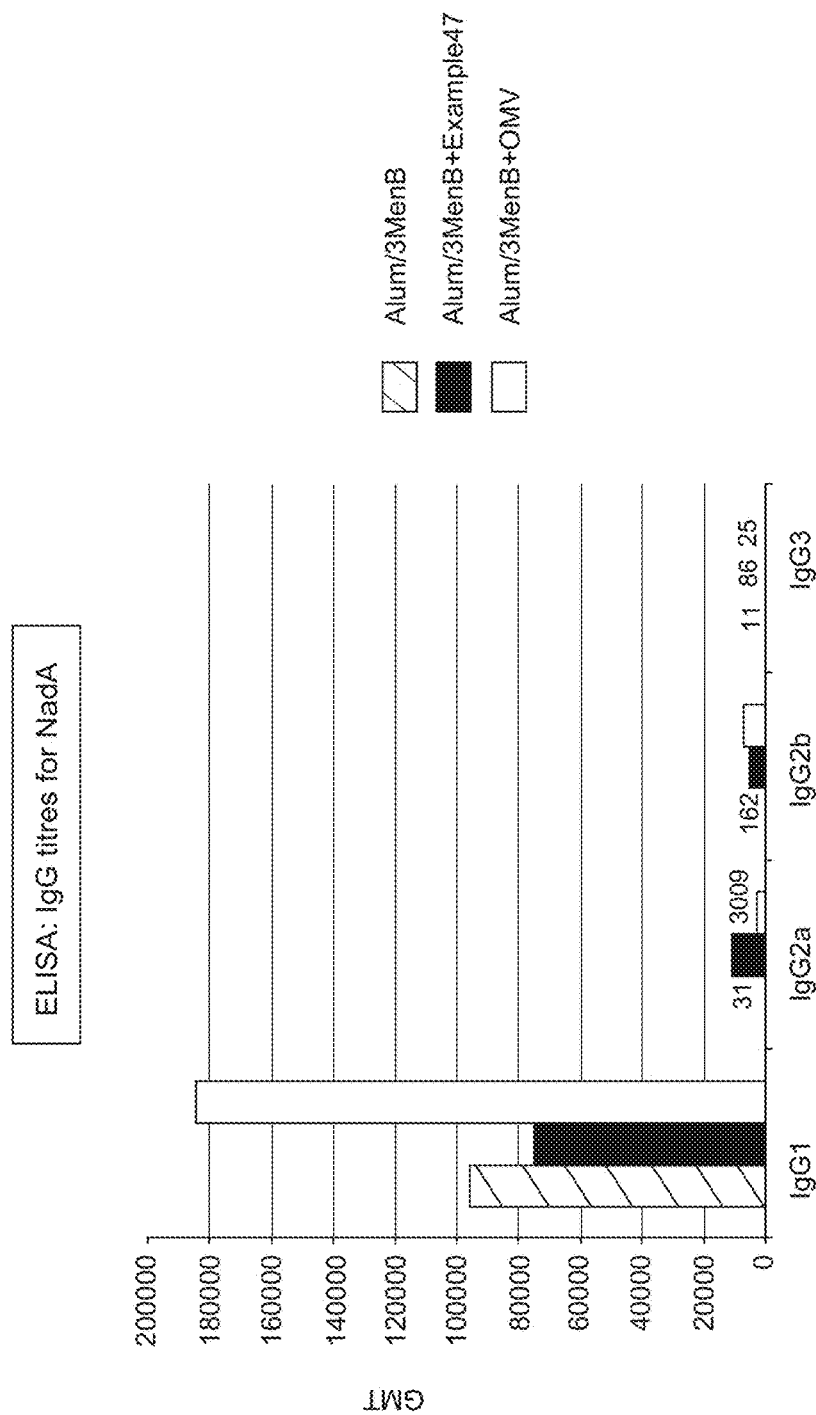

FIGS. 7A-7C shows the IgG1/IgG2a ratios in the MenB mouse model in vivo. Total IgG titres were calculated by ELISA. FIG. 7A shows the IgG1, IgG2a, IgG2b and IgG3 titres for GNA2132-GNA1030. FIG. 7B shows the IgG1, IgG2a, IgG2b and IgG3 titres for GNA2091-GNA1870. FIG. 7C shows the IgG1, IgG2a, IgG2b and IgG3 titres for NadA. Table 6 summarizes the results from an ELISA assay that demonstrated the ability of Example 47 suspension to induce IgG2a when added to Alum/3MenB. Example 47 enhanced IgG2a isotype switching (decreased ratio of IgG1/IgG2a) when formulated with Alum/3MenB (the lower the number, the bigger the IgG2a fold increase was induced by Example 47 suspension). IgG2a is considered as a surrogate of Th1 response is desirable to elicit.

TABLE 6

| | IgG1/IgG2a ratios | | |
|---|---|---|---|
| | GNA2132-GNA1030 | GNA2091-GNA1870 | NadA |
| Alum/3MenB | 923 | 15 | 308 |
| Alum/3MenB + 100 µg Example 47 | 1 | 2 | 7 |
| Alum/3MenB + OMV | 36 | 6 | 61 |

This Example demonstrates that the Example 47 homogenous suspension can significantly enhance immune responses to Alum/3MenB, with SBA titers comparable to, or better than, Alum/3MenB/OMV at 10 µg/dose, 25 µg/dose, or 100 µg/dose of Example 47 suspension. Further, Example 47 suspension can increase breadth of the immune response, as shown by an increase in the breadth of protection to various Neisseria meningitis strains.

Figure 8:
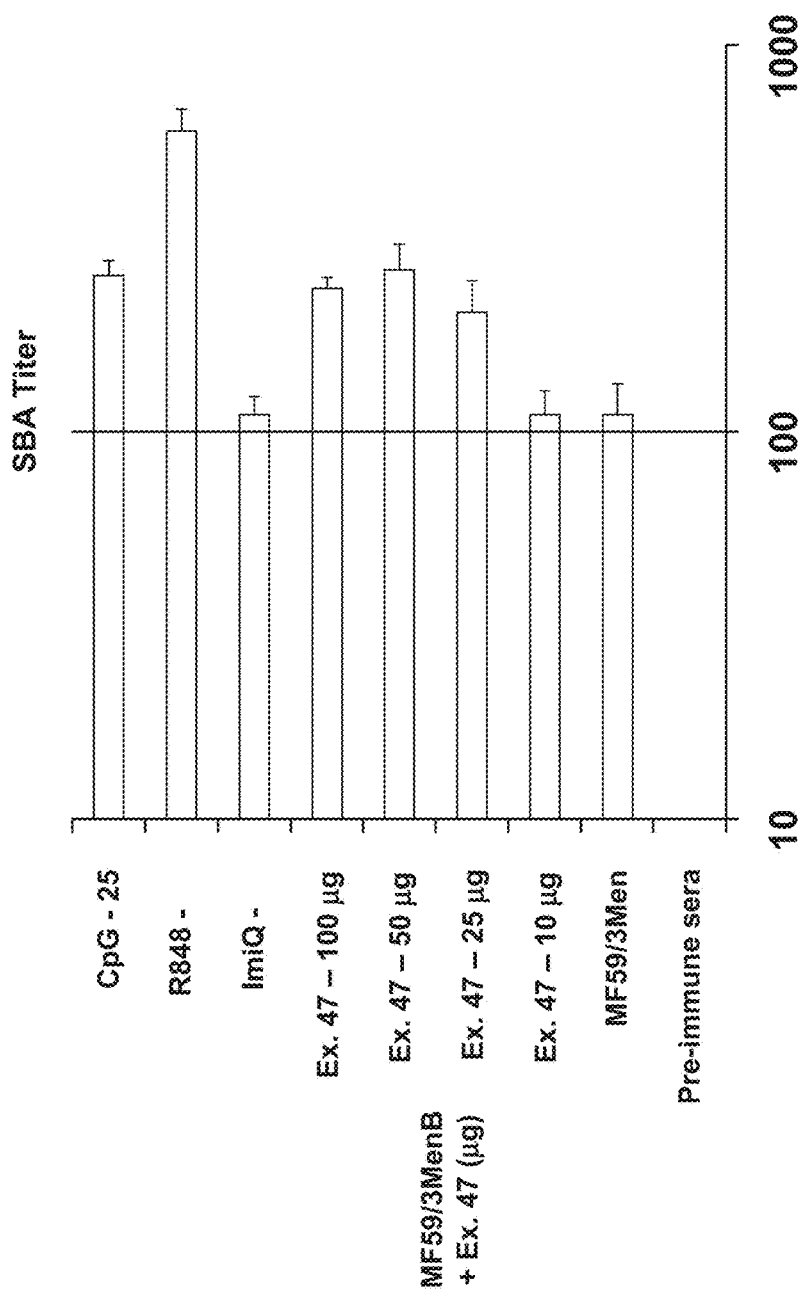
FIG. 8 shows the results of SBA assays using the Example 47 non-homogeneous suspension (prepared in DMSO). Mice were immunized twice via i.m. with MF59/3MenB+ the indicated amount of Example 47. The graph is based on 3 independent SBA studies and depicts average titer±standard deviation at two weeks post-2nd injection. SBA assays were performed with standard CFU method with NZ98 MenB strain.

Significantly, when non-homogeneous Example 47 suspension (prepared in DMSO) were used in conjunction with aluminium-based vaccines and MF59-based vaccines, the non-homogeneous suspension resulted in lower SBA titers when compared to the effects of homogeneous suspension at the same does. In one set of studies using the MenB mouse model, SBA titers upon addition of 10 µg/dose of non-homogeneous Example 47 suspension was comparable to that of MF59/3MenB alone (FIG. 8). In another set of studies, non-homogeneous Example 47 suspension showed only a borderline adjuvant effect. Therefore, the homogeneous suspensions described in this invention not only reduced the high degree of variability between the replicate animals and increase bioavailability of the molecules to immune cells post immunization, but also provide immunostimulatory effect at lower doses (e.g., 10 µg/dose or less).

Example (VI): Efficacy of Homogeneous Suspension of Example 47 in In Vivo RSV Model In this example, the in vivo efficacy of Example 47, delivered as homogeneous suspension, was evaluated using an RSV model.

A. Study 1

In one study, RSV F-subunit antigen was adsorbed on Al—H at a target concentration of 50 µg/mL or 10 µg/mL in 10 mM Histidine buffer. These alum formulations were prepared at 75% volume to allow addition of various adjuvants. Example 47 homogeneous suspension (4 mg/mL) at 25 and 100 µg doses, R848 (1 mg/mL) at 25 µg dose and CpG1826 (10 mg/mL) at 25 µg dose were added to the alum formulations or to F-subunit protein within 2 hours prior to immunization. Balb/c mice were immunized intramuscularly on days 0 and 14 with 100 µL immunization volume (50 µL/leg). Mice were bled retro-orbitally on day 28. ELISA titers were measured by serial dilutions of the sera on F-subunit protein adsorbed to the substrate. Neutralizing titers against RSV virus were measured based on the reduction in plaque numbers when incubated with various serum dilutions. FIRSV, R848 and CpG were used as the benchmarks in the study.

Figure 9A:
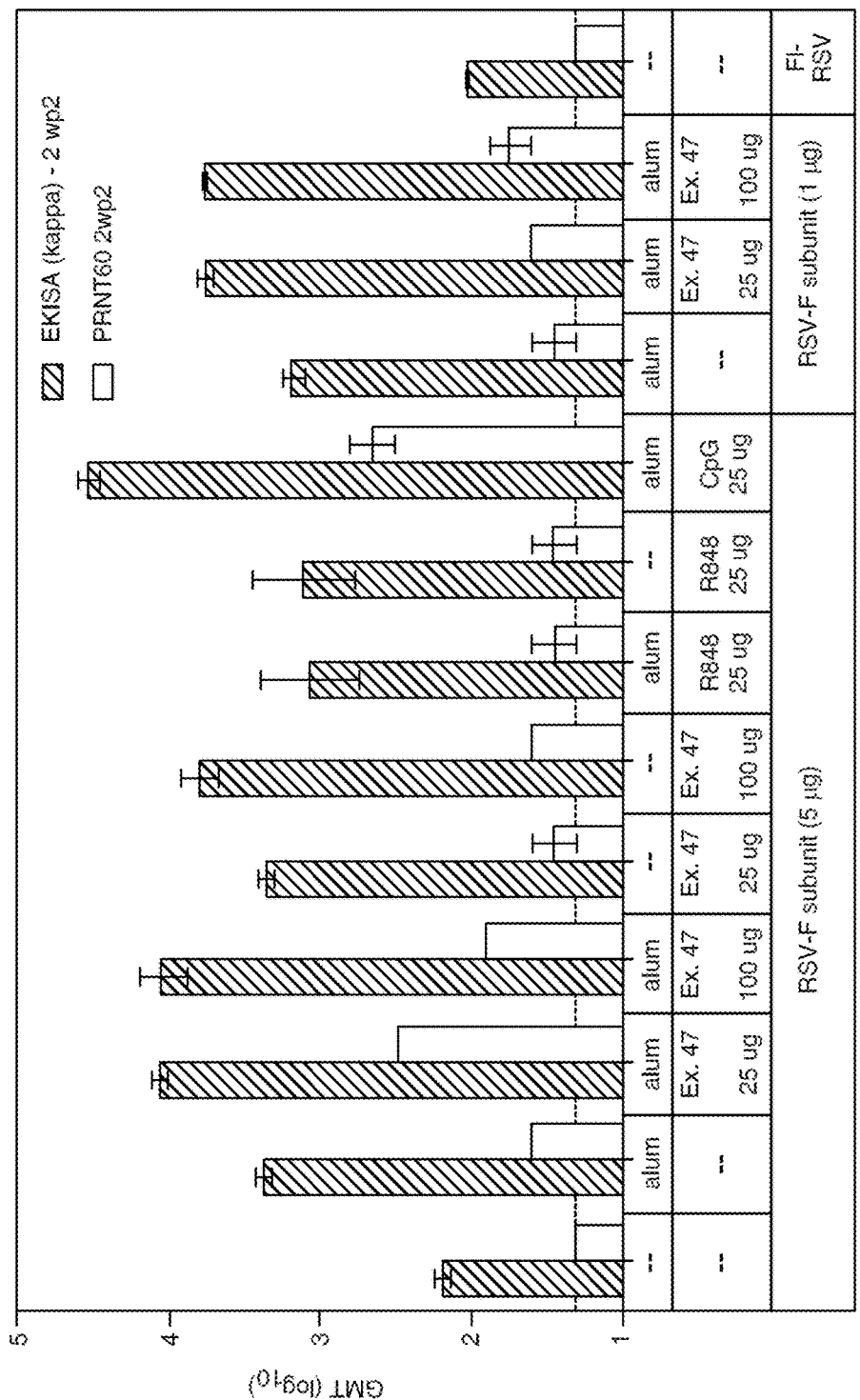
FIG. 9A is a graph summarizing the results of one study that demonstrated the ability of the Example 47 suspension to elicit an immune response against RSV F-antigen. The readouts represent total anti-F antibody (kappa) and neutralizing antibody (PRNT60).

As shown in FIG. 9A, Example 47 suspension increased the total antibody titers for all samples, and increases the neutralizing titers when the F-antigen was adsorbed to Al—H. FIG. 9A shows both the total anti-F antibody (ELISA-kappa) and neutralizing antibody (PRNT60) titres. Highest neutralizing titers were observed for the 25 µg dose of Example 47. Furthermore, addition of the Example 47 homogeneous suspension also enhanced IgG2a isotype switching with RSV F antigen alone or formulated with Al—H.

B. Study 2

Figure 9B:
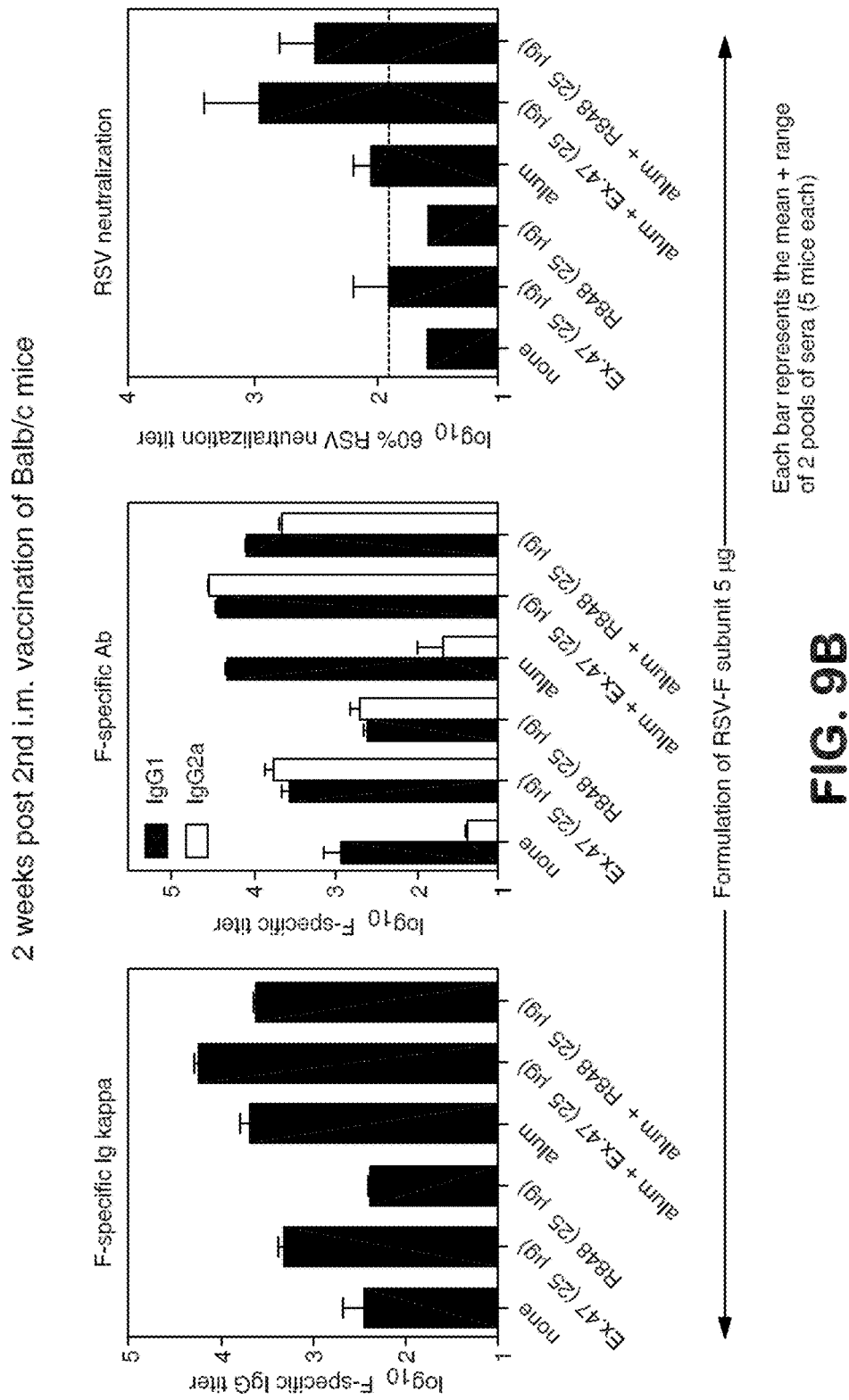
FIG. 9B shows that in another study, the Example 47 suspension enhanced F-specific antibody, class switching to IgG2a, and neutralizing antibody.

Similar results were obtained from another study. As shown in FIG. 9B, Example 47 homogeneous suspension increased the total antibody titers for all samples, and increased the neutralizing titers when the F-antigen was adsorbed to Al—H. Furthermore, addition of the Example 47 suspension also enhanced IgG2a isotype switching with RSV F antigen alone or formulated with Al—H.

Example (VII): Investigation of Strain Coverage for MenB Formulations

The in vivo efficacy of Example 47, delivered as homogeneous suspension at a dose of 25 µg/mouse, was evaluated using a MenB model. The studies were performed in two mouse strains, one study used CD1 mice and the other used C57/BL6 mice. The evaluation was carried out with a modified 5CVMB in which the GNA2091-GNA1870 fusion protein was replaced by the "936-10A-10A" protein disclosed in International Patent Application No. PCT/IB2010/002260 (filed Aug. 27, 2010, claiming priority from U.S. Ser. No. 61/237,576) (SEQ ID NO: 126 therein; SEQ ID NO: 4 herein). The modified 5CVMB was delivered with Al—H. The MenB antigens were tested for in vivo immunogenic potency using a SBA assay.

CD1 mice (Experiment I) or CD57/BL6 mice (Experiment II) were immunized intramuscularly on days 0 and 14 with 100 µL immunization volume (50 µL/leg) containing 10 µg of the three MenB polypeptides and 25.0 µg of Example 47 homogenous suspension. Mice were bled retro-orbitally on day 28 and SBA titers were measured. Alum/3MenB* with 25% of the standard clinical OMV dose was used as a benchmark. In this example, 3MenB* refers to a MenB vaccine made from the following three separate polypeptides: GNA2132-GNA1030, 936-10C-10C and NadA.

Table 7 summarizes the immunization of CD1 mice (Experiment I)

TABLE 7

| Groups | adult mice 6/group |
|---|---|
| 1 | Alum |
| 2 | Alum/3MenB* |
| 3 | Alum/3MenB* + Example 47 (25.0 µg) homogeneous suspension |
| 5 | Alum/3MenB* + ¼ D-OMV (1.25 µg) |

Immunization Protocols:
for i.m. immunization: injection of 100 µl (2 × 50 µl) per mouse
Number of immunizations: 2
Schedule for immunization: day 0, 14
Bleed Days: −1, 13, 28

Table 8 summarizes the immunization of C57/BL6 mice (Experiment II)

TABLE 8

| Groups | adult mice 6/group |
|---|---|
| 1 | Alum |
| 2 | Alum/3MenB* |
| 3 | Alum/3MenB* + Example 47 (25.0 µg) homogeneous suspension |
| 5 | Alum/3MenB* + ¼ D-OMV (1.25 µg) |

Immunization Protocols:
for i.m. immunization: injection of 100 µl (2 × 50 µl) per mouse
Number of immunizations: 2
Schedule for immunization: day 0, 14
Bleed Days: −1, 13, 28

Alum/3MenB* formulations (groups G2, G3, G5 in Table 9) were prepared at 75% volume, and Example 47 homogeneous suspension was added in order to reach a 20 dose, within 2 hours prior to immunization. The addition of Example 47 homogeneous suspension to Alum/3MenB* did not alter the quality of the formulations in terms of pH and osmolarity as the values were consistently within an acceptable range for preclinical and clinical evaluations. The Example 47 homogeneous suspension was compatible with the antigens used and the endotoxin content was less than 5 EU/dose. Table 9 shows that the standard formulations of MenB were well adsorbed on Alum (>95%) both alone and formulated with OMV. Formulations with Example 47 showed a desorption of the antigens after addition of the homogeneous suspension of Example 47, but adsorption remained >90%.

TABLE 9

| Formulation Characterization Overview | |
|---|---|
| G1 | Alum |
| Ags | Osmolarity |

TABLE 9-continued

Formulation Characterization Overview

|  | Adsorption | mOsm/ml | pH |
|---|---|---|---|
| 1st imm (Exp. I) | n/a | 245 | 7.0 |
| 2nd imm (Exp. I) | n/a | 260 | 7.0 |
| 1st imm (Exp. II) | n/a | 282 | 7.0 |
| 2nd imm (Exp. II) | n/a | 265 | 7.0 |

| | G2 Ags Adsorption | Alum/3MenB* Osmolarity mOsm/ml | pH |
|---|---|---|---|
| 1st imm (Exp. I) | >95% | 296 | 7.3 |
| 2nd imm (Exp. I) | >95% | 278 | 7.4 |
| 1st. imm (Exp. II) | >95% | 293 | 7.4 |
| 2nd imm (Exp. II) | >95% | 290 | 7.2 |

| | G3 Ags Adsorption | Alum/3MenB* Example 47 Osmolarity mOsm/ml | pH |
|---|---|---|---|
| 1st imm (Exp. I) | >90% | 294 | 7.3 |
| 2nd imm (Exp. I) | >90% | 280 | 7.4 |
| 1st imm (Exp. II) | >90% | 279 | 7.3 |
| 2nd imm (Exp. II) | >90% | 285 | 7.3 |

| | G5 Ags Adsorption | Alum/3MenB* + ¼ D-OMV Osmolarity mOsm/ml | pH |
|---|---|---|---|
| 1st imm (Exp. I) | >95% | 258 | 7.2 |
| 2nd imm (Exp. I) | >95% | 270 | 7.3 |
| 1st imm (Exp. II) | >95% | 285 | 7.3 |
| 2nd imm (Exp. II) | >95% | 280 | 7.3 |

Tables 10-13 show bactericidal titers against five different strains of Neisseria meningitides after immunization with formulations comprising the three polypeptides combined with (2) Al—H alone, (3) Al—H+250 mcg/ml Example 47 or (5) Al—H and MenB outer membrane vesicles.

TABLE 10 serum bacterial antibody (SBA) analysis of Experiment I (CD1 nice)
Exp. I CD1

| Group | Immunization | MC58 | NZ98/254 | 961-5945 | UK355 | 5-99 |
|---|---|---|---|---|---|---|
| 1 | IM | <16 | <16 | <16 | <16 | <16 |
| 2 | IM | <16 | <16 | <16 | <16 | <16 |
| 3 | IM | <16 | <16 | <16 | <16 | <16 |
| 5 | IM | <16 | <16 | <16 | <16 | <16 |

TABLE 11 serum bacterial antibody (SBA) analysis of Experiment II
(C57/BL6 mice)
Exp. II C57/BL6

| Group | Immunization | MC58 | NZ98/254 | 961-5945 | UK355 | 5-99 |
|---|---|---|---|---|---|---|
| 1 | IM | <16 | <16 | <16 | <16 | <16 |
| 2 | IM | <16 | <16 | <16 | <16 | <16 |
| 3 | IM | <16 | <16 | <16 | <16 | <16 |
| 5 | IM | <16 | <16 | <16 | <16 | <16 |

TABLE 12 serum bacterial antibody (SBA) analysis of Experiment I (CD1 nice)
Exp. I CD1; Post 2nd

| Group | Immunization | MC58 | NZ98/254 | 961-5945 | UK355 | 5-99 |
|---|---|---|---|---|---|---|
| 1 | Alum/PBS | <16 | <16 | <16 | <16 | <16 |
| 2 | Alum/3MenB* | 2048 | 64 | 1024 | <64 | 8192 |
| 3 | Alum/3MenB* + Example 47 (250 mcg/ml) | 8192 | 1024 | 16384 | 2048 | >32768 |
| 5 | Alum/3 MenB* + D-OMV | 4096 | 1024 | 2048 | 128 | >32768 |

TABLE 13 serum bacterial antibody (SBA) analysis of Experiment II
(C57/BL6 mice)
Exp. II C57/BL6; Post 2nd

| Group | Immunization | MC58 | NZ98/254 | 961-5945 | UK355 | 5-99 |
|---|---|---|---|---|---|---|
| 1 | Alum/PBS | <16 | <16 | <16 | <16 | <16 |
| 2 | Alum/3MenB* | <64 | <64 | <64 | <16 | 128 |
| 3 | Alum/3MenB* + Example 47 (250 mcg/ml) | 512 | 128 | 2048 | <16 | 32768 |
| 5 | Alum/3 MenB* + D-OMV | 128 | 1024 | 64 | <16 | 512 |

SBA titers for Example 47 formulations were higher than for Alum/3MenB baseline, and were comparable to Alum/3MenB+D-OMV. As shown in Tables 10-13, addition of Example 47 homogeneous suspension (Group 3) led to a superior breadth of vaccine coverage when compared to the Alum/3MenB group (Group 2), and better or comparable coverage compared to the group formulated with OMV (Group 5).

The amino acid sequences of NadA, GNA2132-GNA1030, GNA2091-GNA1870, and 936-10A-10A are presented below.

```
(Amino acid sequence for NadA)
                                       SEQ ID NO: 1
ATNDDDVKKAATVAIAAAYNNGQEINGFKAGETIYDIDEDGTITKKDATA

ADVEADDFKGLGLKKVVTNLTKTVNENKQNVDAKVKAAESEIEKLTTKLA

DTDAALADTDAALDATTNALNKLGENITTFAEETKTNIVKIDEKLEAVAD

TVDKHAEAFNDIADSLDETNTKADEAVKTANEAKQTAEETKQNVDAKVKA

AETAAGKAEAAAGTANTAADKAEAVAAKVTDIKADIATNKDNIAKKANSA

DVYTREESDSKFVRIDGLNATTEKLDTRLASAEKSIADHDTRLNGLDKTV

SDLRKETRQGLAEQAALSGLFQPYNVG (Amino acid sequence for GNA2132-GNA1030)
                                       SEQ ID NO: 2
MASPDVKSADTLSKPAAPVVSEKETEAKEDAPQAGSQGQGAPSAQGGQDM

AAVSEENTGNGGAAATDKPKNEDEGAQNDMPQNAADTDSLTPNHTPASNM

PAGNMENQAPDAGESEQPANQPDMANTADGMQGDDPSAGGENAGNTAAQG

TNQAENNQTAGSQNPASSTNPSATNSGGDFGRTNVGNSVVIDGPSQNITL

THCKGDSCSGNNFLDEEVQLKSEFEKLSDADKISNYKKDGKNDGKNDKFV
```

-continued

```
GLVADSVQMKGINQYIIFYKPKPTSFARFRRSARSRRSLPAEMPLIPVNQ

ADTLIVDGEAVSLTGHSGNIFAPEGNYRYLTYGAEKLPGGSYALRVQGEP

SKGEMLAGTAVYNGEVLHFHTENGRPSPSRGRFAAKVDFGSKSVDGIIDS

GDGLHMGTQKFKAAIDGNGFKGTWTENGGGDVSGKFYGPAGEEVAGKYSY

RPTDAEKGGFGVFAGKKEQDGSGGGGATYKVDEYHANARFAIDHENTSTN

VGGFYGLTGSVEFDQAKRDGKIDITIPVANLQSGSQHFTDHLKSADIFDA

AQYPDIREVSTKENENGKKLVSVDGNLTMHGKTAPVKLKAEKFNCYQSPM

AKTEVCGGDFSTTIDRTKWGVDYLVNVGMTKSVRIDIQIEAAKQ (Amino acid sequence for GNA2091-GNA1870)
                                        SEQ ID NO: 3
MVSAVIGSAAVGAKSAVDRRTTGAQTDDNVMALRIETTARSYLRQNNQTK

GYTPQISVVGYDRHLLLLGQVATEGEKQFVGQIARSEQAAEGVYNYITVA

SLPRTAGDIAGDTWNTSKVRATLLGISPATRARVKIVTYGNVTYVMGILT

PEEQAQITQKVSTTVGVQKVITLYQNYVQRGSGGGGVAADIGAGLADALT

APLDHKDKGLQSLTLDQSVRKNEKLKLAAQGAEKTYGNGDSLNTGKLKND

KVSRFDFIRQIEVDGQLITLESGEFQVYKQSHSALTAFQTEQIQDSEHSG

KMVAKRQFRIGDIAGEHTSFDKLPEGGRATYRGTAFGSDDAGGKLTYTID

FAAKQGNGKIEHLKSPELNVDLAAADIKPDGKRHAVISGSVLYNQAEKGS

YSLGIFGGKAQEVAGSAEVKTVNGIRHIGLAAKQ (Amino acid sequence for 936-10A-10A)
                                        SEQ ID NO: 4
MVSAVIGSAAVGAKSAVDRRTTGAQTDDNVMALRIETTARSYLRQNNQTK

GYTPQISVVGYDRHLLLLGQVATEGEKQFVGQIARSEQAAEGVYNYITVA

SLPRTAGDIAGDTWNTSKVRATLLGISPATRARVKIVTYGNVTYVMGILT
```

-continued

```
PEEQAQITQKVSTTVGVQKVITLYQNYVQRGSGGGGVAADIGAGLADALT

APLDHKDKGLQSLTLDQSVRKNEKLKLAAQGAEKTYGNGDSLNTGKLKND

KVSRFDFIRQIEVDGQLITLESGEFQVYKQSHSALTAFQTEQIQDSEHSG

KMVAKRQFRIGDLGGEHTAFNQLPDGKAEYRGTAFGSDDAGGKLTYTIDF

TKKQGNGKIEHLKSPELNVELASAEIKADGKSHAVILGDVRYGSEEKGSY

SLGIFGGRAQEVAGSAEVKTVNGIRHIGLAAKQGSGGGGVAADIGAGLAD

ALTAPLDHKDKGLQSLTLDQSVRKNEKLKLAAQGAEKTYGNGDSLNTGKL

KNDKVSRFDFIRQIEVDGQLITLESGEFQVYKQSHSALTAFQTEQIQDSE

HSGKMVAKRQFRIGDLGGEHTAFNQLPDGKAEYRGTAFGSDDAGGKLTYT

IDFTKKQGNGKIEHLKSPELNVELASAEIKADGKSHAVILGDVRYGSEEK

GSYSLGIFGGRAQEVAGSAEVKTVNGIRHIGLAAKQ
```

Those skilled in the art will recognize, or be able to ascertain using no more than routine experimentation, many equivalents to the specific embodiments of the invention described herein. Such equivalents are intended to be encompassed by the following embodiments.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supercede any such material. The citation of any references herein is not an admission that such references are prior art to the present invention.

What is claimed:

1. An immunogenic composition comprising a homogeneous suspension comprising: (a) a Benzonaphthyridine compound of Formula I or Formula II:

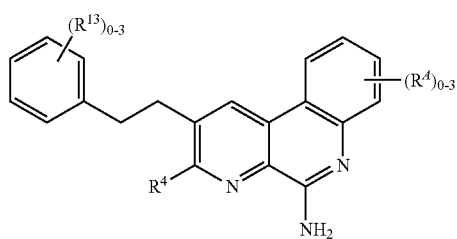

Formula (I)

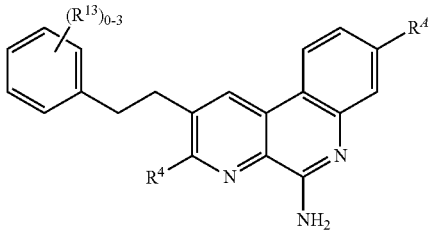

Formula (II)

pharmaceutically acceptable salt, pharmaceutically acceptable solvate, individual isomer or mixture of isomers thereof;

(b) a surfactant, and (c) a viscosity-enhancing suspension agent,
wherein the homogeneous suspension was produced by high pressure homogenization,
wherein the suspension is stable for at least about 4 weeks at 4° C., and, wherein $R^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —CH(R$^{10}$)$_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each $R^9$ is independently selected from H, —C(O)R$^8$, —C(O)OR$^8$, —C(O)R$^{10}$, —C(O)OR$^{10}$, —S(O)$_2$R$^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, R$^8$, —OR$^8$, —C(O)R$^8$, —OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, $C_3$-$C_8$heterocycloalkyl, —S(O)$_2$R$^8$, —S(O)$_2$N(R$^9$)$_2$, —NR$^9$S(O)$_2$R$^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)OR$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$;

each $R^4$ is independently selected from —R$^8$, —R$^7$, —OR$^8$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH═CHCO$_2$R$^8$, —C(═NH)—N(R$^9$)$_2$, and —(CH$_2$)$_n$NHC(O)R$^8$; or in Formula I two adjacent $R^4$ substituents on the ring to which they are bonded form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

2. The immunogenic composition of claim 1, wherein the homogeneous suspension comprises 0.1% to 10% surfactant.

3. The immunogenic composition of claim 1, wherein the homogeneous suspension comprises 0.1% to 10% viscosity-enhancing suspension agent.

4. The immunogenic composition of claim 1, wherein the homogeneous suspension comprises 0.5 mg/mL to 50 mg/mL Benzonaphthyridine compound.

5. The immunogenic composition of claim 1, wherein the surfactant is selected from Polyoxyethylene-Polyoxypropylene Block Copolymer (Pluronic F-68), Polyoxyethylene sorbitan oleate (polysorbate 80), sodium laureth sulfate, or a combination thereof.

6. The immunogenic composition of claim 1, wherein the viscosity-enhancing suspension agent is selected from carboxymethyl cellulose, hydroxypropyl cellulose, hydroxypropylmethyl cellulose, or a combination thereof.

7. The immunogenic composition of claim 1, wherein the surfactant is polysorbate 80.

8. The immunogenic composition of claim 7, wherein the viscosity-enhancing suspension agent is carboxymethyl cellulose.

9. The immunogenic composition of claim 1, wherein at least 50% of the suspension particles have a diameter of 10 μm or less.

10. The immunogenic composition of claim 1, wherein at least 50% of the suspension particles have a diameter of 2 μm or less.

11. The immunogenic composition of claim 1, wherein the Benzonaphthyridine compound is: 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine; 2-(4-methoxyphenethyl)-8-methylbenzo[f][1,7]naphthyridin-5-amine; or 2-(2-(4-(2-(5-amino-8-methylbenzo[f][1,7]naphthyridin-2-yl)ethyl)-3-methylphenoxy)ethoxy)ethanol.

12. The immunogenic composition of claim 1, wherein the composition further comprises an adjuvant.

13. The immunogenic composition of claim 12, wherein the adjuvant is selected from an oil-in-water emulsion, a liposome, a microparticle, an oligonucleotide, a calcium salt, and a saponin formulation.

14. The immunogenic composition of claim 1, wherein the composition further comprises an antigen.

15. The immunogenic composition of claim 14, wherein the antigen is a bacterial antigen.

16. The immunogenic composition of claim 15, wherein the bacterial antigen is an antigen from *Neisseria meningitides*.

17. The immunogenic composition of claim 14, wherein the antigen is a viral antigen.

18. The immunogenic composition of claim 17, wherein the viral antigen is an antigen from respiratory syncytial virus (RSV).

19. The immunogenic composition of claim 17, wherein the viral antigen is an antigen from Ebola virus.

20. A method of generating an immune response in a subject, comprising administering to said subject the immunogenic composition of claim 14.

* * * * *

SEQUENCE LISTING

```
<160> NUMBER OF SEQ ID NOS: 10

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
```

```
                    115                 120                 125
Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Asp Ile Lys
                180                 185                 190

Pro Asp Gly Lys Arg His Ala Val Ile Ser Gly Ser Val Leu Tyr Asn
                195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245
```

<210> SEQ ID NO 2
<211> LENGTH: 247
<212> TYPE: PRT
<213> ORGANISM: Neisseria meningitidis

<400> SEQUENCE: 2

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
                180                 185                 190

Asp Glu Lys Ser His Ala Val Ile Leu Gly Asp Thr Arg Tyr Gly Ser
                195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240
```

```
Ile Gly Ile Ala Gly Lys Gln
            245
```

<210> SEQ ID NO 3
<211> LENGTH: 250
<212> TYPE: PRT
<213> ORGANISM: Neisseria meningitidis

<400> SEQUENCE: 3

```
Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250
```

<210> SEQ ID NO 4
<211> LENGTH: 644
<212> TYPE: PRT
<213> ORGANISM: Neisseria meningitidis

<400> SEQUENCE: 4

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60
```

-continued

```
Ala Thr Asp Lys Pro Lys Asn Glu Asp Glu Gly Ala Gln Asn Asp Met
 65                  70                  75                  80

Pro Gln Asn Ala Ala Asp Thr Asp Ser Leu Thr Pro Asn His Thr Pro
                 85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
```

```
                    485                 490                 495
Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
            530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
                595                 600                 605

Asp Phe Ser Thr Thr Ile Asp Arg Thr Lys Trp Gly Val Asp Tyr Leu
            610                 615                 620

Val Asn Val Gly Met Thr Lys Ser Val Arg Ile Asp Ile Gln Ile Glu
625                 630                 635                 640

Ala Ala Lys Gln

<210> SEQ ID NO 5
<211> LENGTH: 434
<212> TYPE: PRT
<213> ORGANISM: Neisseria meningitidis

<400> SEQUENCE: 5

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asn Arg His
        50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
                180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
```

```
              210                 215                 220
Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
                260                 265                 270

Gly Glu Phe Gln Val Tyr Lys Gln Ser His Ser Ala Leu Thr Ala Phe
                275                 280                 285

Gln Thr Glu Gln Ile Gln Asp Ser Glu His Ser Gly Lys Met Val Ala
                290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
                340                 345                 350

Ala Lys Gln Gly Asn Gly Lys Ile Glu His Leu Lys Ser Pro Glu Leu
                355                 360                 365

Asn Val Asp Leu Ala Ala Ala Asp Ile Lys Pro Asp Gly Lys Arg His
                370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
                420                 425                 430

Lys Gln

<210> SEQ ID NO 6
<211> LENGTH: 327
<212> TYPE: PRT
<213> ORGANISM: Neisseria meningitidis

<400> SEQUENCE: 6

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
                35                  40                  45

Thr Ala Ala Asp Val Glu Ala Asp Asp Phe Lys Gly Leu Gly Leu Lys
                50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
                100                 105                 110

Leu Asp Ala Thr Thr Asn Ala Leu Asn Lys Leu Gly Glu Asn Ile Thr
                115                 120                 125

Thr Phe Ala Glu Glu Thr Lys Thr Asn Ile Val Lys Ile Asp Glu Lys
                130                 135                 140

Leu Glu Ala Val Ala Asp Thr Val Asp Lys His Ala Glu Ala Phe Asn
```

```
                145                 150                 155                 160
Asp Ile Ala Asp Ser Leu Asp Glu Thr Asn Thr Lys Ala Asp Glu Ala
            165                 170                 175

Val Lys Thr Ala Asn Glu Ala Lys Gln Thr Ala Glu Glu Thr Lys Gln
            180                 185                 190

Asn Val Asp Ala Lys Val Lys Ala Glu Thr Ala Ala Gly Lys Ala
            195                 200                 205

Glu Ala Ala Gly Thr Ala Asn Thr Ala Ala Asp Lys Ala Glu Ala
210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
            245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
            290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Polycationic peptide"

<400> SEQUENCE: 7

Lys Leu Lys Leu Leu Leu Leu Leu Lys Leu Lys
1               5                   10

<210> SEQ ID NO 8
<211> LENGTH: 434
<212> TYPE: PRT
<213> ORGANISM: Neisseria meningitidis

<400> SEQUENCE: 8

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Glu Gly Val Tyr Asn Tyr
            85                  90                  95

Ile Thr Val Ala Ser Leu Pro Arg Thr Ala Gly Asp Ile Ala Gly Asp
            100                 105                 110
```

```
Thr Trp Asn Thr Ser Lys Val Arg Ala Thr Leu Leu Gly Ile Ser Pro
            115                 120                 125

Ala Thr Arg Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
            210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
            355                 360                 365

Asn Val Asp Leu Ala Ala Ala Asp Ile Lys Pro Asp Gly Lys Arg His
            370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 9
<211> LENGTH: 686
<212> TYPE: PRT
<213> ORGANISM: Neisseria meningitidis

<400> SEQUENCE: 9

Met Val Ser Ala Val Ile Gly Ser Ala Val Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45
```

-continued

Thr Lys Gly Tyr Thr Pro Gln Ile Ser Val Val Gly Tyr Asp Arg His
 50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
                115                 120                 125

Ala Thr Arg Ala Arg Val Lys Ile Val Thr Tyr Gly Asn Val Thr Tyr
            130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
    275                 280                 285

Gln Thr Glu Gln Ile Gln Asp Ser Glu His Ser Gly Lys Met Val Ala
            290                 295                 300

Lys Arg Gln Phe Arg Ile Gly Asp Leu Gly Gly Glu His Thr Ala Phe
305                 310                 315                 320

Asn Gln Leu Pro Asp Gly Lys Ala Glu Tyr Arg Gly Thr Ala Phe Gly
                325                 330                 335

Ser Asp Asp Ala Gly Gly Lys Leu Thr Tyr Thr Ile Asp Phe Thr Lys
            340                 345                 350

Lys Gln Gly Asn Gly Lys Ile Glu His Leu Lys Ser Pro Glu Leu Asn
    355                 360                 365

Val Glu Leu Ala Ser Ala Glu Ile Lys Ala Asp Gly Lys Ser His Ala
    370                 375                 380

Val Ile Leu Gly Asp Val Arg Tyr Gly Ser Glu Glu Lys Gly Ser Tyr
385                 390                 395                 400

Ser Leu Gly Ile Phe Gly Gly Arg Ala Gln Glu Val Ala Gly Ser Ala
                405                 410                 415

Glu Val Lys Thr Val Asn Gly Ile Arg His Ile Gly Leu Ala Ala Lys
            420                 425                 430

Gln Gly Ser Gly Gly Gly Val Ala Ala Asp Ile Gly Ala Gly Leu
    435                 440                 445

Ala Asp Ala Leu Thr Ala Pro Leu Asp His Lys Asp Lys Gly Leu Gln
450                 455                 460

Ser Leu Thr Leu Asp Gln Ser Val Arg Lys Asn Glu Lys Leu Lys Leu

```
465                 470                 475                 480
Ala Ala Gln Gly Ala Glu Lys Thr Tyr Gly Asn Gly Asp Ser Leu Asn
                485                 490                 495

Thr Gly Lys Leu Lys Asn Asp Lys Val Ser Arg Phe Asp Phe Ile Arg
                500                 505                 510

Gln Ile Glu Val Asp Gly Gln Leu Ile Thr Leu Glu Ser Gly Glu Phe
                515                 520                 525

Gln Val Tyr Lys Gln Ser His Ser Ala Leu Thr Ala Phe Gln Thr Glu
                530                 535                 540

Gln Ile Gln Asp Ser Glu His Ser Gly Lys Met Val Ala Lys Arg Gln
545                 550                 555                 560

Phe Arg Ile Gly Asp Leu Gly Gly Glu His Thr Ala Phe Asn Gln Leu
                565                 570                 575

Pro Asp Gly Lys Ala Glu Tyr Arg Gly Thr Ala Phe Gly Ser Asp Asp
                580                 585                 590

Ala Gly Gly Lys Leu Thr Tyr Thr Ile Asp Phe Thr Lys Lys Gln Gly
                595                 600                 605

Asn Gly Lys Ile Glu His Leu Lys Ser Pro Glu Leu Asn Val Glu Leu
                610                 615                 620

Ala Ser Ala Glu Ile Lys Ala Asp Gly Lys Ser His Ala Val Ile Leu
625                 630                 635                 640

Gly Asp Val Arg Tyr Gly Ser Glu Glu Lys Gly Ser Tyr Ser Leu Gly
                645                 650                 655

Ile Phe Gly Gly Arg Ala Gln Glu Val Ala Gly Ser Ala Glu Val Lys
                660                 665                 670

Thr Val Asn Gly Ile Arg His Ile Gly Leu Ala Ala Lys Gln
                675                 680                 685

<210> SEQ ID NO 10
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      oligonucleotide"
<220> FEATURE:
<221> NAME/KEY: misc_feature
<222> LOCATION: 1, 3, 5, 7, 9, 11, 13, 15, 17, 19, 21, 23, 25
<223> OTHER INFORMATION: 'n' is INOSINE

<400> SEQUENCE: 10 ncncncnc ncncncncnc ncncnc                                      26
```